(12) United States Patent
Barrat et al.

(10) Patent No.: US 8,940,310 B2
(45) Date of Patent: Jan. 27, 2015

(54) METHODS OF TREATMENT USING TLR7 AND/OR TLR9 INHIBITORS

(75) Inventors: Franck Barrat, San Francisco, CA (US); Robert L. Coffman, Portola Valley, CA (US); Cristiana Guiducci, Albany, CA (US)

(73) Assignee: Dynavax Technologies Corporation, Berkeley, CA (US)

( * ) Notice: Subject to any disclaimer, the term of this patent is extended or adjusted under 35 U.S.C. 154(b) by 0 days.

(21) Appl. No.: 13/704,978

(22) PCT Filed: Jun. 16, 2011

(86) PCT No.: PCT/US2011/040788
§ 371 (c)(1),
(2), (4) Date: Mar. 4, 2013

(87) PCT Pub. No.: WO2011/159958
PCT Pub. Date: Dec. 22, 2011

(65) Prior Publication Data
US 2013/0156814 A1    Jun. 20, 2013

Related U.S. Application Data

(60) Provisional application No. 61/355,547, filed on Jun. 16, 2010, provisional application No. 61/415,289, filed on Nov. 18, 2010, provisional application No. 61/423,076, filed on Dec. 14, 2010.

(51) Int. Cl.
*A61K 31/7125* (2006.01)
*A01N 43/04* (2006.01)
*C12N 15/117* (2010.01)

(52) U.S. Cl.
USPC ........... 424/278.1; 435/6; 435/91.1; 435/455; 514/44; 536/23.1

(58) Field of Classification Search
USPC ............ 435/6, 91.1, 91.31, 455; 514/1, 2, 44; 536/23.1; 424/278.1
See application file for complete search history.

(56) References Cited

U.S. PATENT DOCUMENTS

| | | |
|---|---|---|
| 4,458,066 A | 7/1984 | Caruthers et al. |
| 4,587,329 A | 5/1986 | Tomalia et al. |
| 4,650,675 A | 3/1987 | Borel et al. |
| 4,849,513 A | 7/1989 | Smith et al. |
| 4,910,300 A | 3/1990 | Urdea et al. |
| 4,948,882 A | 8/1990 | Ruth |
| 5,015,733 A | 5/1991 | Smith et al. |
| 5,093,232 A | 3/1992 | Urdea et al. |
| 5,118,800 A | 6/1992 | Smith et al. |
| 5,118,802 A | 6/1992 | Smith et al. |
| 5,124,246 A | 6/1992 | Urdea et al. |
| 5,171,264 A | 12/1992 | Merrill |
| 5,338,532 A | 8/1994 | Tomalia et al. |
| 5,391,723 A | 2/1995 | Priest |
| 5,445,934 A | 8/1995 | Fodor et al. |
| 5,453,496 A | 9/1995 | Caruthers et al. |
| 5,460,831 A | 10/1995 | Kossovsky et al. |
| 5,552,391 A | 9/1996 | Coutts et al. |
| 5,700,637 A | 12/1997 | Southern |
| 5,807,522 A | 9/1998 | Brown et al. |
| 6,080,580 A | 6/2000 | Baker et al. |
| 6,096,722 A | 8/2000 | Bennett et al. |
| 6,117,657 A | 9/2000 | Usman et al. |
| 6,177,414 B1 | 1/2001 | Tomalia et al. |
| 6,225,292 B1 | 5/2001 | Raz et al. |
| 7,118,865 B2 | 10/2006 | Behrens et al. |
| 7,608,395 B2 | 10/2009 | Pascual et al. |
| 2001/0006945 A1 | 7/2001 | Agrawal |
| 2003/0087848 A1 | 5/2003 | Bratzler et al. |
| 2004/0009949 A1 | 1/2004 | Krieg |
| 2004/0053880 A1 | 3/2004 | Krieg |
| 2005/0239733 A1 | 10/2005 | Jurk et al. |
| 2006/0193821 A1 | 8/2006 | Diener et al. |
| 2006/0193869 A1* | 8/2006 | Barrat et al. ............... 424/184.1 |
| 2007/0238678 A1* | 10/2007 | Barrat et al. .................... 514/44 |
| 2009/0060898 A1 | 3/2009 | Kandimalla et al. |
| 2010/0130593 A1 | 5/2010 | Garren et al. |
| 2011/0003885 A1 | 1/2011 | Barrat et al. |
| 2011/0123561 A1 | 5/2011 | Barrat et al. |
| 2011/0182927 A1 | 7/2011 | Raz et al. |

FOREIGN PATENT DOCUMENTS

| | | |
|---|---|---|
| EP | 0 313 219 B1 | 5/1996 |
| EP | 2 154 144 A1 | 2/2010 |
| WO | WO-89/02439 A1 | 3/1989 |
| WO | WO-95/07073 A1 | 3/1995 |

(Continued)

OTHER PUBLICATIONS

Agrawal, S. et al. (1986). "Efficient Methods for Attaching Non-Radioactive Labels to the 5' Ends of Synthetic Oligodeoxyribonucleotides," *Nucleic Acids Research* 14(15):6227-6245.

Agrawal, H. et al. (2009). "Deficiency of Type I IFN Receptor in Lupus-Prone New Zealand Mixed 2328 Mice Decreases Dendritic Cell Numbers and Activation and Protects from Disease," *The Journal of Immunology* 183:6021-6029.

Akira, S. et al. (2003). "Recognition of Pathogen-Associated Molecular Patterns by TLR Family," *Immunology Letters* 85:85-95.

Alexopoulou, L. et al. (2001). "Recognition of Double-Stranded RNA and Activation of NF-κB by Toll-Like Receptor 3," *Nature* 413:732-738.

(Continued)

*Primary Examiner* — Jane Zara
(74) *Attorney, Agent, or Firm* — Morrison & Foerster LLP

(57) ABSTRACT

The application relates to compositions and methods of regulating an immune response comprising inhibitors of TLR7 and/or TLR9, such as immunoregulatory polynucleotides and/or immunoregulatory compounds. The application also relates to compositions and methods for predicting and/or determining responsiveness of a disease to treatment comprising inhibitors of TLR7 and/or TLR9.

33 Claims, 52 Drawing Sheets

(56) References Cited

FOREIGN PATENT DOCUMENTS

| | | |
|---|---|---|
| WO | WO-96/40197 A1 | 12/1996 |
| WO | WO-97/46251 A1 | 12/1997 |
| WO | WO-98/16247 A1 | 4/1998 |
| WO | WO-98/55495 A2 | 12/1998 |
| WO | WO-98/55495 A3 | 12/1998 |
| WO | WO-98/55609 A1 | 12/1998 |
| WO | WO-00/34231 A1 | 6/2000 |
| WO | WO-00/61151 A2 | 10/2000 |
| WO | WO-00/61151 A3 | 10/2000 |
| WO | WO-00/75105 A1 | 12/2000 |
| WO | WO-01/22972 A2 | 4/2001 |
| WO | WO-01/22972 A3 | 4/2001 |
| WO | WO-01/22972 A9 | 4/2001 |
| WO | WO-01/68697 A2 | 9/2001 |
| WO | WO-01/68697 A3 | 9/2001 |
| WO | WO-01/75166 A2 | 10/2001 |
| WO | WO-01/75166 A3 | 10/2001 |
| WO | WO-02/10438 A2 | 2/2002 |
| WO | WO-02/10438 A3 | 2/2002 |
| WO | WO-02/10438 A9 | 2/2002 |
| WO | WO-02/095010 A2 | 11/2002 |
| WO | WO-02/095010 A3 | 11/2002 |
| WO | WO-03/085110 A2 | 10/2003 |
| WO | WO-03/085110 A3 | 10/2003 |
| WO | WO-03/103586 A2 | 12/2003 |
| WO | WO-03/103586 A3 | 12/2003 |
| WO | WO-03/103708 A1 | 12/2003 |
| WO | WO-2004/014322 A2 | 2/2004 |
| WO | WO-2004/014322 A3 | 2/2004 |
| WO | WO-2004/047734 A2 | 6/2004 |
| WO | WO-2004/047734 A3 | 6/2004 |
| WO | WO-2004/058179 A2 | 7/2004 |
| WO | WO-2004/058179 A3 | 7/2004 |
| WO | WO-2005/086835 A2 | 9/2005 |
| WO | WO-2005/086835 A3 | 9/2005 |
| WO | WO-2005/115479 A2 | 12/2005 |
| WO | WO-2005/115479 A3 | 12/2005 |
| WO | WO-2006/028742 A2 | 3/2006 |
| WO | WO-2006/028742 A3 | 3/2006 |
| WO | WO-2006/066003 A2 | 6/2006 |
| WO | WO-2006/066003 A3 | 6/2006 |
| WO | WO-2007/075626 A2 | 7/2007 |
| WO | WO-2007/075626 A3 | 7/2007 |
| WO | WO-2007/095387 A2 | 8/2007 |
| WO | WO-2007/095387 A3 | 8/2007 |
| WO | WO-2007/095387 A8 | 8/2007 |
| WO | WO-2007/117686 A2 | 10/2007 |
| WO | WO-2007/117686 A3 | 10/2007 |
| WO | WO-2008/009693 A1 | 1/2008 |
| WO | WO-2009/055076 A2 | 4/2009 |
| WO | WO-2009/055076 A3 | 4/2009 |
| WO | WO-2009/058361 A1 | 5/2009 |
| WO | WO-2011/159328 A1 | 12/2011 |
| WO | WO-2011/159958 A2 | 12/2011 |
| WO | WO-2011/159958 A9 | 12/2011 |

OTHER PUBLICATIONS

Altmann, S. et al. (1995). "NMR Studies of DNA Duplexes Singly Cross-Linked by Different Synthetic Linkers," *Nucleic Acids Research* 23(23):4827-4835.

Asefa, B. et al. (2004). "The Interferon-inducible p200 Family of Proteins: A Perspective on Their Roles in Cell Cycle Regulation and Differentiation," *Blood Cells, Molecules, and Diseases* 32:155-167.

Ashman, R.F. et al. (2005). "Sequence Requirements for Oligodeoxyribonucleotide Inhibitory Activity," *International Immunology* 17(4):411-420.

Asselin-Paturel, C. (2003). "Mouse Strain Differences in Plasmacytoid Dendritic Cell Frequency and Function Revealed by a Novel Monoclonal Antibody," *The Journal of Immunology* 171:6466-6477.

Athens, J.W. et al. (1961). "Leukokinetic Studies. IV. The Total Blood, Circulating and Marginal Granulocyte Pools and the Granulocyte Turnover Rate in Normal Subjects," *J. Clin. Invest.* 40:989-995.

Atherton, E. et al. (1981). "Synthesis of a 21-Residue Fragment of Human Proinsulin by the Polyamide Solid Phase Method," *Hoppe Seylers Z. Physiol. Chem.* 362:833-839.

Baechler, E.C. et al. (2003). "Interferon-Inducible Gene Expression Signature in Peripheral Blood Cells of Patients with Severe Lupus," *PNAS* 100(5):2610-2615.

Baltaci, M. et al. (2009). "Histologic Features of Cutaneous Lupus Erythematosus," *Autoimmunity Reviews* 8:467-473.

Bamboat, Z.M. et al. (2010). "Toll-Like Receptor 9 Inhibition Confers Protection From Liver Ischemia-Reperfusion Injury," *Hepatology* 51(2):621-632.

Banchereau, J. et al. (2004). "Autoimmunity Through Cytokine-Induced Dendritic Cell Activation," *Immunity* 20:539-550.

Banchereau, J. et al. (2006). "Type I Interferon in Systemic Lupus Erythematosus and Other Autoimmune Diseases," *Immunity* 25:383-392.

Barrat, F.J. et al. (2005). "Nucleic Acids of Mammalian Origin Can Act as Endogenous Ligands for Toll-like Receptors and May Promote Systemic Lupus Erythematosus," *The Journal of Experimental Medicine* 202(8):1131-1139.

Barrat, F.J. et al. (2007). "Treatment of Lupus-prone Mice with a Dual Inhibitor of TLR7 and TLR9 Leads to Reduction of Autoantibody Production and Amelioration of Disease Symptoms," *Eur. J. Immunol.* 37:3582-3586.

Barrat, F.J. et al. (2008). "Development of TLR Inhibitors for the Treatment of Autoimmune Diseases," *Immunological Reviews* 223:271-283.

Barry, W.T. et al. (2005). "Significance Analysis of Functional Categories in Gene Expression Studies: A Structured Permutation Approach," *Bioinformatics* 21(9):1943-1949.

Bartley, J.P. et al. (1997). "Solution Conformation of an Intramolecular DNA Triplex Containing a Nonnucleotide Linker: Comparison With the DNA Duplex," *Biochemistry* 36(47):14502-14511.

Bauer, S et al. (2001). "Human TLR9 Confers Responsiveness to Bacterial DNA via Species-specific CpG Motif Recognition," *PNAS* 98(16):9237-9242.

Bennett, L. et al. (2003). "Interferon and Granulopoiesis Signatures in Systemic Lupus Erythematosus Blood," *J. Exp. Med*, 197(6):711-723.

Bischoff, R. et al. (1987). "Introduction of 5'-Terminal Functional Groups Into Synthetic Oligonucleotides for Selective Immobilization," *Analytical Biochemistry* 164(2):336-344.

Blanks, R. et al. (1988). "An Oligodeoxynucleotide Affinity Column for the Isolation of Sequence Specific DNA Binding Proteins," *Nucleic Acids Research* 16(21):10283-10299.

Blomberg, S. et al. (2001). "Presence of Cutaneous Interferon-α Producing Cells in Patients with Systemic Lupus Erythematosus," *Lupus* 10(7):484-490.

Boor, P.P.C. et al. (2006). "Prednisolone Suppresses the Function and Promotes Apoptosis of Plasmacytoid Dendritic Cells," *American Journal of Transplantation* 6:2332-2341.

Borel, H. et al. (1990). "A Novel Technique to Link Either Proteins or Peptides to Gammaglobulin to Construct Tolerogens," *Journal of Immunological Methods* 126(2):159-168.

Borel, Y. et al. (1995). "Food Allergens Transformed Into Tolerogens," *Int. Arch. Allergy Immunol.* 107(1-3):264-267.

Borel, Y. et al. (1996). "Parenteral and Oral Administration of Tolerogens: Protein-IgG Conjugates," *Ann. N. Y. Acad. Sci.* 778:80-87.

Boujrad, N. et al. (1993). "Inhibition of Hormone-Stimulated Steroidogenesis in Cultured Leydig Tumor Cells by a Cholesterol-Linked Phosphorothioate Oligodeoxynucleotide Antisense to Diazepam-Binding Inhibitor," *Proc. Natl. Acad. Sci. USA* 90(12):5728-5731.

Bousquet, Y. et al. (1999). "Molecular Mechanisms of the Adsorption of a Model Protein (Human Serum Albumin) on Poly(Methylidene Malonate 2.1.2) Nanoparticles," *Pharmaceutical Research* 16(1):141-147.

(56) References Cited

OTHER PUBLICATIONS

Bowie, J.U. et al. (1990). "Deciphering the Message in Protein Sequences: Tolerance to Amino Acid Substitutions," *Science* 247:1306-1310.
Brinkmann, V. et al. (2004). "Neutrophil Extracellular Traps Kill Bacteria," *Science* 303:1532-1535.
Bussemaker, H.J. et al. (2007). "Dissecting Complex Transcriptional Responses Using Pathway-Level Scores Based on Prior Information," *BMC Bioinformatics* 8(Suppl. 6):S6, 7 pages.
Chatham, W.W. et al. (2001). "Treatment of Lupus with Corticosteroids," *Lupus* 10(3):140-147.
Chaturvedi, S. et al. (1996). "Stabilization of Triple-Stranded Oligonucleotide Complexes: Use of Probes Containing Alternating Phosphodiester and Stereo-Uniform Cationic Phosphoramidate Linkages," *Nucleic Acids Research* 24(12):2318-2323.
Chaussabel, D. et al. (2008). "A Modular Analysis Framework for Blood Genomics Studies: Application to Systemic Lupus Erythematosus," *Immunity* 29(1):150-164.
Chavany, C. et al. (1992). "Polyalkylcyanoacrylate Nanoparticles as Polymeric Carriers for Antisense Oligonucleotides," *Pharmaceutical Research* 9(4):441-449.
Chavany, C. et al. (1994). "Adsorption of Oligonucleotides Onto Polyisohexylcyanoacrylate Nanoparticles Protects Them Against Nucleases and Increases Their Cellular Uptake," *Pharmaceutical Research* 11(9):1370-1378.
Cheung, V.G. et al. (1999). "Making and Reading Microarrays," *Nature Genetics* 21(1 Suppl.):15-19.
Choubey, D. et al. (2008). "Interferon-Inducible *Ifi200*-family Genes in Systemic Lupus Erythematosus," *Immunology Letters* 119:32-41.
Clancy, R.M. et al. (2004). "Genetic Association of Cutaneous Neonatal Lupus with HLA Class II and Tumor Necrosis Factor α: Implications for Pathogenesis," *Arthritis & Rheumatism* 50(8):2598-2603.
Cload, S.T. et al. (1991). "Polyether Tethered Oligonucleotide Probes," *J. Am. Chem. Soc.* 113:6324-6326.
Connolly, B.A. (1985). "Chemical Synthesis of Oligonucleotides Containing a Free Sulphydryl Group and Subsequent Attachment of Thiol Specific Probes," *Nucleic Acids Research* 13(12):4485-4502.
Connolly, B.A. (1987). "The Synthesis of Oligonucleotides Containing a Primary Amino Group at the 5'-Terminus," *Nucleic Acids Research* 15(7):3131-3139.
Conrotto, P. et al. (2008). "Proteomic Approaches in Biological and Medical Sciences: Principles and Applications," *Exp. Oncol.* 30(3):171-180.
Cook, P.D. (1999). "Making Drugs Out of Oligonucleotides: A Brief Review and Perspective," *Nucleosides & Nucleotides* 18(6&7):1141-1162.
Corey, D.R. et al. (1987). "Generation of a Hybrid Sequence-Specific Single-Stranded Deoxyribonuclease," *Science* 238(4832):1401-1403.
Cowdery, J.S. et al. (1996). "Bacterial DNA Induces NK Cells to Produce IFN-γ In Vivo and Increases the Toxicity of Lipopolysaccharides," *Journal of Immunology* 156:4570-4575.
Coxon, A. et al. (2001). "FcγRIII Mediates Neutrophil Recruitment to Immune Complexes. A Mechanism for Neutrophil Accumulation in Immune-Mediated Inflammation," *Immunity* 14:693-704.
Crow, M.K. et al. (2003). "Microarray Analysis of Gene Expression in Lupus," *Arthritis Research Therapy* 5(6):279-287.
Crow, M.K. et al. (2008). "Interferon-induced Versus Chemokine Transcripts as Lupus Biomarkers," *Arthritis Research & Therapy* 10(6):126, 2 pages.
Dagneaux, C. et al. (1996). "Parallel and Antiparallel A*A-T Intramolecular Triple Helices," *Nucleic Acids Research* 24(22):4506-4512.
Daley, J.M. et al. (2008). "Use of Ly6G-specific Monoclonal Antibody to Deplete Neutrophils in Mice," *Journal of Leukocyte Biology* 83:64-70.
Datta, S.K. et al. (2003). "The Therapeutic Potential of Antigen-Oligonucleotide Conjugates," *Ann. N.Y. Acad. Sci.* 1002:105-111.

Deane, J.A. et al. (2007). "Control of Toll-like Receptor 7 Expression is Essential to Restrict Autoimmunity and Dendritic Cell Proliferation," *Immunity* 27:801-810.
De Bosscher, K. et al (2003). "The Interplay Between the Glucocorticoid Receptor and Nuclear Factor-κB or Activator Protein-1: Molecular Mechanisms for Gene Repression," *Endocrine Reviews* 24(4):488-522.
Deng, G-M. et al. (1999). "Intra-Articularly Localized Bacterial DNA Containing CpG Motifs Induces Arthritis," *Nature Medicine* 5(6):702-705.
Diebold, S.S. et al. (2004). "Innate Antiviral Responses by Means of TLR7-mediated Recognition of Single-stranded RNA," *Science* 303(5663):1529-1531.
Douglas, S.J. et al. (1987). "Nanoparticles in Drug Delivery," *CRC Critical Reviews in Therapeutic Drug Carrier Systems* 3(3):233-261.
Dumas, V. et al. (1995). "Induction of Tolerance by Administration of Hapten-Immunoglobulin Conjugates is Associated with Decreased IL-2 and IL-4 Production," *Arch. Dermatol. Res.* 287(2):123-128.
Duramad, O. et al. (2003). "IL-10 Regulates Plasmacytoid Dendritic Cell Response to CpG-Containing Immunostimulatory Sequences," *Blood* 102(13):4487-4492.
Duramad, O. et al. (2005). "Inhibitors of TLR-9 Act on Multiple Cell Subsets in Mouse and Man In Vitro and Prevent Death In Vivo from Systemic Inflammation," *The Journal of Immunology* 174(9):5193-5200.
Durand, M. et al. (1990). "Circular Dichroism Studies of an Oligodeoxyribonucleotide Containing a Hairpin Loop Made of a Hexaethylene Glycol Chain: Conformation and Stability," *Nucleic Acids Research* 18(21):6353-6359.
Edwards, A.D. et al. (2003). "Toll-like Receptor Expression in Murine DC Subsets: Lack of TLR7 Expression by $CD8\alpha^+$ DC Correlates with Unresponsiveness to Imidazoquinolines," *Euro J. Immunol* 33:827-833.
Farkas, L. et al. (2001). "Plasmacytoid Dendritic Cells (Natural Interferon-α/β-Producing Cells) Accumulate in Cutaneous Lupus Erythematosus Lesions," *American Journal of Pathology* 159(1):237-243.
Franchin, G. et al. (2006). "Pulse Steroids: How Much is Enough?" *Autoimmunity Reviews* 5:111-113.
Fu, Q. et al. (2008). "Association of Elevated Transcript Levels of Interferon-inducible Chemokines with Disease Activity and Organ Damage in Systemic Lupus Erythematosus Patients," *Arthritis Research & Therapy* 10:R112, 10 pages.
Fuchs, T.A. et al. (2007). "Novel Cell Death Program Leads to Neutrophil Extracellular Traps," *The Journal of Cell Biology* 176(2):231-241.
Furukawa, F. et al. (2005). "Animal Models of Spontaneous and Drug-induced Cutaneous Lupus Erythematosus," *Autoimmunity Reviews* 4:345-350.
Ganguly, D. et al. (2009). "Self-RNA-antimicrobial Peptide Complexes Activate Human Dendritic Cells Through TLR7 and TLR8," *The Journal of Experimental Medicine* 206(9):1983-1994.
Gao, H. et al. (1995). "Circulation of Oligonucleotides by Disulfide Bridge Formation," *Nucleic Acids Research* 23(11):2025-2029.
Geiss, G.K. et al. (2008). "Direct Multiplexed Measurement of Gene Expression with Color-coded Probe Pairs," *Nature Biotechnology* 26(3):317-325.
Geoghegan, K.F. et al. (1992). "Site-Directed Conjugation of Nonpeptide Groups to Peptides and Proteins Via Periodate Oxidation of a 2-Amino Alcohol. Application to Modification at N-Terminal Serine," *Bioconjugate Chem.* 3(2):138-146.
Gnanou, Y. et al. (1988). "Synthesis of Star-Shaped Poly(Ethylene Oxide)," *Makrormol. Chem.* 189:2885-2892.
Godard, G. et al. (1995). "Antisense Effects of Cholesterol-Oligodeoxynucleotide Conjugates Associated with Poly(Alkylcyanoacrylate) Nanoparticles," *Eur. J. Biochem.* 232(2):404-410.
Goldberg, B. et al. (2000). "Beyond Danger: Unmethylated CpG Dinucleotides and the Immunopathogenesis of Disease," *Immunology Letters* 73:13-18.
Goodchild, J. (1990). "Conjugates of Oligonucleotides and Modified Oligonucleotides: A Review of Their Synthesis and Properties," *Bioconjug. Chem.* 1(3):165-187.

(56) References Cited

OTHER PUBLICATIONS

Grabarek, Z. et al. (1990). "Zero-Length Crosslinking Procedure with the Use of Active Esters," *Analytical Biochemistry* 185(1):131-135.

Guiducci, C. et al. (2006). "Properties Regulating the Nature of the Plasmacytoid Dendritic Cell Response to Toll-like Receptor 9 Activation," *The Journal of Experimental Medicine* 203(8):1999-2008.

Guiducci, C. et al. (2008). "PI3K is Critical for the Nuclear Translocation of IRF-7 and Type I IFN Production by Human Plasmacytoid Predendritic Cells in Response to TLR Activation," *Journal of Experimental Medicine* 205(2):315-322.

Guiducci, C. et al. (2008). "Signalling Pathways Leading to IFN-α Production in Human Plasmacytoid Dendritic Cell and the Possible Use of Agonists or Antagonists of TLR7 and TLR9 in Clinical Indications," *Journal of Internal Medicine* 265:43-57.

Guiducci, C. et al. (2010). "TLR Recognition of Self Nucleic Acids Hampers Glucocorticoid Activity in Lupus," *Nature* 465(7300):937-941.

Guiducci, C. et al. (2010). "Autoimmune Skin Inflammation is Dependent on Plasmacytoid Dendritic Cell Activation by Nucleic Acids Via TLR7 and TLR9," *The Journal of Experimental Medicine* 207(13):2931-2942.

Hagiwara, A. et al. (1987). "A New Drug-Delivery-System of Anticancer Agents: Activated Carbon Particles Adsorbing Anticancer Agents," *In Vivo* 1(4):241-252.

Hahn, B.H. (1998). "Antibodies to DNA," *The New England Journal of Medicine* 338(19):1359-1368.

Haralambidis, J. et al. (1990). "The Synthesis of Polyamide-Oligonucleotide Conjugate Molecules," *Nucleic Acids Research* 18(3):493-499.

Haralambidis, J. et al. (1990). "The Preparation of Polyamide-Oligonucleotide Probes Containing Multiple Non-Radioactive Labels," *Nucleic Acids Research* 18(3):501-505.

Hartmann, G. et al. (1999). "CpG DNA: A Potent Signal for Growth, Activation, and Maturation of Human Dendritic Cells," *Proc. Natl. Acad. Sci. USA* 96:9305-9310.

Hayashi, F. et al. (Apr. 26, 2001). "The Innate Immune Response to Bacterial Flagellin is Mediated by Toll-Like Receptor 5," *Nature* 410:1099-1103.

Hayashi, F. et al. (2003). "Toll-like Receptors Stimulate Human Neutrophil Function," *Blood* 102(7):2660-2669.

Heil, F. et al. (2003). "The Toll-like Receptor 7 (TLR7)-Specific Stimulus Loxoribine Uncovers a Strong Relationship Within the TLR7, 8 and 9 Subfamily," *Eur. J. Immunol.* 33:2987-2997.

Heil, F. et al. (2004). "Species-Specific Recognition of Single-Stranded RNA via Toll-like Receptor 7 and 8," *Science* 303(5663):1526-1529.

Hemmi, H. et al. (2000). "A Toll-Like Receptor Recognizes Bacterial DNA," *Nature* 408:740-745.

Hemmi, H. et al. (2002). "Small Anti-Viral Compounds Activate Immune Cells Via the TLR7 MyD88-dependent Signaling Pathway," *Nature Immunology* 3(2):196-200.

Hendry, P. et al. (1994). "Using Linkers to Investigate the Spatial Separation of the Conserved Nucleotides $A_9$ and $G_{12}$ in the Hammerhead Ribozyme," *Biochimica et Biophysica Acta* 1219(2):405-412.

Ho, P.P. et al. (2003). "An Immunomodulatory GpG Oligonucleotide for the Treatment of Autoimmunity via the Innate and Adaptive Immune Systems," *The Journal of Immunology* 171:4920-4926.

Imaeda, A.B. et al. (2009). "Acetaminophen-induced Hepatotoxicity in Mice Is Dependent on Tlr9 and the Nalp3 Inflammasome," *The Journal of Clinical Investigation* 119(2):305-314.

Inman, J.K. (1975). "Thymus-Independent Antigens: The Preparation of Covalent, Hapten-Ficoll Conjugates," *The Journal of Immunology* 114(2 Pt. 1):704-709.

Inoue, J. et al. (2005). "Changes in Immune Responses to Antigen Applied to Tape-Stripped Skin with CpG-Oligodeoxynucleotide in Mice," *Journal of Controlled Release* 108:294-305.

Iyer, R.P. et al. (1990). "The Automated Synthesis of Sulfur-Containing Oligodeoxyribonucleotides Using 3*H*-1,2-Benzodithiol-3-one 1,1-Dioxide as a Sulfur-Transfer Reagent," *The Journal of Organic Chemistry* 55(15):4693-4699.

Jäger, A. et al. (1988). "Oligonucleotide *N*-Alkylphosphoramidates: Synthesis and Binding to Polynucleotides," *Biochemistry* 27(19):7237-7246.

Jarvis, T.C. et al. (1996). "Optimizing the Cell Efficacy of Synthetic Ribozymes: Site Selection and Chemical Modifications of Ribozymes Targeting the Proto-Oncogene *c-myb*," *The Journal of Biological Chemistry* 271(46):29107-29112.

Jäschke, A. et al. (1993). "Automated Incorporation of Polyethylene Glycol into Synthetic Oligonucleotides," *Tetrahedron Letters* 34(2):301-304.

Jin, H. et al. (2009). "IL-21 R is Essential for Epicutaneous Sensitization and Allergic Skin Inflammation in Humans and Mice," *The Journal of Clinical. Investigation* 119(1):47-60.

Jurk, M. et al. (2002). "Human TLR7 or TLR8 Independently Confer Responsiveness to the Antiviral Compound R-848," *Nature Immunology* 3(6):499.

Kadowaki, N. et al. (2001). "Subsets of Human Dendritic Cell Precursors Express Different Toll-like Receptors and Respond to Different Microbial Antigens," *J. Exp. Med.* 194(6):863-869.

Kandimalla, E.R. et al. (2001). "Effect of Chemical Modifications of Cytosine and Guanine in a CpG-motif of Oligonucleotides: Structure-Immunostimulatory Activity Relationships," *Bioorganic & Medicinal Chemistry* 9(3):807-813.

Kessenbrock, K. et al. (2009). "Netting Neutrophils in Autoimmune Small-Vessel Vasculitis," *Nature Medicine* 15(6):623-625.

Klinman, D.M. et al. (1997). "Contribution of CpG Motifs to the Immunogenicity of DNA Vaccines," *The Journal of Immunology* 158(8):3635-3639.

Klinman, D.M. et al. (2003). "Regulation of CpG-induced Immune Activation by Suppressive Oligonucelotides," *Annals New York Academy of Sciences* 1002:112-123.

Kremsky, J.N. et al. (1987). "Immobilization of DNA Via Oligonucleotides Containing an Aldehyde or Carboxylic Acid Group at the 5' Terminus," *Nucleic Acids Research* 15(7):2891-2909.

Krieg, A.M. et al. (1995). "CpG Motifs in Bacterial DNA Trigger Direct B-Cell Activation," *Nature* 374(6522):546-549.

Laakko, T. et al. (2002). "Rapid Changes in the Lymphopoietic and Granulopoietic Compartments of the Marrow Caused by Stress Levels of Corticosterone," *Immunology* 105:111-119.

Lambert, G. et al. (1998). "Effect of Polyisobutylcyanoacrylate Nanoparticles and Lipofectin Loaded with Oligonucleotides on Cell Viability and PKCα Neosynthesis in HepG2 Cells," *Biochimie* 80(12):969-976.

Lambrecht, B.N. et al. (2000). "Induction of Rapid T Cell Activation, Division, and Recirculation by Intratracheal Injection of Dendritic Cells in a TCR Transgenic Model," *The Journal of Immunology* 164:2937-2946.

Lande, R. et al. (2007). "Plasmacytoid Dendritic Cells Sense Self-DNA Coupled with Antimicrobial Peptide," *Nature* 449(7162):564-569.

Latterich, M. et al. (2008). "Proteomics: New Technologies and Clinical Applications," *European Journal of Cancer* 44:2737-2741.

Leadbetter, E.A. et al. (2002). "Chromatin-IgG Complexes Activate B Cells by Dual Engagement of IgM and Toll-Like Receptors," *Nature* 416:603-607.

Lee, A.C. et al. (1980). "A Method for Preparing β-hCG COOH Peptide-Carrier Conjugates of Predictable Composition," *Molecular Immunology* 17(6):749-756.

Lee, J. et al. (2003). "Molecular Basis for the Immunostimulatory Activity of Guanine Nucleoside Analogs: Activation of Toll-like Receptor 7," *PNAS* 100(11):6646-6651.

Lenert, P. et al. (2001). "CpG Stimulation of Primary Mouse B Cells is Blocked by Inhibitory Oligodeoxyribonucleotides at a Site Proximal to NF-κB Activation," *Antisense & Nucleic Acid Drug Development* 11(4):247-256.

Li, W.M. et al. (2003). "Effective Induction of CF8+ T-Cell response Using CpG Oligodeoxynucleotides and HER-2/neu-Derived Peptide Co-Encapsulated in Liposomes," *Vaccine* 21:3319-3329.

(56) References Cited

OTHER PUBLICATIONS

Lipsker, D. et al. (2008). "Neutrophilic Cutaneous Lupus Erythematosus. At the Edge Between Innate and Acquired Immunity?" *Dermatology* 216(4):283-286.

Lockhart, D.J. et al. (1996). "Expression Monitoring by Hybridization to High-Density Oligonucleotide Arrays," *Nature Biotechnology* 14(13):1675-1680.

Lund, J. et al. (2003). "Toll-like Receptor 9-mediated Recognition of Herpes Simplex Virus-2 Plasmacytoid Dendritic Cells," The Journal of Experimental Medicine 198(3):513-520.

Ma, M.Y. et al. (1993). "Design and Synthesis of RNA Miniduplexes Via a Synthetic Linker Approach," *Biochemistry* 32(7):1751-1758.

Ma, M.Y. et al. (1993)."Design and Synthesis of RNA Miniduplexes Via a Synthetic Linker Approach. 2. Generation of Covalently Closed, Double-Stranded Cyclic HIV-1 TAR RNA Analogs with High Tat-Binding Affinity," *Nucleic Acids Research* 21(11):2585-2589.

Maglietta, R. et al. (2007). "Statistical Assessment of Functional Categories of Genes Deregulated in Pathological Conditions by Using Microarray Data," *Bioinformatics* 23(16):2063-2072.

Marshak-Rothstein, A. (2006). "Toll-like Receptors in Systemic Autoimmune Disease," *Nature Reviews Immunology* 6:823-835.

Marshall, J.D. et al. (2003). "Identification of a Novel CpG DNA Class and Motif that Optimally Stimulate B Cell and Plasmacytoid Dendritic Cell Functions," *J. Leukoc. Biol.* 73:781-792.

Martinelli, S.et al. (2004). "Induction of Genes Mediating Interferon-dependent Extracellular Trap Formation During Neutrophil Differentiation," *The Journal of Biological Chemistry* 279(42):44123-44132.

Mathian, A. et al. (2005). "IFN-α Induces Early Lethal Lupus in Preautoimmune (New Zealand Black x New Zealand White) $F_1$ but Not in BALB/c Mice," *The Journal of Immunology* 174:2499-2506.

Matsunaga, Y. et al. (2007). "Establishment of a Mouse Skin Model of the Lichenification in Human Chronic Eczematous Dermatitis," *British Journal of Dermatology* 156(5):884-891.

McCauliffe, D.P. (1996). "Antibody Penetration into the Cells of Mice and Men," *The Journal of Investigative Dermatology* 107(1):3-4.

McCurdy, S. et al. (1991). Deoxyoligonucleotides With Inverted Polarity: Synthesis and Use in Triple-Helix Formation, *Nucleosides & Nucleotides* 10(1-3):287-290.

Means, T.K. et al. (2005). "Human Lupus Autoantibody—DNA Complexes Activate DCs Through Cooperation of CD32 and TLR9," *The Journal of Clinical Investigation* 115(2):407-417.

Miller, P.S. et al. (1971). "Syntheses and Properties of Adenine and Thymine Nucleoside Alkyl Phosphotriesters, the Neutral Analogs of Dinucleoside Monophosphates," *Journal of the American Chemical Society* 93(24):6657-6665.

Montague, J.W. et al. (1995). "Glucocorticoid-Induced Death of Immune Cells: Mechanisms of Action," in *Apoptosis in Immunology*, Kroemer, G. et al. eds., Springer-Verlag, pp. 51-65.

Nelson, P.S. et al. (1989). "A New and Versatile Reagent for Incorporating Multiple Primary Aliphatic Amines into Synthetic Oligonucleotides," *Nucleic Acids Research* 17(18):7179-7186.

Nelson, P.S. et al. (1989). "Bifunctional Oligonucleotide Probes Synthesized Using a Novel CPG Support are Able to Detect Single Base Pair-Mutations," *Nucleic Acids Research* 17(18):7187-7194.

Nelson, J.S. et al. (1996). "Incorporation of a Non-Nucleotide Bridge into Hairpin Oligonucleotides Capable of High-Affinity Binding to the Rev Protein of HIV-1," *Biochemistry* 35(16):5339-5344.

Nelson, J.S. et al. (1997). "N3'→P5' Oligodeoxyribonucleotide Phosphoramidates: A New Method of Synthesis Based on a Phosphoramidite Amine-Exchange Reaction," *J. Org. Chem.* 62(21):7278-7287.

Novak, B.A. et al. (2006). "Pathway Recognition and Augmentation by Computational Analysis of Microarray Expression Data," *Bioinformatics* 22(2):233-241.

Ono, A. et al. (1991). "DNA Triplex Formation of Oligonucleotide Analogues Consisting of Linker Groups and Octamer Segments That Have Opposite Sugar-Phosphate Backbone Polarities," *Biochemistry* 30(41):9914-9921.

O'Shannessy, D.J. et al. (1985). "Specific Conjugation Reactions of the Oligosaccharide Moieties of Immunoglobulins," *Journal of Applied Biochemistry* 7(4-5):347-355.

Overbergh, L. et al. (2003). "The Use of Real-Time Reverse Transcriptase PCR for the Quantification of Cytokine Gene Expression," *Journal of Biomolecular Techniques* 14(1):33-43.

Ozinsky, A. et al. (2000). "Co-Operative Induction of Pro-Inflammatory Signaling by Toll-Like Receptors," *Journal of Endotoxin Research* 6(5):393-396.

Ozinsky, A. et al. (2000). "The Repertoire for Pattern Recognition of Pathogens by the Innate Immune System is Defined by Cooperation Between Toll-Like Receptors," *PNAS* 97(25):13766-13771.

Parker, B.J. et al. (2007). "High Dose Methylprednisolone Therapy for the Treatment of Severe Systemic Lupus Erythematosus," *Lupus* 16:387-393.

Paweletz, C.P. et al. (2001). "Reverse Phase Protein Microarrays which Capture Disease Progression Show Activation of Pro-Survival Pathways at the Cancer Invasion Front," *Oncogene* 20:1981-1989.

Peyrottes, S. et al. (1996). "Oligodeoxynucleoside Phosphoramidates (P-$NH_2$): Synthesis and Thermal Stability of Duplexes with DNA and RNA Targets," *Nucleic Acids Research* 24(10):1841-1848.

Pisetsky, D.S. (1996). "The Immunologic Properties of DNA," *The Journal of Immunology* 156(2):421-423.

Poltorak, A. et al. (1998). "Defective LPS Signaling in C3H/HeJ and C57BL/10ScCr Mice: Mutations in *Tlr4* Gene," *Science* 282(5396):2085-2088.

Popovic, K. et al. (2005). "Increased Expression of the Novel Proinflammatory Cytokine High Mobility Group Box Chromosomal Protein 1 in Skin Lesions of Patients with Lupus Erythematosus," *Arthritis & Rheumatism* 52(11):3639-3645.

Puig, M. et al. (2006). "Use of Thermolytic Protective Groups to Prevent G-Tetrad Formation in CpG ODN Type D: Structural Studies and Immunomodulatory Activity in Primates," *Nucleic Acids Research* 34(22):6488-6495.

Rein, D. et al. (1993). "New Developments in Synthesis of Star Polymers with Poly(Ethylene Oxide) Arms," *Acta Polymer* 44:225-229.

Reynolds, M.A. et al. (1996). "Antisense Oligonucleotide Containing an Internal, Non-Nucleotide-Based Linker Promote Site-Specific Cleavage of RNA," *Nucleic Acids Research* 24(4):760-765.

Richardson. P.L. et al. (1991). "Tethered Oligonucleotide Probes. A Strategy for the Recognition of Structured RNA," *J. Am. Chem. Soc.* 113(13):5109-5111.

Riemekasten, G. et al. (2005). "Key Autoantigens in SLE," *Rheumatology* 44(8):975-982.

Roget, A. et al. (1989). "Synthesis and Use of Labelled Nucleoside Phosphoramidite Building Blocks Bearing a Reporter Group: Biotinyl, Dinitrophenyl, Pyrenyl and Dansyl," *Nucleic Acids Research* 17(19):7643-7651.

Roman, M. et al. (1997). "Immunostimulatory DNA Sequences Function as T Helper-1-Promoting Adjuvants," *Nature Medicine* 3(8):849-854.

Rozzo, S.J. et al. (2001). "Evidence for an Interferon-Inducible Gene, *Ifi202*, in the Susceptibility to Systemic Lupus," *Immunity* 15:435-443.

Salunkhe, M. et al. (1992). "Control of Folding and Binding of Oligonucleotides by Use of a Nonnucleotide Linker," *J. Am. Chem. Soc.* 114(23):8768-8772.

Sano, S. et al. (2005). "Stat3 Links Activated Keratinocytes and Immunocytes Required for Development of Psoriasis in a Novel Transgenic Mouse Model," *Nature Medicine* 11(1):43-49.

Santeliz, J.V. et al. (2002). "Amb a 1-Linked CpG Oligodeoxynucleotides Reverse Established Airway Hyper-responsiveness in a Murine Model of Asthma," *Journal of Allergy Clinical Immunology* 109(3):455-462.

Santiago-Raber, M-L. et al. (2003). "Type-I Interferon Receptor Deficiency Reduces Lupus-like Disease in NZB Mice," *J. Exp. Med.* 197(6):777-788.

(56) References Cited

OTHER PUBLICATIONS

Schacht, E. et al. (1996). "Biomedical Applications of Degradable Polyphosphazenes," *Biotechnology and Bioengineering* 52(1):102-108.
Schroeder, U. et al. (1998). "Efficacy of Oral Dalargin-loaded Nanoparticle Delivery Across the Blood-Brain Barrier," *Peptides* 19(4):777-780.
Schultz, R.G. et al. (1996). "Oligo-2'-Fluoro-2'-Deoxynucleotide N3'→P5' Phosphoramidates: Synthesis and Properties," *Nucleic Acids Research* 24(15):2966-2973.
Segal, E. et al. (2003). "Module Networks: Identifying Regulatory Modules and Their Condition-Specific Regulators from Gene Expression Data," *Nature Genetics* 34(2):166-176.
Segal, E. et al. (2004). "A Module Map Showing Conditional Activity of Expression Modules in Cancer," *Nature Genetics* 36(10):1090-1098.
Shevach, E.M. et al. (2001). "Control of T-Cell Activation by $CD4^+$ $CD25^+$ Suppressor T Cells," *Immunological Reviews* 182:58-67.
Shirota, H. et al. (2000). "Regulation of Murine Airway Eosinophilia and Th2 Cells by Antigen-Conjugated CpG Oligodeoxynucleotides as a Novel Antigen-Specific Immunomodulator," *The Journal of Immunology* 164:5575-5582.
Shodell, M. et al. (2003). "Circulating Human Plasmacytoid Dendritic Cells are Highly Sensitive to Corticosteroid Administration," *Lupus* 12:222-230.
Spergel, J.M. et al. (1999). "Roles of $T_H1$ and $T_H2$ Cytokines in a Murine Model of Allergic Dermatitis," *The Journal of Clinical Investigation* 103(8):1103-1111.
Staros, J.V. et al. (1986). "Enhancement by N-Hydroxysulfosuccinimide of Water-Soluble Carbodiimide-Mediated Coupling Reactions," *Analytical Biochemistry* 156(1):220-222.
Stirchak, E.P. et al. (1989). "Uncharged Stereoregular Nucleic Acid Analogs: 2. Morpholino Nucleoside Oligomers With Carbamate Internucleoside Linkages," *Nucleic Acids Research* 17(15):6129-6141.
Strickland, I. et al. (2001). "High Constitutive Glucocorticoid Receptor β in Human Neutrophils Enables Them to Reduce Their Spontaneous Rate of Cell Death in Response to Corticosteroids," *The Journal of Experimental Medicine* 193(5):585-593.
Stunz, L.L. et al. (2002). "Inhibitory Oligonucleotides Specifically Block Effects of Stimulatory CpG Oligonucleotides in B Cells," *European Journal of Immunology* 32:1212-1222.
Takauji, R. et al. (2002). "CpG-DNA-induced IFN-α Production Involves p38 MAPK-dependent STAT1 Phosphorylation in Human Plasmacytoid Dendritic Cell Precursors," *Journal of Leukocyte Biology* 72:1011-1019.
Takeshita, F. et al. (2001). "Cutting Edge: Role of Toll-Like Receptor 9 in CpG DNA-induced Activation of Human Cells," *The Journal of Immunology* 167:3555-3558.
Tang, J-Y. et al. (2000). "Large-Scale Synthesis of Oligonucleotide Phosphorothioates Using 3-Amino-1,2,4-dithiazole-5-thione as an Efficient Sulfur-Transfer Reagent," *Organic Process Research & Development* 4(3):194-198.
Tian, L. et al. (2005). "Discovering Statistically Significant Pathways in Expression Profiling Studies," *PNAS* 102(38):13544-13549.
Tomalia, D.A. et al. (1990). Starburst Dendrimers: Molecular-Level Control of Size, Shape, Surface Chemistry, Topology, and Flexibility from Atoms to Macroscopic Matter, *Angew. Chem. Int. Ed. Engl.* 29:138-175.
Trottier, M.D. et al. (2008). "Natural Glucocorticoids Induce Expansion of All Developmental Stages of Murine Bone Marrow Granulocytes Without Inhibiting Function," *PNAS* 105(6):2028-2033.
Tsuboi, N. et al. (2008). "Human Neutrophil Fcγ Receptors Initiate and Play Specialized Nonredundant Roles in Antibody-Mediated Inflammatory Diseases," *Immunity* 28:833-846.
Tucci, M. et al. (2008). "Glomerular Accumulation of Plasmacytoid Dendritic Cells in Active Lupus Nephritis. Role of Interleukin-18," *Arthritis & Rheumatism* 58(1):251-262.
Tung, C-H. et al. (1991). "Preparation of Oligonucleotide-Peptide Conjugates," *Bioconjugate Chem.* 2(6):464-465.

Ueki, H. (2005). "Koebner Phenomenon in Lupus Erythematosus with Special Consideration of Clinical Findings," *Autoimmunity Reviews* 4:219-223.
Ueno, H. et al. (2007). "Dendritic Cell Subsets in Health and Disease," *Immunological Reviews* 219:118-142.
Waldner, H. et al. (2004). "Activation of Antigen-Presenting Cells by Microbial Products Breaks Self Tolerance and Induces Autoimmune Disease," *The Journal of Clinical Investigation* 113(7):990-997.
Walker, L.S.K. et al. (2002). "The Enemy Within: Keeping Self-reactive T Cells at Bay in the Periphery," *Nature Reviews Immunology* 2:11-19.
Wang, Y. et al. (1991). "Multinuclear Nuclear Magnetic Resonance Studies of Na Cation-stabilized Complex Formed by d(G-G-T-T-T-T-C-G-G) in Solution. Implications for G-tetrad Structures," *J. Mol. Biol.* 222:819-832.
Wang, Y. et al. (1994). "Solution Structure of the *Tetrahymena* Telomeric Repeat $d(T_2G_4)_4$ G-tetraplex," *Structure* 2(12):1141-1156.
Wang, S. et al. (1994). "Circular RNA Oligonucleotides. Synthesis, Nucleic Acid Binding Properties, and a Comparison with Circular DNAs," *Nucleic Acids Research* 22(12):2326-2333.
Warner, B.D. et al. (1984). "Construction and Evaluation of an Instrument for The Automated Synthesis of Oligodeoxyribonucleotides," *DNA* 3(5):401-411.
Wartha, F. et al. (2008). "ETosis: A Novel Cell Death Pathway," *Science Signaling* 1(21):pe25, 3 pages.
Watwe, R.M. et al. (1995). "Manufacture of Liposomes: A Review," *Curr. Sci.* 68(7):715-724.
Wenzel, J. et al. (2007). "Identification of Type I Interferon-associated Inflammation in the Pathogenesis of Cutaneous Lupus Erythematosus Opens Up Options for Novel Therapeutic Approaches," *Experimental Dermatology* 16:454-463.
Wenzel, J. et al. (2008). "An IFN-Associated Cytotoxic Cellular Immune Response Against Viral, Self-, or Tumor Antigens is a Common Pathogenetic Feature in 'Interface Dermatitis'," *Journal of Investigative Dermatology* 128:2392-2402.
Werth, V.P. et al. (2002). "Associations of Tumor Necrosis Factor α and HLA Polymorphisms with Adult Dermatomyositis: Implications for a Unique Pathogenesis," *The Journal of Investigative Dermatology* 119(3):617-620.
Werth, V.P. (2007). "Cutaneous Lupus: Insights Into Pathogenesis and Disease Classification," *Bulletin of the NYU Hospital for Joint Diseases* 65(3):200-204.
Wyrzykiewicz, T.K. et al. (1994). "Efficiency of Sulfurization in the Synthesis of Oligodeoxyribonucleotide Phosphorothioates Utilizing Various Sulfurizing Reagents," *Bioorganic & Medicinal Chemistry Letters* 4(12):1519-1522.
Yamada, H. et al. (2002). "Effect of Suppressive DNA on CpG-Induced Immune Activation," *The Journal of Immunology* 169:5590-5594.
Yamamoto, S. et al. (1992). "Unique Palindromic Sequences in Synthetic Oligonucleotides are Required to Induce IFN [*Correction of INF*] and Augment IFN-Mediated [*Correction of INF*] Natural Killer Activity," *The Journal of Immunology* 148(12):4072-4076.
Yanagawa, H. et al. (1988). "Analysis of Superhelical Structures of Nucleic Acid-Lipid Conjugates by Image Processing," *Nucleic Acids Symposium Series* 19:189-192.
Zuckermann, R. et al. (1987). "Efficient Methods for Attachment of Thiol Specific Probes to the 3'-Ends of Synthetic Oligodeoxyribonucleotides," *Nucleic Acids Res.* 15(13):5305-5321.
Extended European Search Report mailed on Feb. 23, 2011 for EP Patent Application No. 10011096.4, filed on Aug. 24, 2005, 7 pages.
Extended European Search Report mailed on Jul. 22, 2011 for EP Patent Application No. 11155868.0, filed on Oct. 27, 2008, 9 pages.
International Preliminary Report on Patentability mailed Mar. 6, 2007 for PCT Patent Application No. PCT/US2005/030494 filed Aug. 24, 2005, 9 pages.
International Search Report mailed Aug. 4, 2006 for PCT Patent Application No. PCT/US2005/030494 filed Aug. 24, 2005, 7 pages.
Written Opinion mailed Aug. 4, 2006 for PCT Patent Application No. PCT/US2005/030494 filed Aug. 24, 2005, 8 pages.

(56) References Cited

OTHER PUBLICATIONS

International Preliminary Report on Patentability mailed Jun. 19, 2007 for PCT Patent Application No. PCT/US2005/045433, filed Dec. 16, 2005, 7 pages.
International Search Report mailed Oct. 13, 2006 for PCT Patent Application No. PCT/US2005/045433, filed Dec. 16, 2005, 3 pages.
Written Opinion mailed Oct. 13, 2006 for PCT Patent Application No. PCT/US2005/045433, filed Dec. 16, 2005, 6 pages.
International Preliminary Report on Patentability mailed on May 6, 2010 for PCT Patent Application No. PCT/US2008/012220, filed on Oct. 27, 2008, 13 pages.
International Search Report mailed on Sep. 14, 2009 for PCT Patent Application No. PCT/US2008/012220, filed on Oct. 27, 2008, 7 pages.
Written Opinion mailed on Sep. 14, 2009 for PCT Patent Application No. PCT/US2008/012220, filed on Oct. 27, 2008, 11 pages.
International Preliminary Report on Patentability mailed on Dec. 19, 2012, for PCT Patent Application No. PCT/US2010/060365, filed on Dec. 14, 2010, 9 pages.
International Search Report mailed on Apr. 8, 2011, for PCT Patent Application No. PCT/US2010/060365, filed on Dec. 14, 2010, 7 pages.
Written Opinion mailed on Apr. 8, 2011 for PCT Patent Application No. PCT/US2010/060365, filed on Dec. 14, 2010, 8 pages.
International Preliminary Report on Patentability mailed on Apr. 23, 2013 for PCT Patent Application No. PCT/US2011/040788, filed on Jun. 16, 2011, 4 pages.
Written Opinion mailed on Mar. 22, 2013 for PCT Patent Application No. PCT/US11/40788, filed on Jun. 16, 2011, 3 pages.
Extended European Search Report mailed Mar. 27, 2014 for EP Patent Application No. 11796471.8, filed Jun. 16, 2011, 8 pages.
Office Action mailed Jul. 14, 2014 for U.S. Appl. No. 12/767,692, filed Apr. 26, 2010, 7 pages.

* cited by examiner

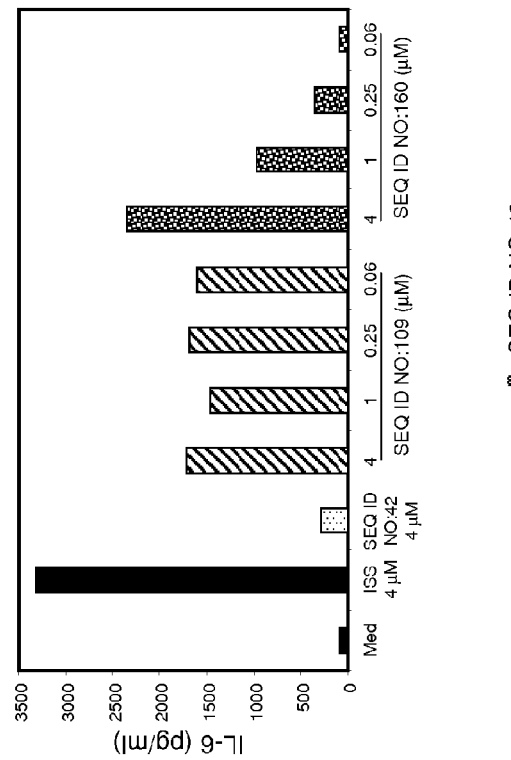
FIG. 1A
FIG. 1B
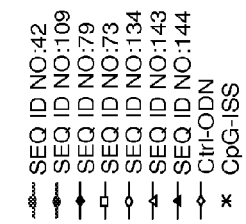
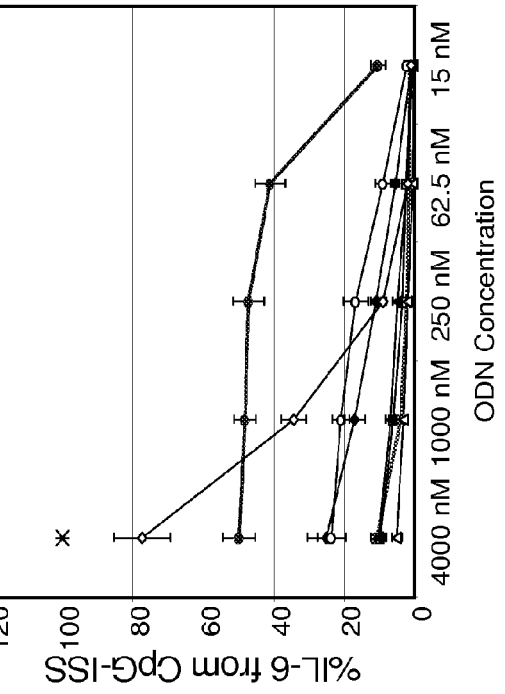
FIG 1C
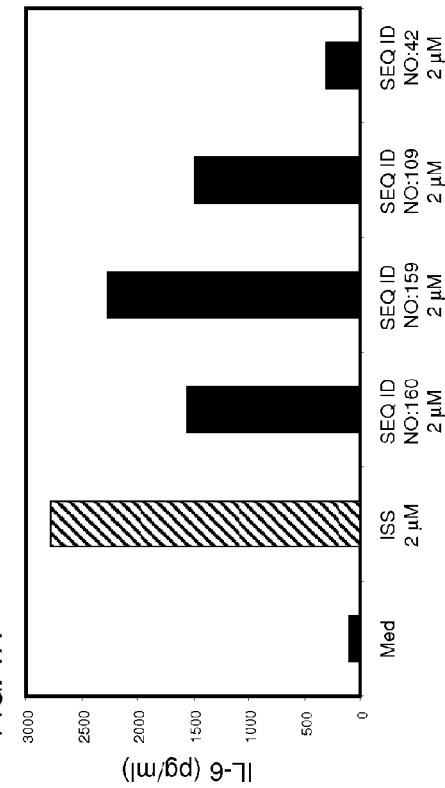

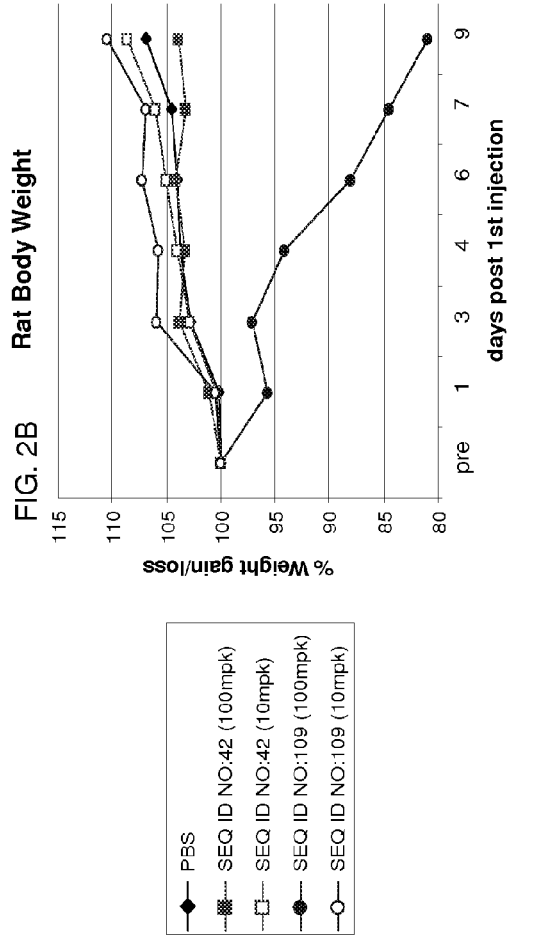
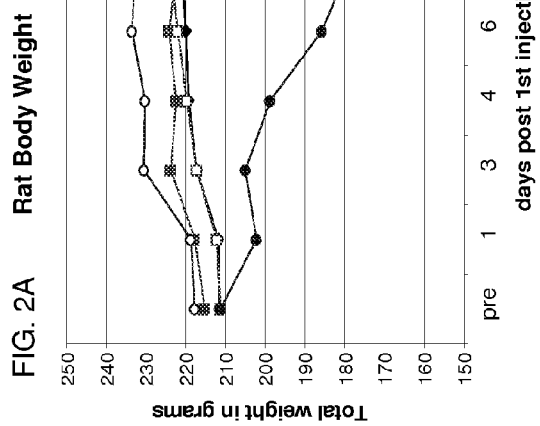
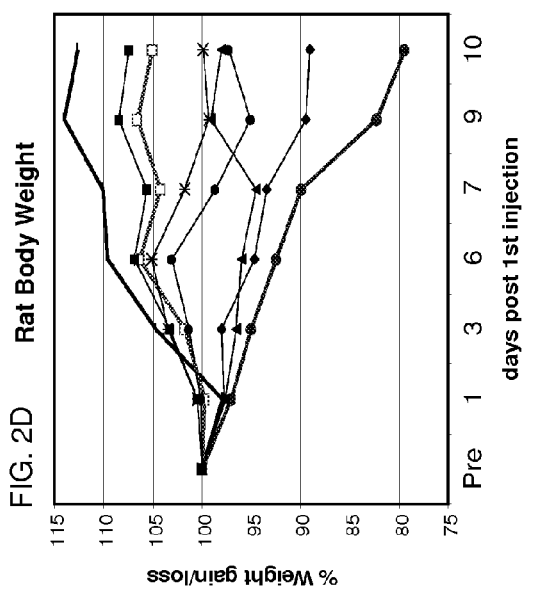
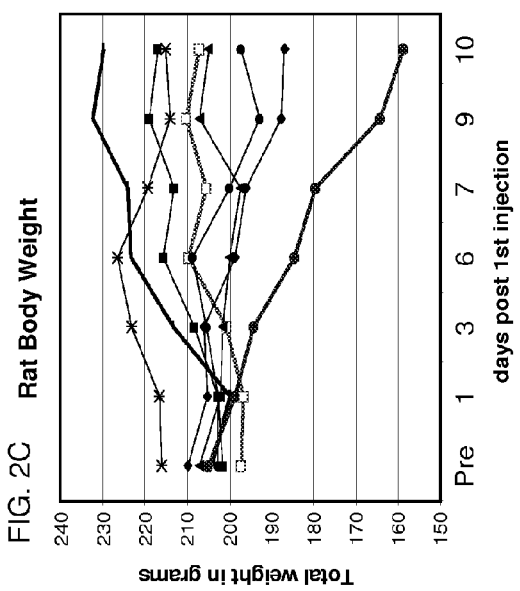

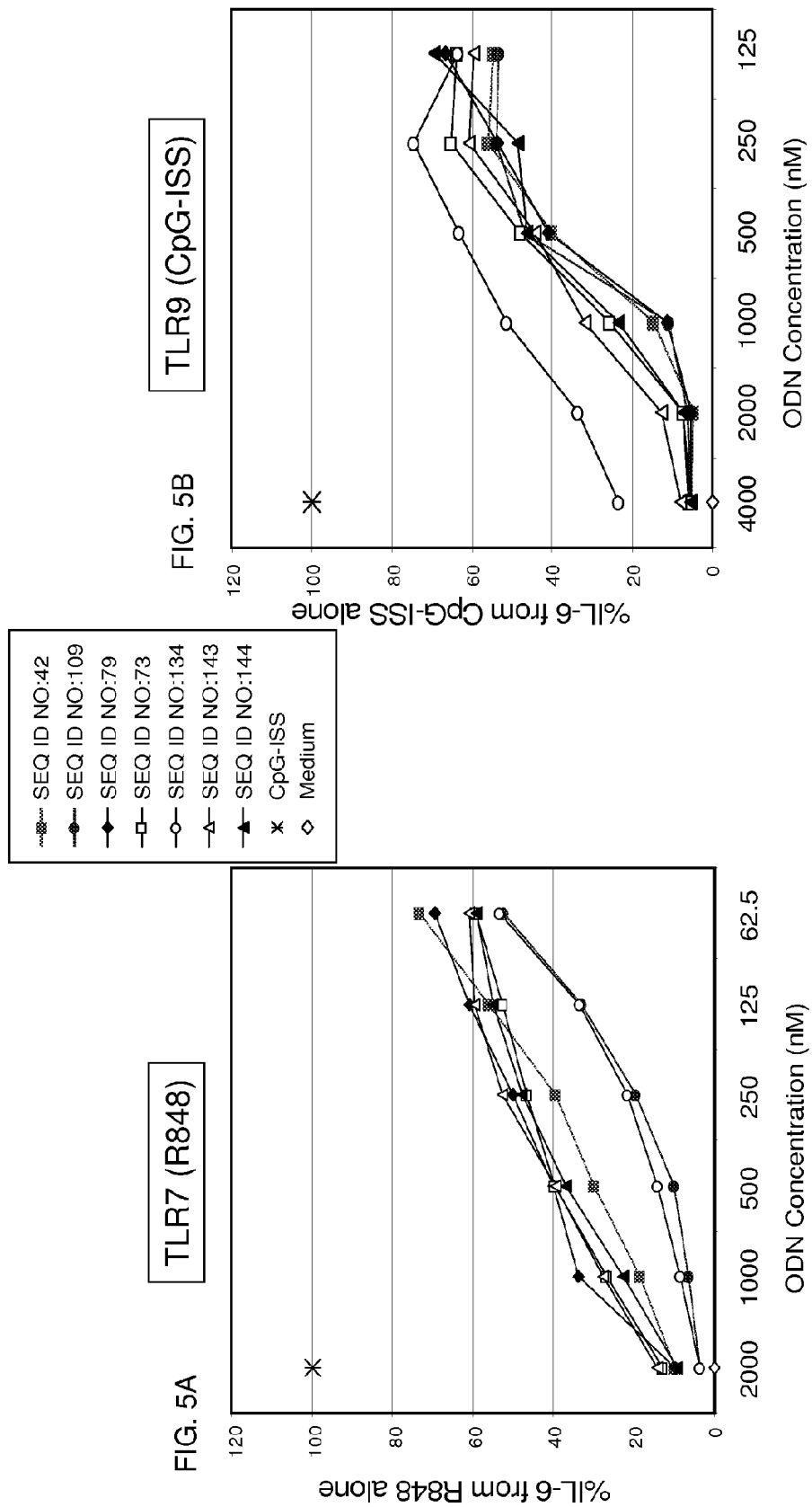

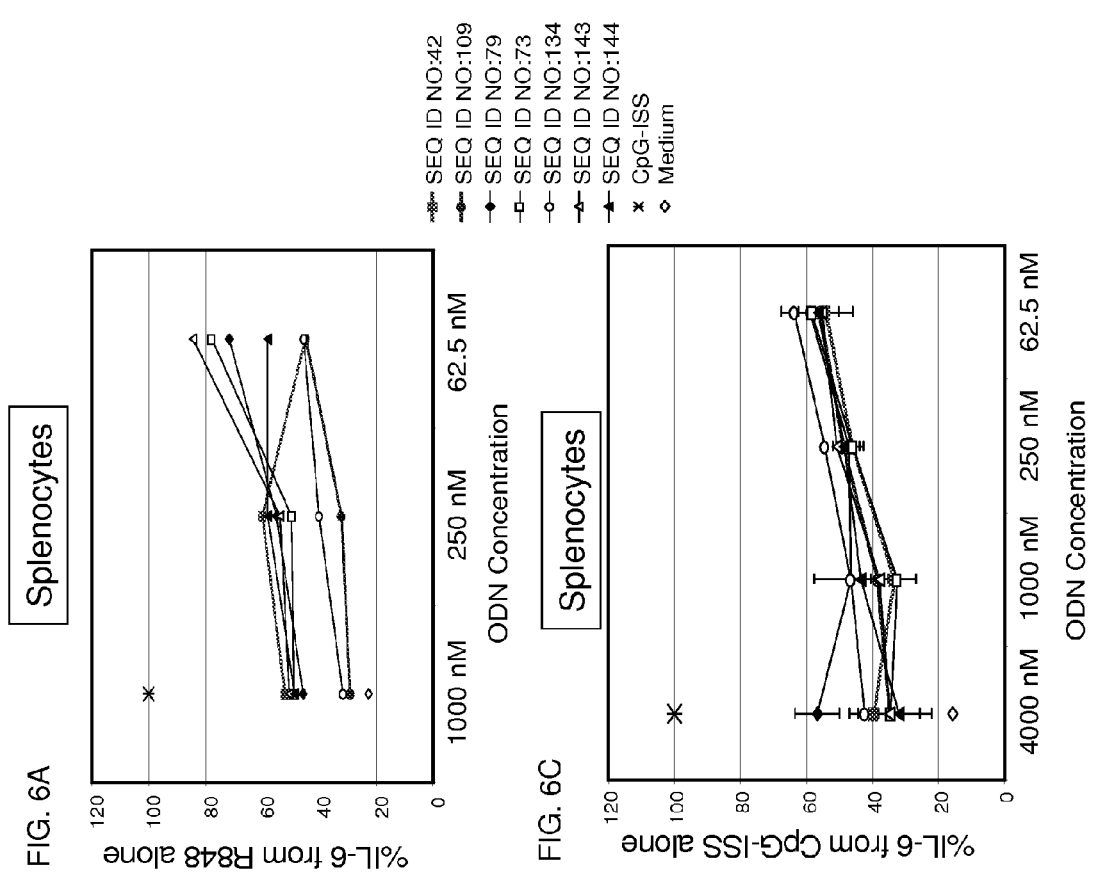

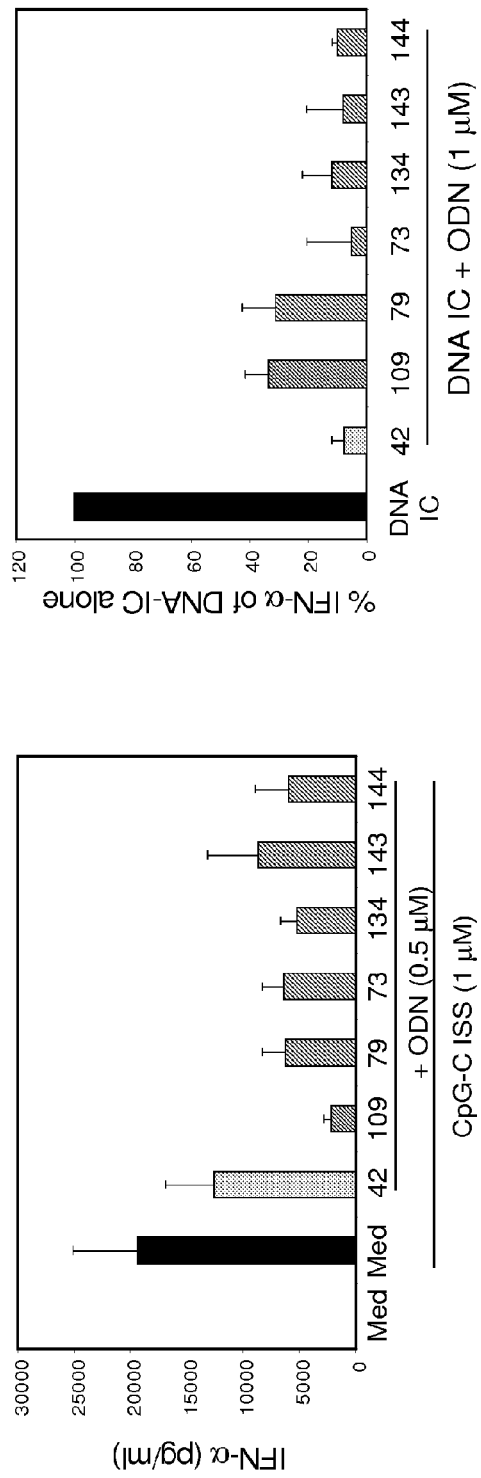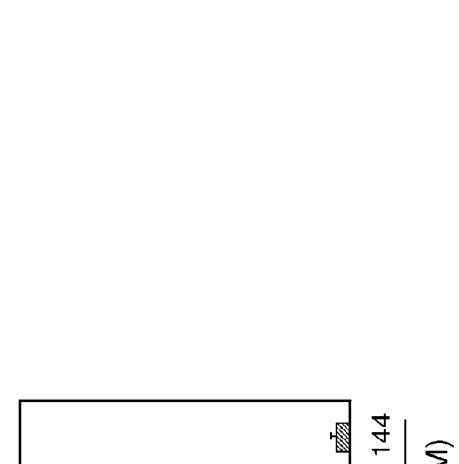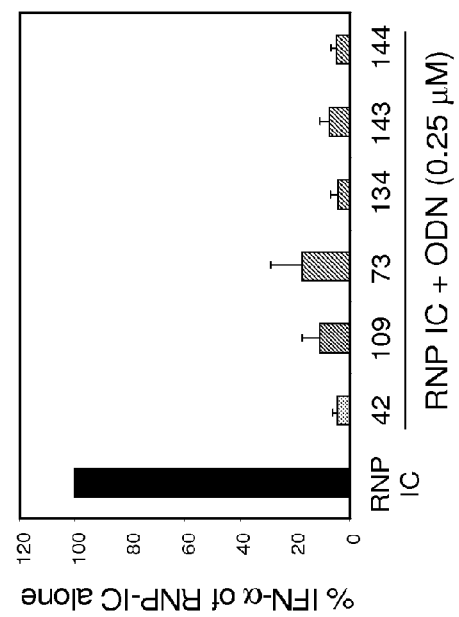
FIG. 8A
FIG. 8B
FIG. 8C

IC50/IC90 Values for the IRS Candidates for PDC (HSV/FLU)

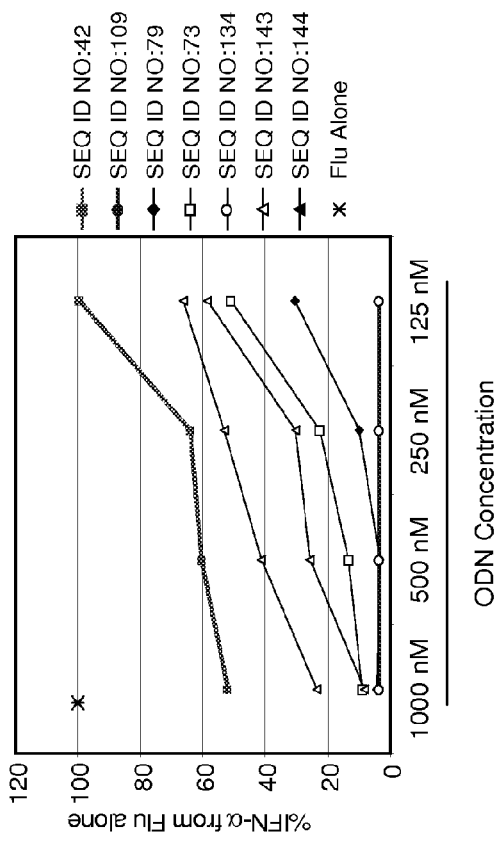
FIG. 10B
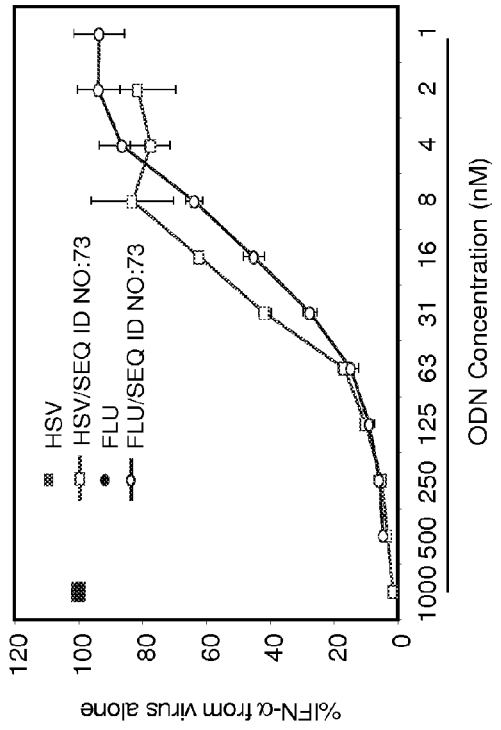
FIG. 10A
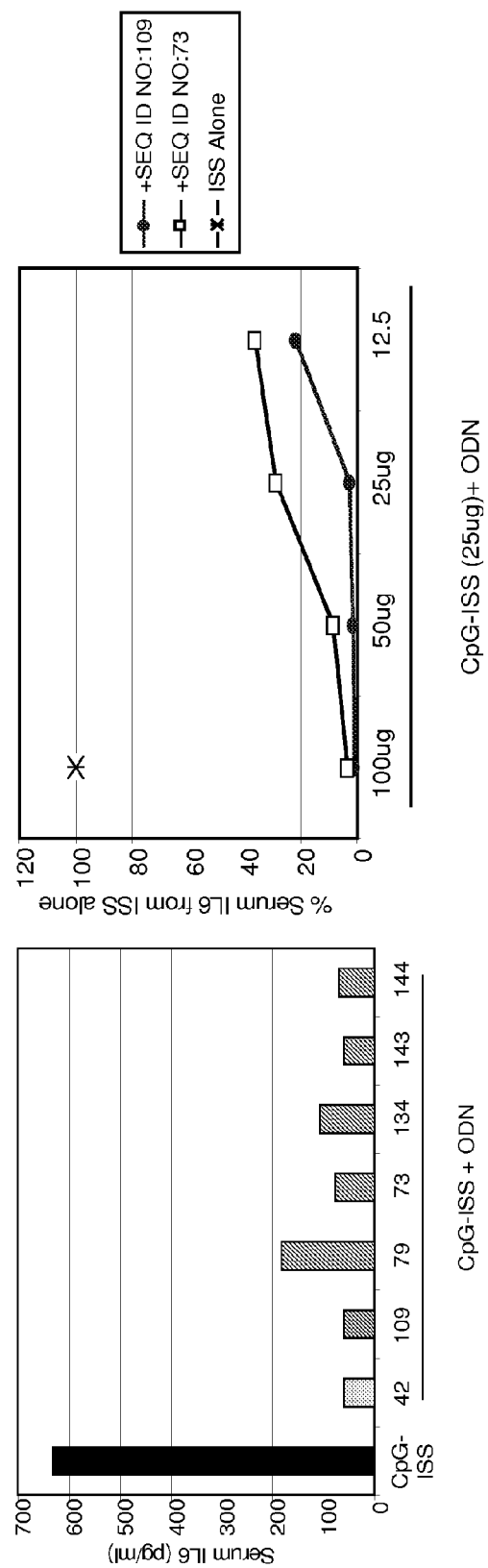
FIG. 10D
FIG. 10C

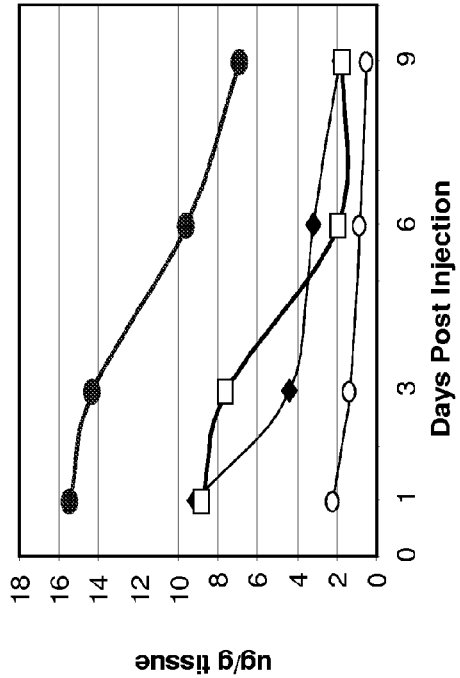
FIG. 11A
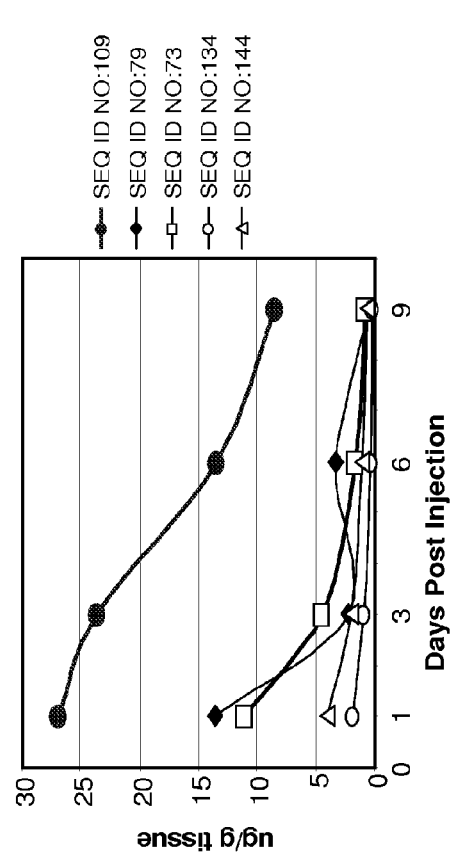
FIG. 11B
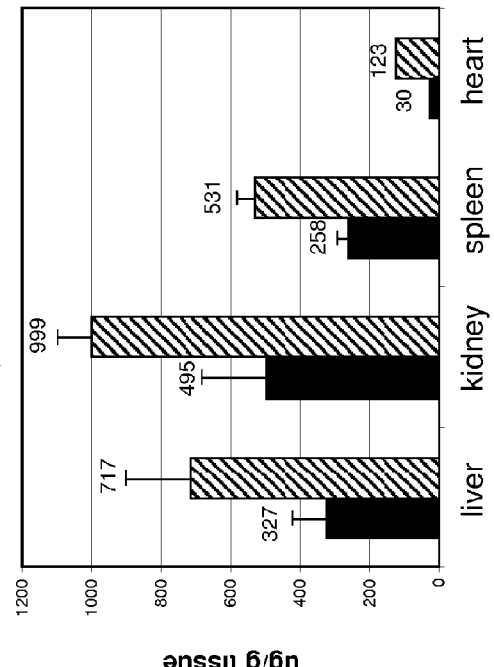
FIG. 11C SEQ ID NO:73
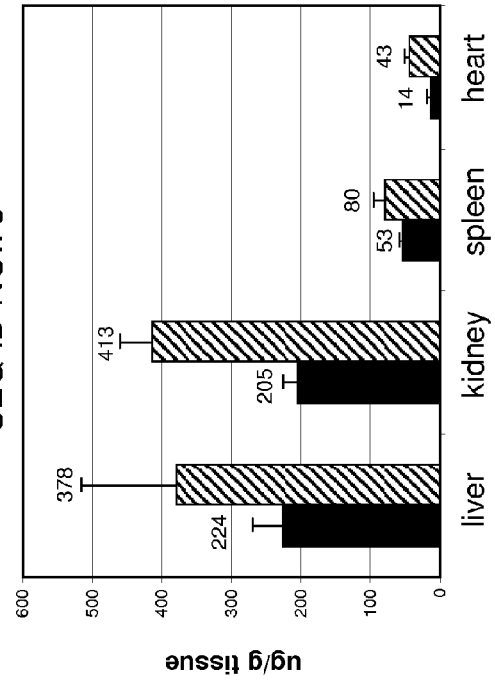
FIG. 11D SEQ ID NO:109

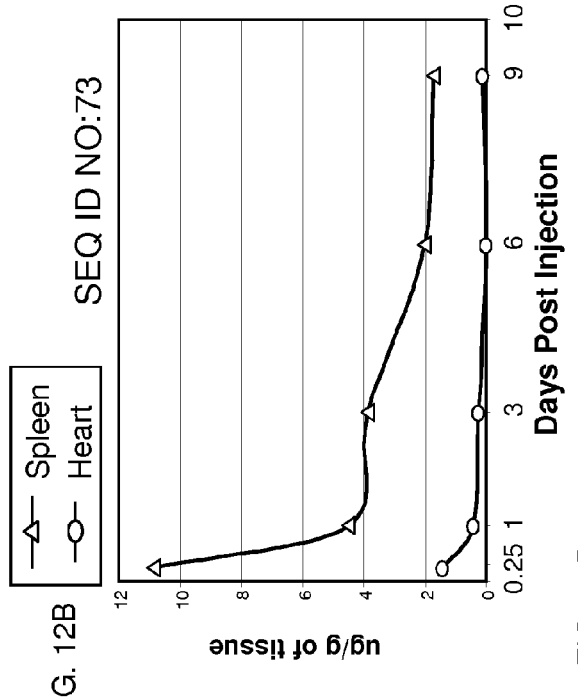
FIG. 12B
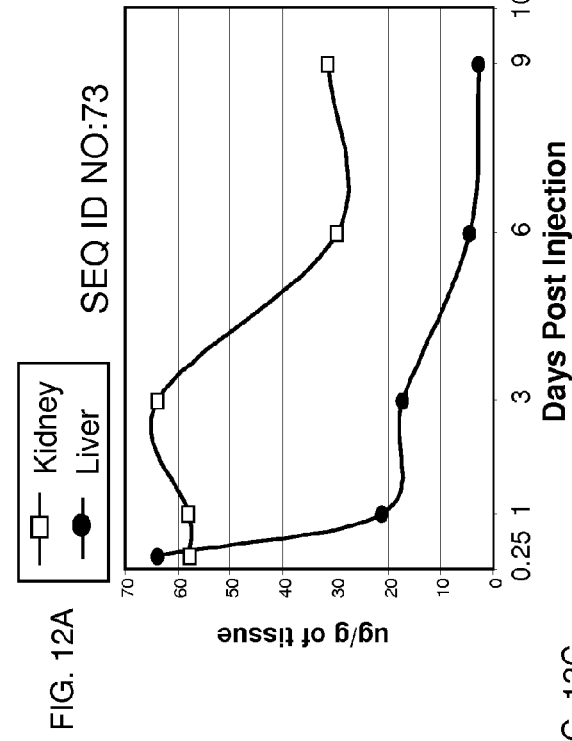
FIG. 12A
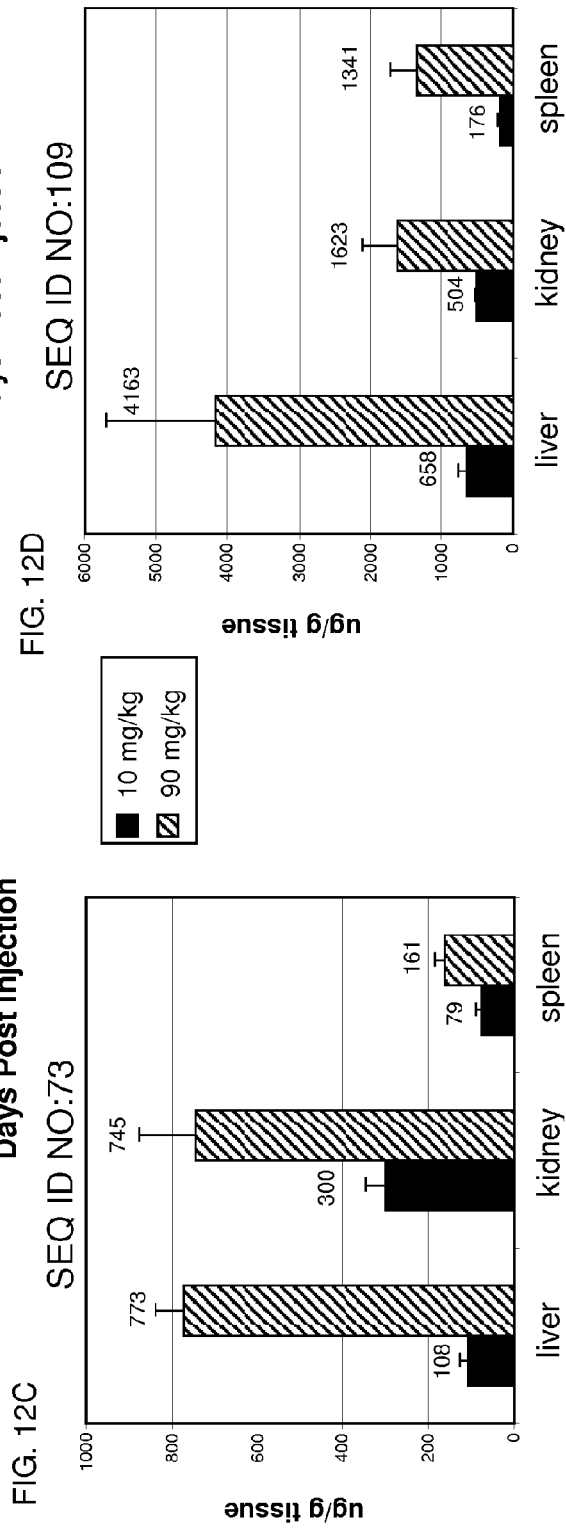
FIG. 12D
FIG. 12C

METHODS OF TREATMENT USING TLR7 AND/OR TLR9 INHIBITORS

CROSS-REFERENCE TO RELATED APPLICATIONS

This application is a U.S. National Phase of PCT/US2011/040788, filed Jun. 16, 2011, which claims benefit of U.S. Provisional Application No. 61/423,076, filed Dec. 14, 2010, U.S. Provisional Application No. 61/415,289, filed Nov. 18, 2010, and U.S. Provisional Application No. 61/355,547, filed Jun. 16, 2010, all of which are incorporated by reference in their entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 377882004700SubSeqListing.txt, date recorded: Feb. 24, 2013, size: 73 KB).

STATEMENT OF GOVERNMENT SUPPORT

This invention was made with government support under Grant Nos. 5R44AI066483 and 5R43AI82839 awarded by the National Institutes of Health. The government has certain rights in the invention.

TECHNICAL FIELD

The application relates to compositions and methods of regulating an immune response comprising inhibitors of TLR7 and/or TLR9, such as immunoregulatory polynucleotides and/or immunoregulatory compounds. The application also relates to compositions and methods for predicting and/or determining responsiveness of a disease to treatment comprising inhibitors of TLR7 and/or TLR9.

BACKGROUND

Immunity can generally be classified as innate immunity or as adaptive immunity. Innate immune responses typically occur immediately upon infection to provide an early barrier to infectious disease whereas adaptive immune responses occur later with the generation of antigen-specific effector cells and often long term protective immunity. Innate immune responses do not generate lasting protective immunity but appear to play a role in the generation of the later arising adaptive immune response.

Toll-like receptors (TLRs) are essential for innate immune responses as they recognize several different antigens and initiate immunological/inflammatory responses such as cytokine production, and dendritic cell and macrophage activation. Especially, TLR2, TLR3, TLR4, TLR7, TLR8, and TLR9 recognize viral or bacterial ligands such as glycoprotein, single- or double-stranded RNA and polynucleotide containing unmethylated 5'-CG-3' sequences. Immunostimulatory nucleic acid molecules stimulate the immune response through interaction with and signaling through the mammalian TLR9 receptor. See Hemmi et al. (2002) *Nat. Immunol.* 3:196-200. Mammalian DNA does not generally possess immunostimulatory activity due apparently to a low frequency of CG sequences and to most of the CG sequences having a methylated cytosine. Mammalian immune system cells thus appear to distinguish bacterial DNA from self DNA through the TLR9 receptor. TLR7 in contrast, is one of the main receptors sensing viral infection by recognizing uridine-rich single-stranded RNA.

The triggering of TLR7 and TLR9 in plasmacytoid dendritic cells precursors (PDC) and B cells by self nucleic acids is key in the pathogenesis of Systemic Lupus Erythematosus (SLE). This leads to the production of type I IFNs from PDC that can be detected by the upregulation of IFN-regulated genes in the blood of patients (IFN-signature) and anti-DNA and anti-RNP antibodies from B cells that form immune complexes (IC) with DNA or RNA from dying cells (Barrat and Coffman, 2008; Marshak-Rothstein, 2006). PDC are the major source of IFN-α induced by nucleic acid-containing ICs. Once activated by self DNA/chromatin or snRNP-containing IC, PDCs migrate from the blood into inflamed tissues including skin and kidney.

IFN-α and PDC have been proposed to contribute to the pathogenesis of other autoimmune diseases characterized by IFN-α signature as well. Indeed, Type I IFN-producing PDC accumulate in the pancreas, muscle and salivary glands of people affected by diabetes mellitus, dermatomyositis and Sjögren's syndrome respectively, strongly suggesting that dysregulated PDC activation could be a more general feature of autoimmune disease (Barrat and Coffman, 2008; Guiducci et al., 2009; Ueno et al., 2007).

SLE patients are often treated with strong immunosuppressive regimens, including cytotoxic drugs, antimalarial compounds and glucocorticoids (GC). Glucocorticoids have strong anti-inflammatory effects on both acquired and innate immune functions. They inhibit B and T cell responses and effector functions of monocytes and neutrophils. At the cellular level, GC inhibit NF-kB activity, thought to be the main mechanism by which GC exert their anti-inflammatory effects. In lupus, GC are typically administered orally on a daily basis, as the typical every other day regimens cannot maintain disease control. When doses greater than 40 mg/day are required, patients receive intravenous methylprednisolone (Solumedrol) pulse therapy (e.g., doses up to 30 mg/kg/day or 1 g/day given each day for 3 days). Such treatment can transiently reduce disease activity, but often does not induce remission or prevent end organ damage. The reason why treatment of SLE requires much higher GC doses than many other autoimmune diseases is not clear.

SUMMARY

The invention relates to inhibitors of TLR9 and/or TLR7 (e.g., immunoregulatory polynucleotides and/or immunoregulatory compounds) and methods of use thereof.

Provided herein are methods of treating a disease in an individual comprising administering to the individual an effective amount of a TLR7 inhibitor and/or TLR9 inhibitor, wherein treatment is based upon interferon signature and/or differential levels of inflammatory cytokines in a sample. Also provided herein are methods of treating a disease comprising: (a) selecting an individual having an IFN signature and/or differential levels of inflammatory cytokines in a sample; and (b) administering to the selected individual an effective amount of a TLR7 inhibitor and/or TLR9 inhibitor. Further provided herein are methods of assessing whether an individual with a disease is more likely to respond or less likely to respond to treatment comprising a TLR7 inhibitor and/or TLR9 inhibitor, the method comprising assessing IFN signature and/or differential levels of inflammatory cytokines in a sample, wherein an IFN signature and/or differential levels of inflammatory cytokines in the sample indicates that the individual is more likely to respond or is less likely to respond to the treatment. Also provided herein are methods of identifying an individual with a disease who is more likely to respond or less likely to respond to treatment comprising an effective amount of a TLR7 inhibitor and/or TLR9 inhibitor, the method comprising: (A) assessing an IFN signature and/or differential levels of inflammatory cytokines in a sample; and (B) identifying the individual having an IFN signature and/or differential levels of inflammatory cytokines in the sample. Also provided herein are methods of treating a disease in an individual comprising administering to the individual an effective amount of a TLR7 inhibitor and/or TLR9 inhibitor, wherein treatment response or lack of treatment response is indicated by IFN signature and/or differential levels of inflammatory cytokines in a sample. Also provided herein are methods of monitoring responsiveness or lack of responsiveness of an individual to a disease treatment comprising an effective amount of a TLR7 inhibitor and/or TLR9 inhibitor, wherein responsiveness is indicated by IFN signature and/or differential levels of inflammatory cytokines in a sample. Further provided herein are methods of identifying an individual as more likely suitable to continue treatment or less likely suitable to continue a disease treatment based upon IFN signature and/or differential levels of inflammatory cytokines in a sample, wherein treatment comprises an effective amount of a TLR7 inhibitor and/or TLR9 inhibitor.

In certain embodiments of any of the methods provided herein the IFN signature is a type I IFN signature. In certain embodiments of any of the methods provided herein, the IFN signature in the sample correlates to an IFN signature of a reference. In certain embodiments of any of the methods provided herein, the IFN signature comprises differential levels in the sample of one or more biomarkers selected from the group consisting of BATF2, CMPK2, CXCL10, DDX60, EPSTI1, HERC5, HES4, IFI44, IFI44L, IFIT1, IFIT3, IFITM3, ISG15, LAMP3, LOC26010, LY6E, MX1, OAS1, OAS2, OAS3, OASL, OTOF, RSAD2, RTP4, SERPING1, TRIM6, XAF1, cl02h05 5, Agencourt-7914287 NIH-MCG__71, ISG20, IFI16, IRF7, and AIM2 compared to a reference. In certain embodiments, the IFN signature comprises differential levels in the sample of one or more biomarkers selected from the group consisting of BATF2, CMPK2, DDX60, EPSTI1, HERC5, HES4, IFI44, IFI44L, IFIT1, IFIT3, IFITM3, ISG15, LAMP3, LOC26010, MX1, OAS1, OAS2, OAS3, OASL, OTOF, RSAD2, RTP4, SERPING1, TRIM6, XAF1, cl02h05 5, Agencourt-7914287 NIH-MCG__71, ISG20, IRF7, and AIM2 compared to a reference. In certain embodiments of any of the methods provided herein, the differential levels of inflammatory cytokines comprise differential levels in the sample of one or more inflammatory cytokine markers selected from the group consisting of IL-1 alpha, IL-1 beta, TNF-alpha, IL-6, and IL-17, IFN-alpha, IFN-omega, IFN-lambda1, IFN-lambda2, and IP-10. In certain embodiments of any of the methods provided herein, the differential levels in the sample are high levels of one or more markers compared to a reference and high levels indicate that a) the individual is more likely to respond to treatment or b) the individual is selected for treatment. In certain embodiments of any of the methods provided herein, the differential levels in the sample are low levels of one or more markers compared to a reference and low levels indicate that a) the individual is less likely to respond to treatment or b) the individual is not selected for treatment. In certain embodiments of any of the methods provided herein, the differential levels in the sample are high levels of one or more markers compared to a reference and high levels indicate that a) the individual is not responsive to treatment or b) the individual is less likely suitable to continue treatment. In certain embodiments of any of the methods provided herein, the differential levels are low levels of one or more markers compared to a reference and low levels indicate that a) the individual is responsive to treatment or b) the individual is more likely suitable to continue treatment. In certain embodiments of any of the methods provided herein, the reference is an IFN signature of a second individual or patient population with the disease. In certain embodiments of any of the methods provided herein, the reference is an IFN signature of the individual at the time of starting treatment. In certain embodiments of any of the methods provided herein, the reference is an IFN signature of a second individual or patient population without the disease. In certain embodiments of any of the methods provided herein, the sample is a sample containing peripheral blood cells or skin tissue.

In certain embodiments of any of the methods or compositions provided herein, the TLR7 inhibitor and/or TLR9 inhibitor is a polynucleotide consisting of a nucleotide sequence of the formula: 5'-$R_\gamma JGCN_z$-3' (SEQ ID NO:147), wherein each R is a nucleotide, $\gamma$ is an integer from about 0 to 10, J is U or T, each N is a nucleotide, and z is an integer from about 1 to about 100. In certain embodiments, $\gamma$ is 0 and z is from about 1 to about 50. In certain embodiments of any of the methods provided herein, the TLR7 inhibitor and/or TLR9 inhibitor is a polynucleotide consisting of a nucleotide sequence of the formula: 5'-$R_\gamma JGCN_z$-3' (SEQ ID NO:147), wherein each R is a nucleotide, $\gamma$ is an integer from about 0 to 10, J is U or T, each N is a nucleotide, and z is an integer from about 1 to about 100. In certain embodiments, $\gamma$ is 0 and z is from about 1 to about 50, which comprises a nucleotide sequence of the formula: 5'-$S_1S_2S_3S_4$-3', wherein $S_1$, $S_2$, $S_3$, and $S_4$ are independently G, I, or 7-deaza-dG. In some embodiments, the polynucleotide consists of a nucleotide sequence of the formula: 5'-$R_\gamma JGCK_\alpha S_1S_2S_3S_4L_\beta$-3' (SEQ ID NO:148), wherein each R, K, and L is a nucleotide, $\gamma$ is an integer from about 0 to 10, J is U or T, $S_1$, $S_2$, $S_3$, and $S_4$ are independently G or a molecule that is capable of preventing G-tetrad formation and/or preventing Hoogsteen base pairing, $\alpha$ is an integer from about 1 to about 20, and $\beta$ is an integer from about 1 to about 20. For example, a polynucleotide comprising a nucleotide sequence of the formula: 5'-$S_1S_2S_3S_4$-3', wherein $S_1$, $S_2$, $S_3$, and $S_4$ are independently G, I, or 7-deaza-dG. In certain embodiments, one or more of $S_1$, $S_2$, $S_3$, and $S_4$ are I. In certain embodiments $S_1$, $S_2$, $S_3$, and $S_4$ are G. In some embodiments, polynucleotide comprising a nucleotide sequence of the formula: 5'-GIGG-3'. In certain embodiments of any of the methods provided herein, the TLR7 inhibitor and/or TLR9 inhibitor is formula 5'-$E_\zeta JGCF_\theta TCCTGGAS_1S_2S_3S_4TT3_\phi$-3' (SEQ ID NO:152), wherein each E, F, and 3 are a nucleotide, $\zeta$, $\theta$, and $\phi$ are an integer from about 0 to 10, J is U or T, S1, S2, S3, and S4 are independently G, I, or 7-deaza-dG.

In certain embodiments of any of the methods or compositions provided herein, one or more nucleotides comprise a modification. In certain embodiments, the modification is 2'-sugar modification. In certain embodiments, the 2'-sugar modification is a 2'-O-methyl sugar modification or a 2'-O-methoxyethyl sugar modification. In certain embodiments, the polynucleotide is comprised of all 2'-deoxyribo polynucleotides. In certain embodiments, the polynucleotide is a 2'-deoxyribo polynucleotide and a 2'-sugar modification chimeric sequence. In certain embodiments, the polynucleotide is a 2'-deoxyribo polynucleotide and a 2'-O-methyl sugar polynucleotide chimeric sequence. In certain embodiments, the polynucleotide is a 2'-deoxyribo polynucleotide and a 2'-O-methyoxyethyl sugar polynucleotide chimeric sequence. In certain embodiments, the polynucleotide has at least one nucleotide comprising a modified phosphate linkage. In certain embodiments, the polynucleotide comprises only phosphorothioate linkages.

In certain embodiments of any of the methods or compositions provided herein that contain the formula: 5'-$S_1S_2S_3S_4$-3', wherein $S_1$, $S_2$, $S_3$, and $S_4$ are independently G, I, or 7-deaza-G, the nucleotides are all deoxyribonucleotides. In certain embodiments containing the formula: 5'-$S_1S_2S_3S_4$-3', wherein $S_1$, $S_2$, $S_3$, and $S_4$ are independently G, I, or 7-deaza-G, the nucleotides are all 2'-deoxyribonucleotides. For instance, for methods and compositions wherein the TLR7 and/or TLR9 inhibitor is a polynucleotide comprising the nucleotide sequence of the formula: R$\gamma$JGCK$\alpha$GIGGL$\beta$-3' (SEQ ID NO:146), wherein each R, K, and L is a nucleotide, J is U or T, $\gamma$ is an integer from about 0 to 10, $\alpha 0$ is an integer from about 1 to about 20, and $\beta$ is an integer from about 1 to about 20, each nucleotide in the GIGG portion of the sequence is a 2'-deoxyribonucleotide (e.g., G is 2'-deoxyguanosine and I is 2'-deoxyinosine). Similarly, in some embodiments, each nucleotide in a GGGG, GIGG or GZ'GG motif, wherein I is inosine and Z' is 7-deaza G is a 2'-deoxyribonucleotide (e.g., G is 2'-deoxyguanosine, I is 2'-deoxyinosine and Z' is 7-deaza-2'-deoxyguanosine).

Also provided herein are methods of regulating an immune response in an individual, comprising administering to the individual a polynucleotide in an amount sufficient to regulate an immune response in the individual, wherein the polynucleotide is selected from the group consisting of SEQ ID NO:64-78, SEQ ID NO:123-135, and SEQ ID NO:141-145. In some embodiments, the polynucleotide comprises one of the group consisting of SEQ ID NO:67, SEQ ID NO:68, SEQ ID NO:69, SEQ ID NO:71, SEQ ID NO:73, SEQ ID NO:78, SEQ ID NO:141, SEQ ID NO:143, and SEQ ID NO:144. In some embodiments, the polynucleotide comprises one of the group consisting of SEQ ID NO:73, SEQ ID NO:134, SEQ ID NO:143, and SEQ ID NO:144.

In certain embodiments, regulating the immune response in the individual treats and/or prevents a disease. In certain embodiments of any of the methods provided herein, an immune response is inhibited. In certain embodiments of any of the methods provided herein, a TLR7 dependent immune response is inhibited. In certain embodiments of any of the methods provided herein, a TLR9 dependent immune response is inhibited. In further embodiments of any of the methods, both TLR7 and TLR9 dependent immune responses are inhibited.

In certain embodiments of any of the methods provided herein, the disease is an autoimmune disease. In certain embodiments, one or more symptoms of the autoimmune disease is ameliorated. In certain embodiments of any of the methods provided herein, development of the autoimmune disease is prevented or delayed. In certain embodiments, the autoimmune disease is selected from the group consisting of systemic lupus erythematosus (SLE), rheumatoid arthritis, dermatomyositis, and Sjogren's syndrome. In certain embodiments of any of the methods provided herein, the disease is associated with inflammation. In certain embodiments, the inflammation is a sterile inflammation. In certain embodiments, the sterile inflammation is sterile inflammation of the liver.

The present invention further encompasses a polynucleotide comprising one or more of the group (of 33 sequences) consisting of SEQ ID NOs:64-78, 123-135, and 141-145. The present invention also encompasses a polynucleotide consisting of one of the group (of 33 sequences) consisting of SEQ ID NOs:64-78, 123-135, and 141-145. In some embodiments, the polynucleotide is comprised of all 2'-deoxyribo polynucleotides. In some embodiments one or more nucleotides of the polynucleotide comprises a modification. In some embodiments, the modification comprises a 2'-sugar modification. In a subset of these embodiments, the 2'-sugar modification comprises a 2'-O-methyl sugar modification or a 2'-O-methoxyethyl sugar modification. In certain embodiments, the polynucleotide is comprised of all 2'-deoxyribo polynucleotides. In certain embodiments, the polynucleotide is a 2'-deoxyribo polynucleotide and a 2'-sugar modification chimeric sequence. In certain embodiments, the polynucleotide is a 2'-deoxyribo polynucleotide and a 2'-O-methyl sugar polynucleotide chimeric sequence. In certain embodiments, the polynucleotide is a 2'-deoxyribo polynucleotide and a 2'-β-methyoxyethyl sugar polynucleotide chimeric sequence. In certain embodiments, the polynucleotide has at least one nucleotide comprising a modified phosphate linkage. In certain embodiments, the polynucleotide comprises only phosphorothioate linkages.

The invention further relates to kits, preferably for carrying out the methods of the invention. The kits of the invention generally comprise an immunoregulatory polynucleotide and/or an immunoregulatory compound of the invention (generally in a suitable container), and may further include instructions for use of the immunoregulatory polynucleotide and/or immunoregulatory compound in immunoregulation of an individual. In some embodiments, the kit further comprises another therapeutic agent.

The present disclosure provides methods of treating an autoimmune disease in an individual comprising administering to the individual an effective amount of a TLR7 inhibitor and/or TLR9 inhibitor, wherein an elevated inflammatory gene expression pattern as compared to that of control sample(s) from healthy subject(s) is present in a sample from the individual at the onset of treatment. In some embodiments the TLR7 and/or TLR9 inhibitor is a polynucleotide comprising or consisting of a nucleotide sequence selected from the group consisting of SEQ ID NOS:1-78, 80-108, and 110-145, or a polynucleotide comprising or consisting of a nucleotide sequence selected from the group consisting of SEQ ID NOS: 64-78, 123-135 and 141-145. In some embodiments the TLR7 and/or TLR9 inhibitor is a polynucleotide comprising the nucleotide sequence of the formula: R$\gamma$JGCK$\alpha$GIGGL$\beta$-3' (SEQ ID NO:146), wherein each of R, K, and L is a nucleotide, J is U or T, $\gamma$ is an integer from about 0 to 10, $\alpha$ is an integer from about 1 to about 20, and $\beta$ is an integer from about 1 to about 20. In some embodiments, each nucleotide of the GIGG of the sequence is a 2'-deoxyribonucleotide (e.g., G is 2'-deoxyguanosine and I is 2'-deoxyinosine). In some embodiments the TLR7 and/or TLR9 inhibitor is a polynucleotide comprising or consisting of a nucleotide sequence selected from the group consisting of SEQ ID NO:67, SEQ ID NO:68, SEQ ID NO:69, SEQ ID NO:71, SEQ ID NO:73, SEQ ID NO:78, SEQ ID NO:141, SEQ ID NO:143 and SEQ ID NO:144. In some embodiments the TLR7 and/or TLR9 inhibitor is a polynucleotide comprising or consisting of a nucleotide sequence selected from the group consisting of SEQ ID NO:71, SEQ ID NO:73, SEQ ID NO:78, SEQ ID NO:143 and SEQ ID NO:144. In some embodiments, the TLR7 and/or TLR9 inhibitor is a polynucleotide comprising or consisting of a nucleotide sequence selected from the group consisting of SEQ ID NO:73, SEQ ID NO:134, SEQ ID NO:143 and SEQ ID NO:144. In some embodiments, the polynucleotide is comprised of all 2'-deoxyribo polynucleotides. In some embodiments one or more nucleotides of the polynucleotide comprises a modification. In some embodiments, the modification comprises a 2'-sugar modification. In a subset of these embodiments, the 2'-sugar modification comprises a 2'-O-methyl sugar modification or a 2'-O-methoxyethyl sugar modification. In certain embodiments, the polynucleotide is comprised of all 2'-deoxyribo polynucleotides. In certain embodiments, the polynucleotide is a 2'-deoxyribo polynucleotide and a 2'-sugar modification chimeric sequence. In certain embodiments, the polynucleotide is a 2'-deoxyribo polynucleotide and a 2'-O-methyl sugar polynucleotide chimeric sequence. In certain embodiments, the polynucleotide is a 2'-deoxyribo polynucleotide and a 2'-O-methyoxyethyl sugar polynucleotide chimeric sequence. In certain embodiments, the polynucleotide has at least one nucleotide comprising a modified phosphate linkage. In certain embodiments, the polynucleotide comprises only phosphorothioate linkages. In some embodiments, the methods further comprise selecting the individual having the elevated inflammatory gene expression pattern, prior to the administering step. In some preferred embodiments, the TLR7 inhibitor and/or TLR9 inhibitor is administered in an amount effective to achieve one or more of the following outcomes: i) reduce the inflammatory gene expression pattern in a post-treatment sample from the individual; ii) reduce a clinical disease activity measure of the autoimmune disease; iii) reduce a serologic disease measure of the autoimmune disease; and iv) increase plasmacytoid dendritic cells in a post-treatment peripheral blood mononuclear cell sample from the individual. In some embodiments, the serologic disease measure comprises complement levels. In some embodiments, the serologic disease measure comprises antinuclear antigen antibodies comprising one or more of the group consisting of anti-dsDNA, anti-Sm (Smith antigen), anti-histone, anti-RNP, anti-Ro (SSA), and anti-La (SSB). In some embodiments, the methods further comprise administering a second therapeutic agent. In some preferred embodiments, the second therapeutic agent is selected from the group consisting of a corticosteroid, a nonsteroidal anti-inflammatory drug (NSAID), an IFN-alpha inhibitor, and an anti-malarial. In some embodiments, the individual is a human patient. In some embodiments, the autoimmune disease is systemic lupus erythematosus (SLE) or cutaneous lupus erythematosus (CLE). In some embodiments, the autoimmune disease is selected from the group consisting of SLE, systemic sclerosis, polymyositis, dermatomyositis, rheumatoid arthritis and Sjorgren syndrome.

Also provided by the present disclosure are methods of treating an autoimmune disease in an individual comprising-administering to the individual an amount of a TLR7 inhibitor and/or TLR9 inhibitor effective to reduce glucocorticoid use by the individual, wherein an elevated inflammatory gene expression pattern as compared to that of control sample(s) from healthy subject(s) is present in a sample from the individual at the onset of treatment. The present disclosure further provides methods of assessing whether an individual having an autoimmune disease is likely to respond to a treatment comprising an effective amount of a TLR7 inhibitor and/or TLR9 inhibitor, the method comprising measuring an inflammatory gene expression pattern in a sample from the individual, wherein an elevated inflammatory gene expression pattern as compared to that of control sample(s) from healthy subject(s) indicates that the individual is likely to respond to the treatment. Additionally the present disclosure provides methods of monitoring responsiveness of an individual having an autoimmune disease to a treatment comprising an effective amount of a TLR7 inhibitor and/or TLR9 inhibitor, the method comprising measuring an inflammatory gene expression pattern in a sample from the individual pre- and post-treatment, wherein when the inflammatory gene expression pattern is reduced in the post-treatment sample as compared to the pre-treatment sample, the individual is determined to be responsive to the treatment. In some embodiments the TLR7 and/or TLR9 inhibitor is a polynucleotide comprising or consisting of a nucleotide sequence selected from the group consisting of SEQ ID NOS:1-78, 80-108, and 110-145, or a polynucleotide comprising or consisting of a nucleotide sequence selected from the group consisting of SEQ ID NOS:64-78, 123-135 and 141-145. In some embodiments the TLR7 and/or TLR9 inhibitor is a polynucleotide comprising the nucleotide sequence of the formula: RγJGCKαGIGGLβ-3' (SEQ ID NO:146), wherein each R, K, and L is a nucleotide, J is U or T, γ is an integer from about 0 to 10, α is an integer from about 1 to about 20, and β is an integer from about 1 to about 20. In some embodiments, each nucleotide of the GIGG of the sequence is a 2'-deoxyribonucleotide (e.g., G is 2'-deoxyguanosine and I is 2'-deoxyinosine). In some embodiments the TLR7 and/or TLR9 inhibitor is a polynucleotide comprising or consisting of a nucleotide sequence selected from the group consisting of SEQ ID NO:67, SEQ ID NO:68, SEQ ID NO:69, SEQ ID NO:71, SEQ ID NO:73, SEQ ID NO:78, SEQ ID NO:141, SEQ ID NO:143 and SEQ ID NO:144. In some embodiments the TLR7 and/or TLR9 inhibitor is a polynucleotide comprising or consisting of a nucleotide sequence selected from the group consisting of SEQ ID NO:71, SEQ ID NO:73, SEQ ID NO:78, SEQ ID NO:143 and SEQ ID NO:144. In some embodiments, the TLR7 and/or TLR9 inhibitor is a polynucleotide comprising or consisting of a nucleotide sequence selected from the group consisting of SEQ ID NO:73, SEQ ID NO:134, SEQ ID NO:143 and SEQ ID NO:144. In some embodiments, the polynucleotide is comprised of all 2'-deoxyribo polynucleotides. In some embodiments one or more nucleotides of the polynucleotide comprises a modification. In some embodiments, the modification comprises a 2'-sugar modification. In a subset of these embodiments, the 2'-sugar modification comprises a 2'-O-methyl sugar modification or a 2'-O-methoxyethyl sugar modification. In certain embodiments, the polynucleotide is comprised of all 2'-deoxyribo polynucleotides. In certain embodiments, the polynucleotide is a 2'-deoxyribo polynucleotide and a 2'-sugar modification chimeric sequence. In certain embodiments, the polynucleotide is a 2'-deoxyribo polynucleotide and a 2'-O-methyl sugar polynucleotide chimeric sequence. In certain embodiments, the polynucleotide is a 2'-deoxyribo polynucleotide and a 2'-O-methyoxyethyl sugar polynucleotide chimeric sequence. In certain embodiments, the polynucleotide has at least one nucleotide comprising a modified phosphate linkage. In certain embodiments, the polynucleotide comprises only phosphorothioate linkages. In some embodiments, the individual is a human patient. In some embodiments, the autoimmune disease is systemic lupus erythematosus (SLE) or cutaneous lupus erythematosus (CLE). In some embodiments, the autoimmune disease is selected from the group consisting of SLE, systemic sclerosis, polymyositis, dermatomyositis, rheumatoid arthritis and Sjorgren syndrome.

Moreover, the present disclosure provides embodiments of any of the methods provided in the preceding paragraphs in which the elevated inflammatory gene expression pattern comprises an interferon (IFN) signature comprising elevated levels in the sample of one or more biomarkers selected from the group consisting of BATF2, CMPK2, CXCL10, DDX60, EPSTI1, HERC5, HES4, IFI44, IFI44L, IFIT1, IFIT3, IFITM3, ISG15, LAMP3, LOC26010, LY6E, MX1, OAS1, OAS2, OAS3, OASL, OTOF, RSAD2, RTP4, SERPING1, TRIM6, XAF1, cl02h05 5, Agencourt-7914287 NIH-MCG__71, ISG20, IFI16, IRF7, and AIM2, as compared to the control sample(s). In some embodiments, the elevated inflammatory gene expression pattern comprises an interferon (IFN) signature comprising elevated levels in the sample of one or more biomarkers selected from the group consisting of BATF2, CMPK2, DDX60, EPSTI1, HERC5, HES4, IFI44, IFI44L, IFIT1, IFIT3, IFITM3, ISG15, LAMP3, LOC26010, MX1, OAS1, OAS2, OAS3, OASL, OTOF, RSAD2, RTP4, SERPING1, TRIM6, XAF1, cl02h05 5, Agencourt-7914287 NIH-MCG__71, ISG20, IRF7, and AIM2, as compared to the control sample(s). In some embodiments, the elevated inflammatory gene expression pattern comprises elevated levels in the sample of one or more cytokines selected from the group consisting of IL-1alpha, IL-1 beta, TNF-alpha, IL-6, IL-17, IFN-alpha, IFN-omega, IFN-lambda1, IFN-lambda2, and IP-10, as compared to the control sample(s). In some embodiments, the elevated inflammatory gene expression pattern comprises elevated levels in the sample of one or more biomarkers selected from the group consisting of: IFIT1 (Interferon-induced protein with tetratricopeptide repeats-1), OASL (2'-5'-oligoadenylate synthetase-like), LY6E (Lymphocyte antigen 6 complex, locus E), OAS2 (2'-5'-oligoadenylate synthetase), OAS3 (2'-5'-oligoadenylate synthetase), IFI44 (Hepatitis C microtubular aggregate protein), MX1 (Myxovirus resistance 1), G1P3 (Interferon, alpha-inducible protein or IFI-6-16), PRKR (Protein kinase, interferon-α-inducible double-stranded RNA-dependent), IFIT4 (Interferon-induced protein with tetratricopeptide repeats 4), PLSCR1 (Phospholipid scramblase 1), C1ORF29 (Hypothetical protein expressed in osteoblasts, similar to IFI44), HSXIAPAF1 (XIAP-associated factor-1), G1P2 (Interferon, alpha-inducible protein or IFI-15K), Hs. 17518 (Cig5 or Viperin), IRF7 (Interferon regulatory factor 7), CD69 (Early T-cell activation antigen), LGALS3BP (Lectin, galactoside-binding, soluble, 3 binding protein), IL1RN (Interleukin-1 receptor antagonist), APOBEC3B (Phorbolin 1-like), RGS1 (Regulator of G-protein signaling 1), AGRN (Agrin), EREG (Epiregulin), THBS1 (Thrombospondin 1), ETS1 (v-ets erythroblastosis virus E26 oncogene homolog 1), ADAM9 (A disintegrin and metalloproteinase domain 9), SERPING1 (Serine or cysteine proteinase inhibitor (C1 inhibitor)), and FCGR1A (Fc fragment of IgG, high-affinity Ia receptor) as compared to the control sample(s). In some embodiments, the IFN signature is part of a SLE signature. In some embodiments, the SLE signature comprises elevated levels in the sample of one or more biomarkers selected from the group consisting of GTPBP2, PCTAIRE2BP, DNAPTP96, GPR84, B4GALT5, FRAT2, and PAFAH1B as compared to the control sample(s). In some embodiments, the SLE signature comprises elevated levels in the sample of one or more biomarkers selected from the group consisting of: Table 1B (185 markers), Table 2B (1253 marker), Table 3B (18 markers), and Table 4 (6 markers) all of U.S. Pat. No. 7,608,395 (and as reproduced in the description) as compared to the control sample(s). In some embodiments, the SLE signature comprises reduced levels in the sample of one or more biomarkers selected from the group consisting of: Table 1A (160 markers), Table 2A (1751 marker), and Table 3A (27 markers) all of U.S. Pat. No. 7,608,395 (and as reproduced in the description) as compared to the control sample(s). In some embodiments, elevated levels refer to a change in the expressed level of at least 2.0 fold, at least 2.25 fold, at least 2.5 fold or, at least 3 fold, at least 3.5 fold, at least 4 fold, at least 5-fold, or at least 10 fold, greater than that in the control sample(s). In other embodiments, reduced levels refer to expression at a level that is at least 50% less, at least 60%, at least 70%, at least 80%, at least 90% or at least 95% less than that in the control sample(s). In some embodiments, the one or more biomarkers comprise at least two, three, four, five, six, seven, eight, nine, ten, fifteen, twenty, or twenty-five biomarkers. In some embodiments, the control sample(s) from healthy subject(s) comprises PBMC from at least 10, 15, 20, or 25 healthy human subjects. In some embodiments, the sample comprises peripheral blood mononuclear cells (PBMC) or skin tissue. In some embodiments, the elevated inflammatory gene expression pattern is determined by measuring mRNA expressed from a gene of the biomarker. In other embodiments, the elevated inflammatory gene expression pattern is determined by measuring protein expression from a gene of the biomarker. In some embodiments, the elevated inflammatory gene expression pattern is determined by a technique selected from but not limited to the group consisting of nanostring analysis, enzyme-linked immunosorbent assay (ELISA), and flow cytometry.

The present disclosure further provides compositions for use in the methods of the preceding paragraphs comprising a TLR7 inhibitor and/or a TLR9 inhibitor for use in treating an autoimmune disease in an individual, wherein an elevated inflammatory gene expression pattern as compared to that of control sample(s) from healthy subject(s) is present in a sample from the individual at the onset of treatment, wherein the TLR7 and/or TLR9 inhibitor is a polynucleotide comprising the nucleotide sequence of the formula: RγJGCKαGIG-GLβ-3' (SEQ ID NO:146), wherein each R, K, and L is a nucleotide, J is U or T, γ is an integer from about 0 to 10, α is an integer from about 1 to about 20, and β is an integer from about 1 to about 20. In some embodiments, each nucleotide of the GIGG of the sequence is a 2'-deoxyribonucleotide (e.g., G is 2'-deoxyguanosine and I is 2'-deoxyinosine).

The present disclosure also provides compositions for use in the methods of the preceding paragraphs comprising a TLR7 inhibitor and/or a TLR9 inhibitor for use in treating an autoimmune disease in an individual, wherein an elevated inflammatory gene expression pattern as compared to that of control sample(s) from healthy subject(s) is present in a sample from the individual at the onset of treatment, wherein the TLR7 and/or TLR9 inhibitor is a polynucleotide comprising the nucleotide sequence of the formula: 5'-$N_m$-$N_3N_2N_1$CGN$^1$N$^2$N$^3$—N$^m$-3' (SEQ ID NO:205), wherein CG is an oligonucleotide motif that is CpG, C*pG, C*pG*, or CpG*, wherein C is cytosine, C* is a pyrimidine nucleotide derivative, G is guanosine, G* is a purine nucleotide derivative; $N_1$ is a nucleotide derivative or non-nucleotide linkage modification that suppresses the activity of the oligonucleotide motif, $N_2$—$N_3$ at each occurrence is a nucleotide, nucleotide derivator, or non-nucleotide linkage modification that suppresses the activity of the oligonucleotide motif, $N^1$—$N^3$ at each occurrence is a nucleotide or nucleotide derivative, and $N_m$ and $N^m$ at each occurrence is a nucleotide, nucleotide derivator, or non-nucleotide linkage.

The present disclosure additionally provides compositions for use in the methods of the preceding paragraphs comprising a TLR7 inhibitor and/or a TLR9 inhibitor for use in treating an autoimmune disease in an individual, wherein an elevated inflammatory gene expression pattern as compared to that of control sample(s) from healthy subject(s) is present in a sample from the individual at the onset of treatment, wherein the TLR7 and/or TLR9 inhibitor is a polynucleotide comprising the nucleotide sequence of the formula: $X_aCCN_1N_2N_3Y_bN_4GGGZ_c$ (SEQ ID NO:206), wherein: each C is cytidine or a derivative thereof, wherein at least one C is a cytidine derivative; each G is guanosine or a deaza derivative thereof; $X_a$ is any nucleotide sequence a nucleotides long, wherein α is an integer between 0-12, inclusive, and each nucleotide is selected independently of any other in $X_a$; $Y_b$ is any nucleotide sequence b nucleotides long, wherein b is an integer between 0-21, inclusive, and each nucleotide is selected independently of any other in $Y_b$; $Z_c$ is any nucleotide sequence c nucleotides long, wherein c is an integer between 0-12, inclusive, and each nucleotide is selected independently of any other in $Z_c$; and $N_1$, $N_2$, $N_3$, and $N_4$ are each independently any nucleotide.

BRIEF DESCRIPTION OF THE DRAWINGS

FIGS. 1A-C depicts IL-6 levels (pg/ml) in mouse splenocytes following TLR7 ligand stimulation by R848 either alone or in the presence of tested IRPs.

FIGS. 2A-D shows rat body weight gain/loss over time after administration of SEQ ID NO:42 or SEQ ID NO:109 (IRS) at 10 mpk and 100 mpk (A, B) and after administration of SEQ ID NO:42, SEQ ID NO:109, SEQ ID NO:79, SEQ ID NO:73, SEQ ID NO:134, SEQ ID NO:143 and SEQ ID NO:144 at 90 mpk (C, D).

FIGS. 5A-B shows the percentage of IL-6 produced (A) compared to R848 alone when stimulated with R848 either alone or in the presence of the tested IRPs and (B) compared to CpG-ISS alone when stimulated with CpG-ISS either alone or in the presence of the tested IRPs.

FIGS. 6A-B shows the percentage of IL-6 produced compared to R848 alone or level of IL-6 (pg/ml) produced when stimulated with R848 either alone or in the presence of the testd IRPs in splenocytes and B-cells, respectively. FIGS. 6C and D show the percentage of IL-6 produced compared to CpG-ISS alone or level of IL-6 (pg/ml) produced when stimulated with CpG-ISS either alone or in the presence of the testd IRPs in splenocytes and B-cells, respectively.

FIG. 8A shows the level of IFN-α produced compared when stimulated with CpG-ISS alone or in the presence of the tested IRPs. FIGS. 8B-C shows the percentage of IFN-α produced compared to DNA-IC alone when stimulated with DNA-IC (B) or RNP-IC (C) either alone or in the presence of the tested IRPs.

FIG. 10A shows dose response curves of human PDC stimulated with TLR9L HSV or TLR71FLU either alone or in the presence of various concentration of SEQ ID NO:73. FIG. 10B shows the percentage of IFN-α produced compared to virus alone when stimulated with influenza virus, either alone or in the presence of the tested IRPs. FIGS. 10C and D show the level of IL-6 (pg/ml) produced or the percentage of IL-6 produced compared to CpG-ISS alone when stimulated with CpG-ISS either alone or in the presence of the tested IRPs.

FIGS. 11A-B shows tissue concentrations of tested IRPs in liver and kidney. FIGS. 11 C and D show tissue concentrations of SEQ ID NO:73 and SEQ ID NO:109 in the liver, kidney, spleen and heart at the tested doses.

FIGS. 12A-B shows tissue concentrations of SEQ ID NO:73 for the liver, kidney, spleen and heart over time at the tested doses. FIGS. 12C and D show tissue concentrations of SEQ ID NO:73 and 109 in liver, kidney and spleen at the end of the study.

(A-B) normal (closed symbols) and lupus-prone (open symbols) animals were either left untreated or treated with Dexamethasone (GC). Cell numbers in blood (A, fold change to pre-bleed) and spleens (B, fold change to untreated) was assessed 18 hr later. Cumulative data of at least three independent experiments is shown. *** p≤0.001 indicate differences between both lupus strains from either normal strains. (C) (NZBxNZW)$F_1$ and (D) TLR7.Tg.6 mice were left untreated or treated with GC alone or in the presence of IRS or control (CTRL) ODN (100 μg/mouse s.c.) given every 3 days for 10 days prior to the GC treatment. Viability was assessed in the spleen 18 hr post DEX. Cumulative data of two independent experiments is shown.

Figure 17:
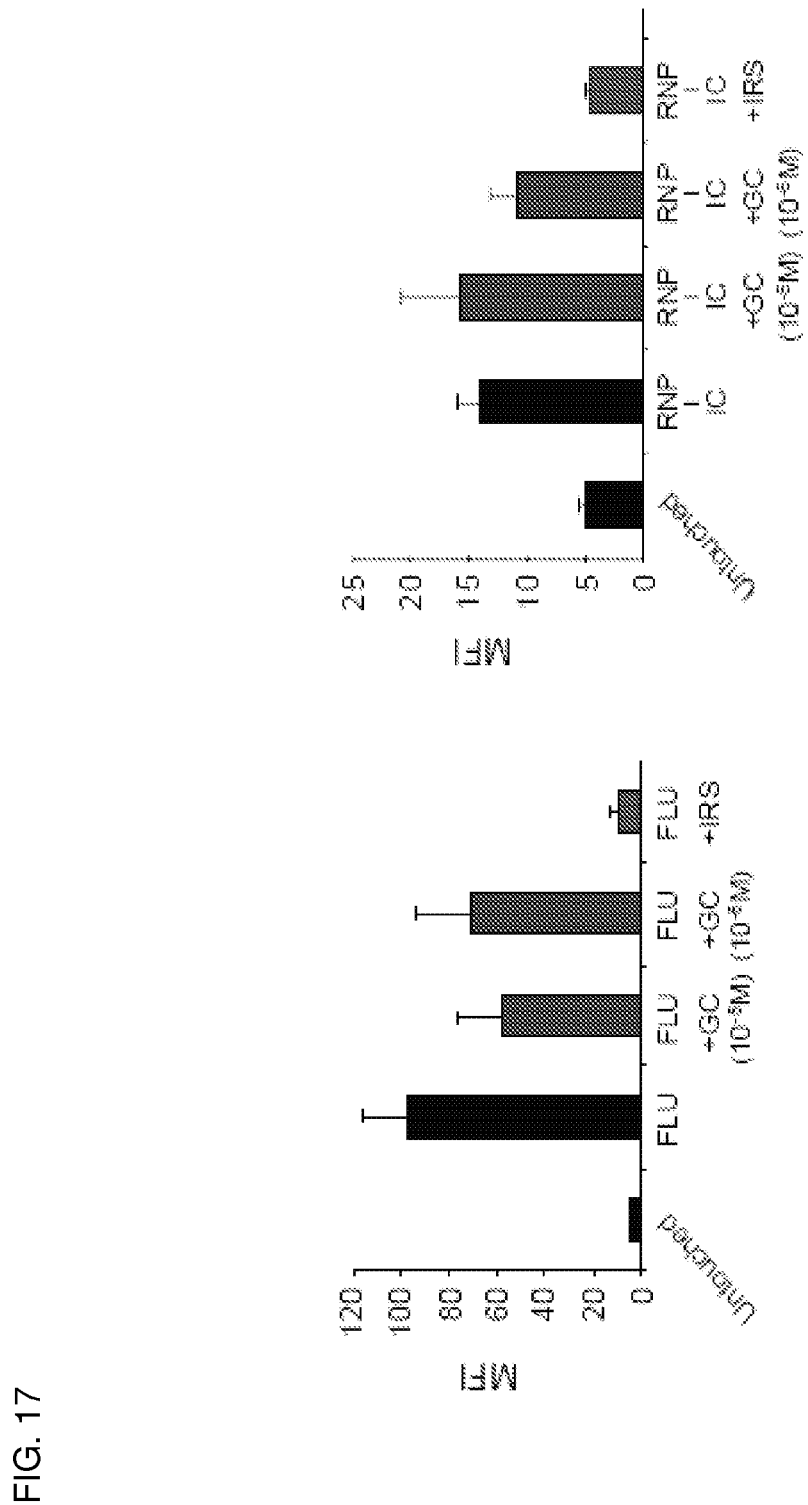

FIG. 17 shows the transient levels of the PDC-induced IFN signature in GC-treated SLE patients. Purified human PDC were cultured alone or in the presence of Flu (2 MOI) or purified anti-RNP IC isolated from SLE patients either alone or combined with GC ($10^{-5}$M or $10^{-6}$M or IRS (0.5 μM). After 3 hr, cells were assayed for IFN-α secretion and cumulative data of five donors shown as MFI (mean±standard error of the mean).

FIGS. 18A-E shows that TLR-induced signal protected PDC from GC-induced cell death. IRS inhibited IFN-α production in TLR7/9 stimulated human PDC but did not induce cell death and exogenous IFN-α did not rescue PDC in absence of NF-kB activation. (A) Purified human PDC were cultured with CpG-C ISS (0.5 μM), IL-3 (5 ng/ml), TNF-α (20 ng/ml), IL-7 (10 ng/ml), FTL-3L (10 ng/ml) alone (white bar) or in the presence of GC ($10^{-5}$M) (black bar). Viability was assessed after 24 hr. Average of 10 (left panel) and 13 (right panel) independent donors±standard error of the mean in five independent experiments is shown  p≤0.01, * p≤0.001. P values are between CpG+GC and cytokines+GC groups. (B) Purified human PDC were cultured with CpG-C ISS (0.5 μM), Flu (2 MOD either alone or in combination with various concentration of GC. Viability and production of IFN-α was assessed after 24 hr. Average of 10 independent donors is shown. (C, D) Purified PDC were cultured with CpG-C ISS (0.5 μM), Flu (2 MOI) or RNP-IC (0.5 mg/ml) either alone or in the presence of IRS (1 μM) (C) Viability was assessed after 24 hr. (D) IFN-α was measured by ELISA. Cumulative data of three independent experiments is shown. n=10. (E) Purified PDC were cultured with CpG-C ISS (0.5 μM) with or without soluble IFN-α (20 ng/ml) either alone or in the presence of the NF-kB inhibitor IKK-2 at the indicated concentrations. Viability was assessed after 24 hr. Average±standard error of the mean of 10 independent donors is shown.

Figure 19:
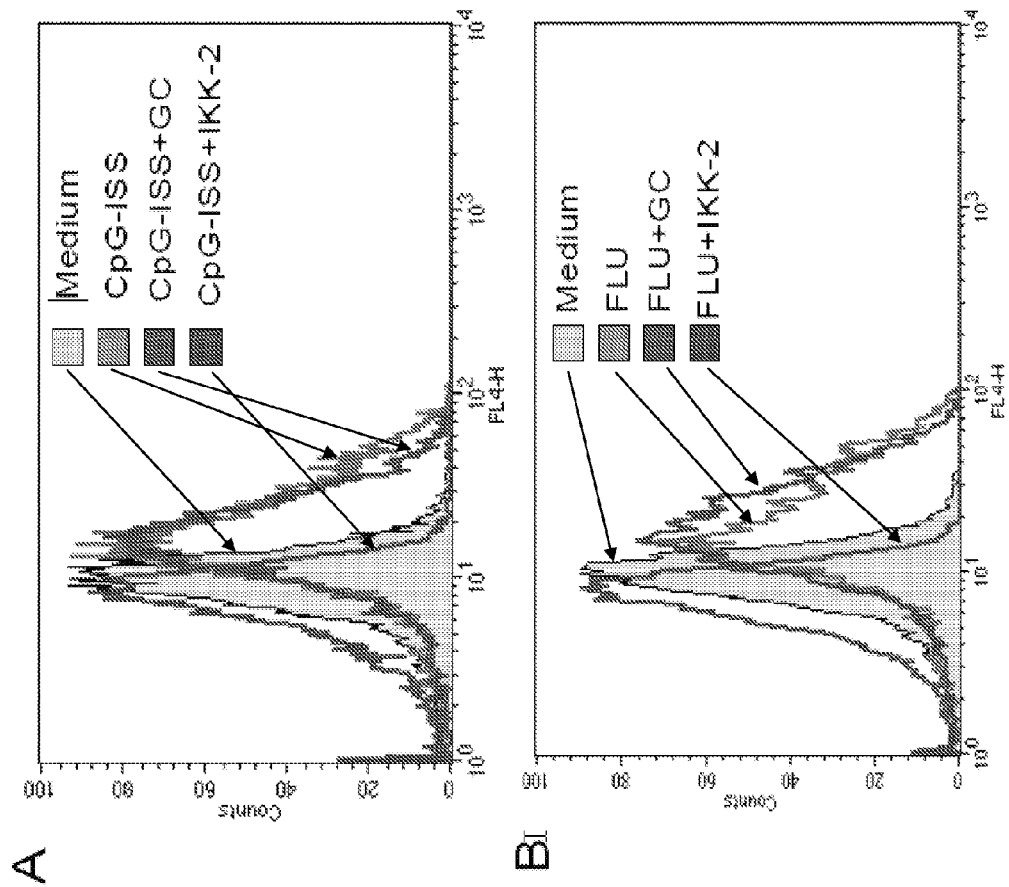

FIG. 19 shows that GC did not affect TLR-induced p65 phosphorylation in PDC. Negatively purified PDC were either left untreated or cultured with CpG-C ISS (0.5 μM) (A), Flu (2 MOI) (B) either alone or in the presence of GC ($10^{-5}$M) or NF-kB inhibitor IKK-2 (0.5 μM) for 90 min after which cells were fixed immediately permabilized with PermBuffer III for 30 minutes on ice and stained with either Alexa-647 anti-human NF-kB p65 (pS529) (BD Bioscience) and then analyzed by flow cytometry. Representative histograms of at least three separate experiments.

Figure 20:
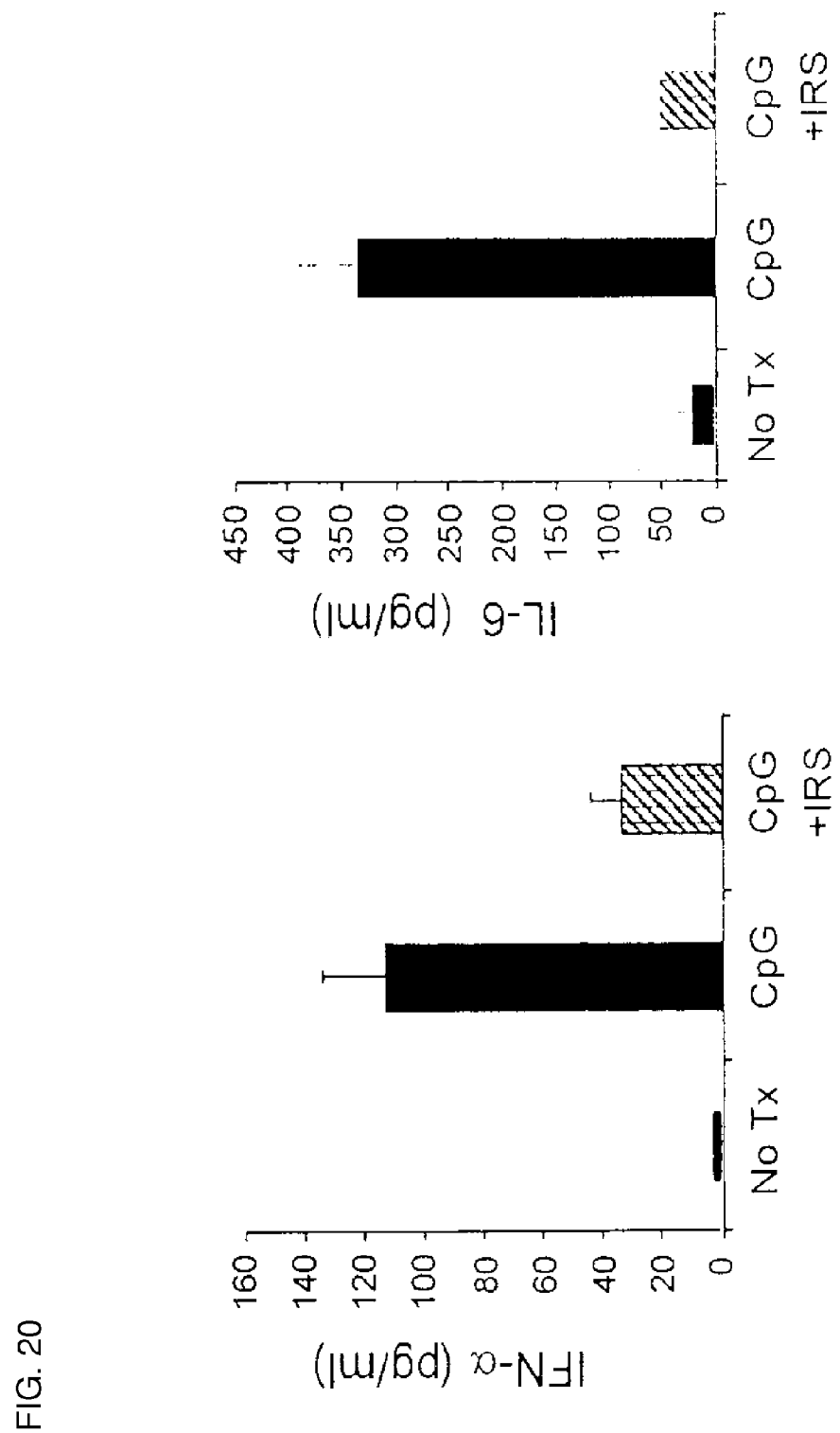

FIG. 20 shows that IRS significantly reduced CpG-C ISS-mediated induction of cytokines in vivo. 129 mice were either left untreated or treated with CpG-C ISS (50 μg/mice) alone or with IRS (50 μg/mice) and serum was collected 6 hr later. IFN-α and IL-6 was evaluated by ELISA. n=6 mice per group±standard error of the mean.

Figure 21:
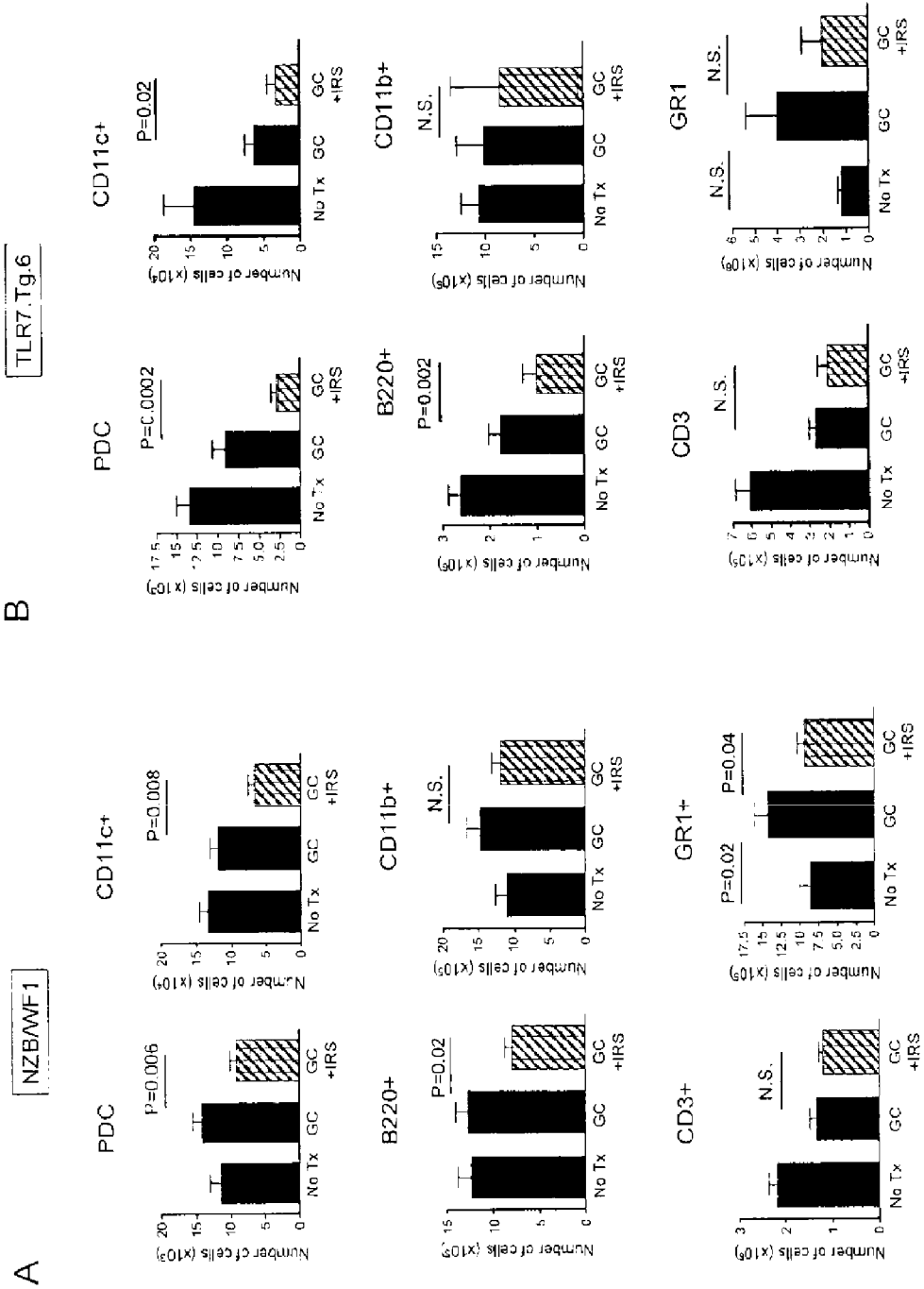

FIG. 21 shows that increased resistance of PDC in lupus-prone mice was due to TLR7&9 stimulation. (A) (NZBxNZW)$F_1$ and (B) TLR7.Tg.6 mice were left untreated or treated with GC (0.5 mg) alone or with IRS. IRS (100 μg/mice s.c.) was administered every 3 days for 10 days prior to the GC treatment. Viability of the different cell subsets was assessed 18 hr after the injection of GC. Data refers to cell number/ml in the blood. Cumulative data±standard error of the mean of two independent experiments n=8-12 mice/group.

Figure 16:
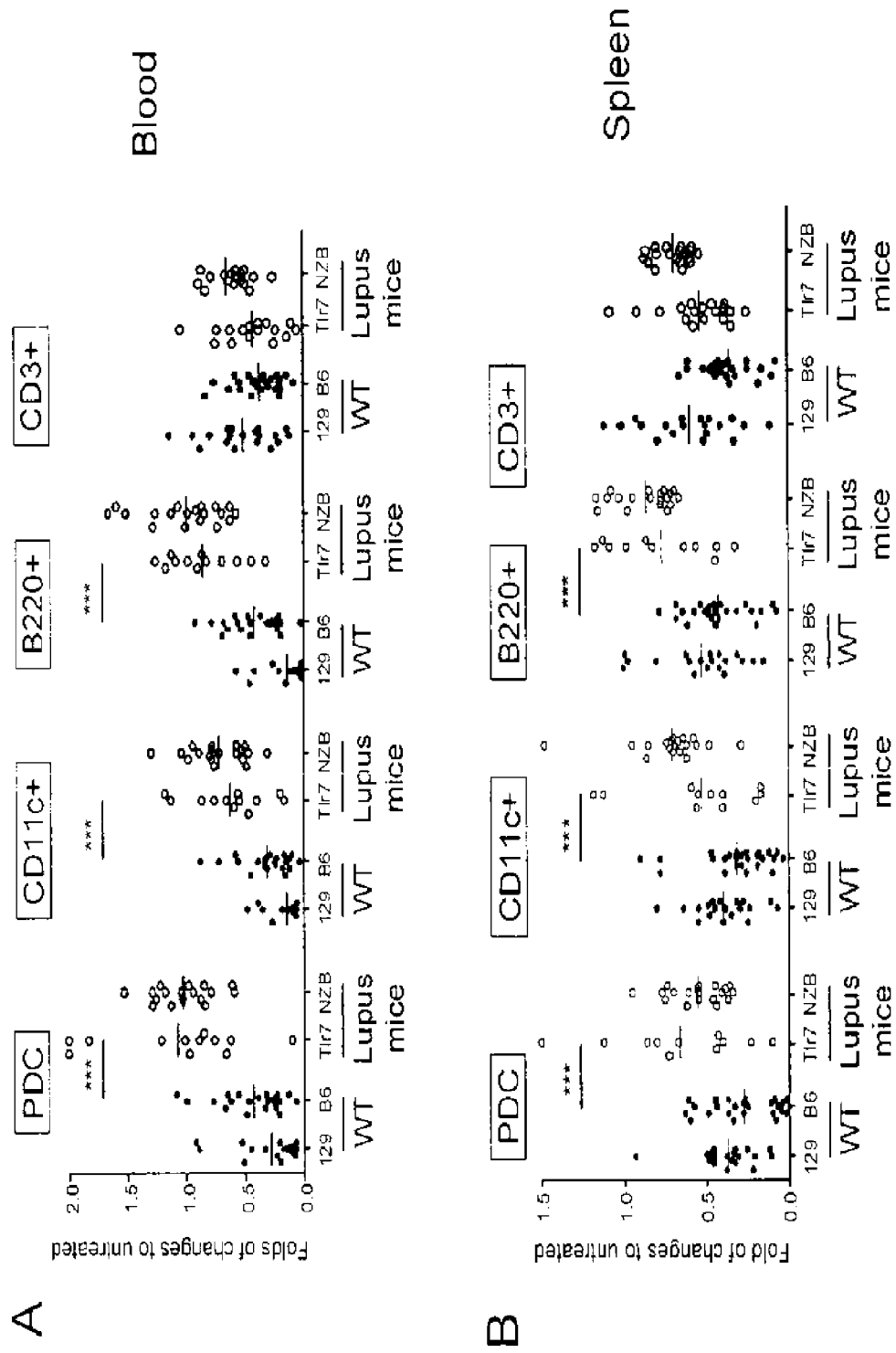
FIGS. 16A-D shows that PDC form lupus prone mice had intrinsic resistance to GC-induced cell death as compare to WT mice due to TLR7&9 activation by self-nucleic acid.
Figure 16:
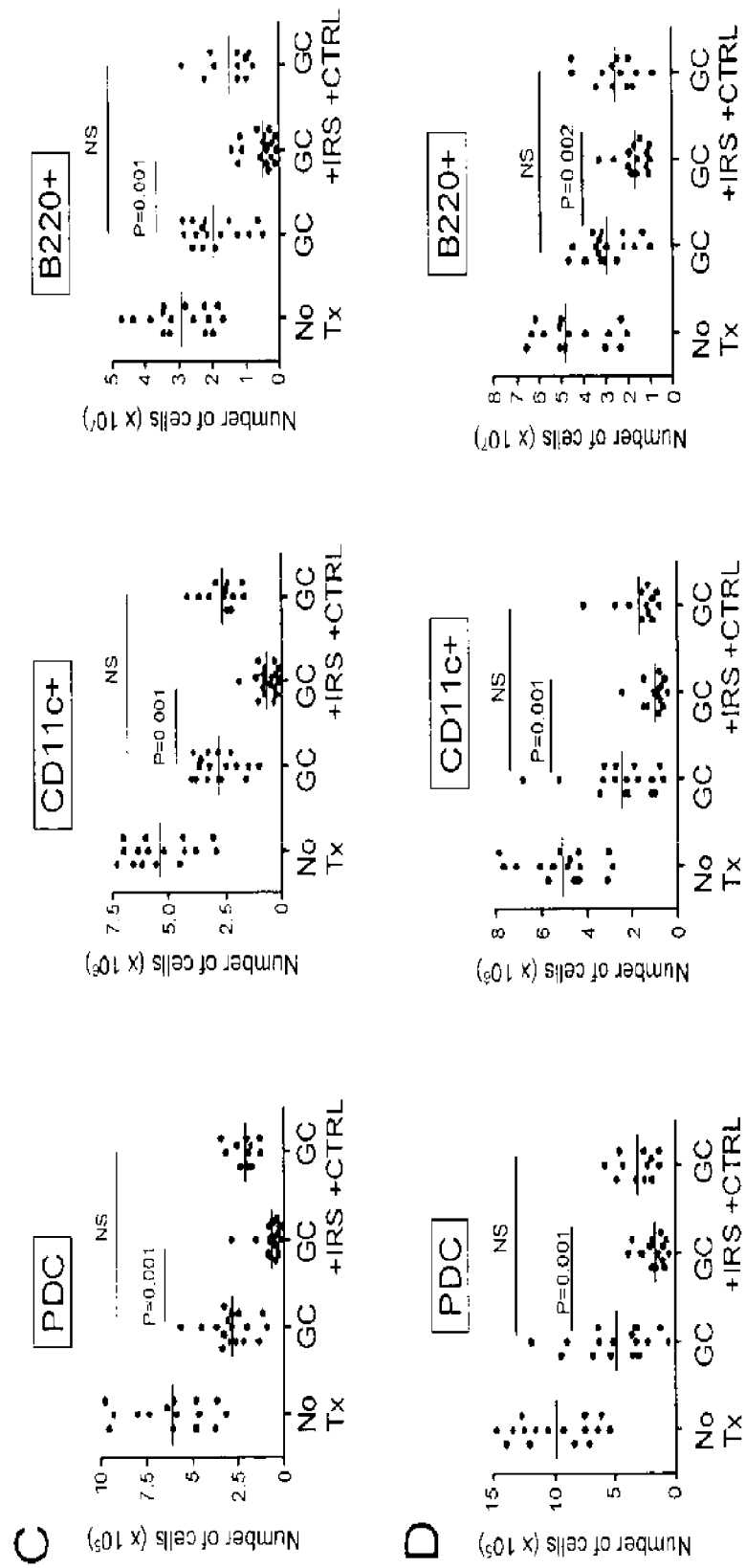

FIGS. 22A-D shows that treatment of lupus-prone mice with TLR inhibitors did not affect viability in vivo in absence of GC in lupus-prone mice and does not have any effect on GC-treated WT mice. Resistance of PDC to GC-induced cell death in lupus mice require cellular activation. (A) (NZBxNZW)$F_1$ or (B) TLR7.Tg.6 were either left untreated or treated every 3 days for 10 days with IRS (100 μg/mice s.c.) and the cell number was measured by flow cytometry in the spleen 18 hr after last IRS administration. Data refers to the average±standard error of the mean of the total cell number in spleens n=6 mice per group. Similar data were obtained in the blood stream (not shown). (C) 129 mice were left untreated or treated with GC 0.5 mg or GC plus IRS (100 μg/mice s.c.) as described in FIG. 16. Viability of PDC was assessed 18 hr after the injection of GC .n=6 mice per group. (D) 129 or the (NZBxNZW)$F_1$ lupus-prone animals (3 weeks or 16 weeks old) were either left untreated or treated with GC as in FIG. 16. Here, the dose of GC was adjusted based on weight of mice and 3 weeks old mice received 0.25 mg while adult mice received 0.5 mg. PDC cell numbers in blood and spleens was assessed 18 hr later. Data are expressed as fold of change to untreated mice for each mouse.

Figure 23:
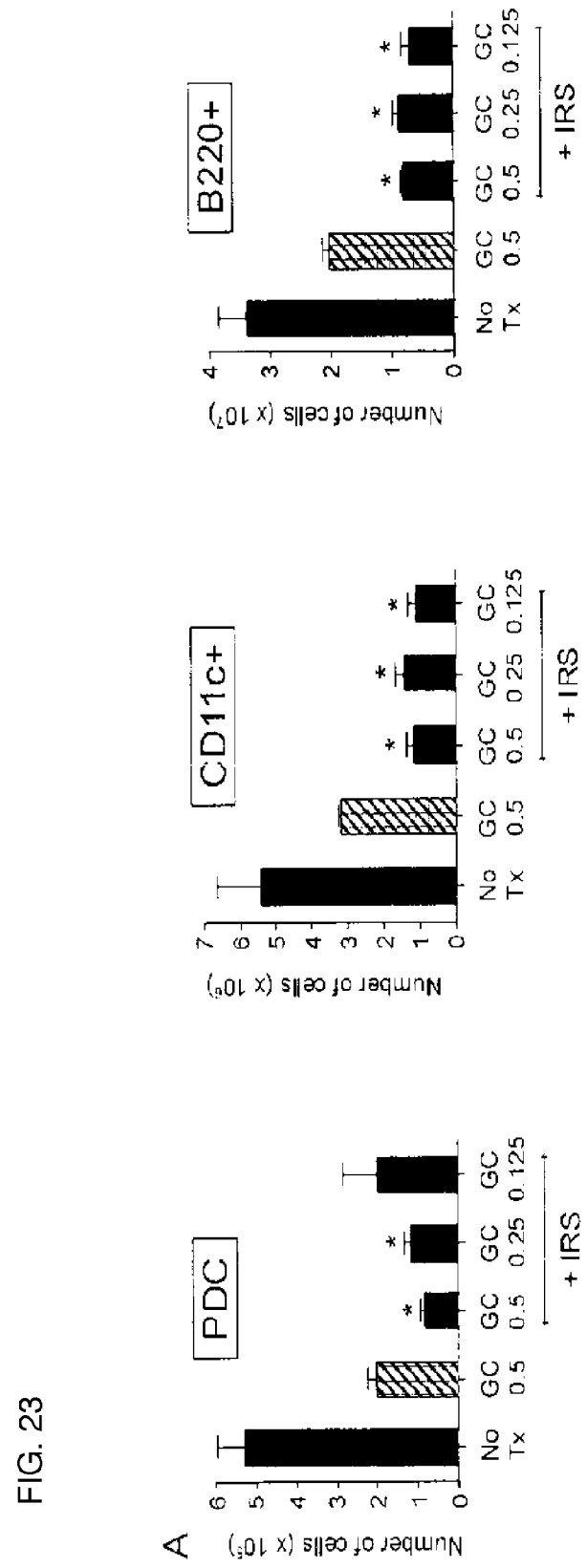
Figure 23:
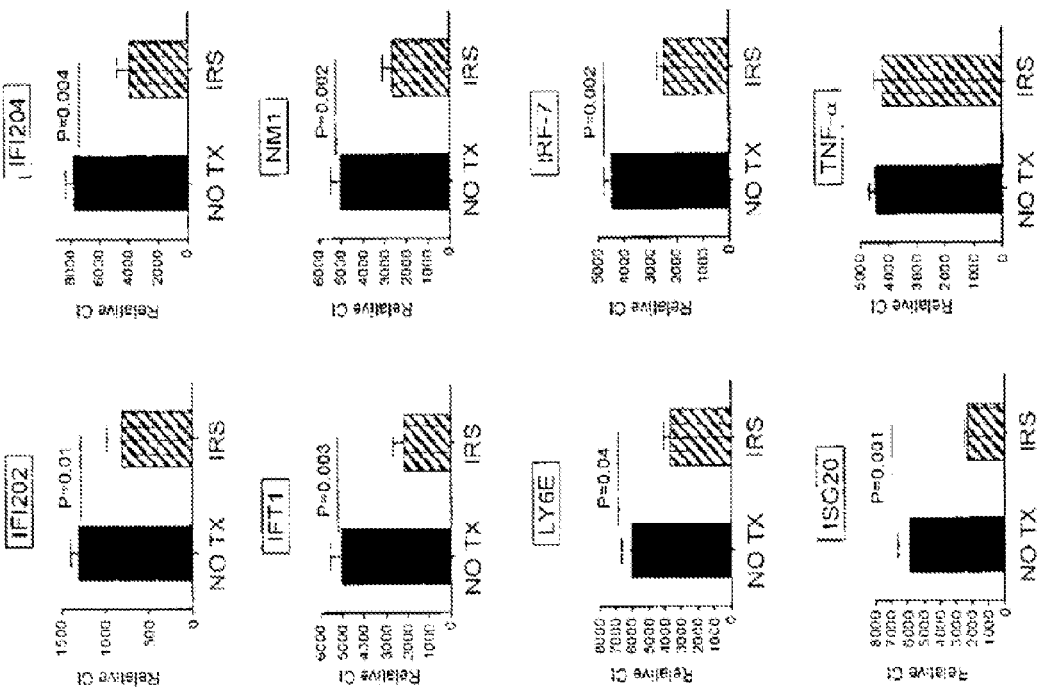
Figure 23:
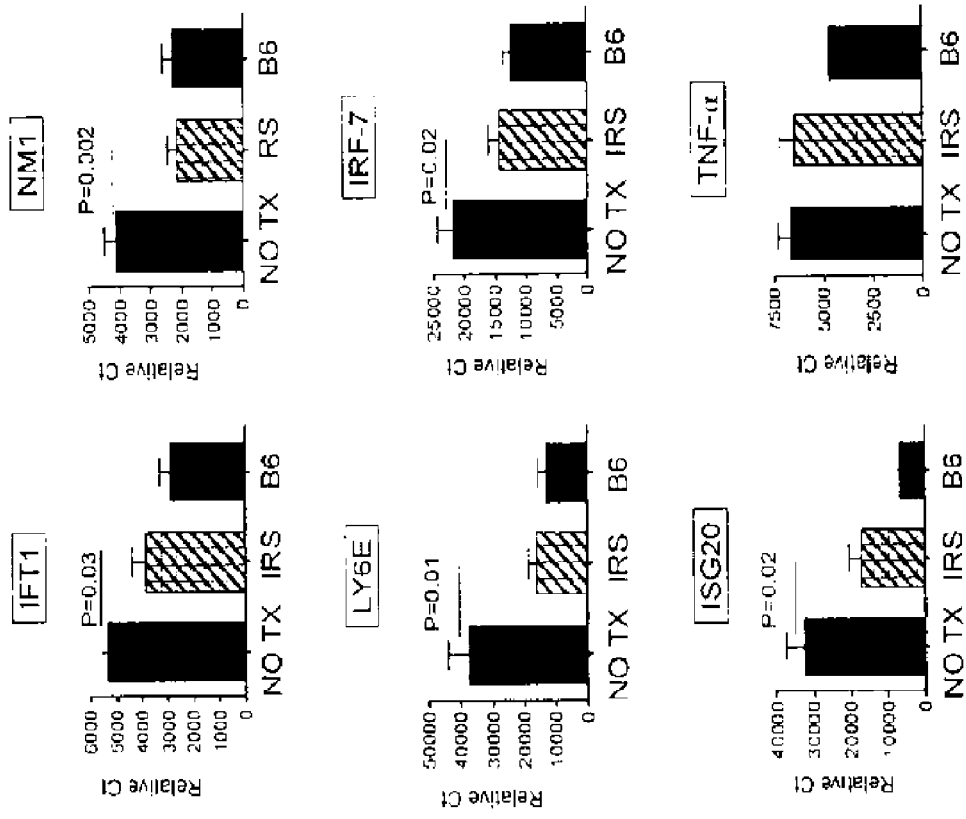

FIGS. 23A-C shows that treatment of lupus-prone mice with TLR inhibitors reduced levels of IFN-inducible genes. (A) (NZBxNZW)$F_1$ mice were treated as described in FIG. 16 but when mice received IRS, different doses of GC were used (in mg per mouse here) (B) (NZBxNZW)$F_1$ and (C) TLR7.Tg.6 mice were left untreated or treated with IRS (100 μg/mice s.c) every 3 days for 10 days and spleens were harvested 18 hr after the last IRS injection. RNA was prepared from the spleens of the animals and the levels of type I IFN-regulated genes were measured by quantitative analysis (Taqman). Averages±standard error of the mean for n=6-10 mice per group.

FIGS. 24A-F shows that skin injury provoked leukocytes infiltration and activation including production of IFN-α by PDC and secretion of NETs by neutrophils. (A) Cellular infiltrate in the skin of 129 mice was characterized 24 hr post inflammation via tape-stripping by flow cytometry. PDC were identified as CD11C+PDCA1+120G8+, cDC as CD11c+PDCA1−120G8−, neutrophils as LY6G+(1A8) F480−, skin macrophages as F480+LY6G low, T cells as CD4+CD3+ and CD8+CD3+. Representative FACS plots of at least 10 mice is shown. (B) 129 mice were tape stripped and 24 hr later PDC infiltrating cells were assessed for IFN-α production by flow cytometry analysis. Neutrophils (LY6G+) and T cells (CD3+) were used as negative control. Cultured bone marrow derived PDC stimulated for 3 hr with CpG-ISS were used as positive control. A representative of three independent experiments with similar results is shown. The ability of neutrophils to form NETs when isolated from (C) bone marrow (as source of inactivated neutrophils) or (D) the skin of mice 24H post tape stripping was determined by immunostaining using Ly6G to detect neutrophils and the SyTox dye to stain DNA. The presence of LL-37-containing DNA (E) or RNA (F) NET fiber was detected by immunostaining using specific dyes. Representative of 10 mice is shown.

FIGS. 25A-B show that MyD88 signaling pathway was necessary for the upregulation of both Type I IFN-regulated and pro-inflammatory genes. A) MyD88$^{-/-}$ (stripped histograms) and age matched WT C57/BL6 mice (black histograms) were either left untreated (naive) or tape stripped to provoke inflammation. 24 hr later, skin biopsies were isolated and the levels of proinflammatory genes evaluated by Taqman. IFNAR$^{-/-}$ mice (stripped histograms) and age matched WT 129 mice (black histograms) were either left untreated (naïve) or tape stripped to provoke inflammation. 24 hr later, skin biopsies were isolated and the levels of proinflammatory genes evaluated by Taqman. Cumulative data from at least two independent experiments n=15-20 per group is shown (Mean±SEM). * p≤0.05;  p≤0.01; * p≤0.001. Naïve (untreated) groups are shown for C57/BL6 and 129 mice only. Cumulative data from at least two independent experiments n=15-20 is shown (Mean±SEM). * p≤0.05;  p≤0.01; * p≤0.001.

FIGS. 26A-B shows that stimulation of TLR7 and TLR9 was required for the induction of skin inflammation but not for the cellular infiltration following skin injury. 129 mice were either left untreated (naïve, white histograms), tape stripped (Tape, black histograms) or tape stripped immediately after treatment (s.c) with the dual TLR7 and TLR9 inhibitor SEQ ID NO:42 (IRS) (100 µg; sc). A) 24 hr later skin infiltrating cells were isolated and PDC and neutrophils identified as in FIG. 24A. Histograms show total cell number obtained from 2×2 cm skin biopsy (n=10 mice) (Mean±SEM). B) Gene expression levels were evaluated by Taqman. Cumulative data from at least two independent experiments n=10-15 mice is shown (Mean±SEM). * p≤0.05;  p≤0.01; * p≤0.001.

FIGS. 27A-B shows that the activation of both PDC and neutrophils was critical for the burst of inflammatory genes following tape-stripping injury. 129 mice were either left untreated or tape stripped PDC and/or neutrophils were depleted prior to tape stripping using specific antibodies. Mice were injected with 250 µg given i.p. at day −2 and day 0, eight hours before tape stripping with the anti-120G8 Ab for depletion of PDC, or anti-GR1-LY6G Ab for depletion of neutrophils. Over 95% cellular depletion was achieved in both blood stream and skin infiltrate. 24 hr post tape-stripping, gene expression levels were measured in skin infiltrating cells (A) and skin biopsies (B). Naïve groups are shown for untreated mice only. Cumulative data from three independent experiments n=14 mice is shown (Mean±SEM). * p≤0.05;  p≤0.01; * p≤0.001.

FIGS. 28A-H shows that lupus prone (NZBxNZW)F1 mice developed a severe and chronic skin disease resembling human CLE following tape-stripping. (A) Lupus prone mice (NZBxNZW)F$_1$ and age matched 129 and C57/BL6 mice were tape stripped and skin biopsies were collected 24 hr, 4 days and 20 days later and gene expression evaluated (IRF7, ISG15 and IFIT were analyzed as Type I IFN regulated genes and TNF-α, IL1-A, IL1B as inflammatory genes). Levels of gene expression at 24 hr were set as 100 and compared to levels obtained at 4 days and 20 days post tape stripping. Cumulative data from three independent experiments is shown n=10 (Mean±SEM)* p≤0.05;  p≤0.01; * p≤0.001. (B) Quantification of area with open lesions 15-23 days after tape stripping in (NZBxNZW)F$_1$, 129 and C57/BL6 mice. Cumulative data of at least two independent experiments n=15 (Mean±SEM). (C-H) Representative sections of skin from (C) untouched (NZBxNZW)F1 mice, or from the skin of (D) 129, (E) C57/BL6 or (F-H) (NZBxNZW)F1 mice 15-23 days after tape stripping. Scale bar 200 µm.

FIGS. 29A-G shows that PDC and TLR7&9 signaling were required for cutaneous disease formation in lupus prone mice. (A) Quantification of area with open macroscopical skin lesions lesions 15-23 days following tape-stripping in (NZBxNZW)F$_1$ mice (untreated), (NZBxNZW)F$_1$ treated with weekly injection of SEQ ID NO:42 (IRS) and (NZBx-NZW)F$_1$ mice in which PDC have been depleted during the course of the experiment (PDC depleted). Cumulative data of at least two independent experiments n=12 (Mean±SEM) is shown. Representative sections of skin from (B) untouched (NZBxNZW)F$_1$ (naive) or from skin isolated 15-23 days after tape stripping from (C) (NZBxNZW)F$_1$ left untreated or (D-E) treated with IRS or (F-G) depleted of PDC. Scale bar 200 µm.

FIGS. 30A-E shows that therapeutic treatment of lupus-prone mice with chronic skin inflammation using SEQ ID NO:42 (IRS) significantly ameliorated CLE-like phenotype. (A) Quantification of area with open lesions 15-23 days after tape stripping in (NZBxNZW)F$_1$ mice left untreated or (NZBxNZW)F$_1$ mice treated from day 4-20 with IRS in a therapeutic setting (scheme of treatment in FIG. 36). Cumulative data of two independent experiments n=12 (Mean±SEM). Representative sections of skin from (NZBx-NZW)F$_1$ either (B, C) left untreated or (D, E) treated from day 4 with SEQ ID NO:42 (IRS). Scale bar 200 µm.

FIGS. 31A-B shows that MyD88 signaling pathway was necessary for the upregulation of both Type I IFN-regulated and pro-inflammatory genes in leukocytes infiltrating injured skin. A) MyD88$^{-/-}$ (stripped histograms) and age matched WT C57/BL6 mice (black histograms) were either left untreated (naive) or tape stripped to provoke inflammation. 24 hr later, infiltrating leukocytes were isolated and the levels of proinflammatory genes evaluated by Taqman. IFNAR$^{-/-}$ mice (stripped histograms) and age matched WT 129 mice (black histograms) were either left untreated (naïve) or tape stripped to provoke inflammation. 24 hr later, skin biopsies were isolated and the levels of proinflammatory genes evaluated by Taqman. Cumulative data from at least two independent experiments n=15-20 per group is shown (Mean±SEM). * p≤0.05;  p≤0.01; * p≤0.001. Naïve (untreated) groups are shown for C57/BL6 and 129 WT mice only. Cumulative data from at least three independent experiments n=15-20 is shown (Mean±SEM). * p≤0.05;  p≤0.01; * p≤0.001.

Figure 24:
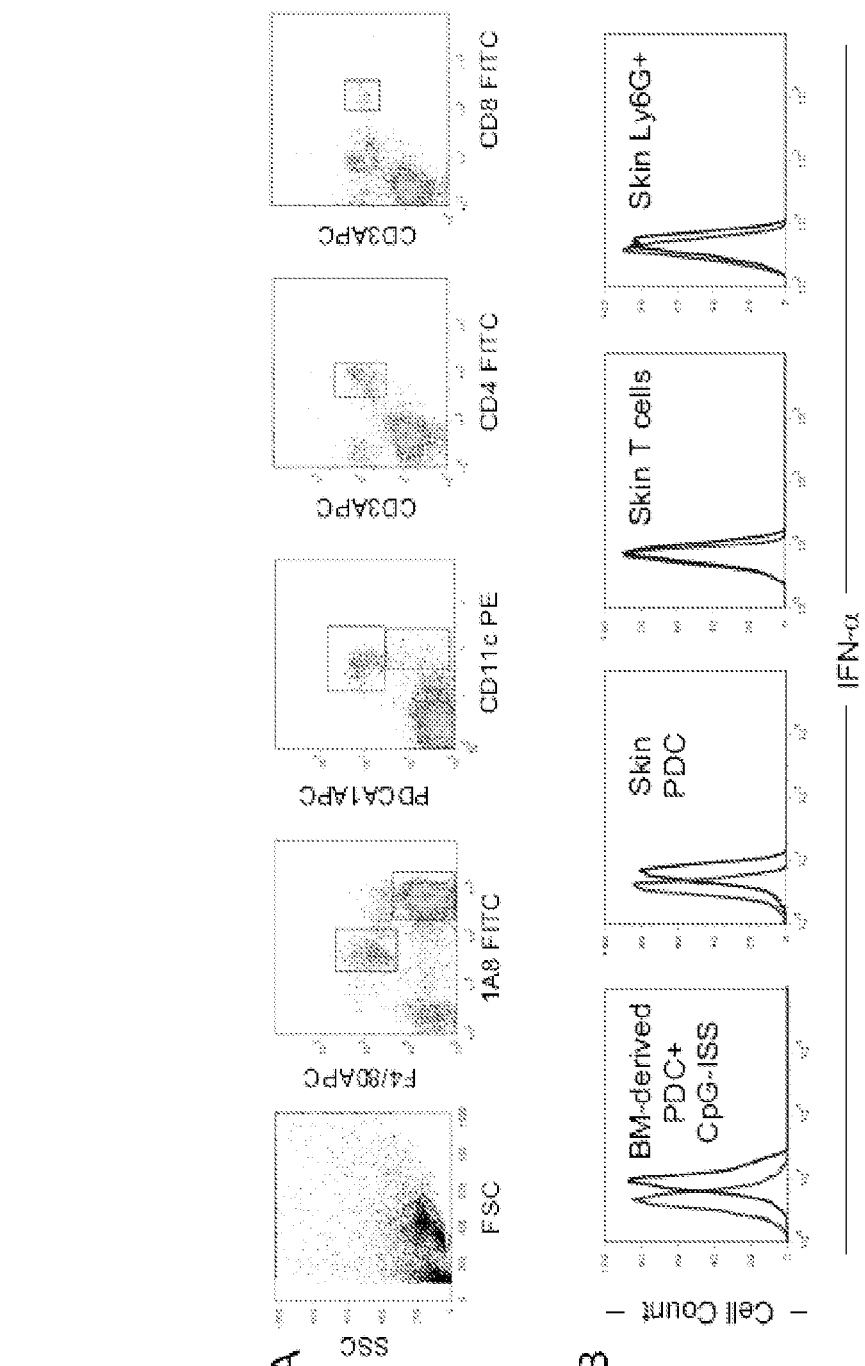
Figure 24:
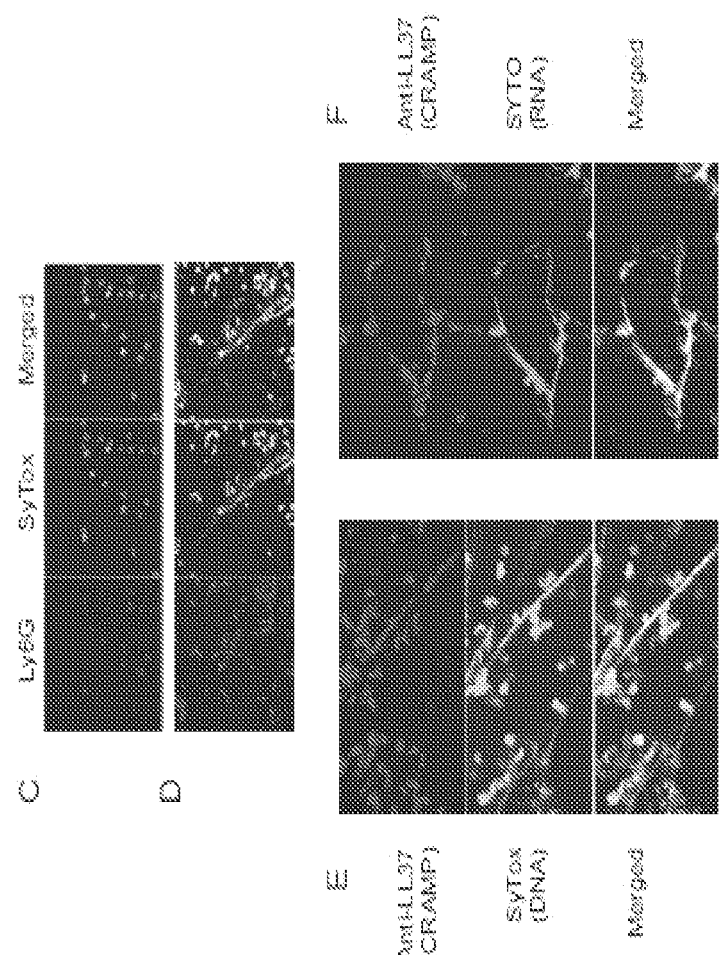
Figure 32:
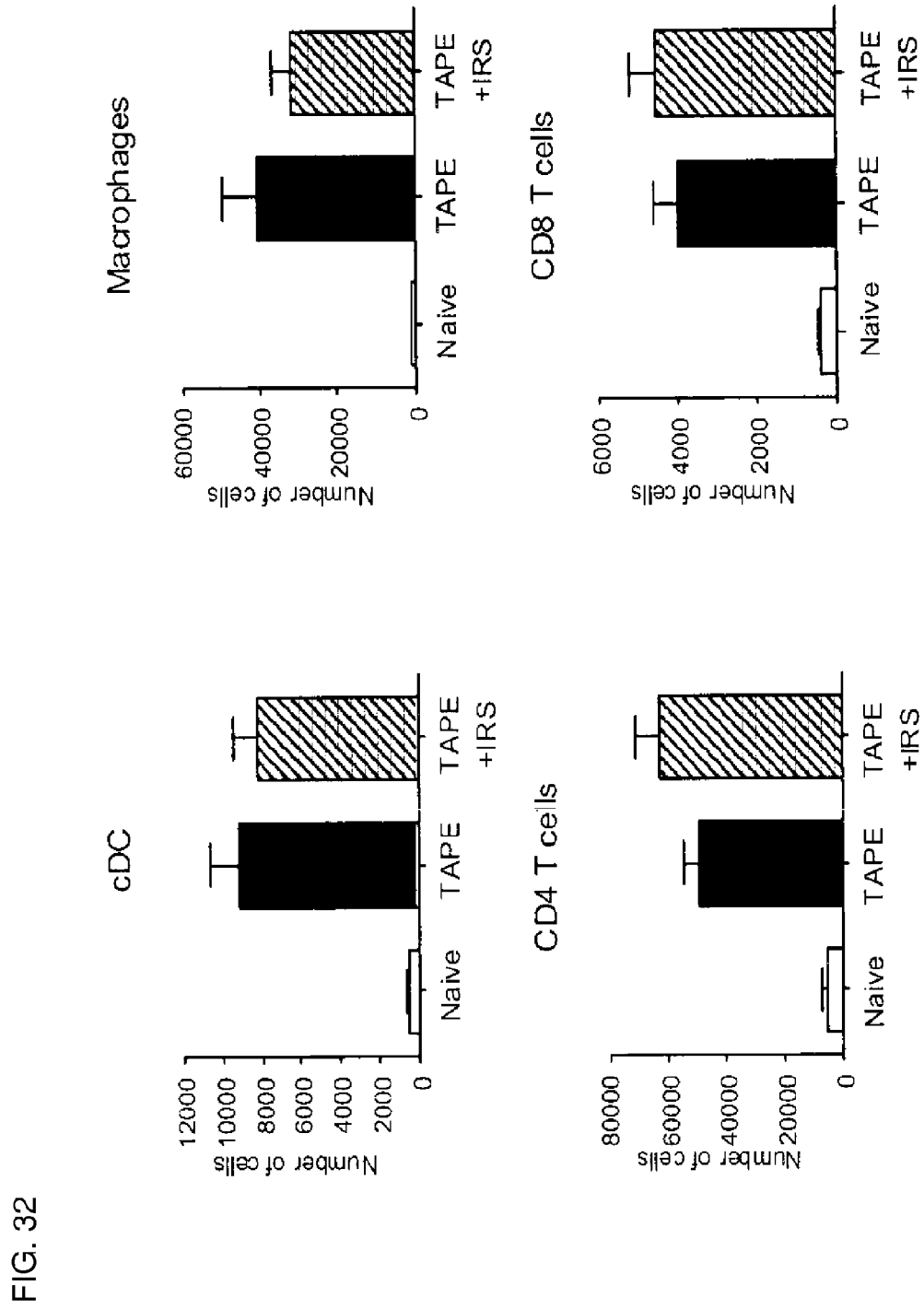

FIG. 32 shows that TLR7 and TLR9 stimulation was not required for the cellular infiltration following skin stripping. 129 mice were either left untreated (naïve, white histograms), tape stripped (Tape, black histograms) or tape stripped immediately after treatment (s.c) with the dual TLR7 and TLR9 inhibitor SEQ ID NO:42 (IRS) (100 µg; sc) as in FIG. 26. 24 hr later skin infiltrating cells were isolated and cell population identified as in FIG. 24A. Histograms show total cell number obtained from 2×2 cm skin biopsy (n=10 mice) (Mean±SEM).

Figure 26:
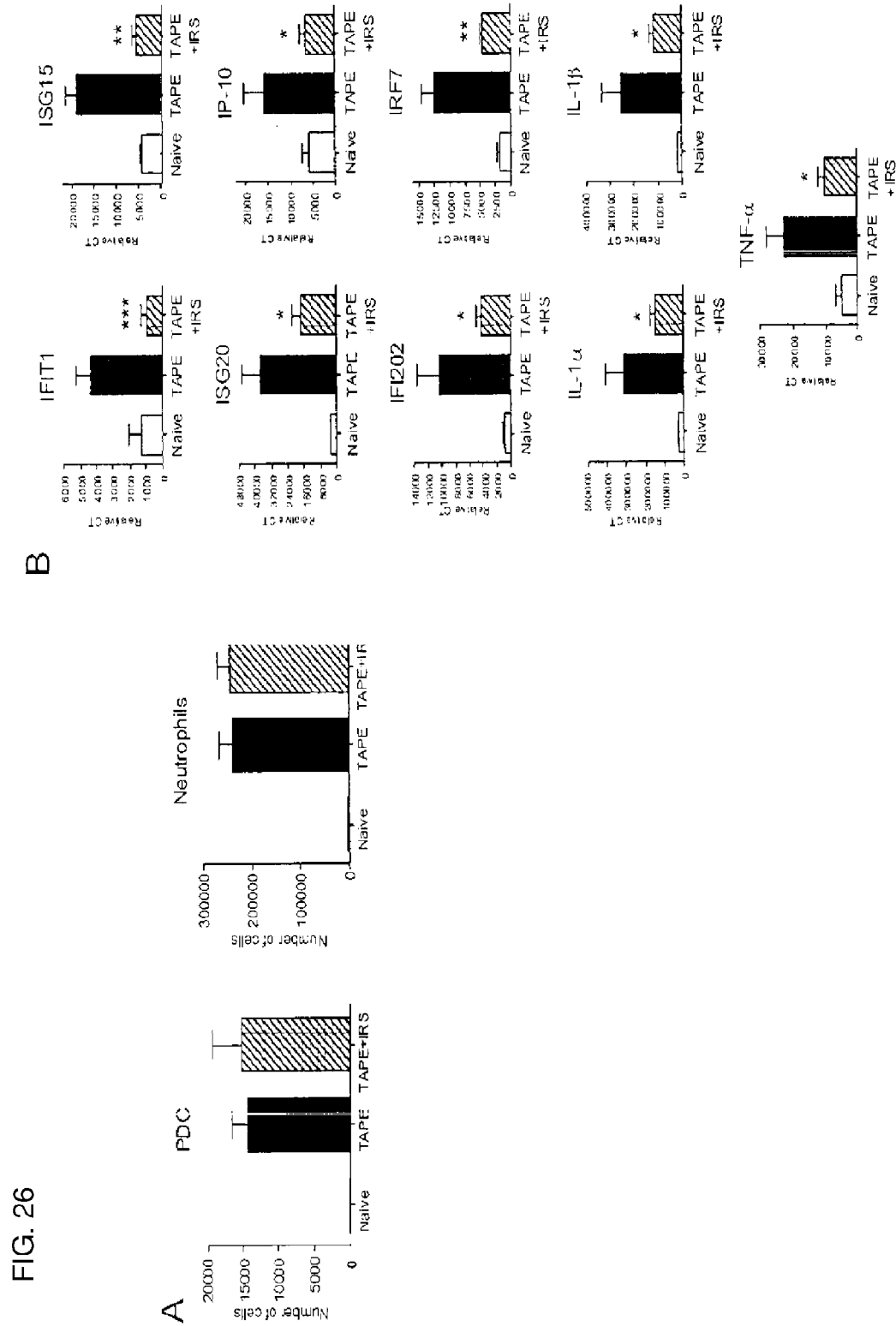
Figure 33:
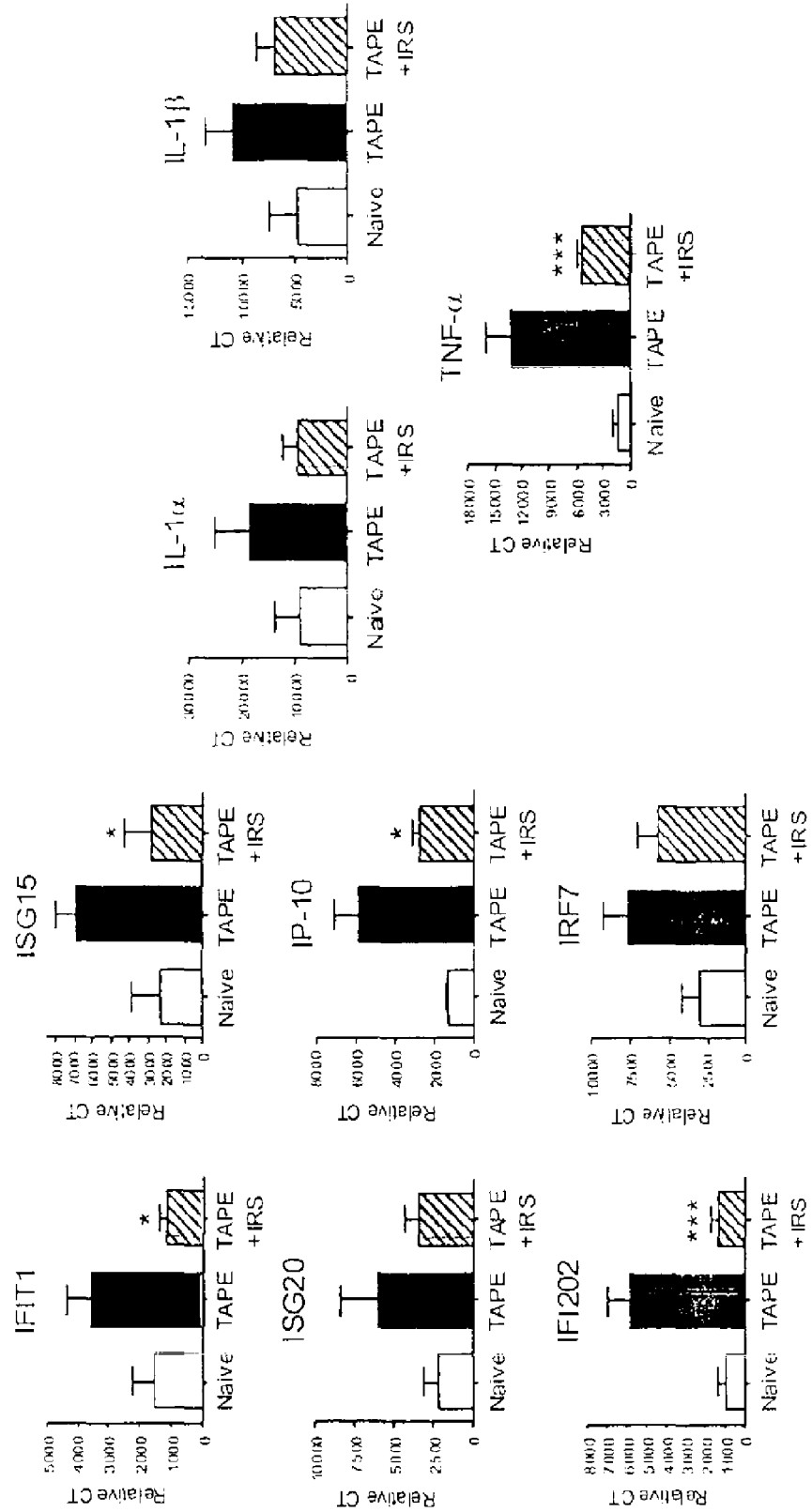

FIG. 33 shows that stimulation of TLR7 and TLR9 was required for the induction of skin inflammation. 129 WT mice were treated as described in FIG. 26. Genes were measured by Taqman in skin biopsies. Cumulative data from at least two independent experiments (n=10-15 mice) is shown (Mean±SEM). * p≤0.05; *** p≤0.001.

FIGS. 34A-D shows that tape stripping of the skin of (NZBxNZW)F$_1$ mice provoked a robust inflammatory response that can be inhibited with SEQ ID NO:42 (IRS). Characterization of the skin cellular infiltrate following inflammation via tape-stripping in lupus-prone mice. (NZBx-NZW)F$_1$ were shaved and either left untreated (A) or tape stripped (B, C); 24 hr later skin infiltrating cells were isolated (B, C) and gene expression levels (D) were evaluated by Taqman. Cells were characterized as described in FIG. 24A. (C) Histograms show total cell number obtained from 2×2 cm skin biopsy (n=8 mice) (Mean±SEM). (D) (NZBxNZW)F$_1$ mice were either left untreated (naïve, white histograms), tape stripped (Tape, black histograms) or tape stripped immediately after treatment with the dual TLR7 and TLR9 inhibitor SEQ ID NO:42 (IRS). 24 hr later gene expression levels were evaluated by Taqman. n=6 mice is shown (Mean±SEM). * p≤0.05.

FIGS. 35A-F shows details of hystopathological features of lesions in (NZBxNZW)F$_1$ 20 days after tape stripping. Representative sections of skin from (NZBxNZW)F$_1$ 15-23 days post tape-stripping. (A-C) Hyperplasia and hyperkeratosis with fibrosclerosis and marked inflammatory infiltration of the dermis (original magnification 100×). (D) Alterations of the dermal epidermis junction characterized by inflammatory infiltrate and degenerative modifications of the adipous tissue (original magnification 100×). (E, F) Details of infiltrate in the deeper dermis consisting of lymphocytes abundant neutrophils (nuclear dust is indicated with an arrow in E) and macrophages (boxed area in F) (original magnification 400×).

Figure 36:
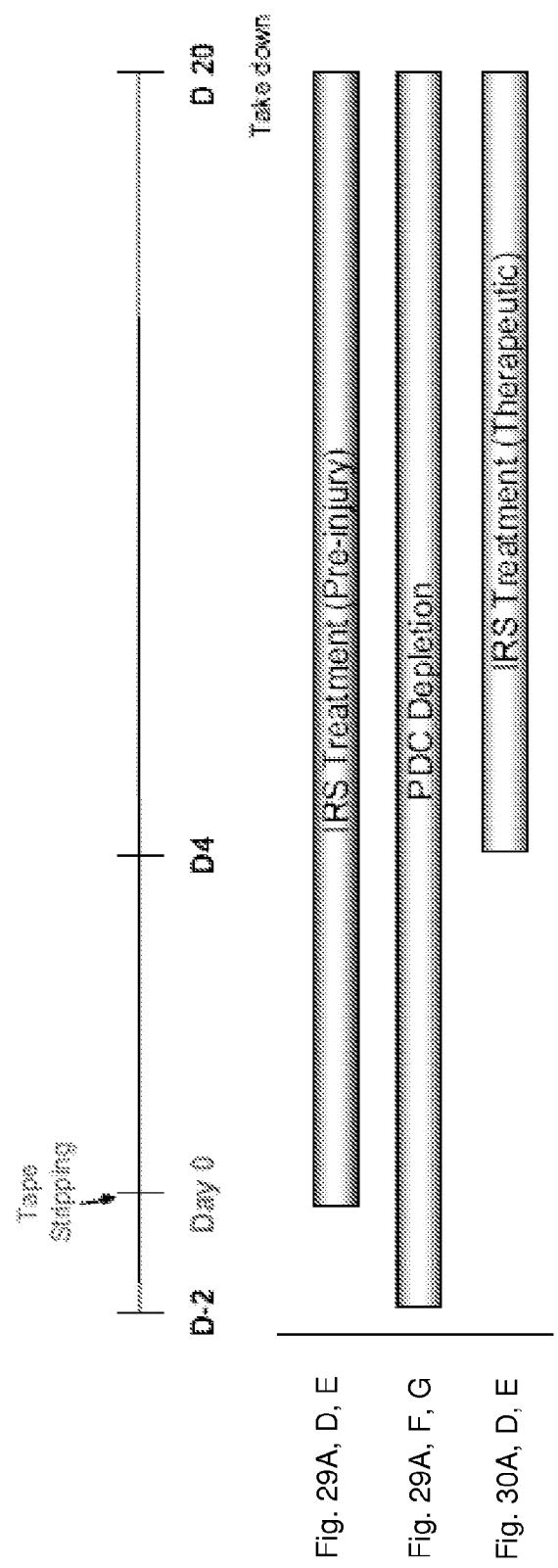

FIG. 36 shows the scheme for treatment protocols in (NZBxNZW)F$_1$ with the TLR7&9 inhibitor SEQ ID NO:42 (IRS) and in the PDC-depleting experiments. SEQ ID NO:42 (IRS) was used starting the day of the tape stripping during the entire course of the experiments (FIGS. 29A,D,E) or starting at 4 days post injury when the disease is already established (FIGS. 30A,D,E). In both cases SEQ ID NO:42 (IRS) (100 µg; s. c.) was administered twice a week. Also described is the timing of PDC depletion experiments described in FIGS. 29A,F,G. Depleting antibody to PDC anti-120G8 (250 µg; i.p.) were given at day −2 and day 0, eight hours before tape stripping and then given twice a week for the entire duration of the experiment. Experiments were stopped in between 15-23 days after initial tape stripping depending on the progression of the lesions in the untreated groups.

Figure 37:
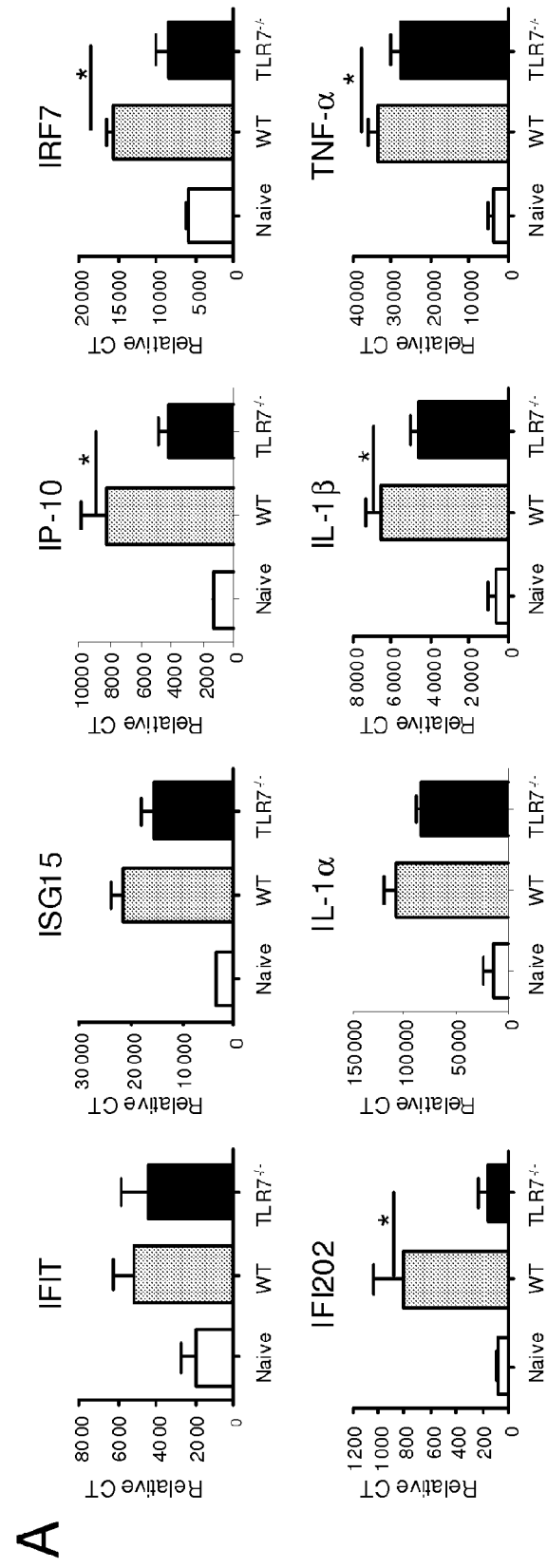
Figure 37:
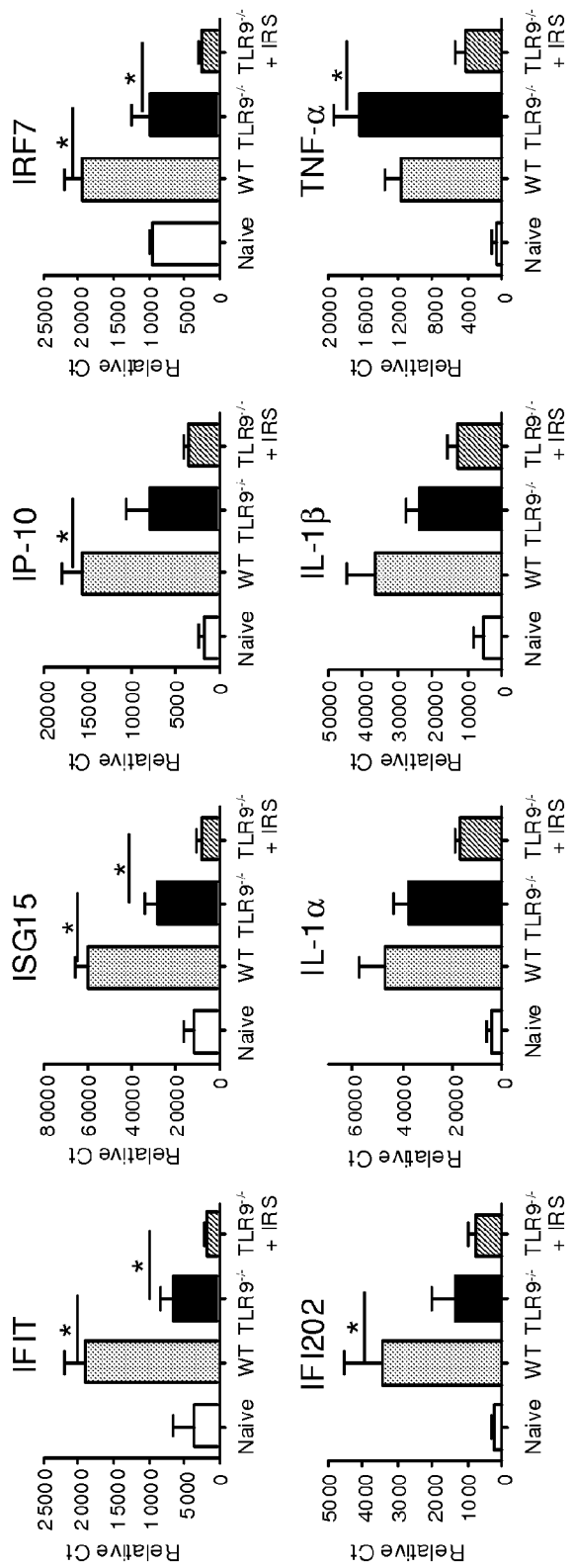

FIG. 37 shows that TLR7 and TLR9 signaling were both required for the induction of skin inflammation. (A) TLR7−/− (black histograms) and age matched WT C57/BL6 mice (grey histograms) were either left untreated (naive) or tape stripped to provoke inflammation. 24 hr later, skin biopsies were isolated and the levels of proinflammatory genes evaluated by Taqman. n=10 mice is shown (Mean±SEM); * p≤0.05. B) TLR9−/− were tape stripped (black histograms) or tape stripped immediately after treatment (s.c) with the dual TLR7 and TLR9 inhibitor IRS 954 (100 µg; sc) (dashed histograms). Age matched WT C57/BL6 mice were either left untreated (naïve; white histograms) or tape stripped (grey histograms). 24 hr later, skin biopsies were isolated and the levels of proinflammatory genes evaluated by Taqman. n=10 mice is shown (Mean±SEM); * p≤0.05.

FIGS. 38A-B shows (A) Module level analysis from whole blood from 29 SLE patients with (n=18) or without (n=11) oral GC treatment as described. Disease activity index (SLEDAI) and therapy used are indicated at the bottom. Modules with slashes correspond to underexpression of genes while modules without slashes correspond to relative overexpression to genes normalized to controls. (B) Nanostring Counter system was used to assess the longitudinal blood gene expression levels in healthy donors and SLE patients. Probes corresponding to 12 IFN-inducible genes were included in Nanostring codeset (see Table I). Gene expression levels were normalized to control genes and to healthy donors. Heatmap (log 2 scale) corresponding to 8 SLE patient longitudinal samples (individual columns) is shown. Samples corresponding to patients SLE 184, 190, 212, 252, 133 and 231 were obtained at 2-3 month intervals. These patients were receiving oral GC but no IV Methylprednisolone pulses. SLE 242 was analyzed the day before an IV pulse, 8 days after 2 independent IV pulses (marked as 0), and 2 additional times while on oral GC. SLE 249 was analyzed the day before and the day after an IV pulse (marked as *), and two additional times while on oral GC. Only the day after IV pulse there was a decrease in the expression levels of IFN-inducible genes. No slashes: over expression. Slashes: under expression.

DETAILED DESCRIPTION

The invention provides inhibitors of TLR7 and/or TLR9, such as immunoregulatory polynucleotides and/or immunoregulatory compounds, and methods of regulating immune responses in individuals, particularly humans, using these inhibitors. In some embodiments, the immunoregulatory polynucleotides and/or immunoregulatory compounds comprise an immunoregulatory sequence (IRS). In some embodiments, the immunoregulatory polynucleotides and/or immunoregulatory compounds comprise an unmodified IRS. The immunoregulatory polynucleotides and/or immunoregulatory compounds of the invention particularly inhibit innate immune responses, including those responses that involve signaling through TLR7 and/or TLR9. Immunoregulatory polynucleotides and/or immunoregulatory compounds of the invention can effectively suppress cytokine production, including IFN-α and/or IL-6, from human cells. Immunoregulatory polynucleotides and/or immunoregulatory compounds described herein also can effectively suppress proliferation and/or maturation of cells stimulated with an immunostimulatory nucleic acid.

Provided herein are also methods of treating and preventing autoimmune disorders and inflammatory disorders, such as chronic inflammatory disorders, in an individual by administering an immunoregulatory polynucleotide and/or immunoregulatory compound described herein to the individual. Provide herein are also methods for predicting and/or determining responsiveness of a disease to treatment comprising inhibitors of TLR7 and/or TLR9. In some embodiments, the immunoregulatory polynucleotide and/or immunoregulatory compound is administered in combination with another therapeutic agent. In some embodiments, the other therapeutic agent is a corticosteroid. In some embodiments, the immunoregulatory compounds and/or the immunoregulatory polynucleotides comprise at least one modified immunoregulatory compounds.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *The Immunoassay Handbook* (D. Wild, ed., Stockton Press NY, 1994); *Bioconjugate Techniques* (Greg T. Hermanson, ed., Academic Press, 1996); and *Methods of Immunological Analysis* (R. Masseyeff, W. H. Albert, and N. A. Staines, eds., Weinheim: VCH Verlags gesellschaft mbH, 1993).

DEFINITIONS

As used interchangeably herein, the terms "nucleic acid," "polynucleotide" and "oligonucleotide" include single-stranded DNA (ssDNA), double-stranded DNA (dsDNA), single-stranded RNA (ssRNA) and double-stranded RNA (dsRNA), modified polynucleotides and polynucleosides or combinations thereof. The polynucleotide can be linearly or circularly configured, or the polynucleotide can contain both linear and circular segments. Polynucleotides are polymers of nucleosides joined, generally, through phosphodiester linkages, although alternate linkages, such as phosphorothioate esters may also be used in polynucleotides. A nucleoside consists of a purine (adenine (A) or guanine (G) or derivative thereof) or pyrimidine (thymine (T), cytosine (C) or uracil (U), or derivative thereof) base bonded to a sugar. The four nucleoside units (or bases) in DNA are called deoxyadenosine, deoxyguanosine, thymidine, and deoxycytidine. A nucleotide is a phosphate ester of a nucleoside.

The term "immunostimulatory nucleic acid" or "immunostimulatory polynucleotide" as used herein refers to a nucleic acid molecule (e.g., polynucleotide) that effects and/or contributes to a measurable immune response as measured in vitro, in vivo and/or ex vivo. Examples of measurable immune responses include, but are not limited to, antigen-specific antibody production, secretion of cytokines, activation or expansion of lymphocyte populations such as NK cells, CD4+ T lymphocytes, CD8+ T lymphocytes, B lymphocytes, and the like. Immunostimulatory nucleic acid (ISNA) sequences are known to stimulate innate immune responses, in particular, those response occur through TLR-9 signaling in the cell. As known in the art, immunostimulatory nucleic acid (ISNA) molecules can be isolated from microbial sources, such as bacteria, can be present in nucleic acid vectors for use in gene therapy, or can be synthesized using techniques and equipment described herein and known in the art. Generally, an immunostimulatory nucleic acid sequence include at least one CG dinucleotide, with the C of this dinucleotide being unmethylated. Accordingly, microbial infection and administered DNA can in some cases result in stimulation of innate immune responses.

The term "immunostimulatory" or "stimulating an immune response" as used herein includes stimulation of cell types that participate in immune reactions and enhancement of an immune response to a specific antigenic substance. An immune response that is stimulated by an immunostimulatory nucleic acid is generally a "Th1-type" immune response, as opposed to a "Th2-type" immune response. Th1-type immune responses are normally characterized by "delayed-type hypersensitivity" reactions to an antigen and activated macrophage function and can be detected at the biochemical level by increased levels of Th1-associated cytokines such as IFN-γ, IL-2, IL-12, and TNF-α. Th2-type immune responses are generally associated with high levels of antibody production, especially IgE antibody production and enhanced eosinophils numbers and activation, as well as expression of Th2-associated cytokines such as IL-4, IL-5 and IL-13.

The term "innate immune response" or "innate immunity" as used herein includes a variety of innate resistance mechanisms by which a cell or individual recognizes and responds to the presence of a pathogen. As used herein, an "innate immune response" includes the intracellular and intercellular events and reactions that occur when the cell recognizes pathogen associated molecular patterns or signals. Cellular receptors active in an innate immune response include a family of Toll-like receptors (TLRs) and microbial ligands have been identified for several TLRs, as described herein.

The term "immunoregulatory sequence" or "IRS", as used herein, refers to a nucleic acid sequence that inhibits and/or suppresses a measurable innate immune response as measured in vitro, in vivo, and/or ex vivo. The term "immuno-regulatory sequence" or "IRS", as used herein, refers to both nucleic acid sequences that comprise a modification (i.e., modified IRS) as well as nucleic acids which do not comprise a modification (i.e., unmodified IRS). Modified IRS can include modifications to the sugar, base or backbone.

The term "immunoregulatory polynucleotide" or "IRP", as used herein, refers to a polynucleotide comprising at least one IRS that inhibits and/or suppresses a measurable innate immune response as measured in vitro, in vivo, and/or ex vivo. The term "immunoregulatory polynucleotide" or "IRP", as used herein, may comprise a modified and/or unmodified IRS. Modified IRS can include modifications to the sugar, base or backbone Inhibition of a TLR, e.g., TLR-7 or 9, includes without limitation inhibition at the receptor site, e.g., by blocking ligand-receptor binding, and inhibition of the downstream signal pathway after ligand-receptor binding. Examples of measurable innate immune responses include, but are not limited to, secretion of cytokines, activation or expansion of lymphocyte populations such as NK cells, CD4+ T lymphocytes, CD8+ T lymphocytes, B lymphocytes, maturation of cell populations such as plasmacytoid dendritic cells and the like.

The term "immunoregulatory compound" or "IRC", as used herein, refers to a molecule which has immunoregulatory activity and which comprises a nucleic acid moiety comprising an IRS, as well as a non-nucleotide spacer. The IRC may consist of non-nucleotide spacer, and a nucleic acid moiety that comprises more than one IRS or consists of at least one IRS. The IRC may comprise a modified and/or unmodified IRS. Modified IRS can include modifications to the sugar, base or backbone. Accordingly, the term IRC includes compounds which incorporate one or more nucleic acid moieties, at least one of which comprises an IRS, covalently linked to a non-nucleotide spacer moiety.

The term "3'" generally refers to a region or position in a polynucleotide or oligonucleotide 3' (downstream) from another region or position in the same polynucleotide or oligonucleotide. The term "3' end" refers to the 3' terminus of the polynucleotide.

The term "5'" generally refers to a region or position in a polynucleotide or oligonucleotide 5' (upstream) from another region or position in the same polynucleotide or oligonucleotide. The term "5' end" refers to the 5' terminus of the polynucleotide.

The term "conjugate" refers to a complex in which an IRP and/or an IRC are linked Such conjugate linkages include covalent and/or non-covalent linkages.

"Adjuvant" refers to a substance which, when added to an immunogenic agent such as antigen, nonspecifically enhances or potentiates an immune response to the agent in the recipient host upon exposure to the mixture.

The term "peptide" refers to polypeptides that are of sufficient length and composition to effect a biological response, e.g., antibody production or cytokine activity whether or not the peptide is a hapten. Typically, the peptides are at least six amino acid residues in length. The term "peptide" further includes modified amino acids (whether or not naturally or non-naturally occurring), such modifications including, but not limited to, phosphorylation, glycosylation, pegylation, lipidization and methylation.

A "delivery molecule" or "delivery vehicle" is a chemical moiety which facilitates, permits, and/or enhances delivery of an IRP and/or IRC to a particular site and/or with respect to particular timing.

An "individual" is a mammal, more preferably a human. Mammals include, but are not limited to, humans, primates, farm animals, sport animals, rodents and pets.

An "effective amount" or a "sufficient amount" of a substance is that amount sufficient to effect beneficial or desired results, including clinical results, and, as such, an "effective amount" depends upon the context in which it is being applied. In the context of administering a composition that suppresses a TLR9 dependent immune response, an effective amount is an amount sufficient to inhibit or decrease a cellular response to stimulation through TLR9. In the context of administering a composition that suppresses a TLR7 dependent immune response, an effective amount is an amount sufficient to inhibit or decrease a cellular response to stimulation through TLR7. An effective amount can be administered in one or more administrations.

The term "co-administration" as used herein refers to the administration of at least two different substances sufficiently close in time to regulate an immune response. Preferably, co-administration refers to simultaneous administration of at least two different substances.

"Suppression" or "inhibition" of a response or parameter includes decreasing that response or parameter when compared to otherwise same conditions except for a condition or parameter of interest, or alternatively, as compared to another condition. For example, a composition comprising an IRP which suppresses immunostimulatory nucleic acid induced cytokine production reduces cytokine production as compared to, for example, cytokine production induced by the immunostimulatory nucleic acid alone. As another example, a composition comprising an IRP which suppresses cytokine production associated with an innate immune response reduces the extent and/or levels of cytokine production as compared to, for example, extent and/or levels of cytokine produced by the innate immune response alone. Inhibition of a TLR response, e.g., a TLR7 or 9 response, includes, but is not limited to, inhibition at the receptor site, e.g., by preventing or blocking effective ligand-receptor binding, and inhibition of the downstream signal pathway, e.g., after effective ligand-receptor binding.

"Stimulation" of a response or parameter includes eliciting and/or enhancing that response or parameter. For example, "stimulation" of an immune response, such as innate immune response or Th1 response, means an increase in the response, which can arise from eliciting and/or enhancement of a response. Similarly, "stimulation" of a cytokine or cell type (such as CTLs) means an increase in the amount or level of cytokine or cell type, such as IL-6 and/or TNF-α.

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder. Especially in the autoimmune disease context, as is well understood by those skilled in the art, palliation may occur upon regulation or reduction of the unwanted immune response. Further, palliation does not necessarily occur by administration of one dose, but often occurs upon administration of a series of doses. Thus, an amount sufficient to palliate a response or disorder may be administered in one or more administrations.

The term "biomarker" as used herein refers to the differential expression of a gene of interest either at the level of transcription (mRNA) or translation (protein).

The term "IFN signature" as used herein refers to the presence of one or more interferon-inducible biomarkers. In some embodiments, the interferon-inducible biomarkers comprise type I interferon-upregulated genes, as compared to the expression of one or more biomarkers that are essentially unregulated by type I interferons. As used herein, an "IFN signature" is part of an elevated inflammatory gene expression pattern.

The term "elevated inflammatory gene expression pattern" as used herein refers to the presence of two or more biomarkers that are upregulated as part of an inflammatory response: a biomarker of an IFN signature; and a further biomarker (e.g., not directly interferon-inducible). Thus, the term "elevated inflammatory gene expression pattern" encompasses an IFN-signature, as well as elevated levels of proinflammatory mediators such as chemokines, and chemokine-inducible biomarkers (Crow and Kirou, Arthritis Res Ther, 2008 10:126, and Fu et al., Arthritis Res Ther, 2008, 10:R112). For instance, the non-interferon-inducible biomarker comprises signatures from activated leukocytes selected from the group consisting of neutrophils, granulocytes, macrophages, and plasma cells. The term "elevated inflammatory gene expression pattern" as used herein is part of an "autoimmune disease signature" such as the heretofore well described "SLE signature." Although termed a "SLE signature," a plurality of biomarkers are common to flares of other systemic autoimmune diseases such as systemic sclerosis, polymyositis, dermatomyositis, rheumatoid arthritis and Sjorgren syndrome. As such, the compositions and methods of the present disclosure find use in the context of multiple systemic autoimmune diseases.

"Correlate" or "correlating" is meant comparing, in any way, the performance and/or results of a first analysis or protocol with the performance and/or results of a second analysis or protocol. For example one may use the results of a first analysis or protocol to determine whether a second analysis or protocol should be performed. With respect to the embodiment of gene expression analysis or protocol, one may use the results of the gene expression analysis or protocol to determine whether a specific therapeutic regimen should be performed.

"Predicting" or "prediction" is used herein to refer to the likelihood that an individual is likely to respond either favorably or unfavorably to a treatment regimen.

As used herein, "at the time of starting treatment" or "baseline" refers to the time period at or prior to the first exposure to the treatment.

As used herein, "based upon" includes assessing, determining, or measuring the individual's characteristics as described herein (and preferably selecting an individual suitable for receiving treatment).

A method of "aiding assessment" as used herein refers to methods that assist in making a clinical determination and may or may not be conclusive with respect to the assessment.

"Likely to respond" or "responsiveness" as used herein refers to any kind of improvement or positive response either clinical or non-clinical selected from, but not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable.

When a marker is "used as a basis" for selection, assessing, measuring, or determining method of treatment as described herein, the biomarker is measured before and/or during treatment, and the values obtained are used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; or (g) predicting likelihood of clinical benefits. As would be well understood by one in the art, an evaluation of an individual's health-related quality of life in a clinical setting is a clear indication that this parameter was used as a basis for initiating, continuing, adjusting and/or ceasing administration of the treatments described herein.

As used herein, "sample" refers to a composition which contains a molecule which is to be characterized and/or identified, for example, based on physical, biochemical, chemical, physiological, and/or genetic characteristics.

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X+/−1% of X".

As used herein and in the appended claims, the singular forms "a," "or," and "the" include plural referents unless the context clearly dictates otherwise. For example, "an" IRP includes one or more IRP.

As is apparent to one skilled in the art, an individual assessed, selected for, and/or receiving treatment is an individual in need of such activities.

Biomarkers

Biomarkers evaluated herein include, but are not limited to the biomarkers in Table I. In some embodiments, an "IFN signature" comprises elevated levels of one or more biomarkers of Table I, as compared to a reference. In further embodiments, an "IFN signature" may further comprise reduced levels of one or more biomarkers as compared to a reference.

TABLE I

IFN Module Gene List

| Probe ID | Gene Symbol | Entrez gene | Description |
|---|---|---|---|
| 1010242 | BATF2 | 116071 | Basic leucine zipper transcription factor, ATF-like 2 (BATF2) |
| 5720438 | CMPK2 | 129607 | Cytidine monophosphate (UMP-CMP) kinase 2, mitochondrial (CMPK2), nuclear gene encoding mitochondrial protein |
| 7380544* | CXCL10 | 3627 | Chemokine (C-X-C motif) ligand 10 (CXCL10) |
| 1260681 | DDX60 | 55601 | DEAD (Asp-Glu-Ala-Asp) box polypeptide 60 (DDX60) |
| 6200273 | EPSTI1 | 94240 | Epithelial stromal interaction 1 (breast) (EPSTI1), transcript varian2 |
| 1710259* | HERC5 | 51191 | Hect domain and RED 5 (HERC5) |
| 4280725 | HES4 | 57801 | Hairy and enhancer of split 4 (*Drosophila*) (HES4) |
| 5870221* | IFI44 | 10561 | Interferon-induced protein 44 (IFI44) |
| 7200255 | IFI44L | 10964 | Interferon-induced protein 44-like (IFI44L) |
| 1780632 | IFIT1 | 3434 | Interferon-induced protein with tetratricopeptide repeats 1 (IFIT1), transcript variant 2 |
| 6220673* | IFIT1 | 3434 | Interferon-induced protein with tetratricopeptide repeats 1 (IFIT1), transcript variant 2 |
| 430021 | IFIT3 | 3437 | Interferon-induced protein with tetratricopeptide repeats 3 (IFIT3) |
| 2690452* | IFIT3 | 3437 | Interferon-induced protein with tetratricopeptide repeats 3 (IFIT3) |
| 3830041 | IFIT3 | 3437 | Interferon-induced protein with tetratricopeptide repeats 3 (IFIT3) |
| 4210291 | IFITM3 | 10410 | Interferon induced transmembrane protein 3 (1-8U) (IFITM3) |
| 1070528* | ISG15 | 9636 | ISG15 ubiquitin-like modifier (ISG15) |
| 1500204 | LAMP3 | 27074 | Lysosomal-associated membrane protein 3 (LAMP3) |
| 5810709 | LOC26010 | 26010 | Viral DNA polymerase-transactivated protein 6 (LOC26010), transcript variant 2 |
| 2940022* | LY6E | 4061 | Lymphocyte antigen 6 complex, locus E (LY6E) |
| 2630110 | MX1 | 4599 | Myxovirus (influenza virus) resistance 1, interferon-inducible protein p78 (mouse) (MX1) |
| 3940731 | OAS1 | 4938 | 2',5'-oligoadenylate synthetase 1, 40/46 kda (OAS1), transcript variant 3 |
| 4040632 | OAS1 | 4938 | 2',5'-oligoadenylate synthetase 1, 40/46 kda (OAS1), transcript variant 2 |
| 6560494* | OAS1 | 4938 | 2',5'-oligoadenylate synthetase 1, 40/46 kda (OAS1), transcript variant 1 |
| 1240754 | OAS2 | 4939 | 2'-5'-oligoadenylate synthetase 2, 69/71kda (OAS2), transcript variant 1 |
| 7330373* | OAS2 | 4939 | 2'-5'-oligoadenylate synthetase 2, 69/71 kda (OAS2), transcript variant 2 |
| 4220435* | OAS3 | 4940 | 2'-5'-oligoadenylate synthetase 3, 100 kda (OAS3) |
| 6370035* | OASL | 8638 | 2'-5'-oligoadenylate synthetase-like (OASL), transcript variant 2 |
| 7150196 | OASL | 8638 | 2'-5'-oligoadenylate synthetase-like (OASL), transcript variant 1 |

TABLE I-continued

IFN Module Gene List

| Probe ID | Gene Symbol | Entrez gene | Description |
|---|---|---|---|
| 3710184* | OTOF | 9381 | Otoferlin (OTOF), transcript variant 4 |
| 6620711 | RSAD2 | 91543 | Radical S-adenosyl methionine domain containing 2 (RSAD2) |
| 770364 | RTP4 | 64108 | Receptor (chemosensory) transporter protein 4 (RTP4) |
| 4390575 | SERPING1 | 710 | Serpin peptidase inhibitor, clade G (C1 inhibitor), member 1, (angioedema, hereditary) (SERPING1), transcript variant 2 |
| 380386 | TRIM6 | 117854 | Tripartite motif-containing 6 (TRIM6), transcript variant 2 |
| 1740341 | XAF1 | 54739 | XIAP associated factor 1 (XAF1), transcript variant 2 |
| 940673 | | | Erythroid Precursor Cells (LCB: cl library) cdna clone cl02h05 5 |
| 6900603 | | | AGENCOURT_7914287 NIH_MGC_71 cdna clone IMAGE: 6156595 5, mrna sequence |
| | IFI16 | 3428 | Gamma-interferon-inducible protein 16 |
| | AIM2 | 9447 | Interferon-inducible protein AIM2, |
| | ISG20 | 3669 | Interferon stimulated exonuclease gene 20 kDA |
| | IRF7 | 3665 | Interferon regulatory factor 7 |

*The term "biomarker" as used herein, replaces the term "genetic marker" as used in the priority provisional patent applications.

In some embodiments, an "IFN signature" comprises elevated levels of one or more markers of Table I. Alternatively or additionally, an "IFN signature" comprises elevated levels of one or more biomarkers selected from the group consisting of: IFIT1 (Interferon-induced protein with tetratricopeptide repeats-1), OASL (2'-5'-oligoadenylate synthetase-like), LY6E (Lymphocyte antigen 6 complex, locus E), OAS2 (2'-5'-oligoadenylate synthetase), OAS3 (2'-5'-oligoadenylate synthetase), IFI44 (Hepatitis C microtubular aggregate protein), MX1 (Myxovirus resistance 1), G1P3 (Interferon, alpha-inducible protein or IFI-6-16), PRKR (Protein kinase, interferon-α-inducible double-stranded RNA-dependent), IFIT4 (Interferon-induced protein with tetratricopeptide repeats 4), PLSCR1 (Phospholipid scramblase 1), C1ORF29 (Hypothetical protein expressed in osteoblasts, similar to IFI44), HSXIAPAF1 (XIAP-associated factor-1), G1P2 (Interferon, alpha-inducible protein or IFI-15K), Hs. 17518 (Cig5 or Viperin), IRF7 (Interferon regulatory factor 7), CD69 (Early T-cell activation antigen), LGALS3BP (Lectin, galactoside-binding, soluble, 3 binding protein), IL1RN (Interleukin-1 receptor antagonist), APOBEC3B (Phorbolin 1-like), RGS1 (Regulator of G-protein signaling 1), AGRN (Agrin), EREG (Epiregulin), THBS1 (Thrombospondin 1), ETS1 (v-ets erythroblastosis virus E26 oncogene homolog 1), ADAMS (A disintegrin and metalloproteinase domain 9), SERPING1 (Serine or cysteine proteinase inhibitor (C1 inhibitor)), and FCGR1A (Fc fragment of IgG, high-affinity Ia receptor) (see, Table 2 of Crow and Wohlgemuth, Arthritis Res Ther, 5:279-287, 2003).

In some embodiments, an "IFN signature" is part of a "SLE signature." In some embodiments, a "SLE signature" comprises elevated levels of one or more biomarkers of: Table 1B (185 markers), Table 2B (1253 marker), Table 3B (18 markers), and Table 4 (6 markers) all of U.S. Pat. No. 7,608,395, and as reproduced below. In some embodiments, a "SLE signature" comprises elevated levels of one or more biomarkers selected from the group (of 7 biomarkers) consisting of: GTPBP2 (NM_019096), PCTAIRE2BP ( ) DNAPTP6 (AK002064.1), GPR84 (AF237762), B4GALT5 (NM_004776.1), FRAT2 (AB045118.1), and PAFAH1B (L13386.1). GTPBP2, PCTAIRE2BP and DNAPTP6 were previously reported to be IFN-regulated genes whose level of expression correlates with the SLEDAI index, while GPR84, B4GALT5, FRAT2 and PAGAH1B were previously reported to be non IFN-regulated genes whose level of expression correlates with the SLEDAI index (see Table 4 of U.S. Pat. No. 7,608,395). Additionally or alternatively, a "SLE signature" comprises elevated levels of one or more biomarkers selected from the group (of 18 biomarkers) consisting of: MARK3 (AI745639), USP15 (AF153604.1), MCOLN2 (AV713773), BUP (NM_012071), CAPN2 (M23254.1), TOR1B (AF317129.1), SQRDL (NM_021199), GLB1 (NM_000404), PTTG1 IP (NMJJ04339), RTN4 (AB015639.1), RAB31 (NM_006868), ANXA1 (NM_000700), SERPINB1 (NM_030666.1), F5 (NM_000130), GPR27 (AI703476), LOC147991 (BF057717), TNFRSF6 (AA164751), and FAM11 B (NM_024121) (see Table 3B of U.S. Pat. No. 7,608,395). Additionally or alternatively, a "SLE signature" comprises elevated levels of one or more biomarkers selected from the group (of 185 biomarkers) consisting of: L14457.1, AF234255.1, AF151024.1, BG482805, NM_016459, BG540628, AW408194, AW404894, NM_005532, BC001886.1, L14456.1, AL555107, M20812, AB037805.1, AJ408433, NM_016448, BG251467, NM_001775, NM_001067.1, NM_001034.1, NM_006010, NM_004523, NM_017709, AF326731.1, BG251467, NM_002105, AW087870, L14454.1, NM_021603, S73498.1, NM_014736, NM_004219, NM_003003.1, NM_016359, AA292789, NM_014333.1, NM_001827, AY029179.1, NM_012485, BF110588, BG492359, BC000323.1, AA742244, NM_030920, BF001806, BG165011, U16996.1, NM_006979, AA181060, 5 NM_016185, NM_014875, AF151075.1, BCOO1 144.1, NM_002794, NM_007019, AK022820.1, NM_001071, NM_003558, NM_003920, AI921320, BG478677, NM_013351, BF589413, NM_007295, NM_000942, NM_022109.1, J04162.1, AK002195.1, AI651594, AI813331, BF983948, AI678096, BC006344.1, M31523.1, AL536986, NM_000942, NM_003003.1, NM_003523, NM_018227.1, NM_016199, BE961916, NM_003542, BG393795, NM_022346, 1.0 BC006405.1, BC000755.1, NM_000173, N25325, NM_024918, NM_002661, AI560720, NM_016123, NM_012177, BC001689.1, BE311760, AI147740, BF540954, BC000941.1, R75637, NMJD00791, BE561798, NM_004146, AW291664, NM_014260.1, AF151037.1, NM_005156, U29343.1, AI887866, NM_004499, NM_012459, AF286162.1, NM_006423, BG481459, AB033007.1, BE966146, BG179991, AI692267, NM_014390, AL119957, AB029031.1, NM_014342, NM_016400, AI347000, AF031469.1, BG260658, AW295105, AK026118.1, BC004118.1, NM_001689, NM_014501, NM_002592, NM_014239, AW271713, AI991669, NM_005530, BE397715, AF094700.1, NM_006420.1, BF246115, BC000738.1, NM_003595, NM_004381, NM_018339, AI439695, BC006088.1, NM_030580, NM_018468, BF439618, NM_001866, NM_014393, NM_001536, NM_007241, BF977829, NM_014302, NM_004237, 0 AV702994, AF060511.1, AB022435.1, BC001 817.1, BF348067, U82756.1, BG497776, NM_014721.1, AL036451, AK025697.1, NM_014874, BE856541, NM_002490, NM_006567, AF061729.1, BC004872.1, BC005009.1, AW237172, AK000878.1, NM_013354, AA971514, AK023415.1, AI052257, AL008582, AI557319, NM_022406, BF126155, AW173222, AB037782.1, and BC002711.1 (Table 1B of U.S. Pat. No. 7,608,395). Additionally or alternatively, a "SLE signature" comprises elevated levels of one or more biomarkers selected from the group (of 1253 biomarkers) consisting of: M97935, M97935, M97935, NM_007315, N53555, AW1 89843, AI337069, NM_016323, NM_001549, AI075407, AI742057, NM_006417.1, NM_006820, NMJ302462, NM_004030, NM_005101, AK002064.1, NM_002463, AA633203, NM_006187, NM_002346, NM_016817, AV755522, AF063612.1, BE669858, BE966604, AF307338.1, NM_002534, NM_001548, AA142842, AI738416, AI825926, NM_017414, AI651594, BC001356.1, AA781795, AA131041, NM_003733, BE049439, AA083478, AL121994, BF338947, NM_015907, NM_005532, NM_017912, AA577672, NM_017631, NM_016816, NM_022873, AI631846, NM_005567, AA741307, NM_017654, AI967971, NM_016410, NM_015961, NM_022168, NM_004688, NM_002759, NM_022750, AL035689, AF317129.1, AK023743.1, NM_000062, AI954660, BE645480, AI539443, BC002704.1, NM_001111, AL121829, NM_004223, AW129593, NM_004335, NM_009587, AI859280, AW014593, BC002666.1, NM_000593, NM_002053, H98105, NM_014398, NM_017523, BE888744, AF280094.1, NM_004509, AA749101, NM_003641, AI962367, NM_001953, NM_005138, BG386566, BC003602.1, M10943, NM_005952, NM_002450, AL031602, NM_005953.1, BF217861, AF333388.1, AW664179, NM_000389, BE971383, NM_006435, BC001463.1, BC001165.1, NM_003827, AA056548, NM_001295, NM_017742, NM_012420, N47725, NM_016381, AW014557, AF312735.1, AA768888, NM_021105, NM_006084, BC000080.1, NM_000527, AI925506, R13458, AA150460, NMJ314314, BF055474, AW084937, U88964, NM_002201, NM_003113, AW291023, AI954660, NM_030776, AF129536.1, AU145711, AF1 14264.1, AL161961.1, AA708470, BE563152, L13386.1, AV648669, NM_000161, BE676543, AI984040, AI478268, AA910306, NM_006442, AL121829, BC001362.1, AA628398, AK023724.1, NM_004510, AW139261, AL050374.1, AF300717.1, NM_001565, AB028976.1, NM_003592, AF078844.1, NM_005950, D87433, NM_001908, AF009644.1, AF009635.1, NM_005874, AW271350, AB023430.1, AI041543, NM_016332, NM_013416, NM_001785, NM_000631, NM_024829, AI279062, NM_002631, NM_005621, NM_002432, NM_012198, AI806395, NM_001995, NM_021122, NM_020980, NM_003264, NM_002029, M60721.1, NM_030666.1, NM_003255, NM_030769, NM_018840, NM_001780, AI188653, BC000715.1, BC002342.1, AW001847, BC000373.1, BC004371.1, BC001709.1, BC004564.1, BC001709.1, AL038787, AK023348.1, TMM_002087, BC000324.1, NM_002003, NM_002115, NM_000714, NM_002826, AA923524, BE622952, NM_006729, AF035307.1, NM_006868, BE789881, BE742268, NM_006755, AW206817, NM_012387, AU151342, AI963142, NM_001183, NM_000308, L13974.1, AF134715.1, AW151360, X14355.1, L03419.1, NM_006665, NM_001860, AW135013, NM_005461, NM_012252, AB035482.1, NM_004848, NM_012228, NM_002000, NM_005534, AK022852.1, AW071793, AW241742, BF575514, NM_004049, AL161952.1, NM_015364, NM_002065, NM_001124, NM_005384, M55580.1, BE563442, AW083357, AW083357, AF257318.1, AF263293.1, NM_003059, BC000764.1, BE466274, J04183.1, BF941983, AK026776.1, NM_020179, AK025608.1, BF1 10421, AB046766.1, AW276572, U81501.1, M88107.1, BC002323.1, NM_003461, AL571424, NM_003120, NM_000099, NM_002957.2, NM_021039, NM_005620, AL122066.1, NM_003864, BF247098, NM_004504, Z22969.1, NM_004244, U15555.1, BC005123.1, NM_004427, NM_004633, AF056979.1, NMJ321626, BG150485, AF327923.1, BC004347.1, NM_001909, NM_004893, NM_001903, NM_000632, U70451.1, NM_003494, W03103, AI806395, AA706818, AA613031, W81119, AF356193.1, NM_005896, NM_006793, NM_001833, NM_007096, AI809206, BF339821, AV758614, AI949549, NM_022748, AK000826.1, NM_006065, NM_000081, NM_014863, NM_005857, N40555, AL568449, AB015639.1, N49844, AF062347.1, AI674647, NM_031301, AI141784, NM_003364, AA789296, J03223.1, BF905445, NM_003405, NM_006825, AW029619, AI640483, AI761561, NM_003681, AI797833, AB020677.2, NM_021090, NM_001706, AW016812, AI989512, AB020663.1, NM_000585, NM_005574, H72927, AL520900, AI683900, AF217974.1, NM_018986, NM_000801, NM_000355, BF939474, NM_000713, U83981, NM_014330, BG250721, NM_006732, NM_003407, BC004490.1, NM_025195, AB017493.1, BC005020.1, BE328402, U08626, AF071504.1, NM_021960, W03103, BC005941.1, AA482548, AI761804, BG025248, NM_002664, U84246.1, AA622495, NM_007115, AW188198, NM_006317, NM_001511, NM_005569, NM_005306, AB045118.1, AF100544.1, L33930, AK000168.1, AA761181, M58664.1, BG327863, AW337833, NM_002424, M18728.1, BC005008.1, NM_001925, M63310.1, NM_005564.1, M33326.1, U19970.1, NM_002343, NM_001725, NM_001062, NM_000045, NM_003064, X16354.1, NM_001700.1, NM_000250, NM_001911, NM_002935, M80927.1, L35848.1, AL390736, AL522667, NM_004776.1, NM_000896, NM_004994, NM_005980, M76742.1, NM_004084, NM_005143, J04152, AI867408, AI343467, BF433657, NM_002934, H16791, NMJH8099, AF087942.1, NM_004130, M81635.1, X69397.1, NM_003039, AI537887, NM_020415, W72338, AK022144.1, NM_002852, NM_001629, NM_020406, W84421, NM_003909, AW170571, AL138717, NM_021199, NM_004832, NM_005274, NM_002629, NM_05566, BC001906.1, NM_013252, D12502.1, BF445012, AF240697.1, AF240698.1, BC000181.2, AF305083.1, AI917716, AK023184.1, NM_001924, NM_004776.1, AL078599, NM_024430, NM_022367, BF689355, NM_002965, AI922599, AF1 17234.1, AF085357.1, AI925518, NM_001747, NM_014918, NM_002294, BC000145.1, AF293026.1, NMJH4624, NM_002305, AI492017, AF004231.1, NMJH6230, NMJ001154, AK022697.1, AU144243, AI743880, AI703476, BE465037, BE465037, NM_000404, NM_006409, AI991451, NM_003851, AA352113, BC000896.1, AV699857, M87507.1, AF001362.1, AF208043.1, NM_003810, U57059.1, AI421071, BC003398.1, AF055030.1, BE348597, Z25521.1, AF100741.1, NM_030790, AL136659.1, AK023661.1, NMJH4158, AI935334, AA094434, AB037784.1, BF510588, AL050262.1, AU154202, NM_003516, AA451996, BC002720.1, AF176704.1, NM_004475, BG171064, AA579630, NM_022109.1, AW052084, AI301948, NM_020189, AA418074, AW006934, AL040396, AL161985.1, NM_022162, AW072388, NM_000265, NM_005134, AW207668, N46867, AB037810.1, AI927605, BF063271, AI760166, NM_001315, AA814140, BC002977.1, AW139719, AI734993, NM_024021, AL136924.1, BC001288.1, BE551347, AI873273, AL135735, NM_001779, AL139812, NM_022136, NM_018590, NM_007246, W27419, NM_005451, AA780381, NM_015527, AL023653, NM_014874, AL583909.1, NM_003003, NM_005873, BC000627.1, NM_001999, AK002113.1, NM_001776, NM_006363, BC000674.1, BF111326, BG500396, AF237762.1, N66633, NM_001099, AI740541, NM_000130, BF508702, NM_022003, NM_004800, BE908217, NM_004039, BC001388.1, M23254.1, BC005902.1, NM_000712, BF057717, NM_016516, AB014578.1, NM_005375, NM_002194, AI202327, R64696, AA004799, NM_024984, NM_005078, AA778684, NM_006931, BC000905.1, NM_014247, NM_016255, AA164751, NM_014999, AI796269, AF285167.1, NMJD05502, NM_004388, NM_013254, AI126625, AI761804, AL136733.1, AA460299, AF313911.1, NM_000611, BC005247.1, NM_004508, BC001188.1, NM_003234, AA043552, BF516567, NM_006058, AA772278, J03250.1, AV700891, AB040903.1, AW058600, NM_002661, AL137753.1, AK023204.1, AL137751.1, BC002796.1, AF077614.1, NM_017455, NM_004666, AK023585.1, BE966748, BE737251, NM_017424, BF794958, AI335263, NM_001153, BC000182.1, NM_014248, L19184.1, AA742261, NMJJ07033, NM_020216, AI630178, NM_001920, NM_006748, D86962.1, U64898.1, NM_002491, NM_002337, NM_014184, AI052659, AW974609, BF892532, BF308645, AI393091, AI709406, NM_002356, NM_025201, M79321.1, NM_002350, BF671187, AA515698, BC004188.1, AL565749, AL581768, BC004949.1, NM_003254, NM_000904, NM_000700, NMJH8457, AY007098.1, NM_019009, BC002755.1, NM_006812, NM_005738, AJ243797, NM_005614, U56417, U79458.1, AA810452, AK025603.1, AB051833.1, NM_006176, NM_003528, AI81.0266, BC002842.1, NM_018295, AI215102, NM_001963, NM_003005, BF589413, AL514295, NM_006292, AW070776, J04755.1, NM_002970, AB037925.1, NM_021960.1, AL078599, AL117354, NM_001660, AA808203, BF056105, NM_003664, BC002684.1, AA758755, AI826060, AF299343.1, U28936.1, NM_002733, BG163267, AB049952.1, NM_001219, AI348745, M33197, NM_002794, NM_001749, NM_004074, J02783.1, AU144000, NM_005834, AA209463, AB011112.2, NM_012268, NM_006289, BG340967, NM_002654, BF570210, BC005851.1, NM_004309, AB002559.1, BC000125.1, BC002356.1, NM_006702, NM_017797, NM_004082, NM_003334, NM_004640, NM_003040, NM_005892, NM_003365, BG286973, NM_024872, AL136729.1, NM_006026, NM_005781, M62762, NM_001665, BF525395, NM_013403, NM_004517, AI742164, NM_002339, AC006942, AF104913.1, L37033, AL550657, NM_004214, NM_000402, BC000850.1, U43430.1, NM_019096, NM_018174, NM_024321, NM_014837, AI024869, NM_001425, NM_001707, NM_005354.2, AL513583, S73751.1, NM_001487, AA307731, NM_030930, NM_006801, AB032964.1, AW003280, AI224128, BC002844.1, BG423052, NM_000033, AF029750.1, NM_005902, NM_014045, BE963280, BE348305, AL121829, D88435, NM_005255, AB007859.2, NM_024121, AI263909, AK022888.1, AI761506, AA706815, NM_006067, AA194996, AL136921.1, NM_004339, W60806, NMJH5946, AW050627, AA181053, BE965029, U28169.1, NM_001054, NM_001055, L25275.1, AL035588, BF666325, AW295105, AK025960.1, AF170562.1, NM_016562, NM_012424, NM_001359, AF220028.1, NM_002535, AI928526, NM_003945, BE617588, NM_013451, AK022142.1, AI678096, BE620258, BF591270, M90360.1, AI559696, AW067021, NM_000512, AB007447, AK026913.1, AW268817, NM_002717, NM_001539, AL1 17607.1, BF223703, AI130705, NM_018440.1, AF320070.1, AI831952, BF692332, NM_002758, AL050350, AF151018.1, AI831932, AA034018, NM_004729, NM_003168, AA359612, AI990349, AB051535.1, NM_021941.1, NM_002668, NM_003876, W58365, NM_031210, NM_012080, AK000948.1, AF202092.1, U03891.2, AI561173, AU155094, AI459194, NM_001964, NM_000399, NM_012110, X83493.1, AA868754, AF153604.1, NM_014628, AF155510.1, AL096714, AI242749, AL555107, AF317711.1, AB038950.1, AL046979, NM_016633, NM_000519, NM_003944.1, L36674.1, L36675.1, BG260394, NM_001738, NM_012179, AI133353, NM_000184, NM_000559, N63920, BE677761, NM_015999, AF1 17233.1, NMJH3446, AL046017, BE906054, H69701, AL578551, AW006290, NM_006877, NM_002436, AL561296, U76248.1, BG476661, AL556190, BE888885, AF195624.1, AA531016, NM_004323, NM_014030, R60866, AL514199, AA522681, NM_018447, AV685208, NM_014413, BE552138, BC002649.1, BE857601, AL121747, AI814257, AF087573.1, AI745639, BC000755.1, AL096733.1, NM_002894, AW451624, BF357738, AW058634, AF142419.1, AK023208.1, N40199, NM_014844, AI952357, BC004288.1, NM_005573, NM_001750, M24779.1, NM_019041.1, NM_000376.1, BC002548.1, AF217190.1, NM_005132, NM_021991, AF077973.1, AF016903.1, AL080183.1, BC006456.1, AL553942, AA746320, BF196523, AU158871, BC005364.1, AJ132258.1, NM_004602, BF515963, AI567554, AB002344, All 89587, AW195572, BE927766, BG288330, AA703523, AA760738, R44974, AA468422, AI459177, BF1 11312, BG485129, AI916641, AA262583, AW975051, AW973078, AU146329, AI289774, AW954199, W61007, AI332638, R37337, BF063657, AK022478.1, AI394529, AI394529, AB007931.1, AU146963, AU147903, AI914925, AK023938.1, AW362945, AW372457, AW057518, AW960145, AW449624, AA132172, W87626, AU159474, AL589593, AL137645.1, AI138934, AW842975, AI475803, NM_018062, AB046820.1, NM_014847, NM_024956, NM_014869, AA868729, AI821925, NM_014778, BF530486, AJ406940.1, AL137445.1, AI989530, BE858373, AV700081, NM_006070, AI912190, NM_001458, AI819394, AF063603.1, AI948598, M57731.1, BE551877, AI813331, NM_001069, BF115777, AK001827.1, AF130079.1, NM_024989, NM_003369, T90703, AK027138.1, NM_014883, NM_006519, AI873425, AI057121, AI393759, X63381.1, AF037448.1, NM_015866.1, AL045306, AV713062, BC001139.1, BG260886, AL110252.1, U17496.1, D43949.1, NM_015556, BF209668, AA805681, AI671238, AK025562.1, N93399, NM_006263, M64571, AW469714, AV713773, AK023161.1, NM_017994, NM_002800, NM_004872, NM_017582, NM_002539, NM_000496, NM_020642, AA744124, AF255649.1, AI819734, AI401105, AA742244, L21961.1, U96394.1, AF043583.1, AF103529.1, AW404894, M85256.1, AJ249377.1, D84143.1, AB001733.1, L14458.1, AF151024.1, AW408194, NM_030810, AL022324, X93006.1, L14452.1, X79782.1, AV698647, AA680302, X57812.1, M87790.1, BG482805, AF234255.1, AB014341.1, BG540628, AF103591.1, M20812, AJ408433, U80139, L23516.1, AW575927, M87789.1, D84140.1, M24669.1, M24668.1, M87268.1, NM_001775, NM_006406, L23518.1, Z00008, BF248364, NM_024629, NMJH6359, BC001886.1, NM_001071, NM_014736, NM_001034.1, NM_001067.1, AF213033.1, NM_004219, NM_007057, NM_004526, AK001261.1, AI924426, NM_001827, AI859865, AL524035, NM_001211, NM_000611.1, BF340083, NM_001826, NM_015895, U63743.1, BG492359, NM_030920, AL135396, AL537042, AW272611, NM_005827, NM_014791, BC001144.1, AK026926.1, BC001312.1, NM_005742, AW087870, NM_003729, NM_002788, NM_006810, NM_001444, AW058617, AF161502.1, AF151039.1, NM_016021, NM_020150, AK025328.1, NM_016021.1, AF131780.1, M23114.1, NM_007002, NM_016021.1, NM_006713.1, AW290940, BF436315, NM_018641, NM_001070, NM_003132, NM_024510, NM_014788, NM_022100.1, NMJ315959, NM_012432, NM_002627, NM_000206, AI798908, NM_003335, AW084510, NM_024602, U87954.1, NM_16096, AB049940.1, AW194729, NM_002189, NM_001712, BC002979.1, AI862887, NM_006854, AK001363.1, BG292367, NM_005703, NM_005334, NM_000194, NM_004581, BC000190.1, T79584, NM_002803, BC005978.1, BC003191.1, AI972475, NM_005034, AK001899.1, AI348935, BE251303, AA643304, AI587307, NMJH2071, Y13786.2, AB023420.1, AL136923.1, N39536, AI807356, BC000903.1, NMJ02266, BC000149.2, AY029179.1, BF001806, AL138828, BG031677, NM_020188, BC004239.1, AF130059.1, N31731, AI656807, AK025504.1, NM_000143, AK026260.1, AF343663.1, NM_004900, NM_002286, AU152456, AV740426, NM_000655, NM_001627.1, AI191920, AF128458.1, NMJ)00100, BC001460.1, NM_006353, BC002877.1, NM_000297, AF092132.1, NM_004258, NM_005789, BC002654.1, AI935115, H95344, AL110209.1, BF732638, W22924, T50399, AA479016, AW514654, AI753638, NM_006865, AU145538, BE793250, and NM_014758 (see Table 2B of U.S. Pat. No. 7,608,395). The biomarkers of any of the above groupings also include their Affymetrix or other genechip equivalents. Additionally or alternatively, an "SLE signature" comprises elevated levels of one or more markers selected from the group consisting of M87434 (71 kD 2'5' OIAS), AB000115 (GS3686), D28195 (Hep C p44), X57352 (1-8U), M33882 (MX1), M30818 (MX2), U66711 (RIGE/TSA1), AB006746 (Phospholipid scramblase), L12691 (DEFA3), X04371 (2'5' OIAS E18 isoform), AL047596 (EST Hute 1), U53831 (IRF 7b), M97935 (ISGF-3), AL022318 (Phorbolin 1 like), U72882 (IF p35), L13210 (MAC-2-BP), X99699 (XIAP associated factor 1), M13755 (ISG-15), X69910 (p63 transmembrane protein), X54486 (C1 inhibitor), X55988 (Eosinophil derived neurotoxin), L09708 (Complement component 2), AF016903 (Agrin), X57522 (TAP1), AF026939 (Cig 49), AI126134 (EST similar to calgranulin), AI225089 (TRIP 14 OIAS), U37518 (TRAIL), M84562 (Formyl peptide receptor-like), AL036554 (DEFA1), Z38026 (FALL-39), AB025254 (Similar to *Drosophila* Tudor), and M24594 (IFI-56)(see Table I of Bennett et al., J Exp Med, 197:711-723, 2003). Additionally or alternatively, an "SLE signature" comprises elevated levels of one or more markers of Table 2 or Table 4 of U.S. Pat. No. 7,118,865, herein incorporated by reference. In some embodiments, elevated levels comprise at least 2-fold higher expression than observed for control(s).

In further embodiments, an "SLE signature" may further comprise reduced levels of one or more markers as of: Table 1A (160 markers), Table 2A (1751 marker), and Table 3A (27 markers) all of U.S. Pat. No. 7,608,395, and as reproduced below. In some embodiments, a "SLE signature" comprises reduced levels of one or more biomarkers selected from the group (of 27 biomarkers) consisting of: BG481877, BF434321, J04132.1, BC002637.1, BE677453, N25621, NM_002967, BG403671, T90771, U38979, NM_031214, NM_003107.1, NM_003107.1, BF345728, NM_015537, AA722878, AW293531, AL523320, AF070526.1, AL050035.1, NM_014612, BE910323, AI694452, AV682940, AK000921.1, AW043594, and NM_004758 (see Table 3A of U.S. Pat. No. 7,608,395). Additionally or alternatively, a "SLE signature" comprises reduced levels of one or more biomarkers selected from the group (of 160 biomarkers) consisting of: AW292752, AA005361, NM_020405, NM_014686, AW138833, D13720.1, AL050166, AW027359, AI652861, AF332595.1, NM_030571, AA205660, AW003635, NM_021038, NM_006445, L41690, BC000580.1, NM_016337, AW157773, BE542684, AA528017, AW614056, NM_024941, NM_004762, AW873606, NM_004281, NM_003423, NM_006625, AI598222, N21364, U19179.1, AL080183.1, AK001039.1, AL136841.1, AV728658, BC000120.1, BC001407.1, NM_020987, AW450901, NM_006226, BE218028, BC004556.1, D89053.1, AW118862, NM_014635, AW189430, NMJH4739, NM_002114, NM_001812, NM_007146.1, AW802645, NM_014415, BG111168, AL356115, AL043571, AI984541, AK024819.1, NM_014315, NM_014153, NM_024419, AL117643.1, AF202092.1, L78132.1, AW591660, NM_004396, AA927480, AI702962, NM_003345.1, NM_018150, AI985751, NM_006802, AK001406.1, D86550.1, NM_006420.1, NM_024835, NM_016628, NM_017917, AF279899.1, AF217190.1, NM_005565, BC004130.1, AF092128.1, NM_022760.1, BE672700, ABO11154.1, AI659005, NM_014454, AA555096, BF114870, NM_025238, AB007895, BC002737.1, NM_014164, AW134798, AI955119, AI078279, AI738556, AL096828, AV700626, NM_004068, AL583509, AI741415, NM_005198, AL136827.1, NM_012433, AW084068, AI417897, AU144387, NMJH7869, N71116, C14394, NM_001967, AB037811.1, BF056303, AF130099.1, NM_014947, AL034550, NM_003297, NM_018281, NM_002035, NMJH4676, AL096857.1, BC004902.1, NM_012175, D80010.1, NM_018976, N35250, NM_024654, BG231980, NM_017652, NM_005642, Y09216.1, NM_007269, D87450.1, BF431965, NM_006766, BE549532, AI887898, W72060, NM_004592, AA167775, AF226044.1, BG284386, NM_016534, BG389744, NM_030979, AI265967, NM_022781, AI540253, AL133646.1, AA836114, NM_001012, AK026678.1, AK026954.1, L22453.1, AL137450.1, AI554106, AI695595, NM_005776, and NM_016127 (see Table 1A of U.S. Pat. No. 7,608,395). Additionally or alternatively, a "SLE signature" comprises reduced levels of one or more biomarkers selected from the group (of 1751 biomarkers) consisting of: AI654857, AI245026, BC004393.1, AK023981.1, AL036350, BE865517, AA863228, AA156238, AL544688, NM_006817, NM_001469, BE905157, AA044705, AA525163, AF1 12216.1, AL136719.1, AF103800.1, BE962299, BC000967.2, BF345728, BC000533.1, NM_003145, NM_003819, BC006235.1, W05463, AA554827, AI472320, AW085312, AA215381, AI369933, AL109722.1, NM_014710, AW299250, BE966599, D80001.1, AF047473.1, AA130247, AA005361, AK025651.1, AF288571.1, NM_022898, NM_006720, NM_003202, AL559122, M15564.1, AF043179.1, AF036906.1, NM_005356, NM_015953, NM_025228, AI084226, NM_004619, NM_002221, N25986, NM_020379, AI650848, NM_019000, AL576253, NMJ300210, NM_004682, NM_014832, AI346026, AB028973.1, NM_004808, AW293531, BE042354, NM_002300, AB01 1154.1, D89678.1, AF1 16707.1, BE867771, AA456099, AL023584, AW292872, U82828, AW269834, NM_018443, AL161999.1, NM_000884, NM_001838, NM_002341, AV700815, BG170478, NM_021211, NM_006107, BE674119, W73788, AL138444, NM_004512, NM_017952, U26455.1, NM_000051, NM_002971, AA002140, BF739767, BC006436.1, AW614072, AW157773, AA286867, AI913123, AI341165, AI582192, AI745170, AI831675, AK025546.1, NM_002013, NM_003143, NM_015251, D87453.1, AA424065, M31523.1, AL137450.1, BE250348, BF247371, NM_013265, NM_016091, NM_006893, NM_005051, M80261.1, AK025446.1, NM_014886, AI985751, AW148801, AI888672, AL162068.1, NM_002271.1, H12084, AB018268.1, AW237290, AA020010, AI912523, U07236.1, AW779917, AU144305, BG253884, AA126419, BF064224, AA541762, AI275605, BC004355.1, AI249173, AU157224, AW513477, AI016714, AA156797, W60810, AI630799, AI669498, AV725947, BG338251, BF219234, AF072930.1, N20923, BE250417, NM_002719, BE218980, AK024263.1, BC004815.1, U04045.1, BC004344.1, NM_004513.1, NM_007267, NMJ)01130, AI817942, AL353715, BE465433, AF157319.1, AL080063.1, BF512028, BG400596, AI491983, NM_000732.1, NM_001767, M12959.1, AL137145, NM_005816, BF245400, AF146696.1, NM_022731, N80922, D84294.1, AB014731.1, NM_019903, NM_022368, BF219234, NM_004774, AB011154.1, AW134823, Y09216.1, Y09216.1, BC003070.1, N92498, BF131791, NM_005499, NM_002902, NM_018094, NM_022804, NM_003097, NM_021178, NM_016308, Z22551.1, NM_004986, BC005895.1, NMJH2262, AK001846.1, NM_014767, NM_018318, S46622, NM_005605, NM_002893, BF1 14870, NM_000901, AF274753.1, AI824171, AI949392, NM_006159, AA992805, AL575177, AF070526.1, NM_006823, N74222, AW055351, AI923633, NM_003640, AK001731.1, BE856321, AA669799, AI436587, BC001805.1, NM_014169, D25304.1, AF005422.1, NM_015456, BG291039, BF528646, AI184512, M93651, NM_003011, AI278616, AI638155, AI769569, NM_016316, AB042278.1, AL050353.1, NM_000026, AF130102.1, NM_006565, NM_022496, AL109965, AI832363, AU146870, AI699465, AK026898.1, AK025731.1, AU152162, AK023160.1, AI928344, AL133101.1, BF432238, AA888858, NM_000753.1, D83781.1, BF941204, NM_003430, U79240.1, D50925.1, NM_006139, NM_003905, AL529104, AI688812, NM_005825, AI928367, BF529715, AA918317, NM_016265, D84294.1, NM_005611.1, BE796924, NMJH4170, NMJH6302, AF113514.1, BC000229.1, AA523172, T90771, AW296067, AF008936.1, NM_031214, AL574514, NM_020405, U38979, NM_003983.1, AK023264.1, AW963138, NM_021212.1, AK026589.1, H49382, NM_002015, NM_020347, NM_002526, M27877.1, N64802, NM_003611, AK022771.1, AU1 45411, BC001663.1, BG165094, NM_012417, AF130089.1, AL031589, Z97353, AL118510, AL136629.1, M61906.1, BC001971.1, AV682285, AF081567.1, R83000, NM_006265, AF349444.1, NM_021038, BC002387.1, NM_004537, D83702.1, AL136920.1, NM_006451, AF226044.1, NM_022483, AL050331, NM_016045, NMJH6542, NM_006754, R51161, AI935415, AA928506, BC000196.1, BC005975.1, AV701173, AF130089.1, AI535683, AV725365, NM_014563, AI796169, H25097, AI524095, AF251053.1, AA470369, AF161492.1, AF248965.1, AA744771, NM_003416, NM_006696, AI760760, D87078.2, NMJ301896, AI912976, AV756536, AI969697, AL523320, 572904, AI051236, AU149257, BE780075, AL563613, AI357639, AL136681.1, BF969806, AL515061, AI862477, NM_014174, AI431931, AF042386.1, AV712694, AW003508, AV698149, AB033011.1, NM_001762, NM_004964, AI434345, AA044154, NM_004338, AA815089, AA503360, AI744029, AA355179, AI765169, AI277652, NM_006807, BC001149.1, AK027039.1, AA824341, BC002832.1, NM_006994, AW500239, NM_016057, AL050226.1, BF593940, AF131748.1, BF062203, BF984830, NM_015918, AA603344, AA129773, BF437747, NM_005087, BE737030, NM_005327, NM_022476, M30471.1, U80918.1, N90866, NM_004867, AL021786, AI572979, NM_014399, AW575245, BF510692, AW003297, NM_007066, AW134608, AW085505, BF528605, NM_004367, AL581873, AI672159, AW450901, AI912275, All 89509, AI225238, AF261135.1, NM_001400, AF061733.1, R51077, NM_024600, AL043266, AA085764, AI829961, BC002492.1, NM_002405, NM_012227, AL575747, NM_024070, L01087.1, J04132.1, NM_003151, BE502930, NM_020662, BE672676, AV646599, AI939308, AJ224082, AJ224080, BF316352, BG329175, BG339653, NM_003932, AF091085.1, AL136226, NM_004182, NM_006098, AB055804.1, NM_002624, AL121871, NMJH5414, AL118502, BE968801, AL096829, AW582267, AA555113, U27143.1, NM_005340, NM_004597, M19156.1, NM_000421, BG152979, D17652.1, BG339228, NM_000967, BC006483.1, BE963164, NM_001010, AF1 19850.1, NM_001404, BC005817.1, NM_000968, NM_000972, NM_006013, BF683426, BE733979, BG168283, NM_000994, BC004334.1, AW574664, BC004954.1, AA838274, AI200589, NM_001023, BF184532, AI799007, AI925635, NM_001006, NM_001025, NM_001030, AW132023, NM_001003, NM_012423, AI186735, AL568186, BE259729, NM_001022, NM_000980, NM_001024, AF279903.1, NM_002948.1, BF214492, L22453.1, NM_000969, NM_001959, AA961748, NM_015710, NM_001020, AW071997, M30448.1, NM_003756, BC000734.1, BC000514.1, NM_019059, BF976260, NM_005594, AI970731, AA630314, BC000524.1, AL121916, NM_000983, AI560573, NM_001004, NM_001021, AF072098, AL565449, NM_001019, NM_000971, NM_000973, BG389744, Z98200, NM_001012, AA281332, NM_021029, BF026595, BF979419, X74070.1, AA789278, AI613383, BC000733.1, NM_000992, NM_001960, AL121934, NMJ)00978, AF230924.1, AU151801, NM_002512, AI452524, AF116710.1, NM_016947, NM_001861, NM_001013, AF085358.1, AF119846.1, AW083133, BG332462, BG255188, NM_003977, NM_006346.1, M26700.1, MM_006294, NM_024064, NM_003726, AU157515, NM_006870, NM_003866, AA532655, AL562398, AI004246, NM_003753, N32864, NM_007104, BE741754, AI953886, Z98950, NM_014944, BF435123, AI652546, AK025703.1, BE252813, AI814257, AW274445, AF212250.1, BF247054, AL080250, NM_006621, BC000232.1, NM_021136, BG472176, NMJH7829, AK024102.1, NM_021994, NM_006360, AI718295, NM_006360, BF446180, NM_004622.1, NM_006743, T62044, AU145746, BC001169.1, AI742940, NM_017918, AI458020, NM_022766, NM_014315, NM_002271.1, AF090934.1, BG11 1047, NM_013300, AA192361, AL573637, AI151434, AA131793, BE501318, AL136657.1, BE616972, BE965646, T84558, AU146850, AW193600, AK026666.1, AA349848, AA861608, U85430.1, AI471969, AI028602, AI359136, NM_024910, BE972394, NM_025124, NM_024900, AI799018, AA722878, X57198.1, U17714.1, AF070528.1, BF446577, AI672356, AI369389, NM_013341, AK000818.1, BE783723, AC005034, AI805301, AL442092.1, AA001423, D50683.1, NM_020404, AI991103, BC003360.1, AL137162, NM_002693, BC005162.1, BE670097, AV716964, AK024029.1, AF161461.1, NM_006241.1, NM_006145, NM_001280, AL117499.1, NM_006977.1, AF281859.1, AI935162, AB007964.1, W87688, BF224073, NM_003079.1, AL518311, AI928212, AB033091.1, NM_015629, AI675152, AL109698, AB011110.2, NM_030674, AA205660, BE963438, AK024739.1, AL136599.1, BF438417, AW236976, AL524045, AL133580.1, AA780067, AL1 18798, NM_006513, NM_024620, BF514509, NM_019014, BG252666, NM_018097, BC002629.1, NM_017932, NM_000923, AI683552, AL080232.1, AA126763, NM_030972, NM_024026, AK026565.1, AI758888, NM_018304, NM_022487, X92110.1, N31807, NM_006226, NM_002628, NM_001967, NM_016127, AK026954.1, BE515346, NM_024733, BG178775, NM_004755, AL080160.1, BG534527, AF159567.1, BF508739, BF508739, D26488.1, AB051450.1, AL1 10238.1, BC001255.1, AF167438.1, NM_014633, NM_014350, X03348.1, AP000693, NM_004779, NM_001968, BE541042, AB023173.1, NM_007269, BF001666, NM_014704, NM_022781, D87450.1, L48784, NM_018191, U62136.2, NM_003589, R59697, NM_014803, NM_022100.1, AA704004, AB034951.1, AF352832.1, NM_006644, AK026008.1, BG223334, AW514857, BG291649, NM_005887, NM_014499.1, AL353681, Z82202, NM_003339, NM_016584, AI023864, BC002513.1, NM_005059.1, AE000659, AA398139, BF431965, AI081194, NM_015929, NM_001628, AK026487.1, AL050050.1, NMJH4887, BF343852, NM_001536, BC001671.1, NM_014165, BC005938.1, NM_003094, AL570294, AV730849, AA746290, BE464819, NM_015344, AA858297, BE857467, BF513060, NM_004719, AI967981, NM_002109, NM_004649, AI703342, AI676241, BE621524, AV728268, NM_003105, AI149508, AW003635, AL044092, AI089932, BE349017, ABOl 1151.1, BF940192, AW205632, AK000749.1, U70056, BE503392, BG390306, AI302244, NM_003328, N30132, BC000787.1, NMJU7925, NM_004879, AL529672, AL050136.1, NM_016617, AW340096, AI890903, AI458439, AI278629, N30416, AA917672, NM_017875, U93867.1, AI872374, AI806322, NM_024300, NM_014679, AL021707, NM_022840, U79248.1, AI816281, AU155565, W19668, AL036450, BE927772, BF111169, AV707196, AV728606, AL035851, AW263542, AA1 81060, NM_005885, NM_013307, AA243143, BE857772, AA630330, NM_005589, AI347000, AA826288, BC005055.1, NM_017913, NM_017632, NM_003274, AI343248, M65217.1, AA808694, AK026954.1, N80922, NM_003799, AW173157, NM_002958, NM_014166, AF275803.1, NM_007043, BE544748, AK023546.1, NMJB0791, NM_005111, BE910323, AF1 16705.1, NM_006165, AF212995.1, BC001052.1, L00634.1, NM_002731, NM_021038.1, AL545982, AI990766, AI818488, AI763123, BC002637.1, NM_005653, AI218219, NM_001310.1, NM_012319, NM_001417.1, AB000359, AI800983, NM_030799, AL558532, AE000659, AL040935, AA223871, AI204981, BF003112, AT471458, NMJH5537, AF142408.1, NM_003646, BF528646, BE677453, BE888593, NM_030915, AI804118, NM_022756, BE888593, AL515874, AL541302, AF161382.1, AI557467, AI123233, NM_012280, NMJH6048, NM_017489, NM_014885, BE542684, AW082219, BE645241, BC004819.1, BF435952, NM_004401, AK000803.1, NM_005870.2, BC002585.1, AW408767, NM_004379, NM_024570, BF338332, NM_017606, AL080149.1, NM_014577, AB014592.1, NM_014635, NM_003339.1, AI632774, AA143579, BC006240.1, AK021738.1, AF153430.1, BF344265, BE897866, NM_004375, AB026118.1, AI554106, NM_024772, NM_001765, AL050348, N36085, AF039698.1, BG106477, NMJH8060, AF109873.1, BF594371, BE464483, AC002073, AC002073, S74774.1, M14333.1, NM_003079.1, AI040029, AV738806, NM_015897.1, NM_030794, NM_005710, NM_007158, NM_024612, NM_006520, NM_003473, NM_006372.1, NM_004034, AL024509, U83410.1, AL049693, S77356.1, X14487, NM_003345.1, AB051499.1, NM_005730, NM_005760, BE865779, AK023696.1, NM_002271.1, AI806747, BF056303, BF447037, AI632214, AU145061, BE044193, NM_006255, NM_018255.1, AI880633, AI017564, NM_018338, AI056683, NM_015485, AF254083.1, NM_024699, AI927701, AF144638.1, U69127.1, NM_018439, T93113, BE675356, AI744084, NM_004762, AK000004.1, D87077, BC003686.1, NM_001527, NM_003138, AV712602, NM_005999, AU126086, AW008502, AL050035.1, BE677308, AI651969, BC000120.1, AL044097, NM_022759, AI492369, NM_021640, NM_002085, NM_003491, NM_016034, NM_014371, NM_022470, N38751, AK025432.1, AL534972, U79271.1, AA019893, NM_003146, AI817976, D21243.1, AI935915, NM_000027, NM_016402, NM_024108, N25621, U34074.1, L24959.1, NM_003983.1, N95466, AB018308.1, NM_004280, NM_018010, NM_021204, NM_014288, AV699565, NM_003550, NM_003689, NM_014374, NM_016603, AI741469, D50911.2, BG149337, NM_004516, NM_000155, AI984005, AK024823.1, AF235049.1, AK024117.1, AL121916, U52111, AI866717, BF435621, AI392933, AW051527, NM_024928, BE880820, NMJ) 16194, NM_004905, BE501980, NM_005997, U79260.1, AA700485, BF031819, BG532690, AW504569, AW003022, NM_003584, N91520, NM_000696, NM_012231, AC007228, AV705292, AW190479, AI797836, AW043594, NM_020217, AI122852, AI827431, NM_016523, NM_000878, NM_002260, X06557.1, X72501.1, AW007751, AB059408.1, NM_007053, NM_002258.1, NM_002261, AW592266, AF251061.1, AB018580.1, NM_004669, AI814092, NM_006433, NM_012445, AA425358, AK025444.1, NM_002830, NM_002378, AI915947, AK001821.1, AL136553.1, NM_025208, NM_018238, AI569747, AI653730, AL039831, AB01 1152.1, AW008627, AL524467, T67481, AK026674.1, NM_003199, W85912, NM_007371, AA877043, AB037811.1, NM_020117, NM_018282, NM_016399, NM_016305, BE348997, AL078633, AF241788.1, NM_004960, U69645.1, NM_006899, NM_005463, NM_014952, AI961224, AA916851, NM_001961, AU152194, AW675725, NM_014061, NM_006117, AA524093, NM_018113, NM_003954, AI668672, AW025150, AB020635.1, AF070592.1, NM_003339.1, NM_004760.1, BE999967, NM_024941, BF218804, AI809341, AL117499.1, NM_014011, NM_005388, U92014.1, X79067.1, AV712064, M_015726, NM_007372, AI359466, NM_014233, NM_016199, BE875232, AL555227, BC001818.1, BC003005.1, BG258639, U91543.1, BF724270, AA133277, BG493862, BE646386, AW027812, AI913329, NM_023015, NM_021167, AF197954.1, NM_020313, NM_007357, NM_015919, NM_017714, BC004957.1, BC000832.1, NM_000889, AF212225.1, BC001051.1, NM_004529, AV700191, AC004531, BG480592, AF023265.1, NM_002208, BF673940, NM_003107.1, AA148789, NM_003107.1, BF057084, AI492167, AI262560, BF976290, AA045257, AK025731.1, AV701229, AL561281, AW574933, AL080169.1, AB039327.2, BF512388, BC005871.1, AF131831.1, AI633734, NM_004445, AW270138, BE789346, T52999, NMJB0969, BC000580.1, NM_017646, NM_022838, NMJ)O1 108, NM_024514, D42084.1, W37897, AW074911, BF683512, N80935, AI201594, AW024741, NM_016382, NM_000689.1, NM_000709, NM_018622, BE903880, NM_022356, NM_006344, NM_017933, BC005912.1, M60333.1, M60334.1, NM_002118, NM_003916, M19720, NM_004578, AA651899, NMJH6205, BC002438.1, AL042817, BF058944, AI690169, BC001441.1, AI092931, AF303588.1, AI720705, BC000389.1, BG1 10532, NM_006324, W68720, AK026630.1, BF475280, AK021602.1, AK001934.1, AU150386, AAI14243, AL136619.1, AJ223321, NM_015986, R66534, BE883841, BG500677, AI888503, D55674.1, AF057356.1, BF061275, AA745971, BG166310, BG431266, AK022014.1, AA001543, AL565238, BC000717.1, U08015.1, AA789302, AI568622, AI056895, AI829724, AL133646.1, AW189430, AF090891.1, M31183.1, W68845, N66727, NM_017864, BE856596, NM_017943, AI016355, AU146532, NM_000309, BC000282.1, NM_017773, AI620827, NM_006530, AI766279, BF445127, AF251049.1, D29641.2, NM_016122, BF434321, AW628987, AA126311, Z24459, BC002600.1, AW024383, AL031228, NM_014367, AB006630.1, NM_004951, NM_006925, AW614056, AI695743, AB023208, BF593050, NM_025198.1, AI192379, BE671038, AA824321, BE614908, U19179.1, NM_000305, AI693140, NM_003952, NM_021078, M55575.1, AV700514, U87408, AI569785, BF129093, BF732638, NM_003142, BG402553, AL157437.1, BC006383.1, NM_003801, N21127, BG478726, BE252813, AK000921.1, NM_004708, NM_012458, AF277181.1, BC005400.1, NM_018959, BF507383, AI805069, BG249565, N49233, AI701408, BE673759, NM_020186, BC005250.1, BG286537, NM_030579, NM_000410, AF291676.1, NM_005776, NM_004261, BE676703, AI912238, AW952320, NM_004524, AB020671.1, AA769410, AL137430.1, BC006428.1, BF671883, AI761621, AK025626.1, BE302089, AL137317.1, BF436957, NM_024047, NM_005882, AA504646, N32185, AI762547, NM_022663, AK024949.1, NM_005639.1, AK001155.1, AW139448, X61072.1, NM_006180, NM_005971, NM_002023, AW024467, NM_000136, AL096729.1, N67741, NM_006610, NM_025073.1, U19345.1, AF034956, AI962897, AK023621.1, AB018305.1, NM_025040, NM_000922, NM_021631, AF181985.1, NM_006568, NM_021047, AI937543, NM_005666, NM_005027, AK024108.1, NM_000171, AA845577, NM_014139, NM_003069, AI669379, NM_004300, AL390738, AV691491, AW241832, AL034399, NM_005476, NM_022336, NM_024343, AK024879.1, NM_004944, NM_001353, BG168858, AW593859, AA748492, NM_012199, AI349506, NM_014349, U03494.1, NM_006114, NM_007317, NM_025207, NM_017976, NM_018036, AI797063, AF312230.1, AB011088.1, AF094508.1, BC002752.1, NM_005715, AV694732, AI522311, NM_014913.1, AI694452, U44378.1, NM_022771, BF246917, NM_006371, U89386.1, BG403671, AI191118, AL024509, BG472176, NM_014612, NMJ318221, NM_006738, NM_014766, M74088.1, AA053830, NM_003758, U66046.1, AL390149.1, BC004424.1, AI949220, W74580, NM_000017, NM_001269, AK022046.1, NM_003418, AK023738.1, NM_004758, NM_018507, AL527430, AI299467, AC007277, NM_012405, BF436632, BG537255, AI570531, T89044, AI569766, NM_001123, AB028966.1, AL023553, NM_014242, NM_024033, NM_014239, U80184, U81802.1, M68520.1, NM_015678, AL050204.1, N54448, NM_006023, NM_006320, NM_003093, NM_001551, BF973387, AB037745.1, BF439163, AF161422.1, BE898861, NM_004641, AI632212, BE968576, NM_003366, AK000921.1, AW298170, AI650819, NM_006166, AI005043, BC006110.1, NM_001611, NM_025159, NM_003291, NM_002967, AK024263.1, D87440.1, NM_005741, NM_018321, NM_018195, AI300126, NM_019012, NM_015904.1, BF240652, N64802, AA481044, NM_006414, AF145439.1, BG481877, NM_030954, BC004372.1, M24915.1, NM_022170, NM_006805, NM_023009, BE247450, AI613089, BE550501, AI268231, AL080102.1, AB040915.1, AW590155, NM_030818, AL530441, BF675004, AL137520.1, AJ130971.1, NM_002908, NM_000202, AW131553, NMJH8158, NM_002197, NMJH7656, L19185, X04801, AL109955, AI820101, NM_016532, BG106477, NM_018095, AK026155.1, U40763.1, BF446940, AI339915, R67076, N66669, AI971724, BE218428, AI971694, AI672084, AB037759.1, NM_016281, AF183419.1, NM_020466, AA284075, AV682940, M77498.1, NM_005901, BF057298, NM_002655, AW024095, AI720923, AW025093, NM_014674, NM_017745, NMJ21O3O., NM_024072, AW237172, AI460037, NM_019034, AL390164.1, NM_017660, AW628835, NMJH6026, AI693862, AW055161, BG341575, NM_015909, AB023216.1, U79277.1, AI222805, AI820796, AI888657, BG339050, BG1 12118, NM_005735, NM_007344, AW296162, AK001652.1, BC005370.1, AF183569.1, BF1 14745, AJO1 1307, AI439695, BF240782, AI659219, AB049654.1, AF275813.1, AV751709, AF080579, D49737.1, NM_003001, AF129756, AI814587, NM_016017, BF224247, N92500, L29008.1, AI798846, AW264102, AI762876, BF206389, NM_004843, AB014576.1, NM_025198.1, T75480, AI870866, AB041836.1, N32831, AL354612.1, AW449353, AI760812, AI986239, AW972855, NM_012097, AI638235, AI589978, AI096706, NM_006457, NM_018340, BC002642.1, AF333336.1, AW451502, NM_002162, AW274846, AA152232, NM_018845, NMJH6586, NM_006802, AB023215.1, AU157017, AI868315, BF063821, AI826279, AK025464.1, NM_018465, NM_004546, NM_006886, BC002772.1, N34846, AI939400, AF217197.1, NM_002823, AK023255.1, AI203021, NM_004780, AL049980.1, M14016.1, BE670798, BF589088, D21089.1, AI348010, NM_018312, AI741415, AL567411, BE551193, AA664258, AK001039.1, AB051548.1, AF077048.1, NM_005402.1, M32577.1, NM_004634, AF226990.2, BC001041.1, M27487.1, AA789329, AL157424.1, BC000978.2, AI917328, AW236209, BC003669.1, AI432713, BF676980, AF151842.1, BF972871, AI335267, AA523441, AI435036, BG028884, BG388615, NM_021603, NM_024579, AK022050.1, AI332476, and AI738987 (see Table 2A of U.S. Pat. No. 7,608,395). The biomarkers of any of the above groupings also include their Affymetrix or other genechip equivalents. Additionally or alternatively, an "SLE signature" comprise reduced levels of one or more markers as of Table 3 of U.S. Pat. No. 7,118,865, herein incorporated by reference. In some embodiments, reduced levels comprise 50% lower expression than observed for control(s).

"Differentially expressed" as applied to a gene, refers to the differential production of the mRNA transcribed from the gene and/or translated from the mRNA transcript into the protein product. The difference in gene expression between similar cell types from different subjects may be compared, or the difference in gene expression at a first and second time point in the same subject can be compared. In addition, the expression profile of a subject can be compared to a stored reference expression profile. A differentially expressed gene may be over-expressed (e.g., elevated biomarker expression) or under-expressed (reduced biomarker expression) as compared to the expression level of a normal or control cell. However, in some preferred embodiments, over-expressed is used to refer to a change in the expressed level of at least 2.0 fold, at least 2.25 fold, at least 2.5 fold or, at least 3 fold, at least 3.5 fold, at least 4 fold, at least 5-fold, or at least 10 fold, greater than that in the control cell, tissue or other biological sample. As such, a level that is 2-fold more than X refers to the level that is 2X. In further preferred embodiments, under-expressed refers to expression at a level that is at least 50% less, at least 60%, at least 70%, at least 80%, at least 90% or at least 95% less than that in the control cell or tissue. For example, a level 75% less than X refers to a level that is 0.25X. Differentially expressed also refers to nucleotide and/or protein sequences in a cell or tissue which are expressed where silent in a control cell or not expressed where expressed in a control cell.

The terms "subject," "individual" and "patient" are used interchangeably to refer to a human that may be afflicted with an autoimmune disease such as SLE. The terms "reference" and control are used interchangeably to refer to an alternative subject or sample used for comparison purpose. The term "control" as used in reference to determining whether a biomarker is expressed at an elevated or a reduced level refers to one or more negative controls, such that the control sample in which gene expression is analyzed is from one or more humans that do not have an autoimmune disease. It is preferable to determine the levels of gene expression from the same cell type or types in both the subject and the controls. One or more controls may be used. If more than one control is used, the level expressed in the controls is preferably the average or median level of expression of a gene in the controls. Any number of controls may be used. In one example, at least 10, 20, 30, 40, or at least 50 controls are used. The level of gene expression in a control may be determined at or around the same time that the level of gene expression is determined in a subject. Alternatively, the level expression of a control may be previously determined and stored for subsequent comparison. In another embodiment, the expression level in a subject may be determined and stored prior to determination of the expression level in one or more controls. In some embodiments, the one or more biomarkers include, for example, at least two or more biomarkers, at least three or more biomarkers, at least four or more biomarkers, at least five or more biomarkers, at least ten or more biomarkers, or at least fifteen or more biomarkers.

In some embodiments, expression of the biomarkers is determined using NanoString nCounter gene expression system (Geiss et al., Nature Biotechnology, 26:317-325, 2008, herein incorporated by reference). However, any method can be used to determine whether or not biomarker expression is elevated or reduced in a sample from a subject, as compared to a control or an average level of expression observed in control cells.

Methods of Use

Provided herein are methods of regulating an immune response in an individual comprising administering to the individual an effective amount of an inhibitor of TLR7 and/or TLR9 (e.g., an IRP and/or IRC). The IRP and/or IRC comprises an IRS. For example, the IRS is or comprises the IRS of one of the group consisting of SEQ ID NO: 64-78, SEQ ID NO:123-135, and SEQ ID NO:141-145. In some embodiments, the IRS is the IRS of SEQ ID NO:67, SEQ ID NO:68, SEQ ID NO:69, SEQ ID NO:71, SEQ ID NO:73, SEQ ID NO:78, SEQ ID NO:141, SEQ ID NO:143, or SEQ ID NO:144. In some embodiments, the IRS is the IRS of SEQ ID NO:73, SEQ ID NO:134, SEQ ID NO:143, or SEQ ID NO:144. In some embodiments, the immune response is suppressed and/or inhibited. In some embodiments, the inhibited immune response is associated with the TLR7 signaling pathway and/or TLR9 signaling pathway. In some embodiments of any of the IRPs, the IRP is a 2'-deoxyribo polynucleotide sequence. In some embodiments of any of the IRPs, the IRP is a 2' deoxyribo polynucleotide and/or the 2'-O-Me sugar polynucleotide chimeric sequence. In some embodiments, the IRP has at least one nucleotide comprising a modified phosphate linkage. In some embodiments, IRP comprises only phosphorothioate linkages.

Exemplary methods and compositions are described in Guiducci et al., Nature 465:937-941, 2010 (17 Jun. 2010), and are described in Guiducci et al. J. Exp. Med. 207:2931-2942, 2010 and Nov. 29, 2010 [Epub ahead of print], the disclosures of each of which are incorporated herein by reference in their entirety.

Methods of immunoregulation provided by the invention include those that suppress and/or inhibit an immune response, including, but not limited to, an immune response stimulated by immunostimulatory nucleic acid molecules such as bacterial DNA. The invention also provides methods for inhibiting TLR7 and/or TLR9 induced cell response. The invention also provides methods for ameliorating symptoms associated with unwanted immune activation, including, but not limited to, symptoms associated with autoimmunity.

Immuno-regulation according to the methods described herein may be practiced on individuals including those suffering from a disorder associated with an unwanted activation of an immune response. In some variations, the immune response is an innate immune response. In some variations, the immune response is an adaptive immune response. In some embodiments, the cell is contacted with the polynucleotide in an amount effective to inhibit a response from the cell that contributes to an immune response.

Provided herein are methods of treating or preventing a disease in an individual comprising administering to the individual an effective amount of an inhibitor of TLR7 and/or TLR9 (e.g., an IRP and/or IRC). Further, provided are methods for ameliorating symptoms associated with a disease comprising administering an effective amount of an inhibitor of TLR7 and/or TLR9 (e.g., an IRP and/or IRC) to an individual having a disease. Methods are also provided herein for preventing or delaying development of a disease, comprising administering an effective amount of an inhibitor of TLR7 and/or TLR9 (e.g., an IRP and/or IRC). In some embodiments, the disease is an autoimmune disease. In some embodiments, the autoimmune disease, including SLE, rheumatoid arthritis, dermatomyositis, and Sjögren's syndrome. In some embodiments, the immunoregulatory polynucleotide or immunoregulatory compound effective for suppressing a symptom of SLE comprises an immunoregulatory sequence of the TLR7 class or TLR9 class or TLR7/9 class. In some variation, the disease is an inflammatory disease. In some embodiments, the inflammatory disease is an interface dermatitis. In some embodiments, the interface dermatitis is dermatomyositis, cutaneous lupus, psoriasis, lichen planus, etc. In some embodiments, the inflammatory disease is sterile inflammatory disease such as drug-induced liver inflammation and/or pancreas inflammation. In some embodiments, the inflammatory disease is inflammatory liver disease. In some embodiments, the IRS is or comprises the IRS of one of the group consisting of SEQ ID NO: 64-78, SEQ ID NO:123-135, and SEQ ID NO:141-145. In some embodiments, the IRS is the IRS of SEQ ID NO:67, SEQ ID NO:68, SEQ ID NO:69, SEQ ID NO:71, SEQ ID NO:73, SEQ ID NO:78, SEQ ID NO:141, SEQ ID NO:143, or SEQ ID NO:144. In some embodiments, the IRS is the IRS of SEQ ID NO:73, SEQ ID NO:134, SEQ ID NO:143, or SEQ ID NO:144. In some embodiments of any of the IRPs, the IRP is a 2'-deoxyribo polynucleotide sequence. In some embodiments of any of the IRPs, the IRP is a 2' deoxyribo polynucleotide and/or the 2'-O-Me sugar polynucleotide chimeric sequence. In some embodiments, the IRP has at least one nucleotide comprising a modified phosphate linkage. In some embodiments, IRP comprises only phosphorothioate linkages.

In certain embodiments, the individual suffers from a disorder associated with unwanted immune activation, such as allergic disease or condition, allergy and asthma. An individual having an allergic disease or asthma is an individual with a recognizable symptom of an existing allergic disease or asthma. In any of the methods described herein the IRS-containing polynucleotide may be administered in an amount sufficient to regulate an immune response. As described herein, regulation of an immune response may be humoral and/or cellular, and is measured using standard techniques in the art and as described herein. In some embodiments, provided herein are methods for suppressing, reducing, and/or inhibiting TLR7 and/or TLR9 dependent cell stimulation.

Other embodiments provided herein relate to immuno-regulatory therapy of individuals having been exposed to or infected with a virus. Administration of an IRP or IRC to an individual having been exposed to or infected with a virus results in suppression of virus induced cytokine production.

Provided herein are methods for treating, assessing responsiveness, identifying individuals, and/or selecting individuals for treatment comprising an effective amount of a TLR7 inhibitor and/or TLR9 inhibitor based upon interferon (IFN) signature and/or differential levels of inflammatory cytokines. Also provided herein are methods for treating, assessing responsiveness, identifying individuals, and/or selecting individuals for treatment comprising an effective amount of an IRP and/or IRC based upon interferon (IFN) signature and/or differential levels of inflammatory cytokines.

The present invention provides methods of treating a disease in an individual (e.g., human) comprising administering to the individual an effective amount of a TLR7 inhibitor and/or TLR9 inhibitor, wherein treatment is based upon IFN signature and/or differential levels of inflammatory cytokines. For example, methods of treating a disease in an individual (e.g., human) comprising administering to the individual an effective amount of an IRP and/or IRC, wherein treatment is based upon IFN signature and/or differential levels of inflammatory cytokines. In some embodiments, the IRS is or comprises the IRS of one of the group consisting of SEQ ID NO:67, SEQ ID NO:68, SEQ ID NO:69, SEQ ID NO:71, SEQ ID NO:73, SEQ ID NO:78, SEQ ID NO:141, SEQ ID NO:143, and SEQ ID NO:144. In some embodiments, the disease is an autoimmune disease. In some embodiments, the autoimmune disease, including SLE, rheumatoid arthritis, dermatomyositis, and Sjögren's syndrome. In some variation, the disease is an inflammatory disease. In some embodiments, the inflammatory disease is an interface dermatitis. In some embodiments, the interface dermatitis is dermatomyositis, cutaneous lupus, psoriasis, lichen planus, etc. In some embodiments, the inflammatory disease is sterile inflammatory disease such as drug-induced liver inflammation and/or pancreas inflammation. In some embodiments, the inflammatory disease is inflammatory liver disease. In some embodiments, the IRS is the IRS of SEQ ID NO:73, SEQ ID NO:134, SEQ ID NO:143, or SEQ ID NO:144.

Provided herein are also methods of treating a disease, comprising: (a) selecting an individual having an IFN signature and/or differential levels of inflammatory cytokines; and (b) administering to the selected individual an effective amount of a TLR7 inhibitor and/or TLR9 inhibitor. For example, methods of treating a disease, comprising: (a) selecting an individual having an IFN signature and/or differential levels of inflammatory cytokines; and (b) administering to the selected individual an effective amount of an IRP and/or IRC. In some embodiments, the IRS is or comprises the IRS of one of the group consisting of SEQ ID NO:67, SEQ ID NO:68, SEQ ID NO:69, SEQ ID NO:71, SEQ ID NO:73, SEQ ID NO:78, SEQ ID NO:141, SEQ ID NO:143, and SEQ ID NO:144. In some embodiments, the disease is an autoimmune disease. In some embodiments, the autoimmune disease, including SLE, rheumatoid arthritis, dermatomyositis, and Sjogren's syndrome. In some variation, the disease is an inflammatory disease. In some embodiments, the inflammatory disease is an interface dermatitis. In some embodiments, the interface dermatitis is dermatomyositis, cutaneous lupus, psoriasis, lichen planus, etc. In some embodiments, the inflammatory disease is sterile inflammatory disease such as drug-induced liver inflammation and/or pancreas inflammation. In some embodiments, the inflammatory disease is inflammatory liver disease. In some embodiments, the IRS is the IRS of SEQ ID NO:73, SEQ ID NO:134, SEQ ID NO:143, or SEQ ID NO:144.

Methods are also provided herein of assessing whether an individual with a disease will more likely to respond or less likely to respond to treatment comprises an effective amount of a TLR7 inhibitor and/or TLR9 inhibitor, the method comprising assessing IFN signature and/or differential levels of inflammatory cytokines, wherein the IFN signature and/or differential levels of inflammatory cytokines indicates that the individual is more likely to respond or is less likely to respond to the treatment. For example, methods are also provided herein of assessing whether an individual with a disease will more likely to respond or less likely to respond to treatment comprises an effective amount of an IRP and/or IRC, the method comprising assessing IFN signature and/or differential levels of inflammatory cytokines, wherein the IFN signature and/or differential levels of inflammatory cytokines indicates that the individual is more likely to respond or is less likely to respond to the treatment. In some embodiments, the method comprises administering an effective amount of a TLR7 inhibitor and/or TLR9 inhibitor. In some embodiments, the IRS is the IRS of one of the group consisting of SEQ ID NO:67, SEQ ID NO:68, SEQ ID NO:69, SEQ ID NO:71, SEQ ID NO:73, SEQ ID NO:78, SEQ ID NO:141, SEQ ID NO:143, and SEQ ID NO:144. In some embodiments, the disease is an autoimmune disease. In some embodiments, the autoimmune disease, including SLE, rheumatoid arthritis, dermatomyositis, and Sjogren's syndrome. In some variation, the disease is an inflammatory disease. In some embodiments, the inflammatory disease is an interface dermatitis. In some embodiments, the interface dermatitis is dermatomyositis, cutaneous lupus, psoriasis, lichen planus, etc. In some embodiments, the inflammatory disease is sterile inflammatory disease such as drug-induced liver inflammation and/or pancreas inflammation. In some embodiments, the inflammatory disease is inflammatory liver disease. In some embodiments, the IRS is the IRS of SEQ ID NO:73, SEQ ID NO:134, SEQ ID NO:143, or SEQ ID NO:144.

Methods are also provided herein of aiding assessment of whether an individual with a disease will more likely respond to or is suitable for treatment, wherein the treatment comprises an effective amount of a TLR7 inhibitor and/or TLR9 inhibitor, the method comprising evaluating IFN signature and/or differential levels of inflammatory cytokines, wherein the IFN signature and/or differential levels of inflammatory cytokines indicate that the individual is more likely to respond or suitable for the treatment. In some embodiments, the method comprises administering an effective amount of a TLR7 inhibitor and/or TLR9 inhibitor. In some embodiments, the disease is an autoimmune disease. In some embodiments, the autoimmune disease, including SLE, rheumatoid arthritis, dermatomyositis, and Sjogren's syndrome. In some variation, the disease is an inflammatory disease. In some embodiments, the inflammatory disease is an interface dermatitis. In some embodiments, the interface dermatitis is dermatomyositis, cutaneous lupus, psoriasis, lichen planus, etc. In some embodiments, the inflammatory disease is sterile inflammatory disease such as drug-induced liver inflammation and/or pancreas inflammation. In some embodiments, the inflammatory disease is inflammatory liver disease. In some embodiments, the TLR7 inhibitor and/or TLR9 inhibitor is an IRP and/or IRC as described herein. In some embodiments, the IRS is or comprises the IRS of one of the group consisting of SEQ ID NO:67, SEQ ID NO:68, SEQ ID NO:69, SEQ ID NO:71, SEQ ID NO:73, SEQ ID NO:78, SEQ ID NO:141, SEQ ID NO:143, and SEQ ID NO:144. In some embodiments, the IRS is the IRS of SEQ ID NO:73, SEQ ID NO:134, SEQ ID NO:143, or SEQ ID NO:144.

In addition, methods are provided herein of identifying an individual with a disease more likely to respond or less likely to respond comprising an effective amount of a TLR7 inhibitor and/or TLR9 inhibitor, the method comprising: (A) assessing an IFN signature and/or differential levels of inflammatory cytokines; and (B) identifying the individual having a differential IFN signature and/or differential levels of inflammatory cytokines. In some embodiments, the method comprises administering an effective amount of a TLR7 inhibitor and/or TLR9 inhibitor. In some embodiments, the disease is an autoimmune disease. In some embodiments, the autoimmune disease, including SLE, rheumatoid arthritis, dermatomyositis, and Sjogren's syndrome. In some variation, the disease is an inflammatory disease. In some embodiments, the inflammatory disease is an interface dermatitis. In some embodiments, the interface dermatitis is dermatomyositis, cutaneous lupus, psoriasis, lichen planus, etc. In some embodiments, the inflammatory disease is sterile inflammatory disease such as drug-induced liver inflammation and/or pancreas inflammation. In some embodiments, the inflammatory disease is inflammatory liver disease. In some embodiments, the TLR7 inhibitor and/or TLR9 inhibitor is an IRP and/or IRC as described herein. In some embodiments, the IRS is or comprises the IRS of one of the group consisting of SEQ ID NO:67, SEQ ID NO:68, SEQ ID NO:69, SEQ ID NO:71, SEQ ID NO:73, SEQ ID NO:78, SEQ ID NO:141, SEQ ID NO:143, and SEQ ID NO:144. In some embodiments, the IRS is the IRS of SEQ ID NO:73, SEQ ID NO:134, SEQ ID NO:143, or SEQ ID NO:144.

In addition, methods are provided herein of selecting or not selecting an individual with a disease more likely suitable or less likely suitable for treatment comprising an effective amount of a TLR7 inhibitor and/or TLR9 inhibitor, the method comprising: (A) assessing IFN signature and/or differential levels of inflammatory cytokines; and (B) selecting the individual having a differential IFN signature and/or differential levels of inflammatory cytokines. In some embodiments, the method comprises administering an effective amount of a TLR7 inhibitor and/or TLR9 inhibitor. In some embodiments, the disease is an autoimmune disease. In some embodiments, the autoimmune disease, including SLE, rheumatoid arthritis, dermatomyositis, and Sjogren's syndrome. In some variation, the disease is an inflammatory disease. In some embodiments, the inflammatory disease is an interface dermatitis. In some embodiments, the interface dermatitis is dermatomyositis, cutaneous lupus, psoriasis, lichen planus, etc. In some embodiments, the inflammatory disease is sterile inflammatory disease such as drug-induced liver inflammation and/or pancreas inflammation. In some embodiments, the inflammatory disease is inflammatory liver disease. In some embodiments, the TLR7 inhibitor and/or TLR9 inhibitor is an IRP and/or IRC as described herein. In some embodiments, the IRS is or comprises the IRS of one of the group consisting of SEQ ID NO:67, SEQ ID NO:68, SEQ ID NO:69, SEQ ID NO:71, SEQ ID NO:73, SEQ ID NO:78, SEQ ID NO:141, SEQ ID NO:143, and SEQ ID NO:144. In some embodiments, the IRS is the IRS of SEQ ID NO:73, SEQ ID NO:134, SEQ ID NO:143, or SEQ ID NO:144.

Methods are provided herein of determining whether an individual with a disease more likely suitable or less likely suitable for treatment comprising an effective amount of a TLR7 inhibitor and/or TLR9 inhibitor, the method comprising: assessing an IFN signature and/or differential levels of inflammatory cytokines. In some embodiments, the method comprises administering an effective amount of a TLR7 inhibitor and/or TLR9 inhibitor. In some embodiments, the disease is an autoimmune disease. In some embodiments, the autoimmune disease, including SLE, rheumatoid arthritis, dermatomyositis, and Sjogren's syndrome. In some variation, the disease is an inflammatory disease. In some embodiments, the inflammatory disease is an interface dermatitis. In some embodiments, the interface dermatitis is dermatomyositis, cutaneous lupus, psoriasis, lichen planus, etc. In some embodiments, the inflammatory disease is sterile inflammatory disease such as drug-induced liver inflammation and/or pancreas inflammation. In some embodiments, the inflammatory disease is inflammatory liver disease. In some embodiments, the TLR7 inhibitor and/or TLR9 inhibitor is an IRP and/or IRC as described herein. In some embodiments, the IRS is or comprises the IRS of one of the group consisting of SEQ ID NO:67, SEQ ID NO:68, SEQ ID NO:69, SEQ ID NO:71, SEQ ID NO:73, SEQ ID NO:78, SEQ ID NO:141, SEQ ID NO:143, and SEQ ID NO:144. In some embodiments, the IRS is the IRS of SEQ ID NO:73, SEQ ID NO:134, SEQ ID NO:143, or SEQ ID NO:144.

The present invention provides methods of treating a disease in an individual (e.g., human) comprising administering to the individual an effective amount of a TLR7 inhibitor and/or TLR9 inhibitor, wherein treatment response or lack of treatment response is indicated by an IFN signature and/or differential levels of inflammatory cytokines of a sample. In some embodiments, the disease is an autoimmune disease. In some embodiments, the autoimmune disease, including SLE, rheumatoid arthritis, dermatomyositis, and Sjogren's syndrome. In some variation, the disease is an inflammatory disease. In some embodiments, the inflammatory disease is an interface dermatitis. In some embodiments, the interface dermatitis is dermatomyositis, cutaneous lupus, psoriasis, lichen planus, etc. In some embodiments, the inflammatory disease is sterile inflammatory disease such as drug-induced liver inflammation and/or pancreas inflammation. In some embodiments, the inflammatory disease is inflammatory liver disease. In some embodiments, the TLR7 inhibitor and/or TLR9 inhibitor is an IRP and/or IRC as described herein. In some embodiments, the IRS is or comprises the IRS of one of the group consisting of SEQ ID NO:67, SEQ ID NO:68, SEQ ID NO:69, SEQ ID NO:71, SEQ ID NO:73, SEQ ID NO:78, SEQ ID NO:141, SEQ ID NO:143, and SEQ ID NO:144. In some embodiments, the IRS is the IRS of SEQ ID NO:73, SEQ ID NO:134, SEQ ID NO:143, or SEQ ID NO:144.

The present invention also provides methods of assessing responsiveness or lack of responsiveness of an individual to a disease treatment comprising an effective amount of a TLR7 inhibitor and/or TLR9 inhibitor, wherein responsiveness or lack of responsiveness is indicated by an IFN signature and/or differential levels of inflammatory cytokines of a sample. In some embodiments, the method comprises administering an effective amount of a TLR7 inhibitor and/or TLR9 inhibitor. In some embodiments, the disease is an autoimmune disease. In some embodiments, the autoimmune disease, including SLE, rheumatoid arthritis, dermatomyositis, and Sjogren's syndrome. In some variation, the disease is an inflammatory disease. In some embodiments, the inflammatory disease is an interface dermatitis. In some embodiments, the interface dermatitis is dermatomyositis, cutaneous lupus, psoriasis, lichen planus, etc. In some embodiments, the inflammatory disease is sterile inflammatory disease such as drug-induced liver inflammation and/or pancreas inflammation. In some embodiments, the inflammatory disease is inflammatory liver disease. In some embodiments, the TLR7 inhibitor and/or TLR9 inhibitor is an IRP and/or IRC as described herein. In some embodiments, the IRS is or comprises the IRS of one of the group consisting of SEQ ID NO:67, SEQ ID NO:68, SEQ ID NO:69, SEQ ID NO:71, SEQ ID NO:73, SEQ ID NO:78, SEQ ID NO:141, SEQ ID NO:143, and SEQ ID NO:144. In some embodiments, the IRS is the IRS of SEQ ID NO:73, SEQ ID NO:134, SEQ ID NO:143, or SEQ ID NO:144.

The present invention also provides methods of monitoring responsiveness or lack of responsiveness of an individual to a disease treatment comprising an effective amount of a TLR7 inhibitor and/or TLR9 inhibitor, wherein responsiveness or lack of responsiveness is indicated by an IFN signature and/or differential levels of inflammatory cytokines of a sample. In some embodiments, the method comprises administering an effective amount of a TLR7 inhibitor and/or TLR9 inhibitor. In some embodiments, the disease is an autoimmune disease. In some embodiments, the autoimmune disease, including SLE, rheumatoid arthritis, dermatomyositis, and Sjogren's syndrome. In some variation, the disease is an inflammatory disease. In some embodiments, the inflammatory disease is an interface dermatitis. In some embodiments, the interface dermatitis is dermatomyositis, cutaneous lupus, psoriasis, lichen planus, etc. In some embodiments, the inflammatory disease is sterile inflammatory disease such as drug-induced liver inflammation and/or pancreas inflammation. In some embodiments, the inflammatory disease is inflammatory liver disease. In some embodiments, the TLR7 inhibitor and/or TLR9 inhibitor is an IRP and/or IRC as described herein. In some embodiments, the IRS is or comprises the IRS of one of the group consisting of SEQ ID NO:67, SEQ ID NO:68, SEQ ID NO:69, SEQ ID NO:71, SEQ ID NO:73, SEQ ID NO:78, SEQ ID NO:141, SEQ ID NO:143, and SEQ ID NO:144. In some embodiments, the IRS is the IRS of SEQ ID NO:73, SEQ ID NO:134, SEQ ID NO:143, or SEQ ID NO:144.

Also provided herein are methods of identifying an individual as more likely suitable to continue to receive a disease treatment or less likely suitable to continue to receive treatment based upon an IFN signature and/or differential levels of inflammatory cytokines of a sample, wherein treatment comprises an effective amount of a TLR7 inhibitor and/or TLR9 inhibitor. In some embodiments, the disease is an autoimmune disease. In some embodiments, the autoimmune disease, including SLE, rheumatoid arthritis, dermatomyositis, and Sjogren's syndrome. In some variation, the disease is an inflammatory disease. In some embodiments, the inflammatory disease is an interface dermatitis. In some embodiments, the interface dermatitis is dermatomyositis, cutaneous lupus, psoriasis, lichen planus, etc. In some embodiments, the inflammatory disease is sterile inflammatory disease such as drug-induced liver inflammation and/or pancreas inflammation. In some embodiments, the inflammatory disease is inflammatory liver disease. In some embodiments, the TLR7 inhibitor and/or TLR9 inhibitor is an IRP and/or IRC as described herein. In some embodiments, the IRS is or comprises the IRS of one of the group consisting of SEQ ID NO:67, SEQ ID NO:68, SEQ ID NO:69, SEQ ID NO:71, SEQ ID NO:73, SEQ ID NO:78, SEQ ID NO:141, SEQ ID NO:143, and SEQ ID NO:144. In some embodiments, the IRS is the IRS of SEQ ID NO:73, SEQ ID NO:134, SEQ ID NO:143, or SEQ ID NO:144.

In some embodiments of any of the methods above, more likely responsiveness or more likely suitability for treatment is indicated by correlation with IFN signature of the sample with a reference IFN signature. In some embodiments, less likely responsiveness or less likely suitability is indicated by lack of correlation with IFN signature of the sample with a reference IFN signature.

In some embodiments of any of the methods above, responsiveness is indicated by correlation with IFN signature of the sample with a reference IFN signature. In some embodiments, nonresponsiveness is indicated by lack of correlation with IFN signature of the sample with a reference IFN signature. In some embodiments, responsiveness is indicated by a change in IFN signature of the sample. In some embodiments, lack of responsiveness is indicated by an insignificant change in IFN signature of the sample.

In some embodiments of any of the methods above, the IFN signature is a differential IFN signature in the sample as compared to a reference. In some embodiments, the IFN signature is higher than a reference IFN signature. In some embodiments, the IFN signature is lower than a reference IFN signature. In some embodiments, the reference IFN signature is the IFN signature as described in Chaussabel et al. *Immunity* 29:150-164 (2008), Bennett et al. *J. Exp. Med.* 197(6): 711-723 (2003), or Baechler E C et al., *PNAS* 100(5):2610-5 (2003) which are incorporated by reference in their entirety. In some embodiments, the differential IFN signature comprises differential levels of one or more biomarkers of an IFN signature in the sample compared to a reference. In some embodiments of any of the methods above, the IFN signature is a type I IFN signature.

The IFN signature may include the evaluation of expression levels of one or more of the biomarkers selected from the group consisting of BATF2, CMPK2, CXCL10, DDX60, EPSTI1, HERC5, HES4, IFI44, IFI44L, IFIT1, IFIT3, IFITM3, ISG15, LAMP3, LOC26010, LY6E, MX1, OAS1, OAS2, OAS3, OASL, OTOF, RSAD2, RTP4, SERPING1, TRIM6, XAF1, cl02h05 5, Agencourt-7914287 NIH-MCG__71, ISG20, IFI16, IRF7, and AIM2. In some embodiments, the differential levels are differential levels of one or more biomarkers selected from the group consisting of BATF2, CMPK2, DDX60, EPSTI1, HERC5, HES4, IFI44, IFI44L, IFIT1, IFIT3, IFITM3, ISG15, LAMP3, LOC26010, MX1, OAS1, OAS2, OAS3, OASL, OTOF, RSAD2, RTP4, SERPING1, TRIM6, XAF1, cl02h05 5, Agencourt-7914287 NIH-MCG__71, ISG20, IRF7, and AIM2 compared to a reference. In some embodiments, the expression levels of one or more of biomarker are differential levels compared to a reference. In some embodiments of any of the methods, IFN signature may include evaluating the expression levels of about any of 1, 2, 3, 4, 5, 6, 7, 8, 9, 10, or 15 biomarkers. In some embodiments, the one or more biomarkers include, for example, at least two or more biomarkers, at least three or more biomarkers, at least four or more biomarkers, at least five or more biomarkers, at least ten or more biomarkers, or at least fifteen or more biomarkers.

In some embodiments of any of the methods above, IFN signature comprises differential levels of one or more biomarkers selected from the group consisting of BATF2, CMPK2, CXCL10, DDX60, EPSTI1, HERC5, HES4, IFI44, IFI44L, IFIT1, IFIT3, IFITM3, ISG15, LAMP3, LOC26010, LY6E, MX1, OAS1, OAS2, OAS3, OASL, OTOF, RSAD2, RTP4, SERPING1, TRIM6, XAF1, cl02h05 5, Agencourt-7914287 NIH-MCG__71, ISG20, IFI16, IRF7, and AIM2. In some embodiments of any of the methods, the differential levels are high expression levels of one or more biomarkers selected from the group consisting of BATF2, CMPK2, CXCL10, DDX60, EPSTI1, HERC5, HES4, IFI44, IFI44L, IFIT1, IFIT3, IFITM3, ISG15, LAMP3, LOC26010, LY6E, MX1, OAS1, OAS2, OAS3, OASL, OTOF, RSAD2, RTP4, SERPING1, TRIM6, XAF1, cl02h05 5, Agencourt-7914287 NIH-MCG__71, ISG20, IFI16, IRF7, and AIM2 compared to a reference.

In some embodiments of any of the methods, high expression levels compared to a reference may indicate that the individual is more likely to respond or more likely suitable to treatment comprising an effective amount of a TLR7 inhibitor and/or TLR9 inhibitor. For example, an individual may be selected for treatment if the differential levels are high levels of one or more biomarkers selected from the group consisting of BATF2, CMPK2, CXCL10, DDX60, EPSTI1, HERC5, HES4, IFI44, IFI44L, IFIT1, IFIT3, IFITM3, ISG15, LAMP3, LOC26010, LY6E, MX1, OAS1, OAS2, OAS3, OASL, OTOF, RSAD2, RTP4, SERPING1, TRIM6, XAF1, cl02h05 5, Agencourt-7914287 NIH-MCG__71, ISG20, IFI16, IRF7, and AIM2 compared to a reference. In addition, an individual may be selected not to continue treatment if the differential levels are high levels of one or more biomarkers selected from the group consisting of BATF2, CMPK2, CXCL10, DDX60, EPSTI1, HERC5, HES4, IFI44, IFI44L, IFIT1, IFIT3, IFITM3, ISG15, LAMP3, LOC26010, LY6E, MX1, OAS1, OAS2, OAS3, OASL, OTOF, RSAD2, RTP4, SERPING1, TRIM6, XAF1, cl02h05 5, Agencourt-7914287 NIH-MCG__71, ISG20, IFI16, IRF7, and AIM2 compared to a reference.

In some embodiments, low expression levels compared to a reference may indicate that the individual is less likely to respond or less likely suitable to treatment comprising an effective amount of a TLR7 inhibitor and/or TLR9 inhibitor.

In some embodiments, the differential levels of inflammatory cytokines comprises differential levels in the sample of one or more inflammatory cytokine markers selected from the group consisting of IL-1 alpha, IL-1 beta, TNF-alpha, IL-6, IL-17, IFN-alpha, IFN-omega, IFN-lambda1, IFN-lambda2, and IP-10, as compared to the control sample(s).

The different levels of any of the methods described above may be differential levels of about any of 1, 2, 3, 4, 5, 6, 7, 8, 9, 10, or 15 or all the markers. In some embodiments, the one or more biomarkers include, for example, at least two or more biomarkers, at least three or more biomarkers, at least four or more biomarkers, at least five or more biomarkers, at least ten or more biomarkers, or at least fifteen or more biomarkers. In some embodiments, the one or more biomarkers does not include CXCL10, LY6E, and/or IFI16.

In some embodiments, differential levels are determined by measuring the expression level of a gene of interest in an individual and comparing to a reference (e.g., the median expression level for the given patient population or expression level of a second individual). For example, if the expression level of a gene of interest for the single individual is determined to be above the median expression level of the patient population, that individual is determined to have high expression of the gene of interest. Alternatively, if the expression level of a gene of interest for the single individual is determined to be below the median expression level of the patient population, that individual is determined to have low expression of the gene of interest. In some embodiments, the individual has a disease and the patient population or second individual does not have a disease (i.e., normal). In some embodiments, the individual has a disease and the patient population or second individual has a disease. In some embodiments, the individual is compared to a second individual and/or a patient population which is responsive to treatment. In some embodiments, the individual is compared to a second individual and/or a patient population which is responsive to treatment.

Differential, as used in context of differential cell, gene signature, nucleic acid, or protein refers to a difference compared to a reference (e.g., differential production of a cell or cell type, differential copy number of a gene, differential production of the mRNA transcribed from the gene, or the protein product encoded by the gene compared to a reference.) Differential expression of a gene may be overexpressed (high expression) or underexpressed (low expression) as compared to a reference (e.g., a normal cell, control cell, biological sample, a given patient population or with an internal control gene).

Differential levels may be assessed by evaluating the expression levels of one or more markers in one or more samples from an individual. The expression profile of a sample may be compared to the expression levels of a reference (e.g., reference sample). In some embodiments, the sample is a sample containing tissue sample or blood sample (leukocytes). The expression profile of a sample may be compared to the expression of levels of a reference (e.g., reference sample) for a pre-defined gene set. See e.g., Chaussabel et al. *Immunity* 29:150-164 (2008), Bennett et al. *J. Exp. Med.* 197(6):711-723 (2003), or Baechler E C et al., *PNAS* 100(5): 2610-5 (2003). Gene Set Enrichment Analysis (GSEA) may be used to convert the gene expression data into gene set-expression profiles (signatures).

In some embodiments, Gene Set Enrichment Analysis (GSEA) is performed by i) ranking genes in a data set, e.g., gene expression profiles of a DNA microarray analysis, based on their correlation to a chosen phenotype; ii) identifying all members of the gene set; and iii) calculating an Enrichment Score (ES), which can be a Normalized Enrichment Score (NES), representing the difference between the observed rankings and those that would be expected given a random distribution. After calculating the ES/NES, the method randomizes the sample labels and calculates the ES/NES for the gene set based on the random distribution. This process is repeated multiple times to create a distribution of randomized ES scores. Observed ES/NES scores that significantly outperform the randomized ES/NES scores are considered significant, thereby indicating that the given gene set is deregulated, i.e., up- or downregulated or differentially expressed, between cells having a certain biological phenotype. Software to perform GSEA is freely available online on the world wide web at broad.mit.edu/gsea/msigdb/index.jsp.

Numerous alternative bioinformatics approaches have been developed to assess gene set expression profiles using gene expression profiling data. Methods include but are not limited to those described in Segal, E. et al. *Nat. Genet.* 34:66-176 (2003); Segal, E. et al. *Nat. Genet.* 36:1090-1098 (2004); Barry, W. T. et al. *Bioinformatics* 21:1943-1949 (2005); Tian, L. et al. *Proc Nat'l Acad Sci USA* 102:13544-13549 (2005); Novak B A and Jain A N. *Bioinformatics* 22:233-41 (2006); Maglietta R et al. *Bioinformatics* 23:2063-72 (2007); Bussemaker H J, *BMC Bioinformatics* 8 Suppl 6:S6 (2007).

In some embodiments, the expression level and/or differential level of a marker of interest in a sample is greater than about any of 1.25×, 1.5×, 1.75×, 2×, 3×, 4×, 5×, 6×, 7×, 8×, 9×, 10×, 25×, 50×, or 100× higher or lower than the expression level in reference. In some embodiments, the expression level and/or differential expression in a sample is between about any of 1.25× and 100×, 1.25× and 50×, 1.5× and 100×, 1.5× and 50×, 2× and 100×, 2× and 50×, 1.25× and 10×, 1.5× and 10×, 2× and 10× higher or lower than the expression level in a reference. In some embodiments, the expression level of a marker in a sample from a subject (e.g., individual selected for treatment, individual identified as likely to respond to treatment, or an individual identified as responsive to treatment) is at least 1.25×, 1.5×, 1.75×, 2×, 3×, 4×, 5×, 6×, 7×, 8×, 9×, 10×, 25×, 50×, or 100× higher than the expression level in a reference sample from a normal subject. In some embodiments, the expression level of a marker in a sample from a subject (e.g., individual selected for treatment, individual identified as likely to respond to treatment, or an individual identified as responsive to treatment) is at least 1×, 1.5×, 2×, 2.5×, 3×, 4×, 5×, 6×, 7×, 8×, 9×, 10×, 25×, 50×, or 100× higher than the mean plus standard deviation of the expression level in reference samples from a normal population.

In another embodiment, the expression level of a marker of interest in a sample may be decreased or increased by at least about a 20%, 25%, 30%, 35%, 40%, 50%, 60%, 70%, 80%, 90% or 100%, compared to expression level in a reference.

In some embodiments, the markers are expressed at statistically significant differential levels, underexpressed or overexpressed, the sample versus the reference. In some embodiments, statistical significance is determined at a p-value of 0.1 or less, 0.05 or less, or 0.01 or less. In some embodiments, the p-value is between about any of 0.01 and 0.05 or 0.01 and 0.1. In some embodiments, the p-values are corrected for multiple comparisons. In some embodiments, multiple comparisons are corrected for using Bonferroni correction. In some embodiments, p-values are determined using permutation approaches, which are well known to those in the art. Permutation tests include randomization tests, re-randomization tests, exact tests, the jackknife, the bootstrap and other resampling schemes. In some embodiments, the threshold criterion comprises a correlation value. In some embodiments, the correlation value is r. In some embodiments, r is greater than or equal to about any of 0.95, 0.90, 0.85, 0.80, 0.75, 0.70, 0.65, 0.60, 0.55, 0.50, 0.45, 0.40, 0.35, 0.30 or 0.25.

Expression levels may be measured at the mRNA level and/or the protein level. In some embodiments, the measured expression level of the marker gene is normalized. For example, expression level is normalized against a gene the expression level of which does not change (or does not change significantly) among different samples. In some embodiments, expression levels of one or more housekeeping genes (genes that codes for proteins whose activities are essential for the maintenance of cell function) are used for normalization. These genes are typically similarly expressed in all cell types. Housekeeping genes include, without limitation, ribosomal protein L19 (NP_000972), UBC (Ubiquitin C), glyceraldehyde-3-phosphate dehydrogenase (GAPDH), Cyp1, albumin, actins (e.g., β-actin), tubulins, cyclophilin, hypoxantine phosphoribosyltransferase (HRPT), ribosomal protein L32 (NP_001007075), and ribosomal protein/genes 28S (e.g., Q9Y399) and 18S.

Differential expression and/or expression levels may be determined at the time of starting treatment or during treatment. In some embodiments, "at the time of starting treatment" or "baseline" is about any of six months, three months, second months, one month, or days prior to the treatment. In some embodiments, "at the time of starting treatment" is immediately prior to or coincidental with the first exposure to the treatment.

In some embodiments of any of the methods of treating, assessing responsiveness, identifying individuals, and/or selecting individuals for treatment, the disease is an autoimmune disease. In some embodiments, the autoimmune disease is characterized by serositis (pleuritis or pericarditis), oral ulcers (includes oral or nasopharyngeal ulcers), arthritis (nonerosive arthritis of two or more peripheral joints), photosensitivity, blood-hematologic disorder, hypocomplementemia, renal disorder, antinuclear antibody test positive, immunologic disorder, neurologic disorder (seizures or psychosis), malar rash, or discoid rash. In some embodiments, the autoimmune disease is associated with the skin, muscle tissue, and/or connective tissue. In some embodiment, the autoimmune disease is not evidenced in the individual by skin, muscle tissue, and/or connective tissue symptoms. In some embodiments, the autoimmune disease is systemic.

Autoimmune diseases include, without limitation, rheumatoid arthritis (RA), systemic lupus erythematosus (SLE), type I diabetes mellitus, type II diabetes mellitus, multiple sclerosis (MS), immune-mediated infertility such as premature ovarian failure, scleroderma, Sjogren's disease, vitiligo, alopecia (baldness), polyglandular failure, Grave's disease, hypothyroidism, polymyositis, pemphigus vulgaris, pemphigus foliaceus, inflammatory bowel disease including Crohn's disease and ulcerative colitis, autoimmune hepatitis including that associated with hepatitis B virus (HBV) and hepatitis C virus (HCV), hypopituitarism, graft-versus-host disease (GvHD), myocarditis, Addison's disease, autoimmune skin diseases, uveitis, pernicious anemia, and hypoparathyroidism.

Autoimmune diseases may also include, without limitation, Hashimoto's thyroiditis, Type I and Type II autoimmune polyglandular syndromes, paraneoplastic pemphigus, bullus pemphigoid, dermatitis herpetiformis, linear IgA disease, epidermolysis bullosa acquisita, erythema nodosa, pemphigoid gestationis, cicatricial pemphigoid, mixed essential cryoglobulinemia, chronic bullous disease of childhood, hemolytic anemia, thrombocytopenic purpura, Goodpasture's syndrome, autoimmune neutropenia, myasthenia gravis, Eaton-Lambert myasthenic syndrome, stiff-man syndrome, acute disseminated encephalomyelitis, Guillain-Barre syndrome, chronic inflammatory demyelinating polyradiculoneuropathy, multifocal motor neuropathy with conduction block, chronic neuropathy with monoclonal gammopathy, opsonoclonus-myoclonus syndrome, cerebellar degeneration, encephalomyelitis, retinopathy, primary biliary sclerosis, sclerosing cholangitis, gluten-sensitive enteropathy, ankylosing spondylitis, reactive arthritides, polymyositis/dermatomyositis, mixed connective tissue disease, Bechet's syndrome, psoriasis, polyarteritis nodosa, allergic anguitis and granulomatosis (Churg-Strauss disease), polyangiitis overlap syndrome, hypersensitivity vasculitis, Wegener's granulomatosis, temporal arteritis, Takayasu's arteritis, Kawasaki's disease, isolated vasculitis of the central nervous system, thromboangiutis obliterans, sarcoidosis, glomerulonephritis, and cryopathies. These conditions are well known in the medical arts and are described, for example, in Harrison's Principles of Internal Medicine, 14th ed., Fauci A S et al., eds., New York: McGraw-Hill, 1998.

The systemic disease SLE is characterized by the presence of antibodies to antigens that are abundant in nearly every cell, such as anti-chromatin antibodies, anti-splicesosome antibodies, anti-ribosome antibodies and anti-DNA antibodies. Consequently, the effects of SLE are seen in a variety of tissues, such as the skin and kidneys. Autoreactive T cells also play a role in SLE. For example, studies in a murine lupus model have shown that non-DNA nucleosomal antigens, e.g. histones, stimulate autoreactive T cells that can drive anti-DNA producing B cells. Increased serum levels of IFN-α has been observed in SLE patients and shown to correlate with both disease activity and severity, including fever and skin rashes, as well as essential markers associated with the disease process (e.g., anti-dsDNA antibody titers).

In some situations, peripheral tolerance to an autoantigen is lost (or broken) and an autoimmune response ensues. For example, in an animal model for EAE, activation of antigen presenting cells (APCs) through the immune receptor TLR9 or TLR4 was shown to break self-tolerance and result in the induction of EAE (Waldner et al. (2004) J. Clin. Invest. 113: 990-997).

In certain embodiments treating, assessing responsiveness, identifying individuals, and/or selecting individuals for treatment, the individual is at risk of developing an autoimmune disease. Individuals at risk of developing an autoimmune disease include, for example, those with a genetic or other predisposition toward developing an autoimmune disease. In humans, susceptibility to particular autoimmune diseases is associated with HLA type with some being linked most strongly with particular MHC class II alleles and others with particular MHC class I alleles. For example, ankylosing spondylitis, acute anterior uveitis, and juvenile rheumatoid arthritis are associated with HLA-B27, Goodpasture's syndrome and MS are associated with HLA-DR2, Grave's disease, myasthenia gravis and SLE are associated with HLA-DR3, rheumatoid arthritis and pemphigus vulgaris are associated with HLA-DR4 and Hashimoto's thyroiditis is associated with HLA-DR5. Other genetic predispositions to autoimmune diseases are known in the art and an individual can be examined for existence of such predispositions by assays and methods well known in the art. Accordingly, in some instances, an individual at risk of developing an autoimmune can be identified.

In some embodiments of any of the methods of treating, assessing responsiveness, identifying individuals, and/or selecting individuals for treatment, the TLR7 and/or TLR9 inhibitor (e.g., an IRP or IRC) is administered in an amount effective to delay or prevent the autoimmune disease. In some embodiments of any of the methods of treating, assessing responsiveness, identifying individuals, and/or selecting individuals for treatment, the TLR7 and/or TLR9 inhibitor (e.g., an IRP or IRC) is administered in an amount effective to suppress one or more symptoms of the autoimmune disease, including SLE and rheumatoid arthritis. In some embodiments, the TLR7 and/or TLR9 inhibitor (e.g., an IRP or IRC) used in combination therapy reduces the amount (dosage) of corticosteroid required and/or administered to treat the individual. In some embodiments, the amount (dosages of corticosteroid is reduced by about any of 10%, 20%, 30%, 40%, or 50%.

In some embodiments of any of the methods of treating, assessing responsiveness, identifying individuals, and/or selecting individuals for treatment, the disease is an inflammatory disease. In some embodiments, the inflammatory disease is a sterile inflammatory disease See e.g., Imaeda A B et al. *J Clin Invest.* 119(2):305-14 (2009), which is incorporated herein by reference in its entirety. In some embodiments, the inflammatory disease is a chronic inflammatory disease. In some embodiment, the inflammatory disease is inflammatory liver disease. In some embodiments, the inflammatory response inhibited and/or suppressed is drug-induced inflammation. In some embodiments, the drug-induced inflammation is drug-induced inflammation of the liver. In some embodiments, the inflammatory response inhibited and/or suppressed is infection-induced inflammation. In some embodiments, the disorder is an inflammatory liver disease or an inflammatory pancreatic disorder. Examples of inflammatory liver disorders include, for example, ligalactosemia, Alagille's syndrome, alpha 1-antitrypsin deficiency, neonatal hepatitis, tyrosinemia, hemorrhagic telangiectasia, Reye's syndrome, Wilson's disease, thalassemia, biliary atresia, chronic active hepatitis such as hepatitis A, hepatitis B, or hepatitis C, cancer of the liver, cirrhosis, type I glycogen storage disease, porphyria, hemochromatosis, primary sclerosing cholangitis, sarcoidosis, gallstones, fatty liver disease, alcoholic hepatitis, or alcoholic cirrhosis. Examples of inflammatory pancreatic disorders include, for example, pancreatitis or pancreatic cancer.

Administration of an IRP results in immunomodulation, decreasing levels of one or more immune response associated cytokines, which may result in a reduction of the inflammatory response. Immunoregulation of individuals with the unwanted immune response associated the described disorders results in a reduction or improvement in one or more of the symptoms of the disorder.

In some embodiments of any of the methods of treating, assessing responsiveness, identifying individuals, and/or selecting individuals for treatment, the disease is associated with chronic pathogen stimulation. In some embodiments, the disease is a chronic pathogen infection or disease. In some variations, administration of an immunoregulatory polynucleotide or an immunoregulatory compound suppresses chronic pathogen stimulation in the individual, including that associated with malaria and chronic viral infections.

In some embodiments of any of the methods of treating, assessing responsiveness, identifying individuals, and/or selecting individuals for treatment, the method comprises, comprising administering an effective amount of an immunoregulatory polynucleotide or an immunoregulatory compound described herein to an individual having an inflammatory disease or disorder. In some embodiments, administration of an immunoregulatory polynucleotide ameliorates one or more symptoms of the inflammatory disease or disorder.

In some embodiments of any of the methods of treating, assessing responsiveness, preventing and/or delaying development of a disease, the method comprises combination therapy. In some embodiments, methods are provided for ameliorating one or more symptoms of an autoimmune disease, comprising administering an effective amount of a TLR7 and/or TLR9 inhibitor described herein (e.g., an IRP or IRC) and an other therapeutic agent to an individual having an autoimmune disease. In some variations, the other therapeutic agent is a corticosteroid. In some variations, administration of the combination ameliorates one or more symptoms of the autoimmune disease, including SLE and rheumatoid arthritis. In some variations, the immunoregulatory polynucleotide or immunoregulatory compound used in combination therapy effective for suppressing a symptom of SLE comprises an immunoregulatory sequence of the TLR7 class or TLR9 class or TLR7/9 class.

In some embodiments of any of the methods of treating, assessing responsiveness, preventing and/or delaying development of a disease, the method comprises administering an effective amount of a TLR7 and/or TLR9 inhibitor (e.g., an IRP or IRC) and another therapeutic agent to an individual at risk of developing an autoimmune disease. In some variations, the other therapeutic agent is a corticosteroid. In some variations, administration of the combination prevents or delays development of one or more symptoms of the autoimmune disease, including SLE and rheumatoid arthritis. In some embodiments, the TLR7 and/or TLR9 inhibitor (e.g., an IRP or IRC) used in combination therapy reduces the amount (dosage) of corticosteroid required and/or administered to treat the individual. In some embodiments, the amount (dosages of corticosteroid is reduced by at least about 10%, 20%, 30%, 40%, 50%, 75% or 100%.

In some embodiments of any of the methods of treating, assessing responsiveness, preventing and/or delaying development of a disease, the inhibitor of TLR7 and/or inhibitor of TLR9 is an IRP and/or IRC, which comprises an IRS. In some embodiments of any of the methods of treating, assessing responsiveness, methods are provided for preventing or delaying development of a disease, the inhibitor of TLR7 and/or inhibitor of TLR9 is an immune regulatory oligonucleotide has the structure 5'-$N_m$—$N_3N_2N_1$CG$N^1N^2N^3$-$N^m$-3', wherein CG is an oligonucleotide motif that is CpG, C*pG, C*pG*, or CpG*, wherein C is cytosine, C* is a pyrimidine nucleotide derivative, G is guanosine, G* is a purine nucleotide derivative; $N_1$ is a nucleotide derivative or non-nucleotide linkage modification that suppresses the activity of the oligonucleotide motif, $N_2$-$N_3$ at each occurrence is a nucleotide, nucleotide derivator, or non-nucleotide linkage modification that suppresses the activity of the oligonucleotide motif, $N^1$-$N^3$ at each occurrence is a nucleotide or nucleotide derivative, and $N_m$ and $N^m$ at each occurrence is a nucleotide, nucleotide derivator, or non-nucleotide linkage. In some embodiments, the nonnucleotide linker linking the at least two oligonucleotides at their 3' ends or by a functionalized sugar or by a functionalized nucleobase is Glycerol (1,2,3-Propanetriol), 1,2,4, Butanetriol, 2(hydroxymethyl)-1,3-propanediol, 2-(hydroxymethyl)1,4-butanediol, 1,3,5-Pentanetriol, 1,1,1-Tris(hydroxymethyl)ethane, 1,1,1-Tris(hydroxymethyl)nitromethane, 1,1,1 Tris(hydroxymethyl)propane, 1,2,6-Hexanetriol, 3-Methyl-1,3,5-pentanetriol, 1,2,3-Heptanetriol, 2-Amino-2-(hydroxymethyl)-1,3-propanediol, N-[Tris(hydroxymethyl)methyl]acrylamide, cis-1,3,5-Cyclohexanetriol, Cis-1,3,5-Tri(hydroxymethyl)cyclohexane, 3,5-Di(hydroxymethyl)phenol, 1,3,5-Trihydroxylbenzene, 3,5-Di(hydroxymethyl)benzene, 1,3-Di(hydroxyethoxy)-2-hydroxyl-propane, 1,3-Di(hydroxypropoxy)-2-hydroxyl-propane, 2Deoxy-D-ribose, 1,2,4-Trihydroxyl-benzene, D-Galactoal, 1,6-anhydro-~-D-Glucose, 1,3,5-Tris(2-hydroxyethyl)-Cyanuric acid, Gallic acid, 3,5,7-Trihydroxyflavone, 4,6-Nitropyrogallol, Ethylene glycol, 1,3-Propanediol, 1,2-Propanediol, 1,4-Butanediol, 1,3-Butanediol, 2,3Butanedio-1,1,4-Butanediol, 1,5-Pentanediol, 2,4-Pentanediol, 1,6-Hexanediol, 1,2-Hexanedio-1, 1,5-Hexanediol, 2,5-Hexanediol, 1,7-Heptanediol, 1,8-Octanediol, 1,2-Octanediol, 1,9-Nonanediol, 1,12-Dodecanediol, Triethylene glycol, Tetraethylene glycol, 2-(1-Aminopropyl)1,3-propanediol, or 1,2-Dideoxyribose. In some embodiments, the normucleotide linker linking the at least two oligonucleotides at their 3' ends or by a functionalized sugar or by a functionalized nucleobase is Glycerol (1,2,3-Propanetriol).

In some embodiments, the inhibitor of TLR7 and/or inhibitor of TLR9 has the sequence TCTGACGTTCT (SEQ ID NO:169), TCTGACG$_1$TTCT (SEQ ID NO:170), TCTGACG$_4$TTCT (SEQ ID NO:171), TCTCTGACGTT (SEQ ID NO:172), TCTGUCGTTCT (SEQ ID NO:173), TCTGUCG$_1$TTCT (SEQ ID NO:174), TCTGACG$_4$TTCT (SEQ ID NO:175), TCTGACG$_1$TT (SEQ ID NO:176), UGUCG$_1$TTCT (SEQ ID NO:177), or UGACG$_1$TTCT (SEQ ID NO:178), wherein bold G, A or U=2'-OMe; G$_1$=7-deaza-dG; and G$_4$=araG. In some embodiments, oligonucleotides are linked at their 3' ends to a non nucleotide linker, wherein the inhibitor of TLR7 and/or inhibitor of TLR9 is 5'-(TCTGACGTTCT)$_2$X$_2$ (5'-SEQ ID NO:169-3'-X$_2$-3'-SEQ ID NO:169-5'), 5'-(TCTGACG$_1$TTCT)$_2$X$_2$ (5'-SEQ ID NO:170-3'-X$_2$-3'-SEQ ID NO:170-5'), 5'-(TCTGACG$_4$TTCT)$_2$X$_2$ (5'-SEQ ID NO:171-3'-X$_2$-3'-SEQ ID NO:171-5'), 5'-(TCTCTGACGTT)$_2$X$_2$ (5'-SEQ ID NO:172-3'-X$_2$-3'-SEQ ID NO:172-5'), 5'-(TCTGUCGTTCT)$_2$X$_2$ (5'-SEQ ID NO:173-3'-X$_2$-3'-SEQ ID NO:173-5'), 5'-(TCTGUCG$_1$TTCT)$_2$X$_2$ (5'-SEQ ID NO:174-3'-X$_2$-3'-SEQ ID NO:174-5'), 5'-(TCTGACG$_4$TTCT)$_2$X$_2$ (5'-SEQ ID NO:175-3'-X$_2$-3'-SEQ ID NO:175-5'), 5'-(TCTGACG$_1$TT)$_2$X$_2$ (5'-SEQ ID NO:176-3'-X$_2$-3'-SEQ ID NO:176-5'),5'-(UGUCG$_1$TTM2X$_2$ (5'-SEQ ID NO:177-3'-X$_2$-3'-SEQ ID NO:177-5'), or 5'-(UGACG$_1$TTCT)$_2$X$_2$ (5'-SEQ ID NO:178-3'-X$_2$-3'-SEQ ID NO: 178-5'), wherein bold G, A or U=2'-OMe; G$_1$=7-deaza-dG; X$_2$=glycerol linker, and G$_4$=araG. In some embodiments, the inhibitor of TLR7 and/or inhibitor of TLR9 is a immune regulatory oligonucleotide disclosed in U.S. Patent Application No. 2009/0060898, which is incorporated by reference in its entirety.

In some embodiments of any of the methods, the inhibitor of TLR7 and/or inhibitor of TLR9 is SEQ ID NO:161 (5'-CTATCTGACGTTCTCTGT-3'), SEQ ID NO:162 (5'-CTATCTGUCGTTCTCTGT-3'), SEQ ID NO:163 (5'-CTATCTGACRTTCTCTGT-3'), or SEQ ID NO:164 (5'-CTATCTGUCRTTCTCTGT-3'). In some embodiments, in particular, the inhibitor of TLR7 and/or inhibitor of TLR9 is SEQ ID NO:165 (5'-CTATCTGACGTTCTCTGT-3'), SEQ ID NO:166 (5'-CTATCTGUCGTTCTCTGT-3'), SEQ ID NO:167 (5'-CTATCTGACRTTCTCTGT-3'), SEQ ID NO:168 (5'-CTATCTGUCRTTCTCTGT-3'), wherein R is a 2'-deoxy-7-deazaguanosine linker and bold G/A/U is a 2'O-methyl-ribonucleotide modification.

In some embodiments of any of the methods, the inhibitor of TLR7 and/or inhibitor of TLR9 are as described in US Patent Application US 2005-0239733 which is herein incorporated by reference in its entirety. For example, the inhibitor may be a composition comprising an isolated immunoinhibitory nucleic acid molecule comprising a sequence $X_a CCN_1 N_2 N_3 Y_b N_4 GGGZ_c$ wherein: each C is cytidine or a derivative thereof, wherein at least one C is a cytidine derivative; each G is guanosine or a deaza derivative thereof; $X_a$ is any nucleotide sequence a nucleotides long, wherein a is an integer between 0-12, inclusive, and each nucleotide is selected independently of any other in $X_a$; $Y_b$ is any nucleotide sequence b nucleotides long, wherein b is an integer between 0-21, inclusive, and each nucleotide is selected independently of any other in $Y_b$; $Z_c$ is any nucleotide sequence c nucleotides long, wherein c is an integer between 0-12, inclusive, and each nucleotide is selected independently of any other in $Z_c$; and $N_1$, $N_2$, $N_3$, and $N_4$ are each independently any nucleotide. Additionally, for example, the inhibitor may be a composition comprising an isolated immunoinhibitory nucleic acid molecule comprising a sequence $X_a CCN_1 N_2 N_3 Y_b N_4 GGGZ_c$ wherein: each C of the CC motif is cytidine or a derivative thereof; each G is guanosine or a deaza derivative thereof; $X_a$ is T; $Y_b$ is any nucleotide sequence b nucleotides long, wherein b is an integer between 0-21, inclusive, and each nucleotide is selected independently of any other in $Y_b$; $Z_c$ is any nucleotide sequence c nucleotides long, wherein c is an integer between 0-12, inclusive, and each nucleotide is selected independently of any other in $Z_c$; and $N_1$, $N_2$, $N_3$, and $N_4$ are each independently any nucleotide; and, wherein $N_1 N_2$ is TG.

In some embodiments of any of the methods, the inhibitor of TLR7 and/or inhibitor of TLR9 are as described in WO 2004/047734 which is herein incorporated by reference in its entirety. For example, the inhibitor may be a composition comprising an isolated immunoinhibitory nucleic acid molecule comprising a sequence 5'-Purine-Pyrimidine-[X]-[Y]-Pyrmidine-Pyrmidine-3', wherein X and Y are any naturally occurring or synthetic nucleotides except that X and Y cannot be cytosine-guanine. Additionally, the inhibitor may be a composition comprising an isolated immunoinhibitory nucleic acid molecule having at least one cytosine to noncytosine substitution within a CpG motif, wherein the CpG motif is of the formula comprising a sequence 5'-Purine-Purine-CG-Pyrmidine-Pyrmidine-3', and wherein the cytosine to noncytosine substitution is within the CpG dinucleotide.

In some embodiments of any of the methods, the inhibitor of TLR7 and/or inhibitor of TLR9 are as described in US Patent Application US 2010-0130593 which is herein incorporated by reference in its entirety. For example, the inhibitor may be a pharmaceutical composition comprising: a) an immune modulatory nucleic acid comprising an immune modulatory sequence comprising i) a hexameric sequence 5'-purine-pyrimidine1-XY-pyrimidine-2-pyrimidine-3-3' wherein X and Y are any naturally occurring or synthetic nucleotide, except that: a. X and Y cannot be cytosine-guanine b. X and Y cannot be cytosine-cytosine when pyrimidine-2 is thymidine c. X and Y cannot be cytosine-thymidine when pyrimidine1 is cytosine; ii) a CC dinucleotide 5' to the hexameric sequence wherein the CC dinucleotide is between one to five nucleotides 5' of the hexameric sequence; and iii) a polyG region 3' of the hexameric sequence wherein the polyG comprises at least 3 contiguous Gs and is between two to five nucleotides 3' of the hexameric sequence wherein the immune modulatory sequence does not contain CG sequences and b) a pharmaceutically acceptable carrier. In other embodiments, the inhibitor may be the nucleotide sequence comprising 5'-CCATGTGGTTATGGGT-3' (SEQ ID NO:183).

As demonstrated herein, some IRP and/or IRC suppress both TLR9 dependent cell responses and TLR7 dependent cell responses. In some embodiments, methods are provided for inhibiting a TLR9 dependent immune response and a TLR7 dependent immune response in an individual, comprising administering to an individual an immunoregulatory polynucleotide or an immunoregulatory compound described herein in an amount sufficient to suppress TLR9 dependent cytokine production and TLR7 dependent cytokine production in the individual, wherein the IRP or IRC comprises an IRS of the TLR7/9 class. In some embodiments, the TLR7 and/or TLR9 dependent immune response is an innate immune response. In some embodiments, the TLR7 and/or TLR9 dependent immune response is an adaptive immune response. In some embodiments, the IRP and/or IRC comprise a modified IRS. In some embodiments, the IRP and/or IRC comprise an unmodified IRS. In some embodiments, the IPR and/or IRC comprise both modified and unmodified IRSs.

In some embodiments of any of the methods of treating, assessing responsiveness, preventing and/or delaying development of a disease, the compositions described herein inhibit a response of a B cell or a plasmacytoid dendritic cell. In some embodiments, immune responses inhibited by the compositions described herein include inhibition of cytokine production, such as IL-6 and/or IFN-α, by the cell, inhibition of cell maturation and/or inhibition of cell proliferation. In some embodiments, the compositions described herein inhibit a TLR9 dependent cell response, a TLR7 dependent cell response, and/or a TLR7/9 dependent cell response.

In some embodiments of any of the methods of treating, assessing responsiveness, preventing and/or delaying development of a disease, the IRS has a therapeutically acceptable safety profile and may for example, have a therapeutically acceptable histological profile including an acceptably low, if any, toxicity of the liver, kidney, pancreas, or other organs. It has been observed that IRS can exhibit toxicity to certain organs such as the liver, kidney and pancreas, and certain selected IRS provided herein can offer an improved safety profile that is unexpected and advantageous. In some embodiments, the therapeutically acceptable safety profile includes evaluation of toxicity, histological profile, and/or necrosis (for example, upon evaluation of the liver, kidneys and/or heart). In some embodiments, the IRS has a therapeutically acceptable toxicity. In some embodiments, the IRS has reduced toxicity compared to another IRS as illustrated in the examples provided herein. In some embodiments, the IRS has low or reduced toxicity (for example, compared to another IRS, e.g., SEQ ID NO:79 or SEQ ID NO:109). In some embodiments, the IRS has a therapeutically acceptable reduction in weight compared to the initial weight. In some embodiments, the IRS induces less than about any of 5%, 7.5%, 10%, 12.5, or 15% reduction in weight (for example as determined by the methods described in Example 3). In some embodiments, the IRS has a therapeutically acceptable histology profile. In some embodiments, the IRS has a better (e.g., lower score) histologic profile (for example, compared to another IRS, e.g., SEQ ID NO:79 or SEQ ID NO:109). In some embodiments, the IRS has a better and/or lower score) histologic profile upon evaluation of the liver, kidneys and heart, for example, as determined by the methods described in Example 3. In some embodiments, the IRS has a therapeutically acceptable necrosis score. In some embodiments, the IRS has reduced necrosis and/or better (e.g., lower) necrosis score (for example, compared to another IRS, e.g., SEQ ID NO:79 or SEQ ID NO:109). In some embodiments, the average necrosis score is less than or equal to about 3. In some embodiments, the average necrosis score is less than or equal to about 2. In some embodiments, the average necrosis score is less than or equal to about 1. In some embodiments, the average necrosis score is less than or equal to about 0. In some embodiments, the IRS has reduced renal and/or hepatocellular necrosis and/or better renal and/or hepatocellular necrosis score, for example, as determined by the methods described in Example 3. In some embodiments, the IRS is or comprises the IRS of one of the group consisting of SEQ ID NO:67, SEQ ID NO:68, SEQ ID NO:69, SEQ ID NO:71, SEQ ID NO:73, SEQ ID NO:78, SEQ ID NO:141, SEQ ID NO:143, and SEQ ID NO:144. In some embodiments, the IRS is selected from the group consisting of SEQ ID NO:73, SEQ ID NO:134, SEQ ID NO:143, and SEQ ID NO:144.

In some embodiments of any of the methods of treating, assessing responsiveness, preventing and/or delaying development of a disease, the IRS has a therapeutically acceptable pK. In some embodiments of any of the methods, the IRS has a PK profile or PK similar to another IRS as described in the examples. In some embodiments, the therapeutically acceptable safety profile is determined in mice or rats. In some embodiments, the therapeutically acceptable acceptable safety profile is determined in rats.

In some embodiments of any of the methods of treating, assessing responsiveness, preventing and/or delaying development of a disease, the IRS has a therapeutically acceptable B-cell activation. In some embodiments, the IRS has reduced or low B-cell-related toxicity. In some embodiments, the IRS has reduced or low B-cell activation. In some embodiments, the IRS has reduced or low B-cell activation compared to a positive control polynucleotide (e.g., an immunostimulatory sequence (ISS)), another IRS, or negative control polynucleotide and as illustrated in the examples provided herein. In some embodiments, the IRS does not induce B-cell activation to levels significantly higher than a control, e.g., a negative control polynucleotide. In some embodiments, the IRS induces B-cell activation to levels significantly lower than a control, e.g., a positive control polynucleotide (e.g., an ISS). In some embodiments, the IRS induces B-cell activation in a cell culture assay to levels less than about any of 5%, 10%, 15%, 20%, 25%, 30%, 35%, or 40% compared to a positive control polynucleotide (e.g., an ISS). In some embodiments, the IRS induces B-cell activation in a cell culture assay to levels less than about any of 5%, 10%, 15%, or 20% compared to a positive control polynucleotide (e.g., an ISS). In some embodiments, the B-cell activation of the IRS is normalized to a positive control polynucleotide (e.g., an ISS). In some embodiments normalized results of multiple IRS are compared. In some embodiments, the IRS induces B-cell activation to levels significantly lower than second IRS. In some embodiments, the IRS does not induce B-cell activation in a cell culture assay to levels significantly higher than media alone or to a negative control polynucleotide. In some embodiments, the IRS induces B-cell activation in a cell culture assay to levels significantly less than a positive control polynucleotide (e.g., an ISS). In some embodiments, the IRS shows concentration-dependent, B-cell activation, for example over the range of about 4000 nM to about 15 nM. In some embodiments, the IRS shows low concentration-dependent, B-cell activation, for example over the range of about 4000 nM to about 15 nM. In some embodiments, B-cell activation is determined as described in Example 1 and/or FIG. 1C.

Methods of treatment are provided comprising administering an IRS described herein in an effective amount to treat an individual with an an autoimmune or inflammatory disease characterized by activated B cells and/or PDCs, wherein the IRS lowers the production of TLR9 and/or TLR 7-dependent cytokines, for example IL-6, by B cells and/or PDCs to at least 15% or less compared to the B cells and/or PDCs of an untreated individual with the same autoimmune or inflammatory disease. In some embodiments, the method of treatment comprising administering an IRS described herein in an effective amount to treat an individual with an an autoimmune or inflammatory disease characterized by activated B cells and/or PDCs, wherein the IRS lowers the production of TLR9 and/or TLR 7-dependent cytokines, for example IL-6, by B cells and/or PDCs to at least 20%, 25%, 30%, 35%, 40%, 45%, or 50% or less compared to the B cells and/or PDCs of an untreated individual with the same autoimmune or inflammatory disease.

Additional methods of treatment are provided wherein an IRS described herein has a therapeutically acceptable half maximal inhibitory concentration (IC50) and/or IC90. In some embodiments, the IRS has a reduced IC50 and/or IC90 compared to another IRS (for example, SEQ ID NO:42, SEQ ID NO:79, or SEQ ID NO:109), as illustrated in the examples provided herein (for example, but not limited to, SEQ ID NO:73, SEQ ID NO:134, SEQ ID NO:143. or SEQ ID NO:144). In some embodiments the dosage of IRS required to inhibit TLR-7 and/or TLR-9-dependent cytokine production is less when compared to the dosage required by another IRS as illustrated in the examples provided herein (for example, but not limited to, SEQ ID NO:73, SEQ ID NO:134, SEQ ID NO:143 or SEQ ID NO:144).

Determination of Differential Levels

Differential levels may be determined based on a sample (e.g., sample from the individual or reference sample). In some embodiments, the sample is a biological sample. In some embodiments, the biological sample is a biological fluid sample or a biological tissue sample. In some embodiments of any of the methods, differential levels are determined in skin tissue, blood sample, or other biological sample. In some embodiments, the blood sample may include, for example, platelets, lymphocytes, polymorphonuclear cells, macrophages, and erythrocytes. In some embodiments, differential levels are determined in a skin tissue biopsy.

To practice this method, for example, the sample is an individual's sample containing tissue or fluid. Sample nucleic acid for use in the above-described methods can be obtained from any cell type or tissue of a subject. For example, a subject's bodily fluid (e.g. blood) can be obtained by known techniques (e.g., venipuncture). Alternatively, tests can be performed on dry samples (e.g., hair or skin). The samples may be fresh or frozen. In some embodiments, the sample is fixed and embedded in paraffin or the like.

In some embodiments, the method comprises isolating a sample containing the genetic material to be tested. In some embodiments, the methods comprise determining differential levels in situ. Accordingly, the methods of this application are not to be limited to requiring isolation of the genetic material prior to analysis.

These methods to identify expression levels are not limited by the technique that is used to identify the expression level of the biomarker. Nucleic acid (e.g., RNA or DNA) or protein levels of the gene of interest can be measured. Methods for measuring gene expression and/or determining sequence for detection of polymorphism are well known in the art and include, but are not limited to, immunological assays, nuclease protection assays, northern blots, in situ hybridization, ELISA, reverse transcriptase Polymerase Chain Reaction (RT-PCR), Real-Time Polymerase Chain Reaction, expressed sequence tag (EST) sequencing, cDNA microarray hybridization or gene chip analysis, subtractive cloning, Serial Analysis of Gene Expression (SAGE), Massively Parallel Signature Sequencing (MPSS), Sequencing-By-Synthesis (SBS), aptamer-based assays, western blot, enzyme immunoassays, and Luminex Patform utilizing color. See, e.g., in Ausubel et al. eds., 1995, Current Protocols In Molecular Biology, Units 2 (Northern Blotting), 4 (Southern Blotting), 15 (Immunoblotting) and 18 (PCR Analysis). Diagnostic procedures can also be performed in situ directly upon tissue sections (fixed and/or frozen) of individual's tissue obtained from biopsies or resections.

Microarray technology utilizes nucleic acid hybridization techniques and computing technology to evaluate the mRNA expression profile of thousands of genes within a single experiment. See, e.g., WO 01/75166 published Oct. 11, 2001; U.S. Pat. No. 5,700,637, U.S. Pat. No. 5,445,934, U.S. Pat. No. 5,807,522, Lockart, Nat. Biotech., 14:1675-1680 (1996); Cheung, V. G. et al., Nat. Gen. 21(Suppl):15-19 (1999). DNA microarrays are miniature arrays containing gene fragments that are either synthesized directly onto or spotted onto glass or other substrates. Thousands of genes are usually represented in a single array. A typical microarray experiment involves the following steps: 1) preparation of fluorescently labeled target from RNA isolated from the sample, 2) hybridization of the labeled target to the microarray, 3) washing, staining, and scanning of the array, 4) analysis of the scanned image and 5) generation of gene expression profiles. Currently two main types of DNA microarrays are being used: oligonucleotide (usually 25 to 70 mers) arrays and gene expression arrays containing PCR products prepared from cDNAs. In forming an array, oligonucleotides can be either prefabricated and spotted to the surface or directly synthesized on to the surface (in situ). The Affymetrix GeneChip® system (e.g., GeneChip® Human Genome U133 Plus 2.0 array from Affymetrix, Inc. (catalog no. 900470)) is commercially available and may be used for measuring gene expression levels.

Amplification of polynucleotides includes methods such as PCR, ligation amplification (or ligase chain reaction, LCR) and amplification methods. These methods are known and widely practiced in the art.). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified. In some embodiments, expression of one or more biomarkers may be assayed by RT-PCR. In some embodiments, the RT-PCR may be quantitative RT-PCR (qRT-PCR). In some embodiments, the RT-PCR is real-time RT-PCR. In some embodiments, the RT-PCR is quantitative real-time RT-PCR. In some embodiments, the real-time RT-PCR may be performed using TaqMan® chemistry (Applied Biosystems). In some embodiments, the real-time RT-PCR may be performed using TaqMan® chemistry (Applied Biosystems) and the ABI Prism® 7700 Sequence Detection System (Applied Biosystems). See, e.g., Overbergh, L. et al., J. Biomol. Tech. 14(1): 33-43 (2003).

Reagents and hardware for conducting PCR are commercially available. Primers useful to amplify sequences from a particular gene region are preferably complementary to, and hybridize specifically to sequences in the target region or in its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments is known in the art.

In other embodiments of the invention, gene expression is determined by analysis of expressed protein in a cell by use of one or more antibodies specific for one or more epitopes of individual gene products (proteins), or proteolytic fragments thereof, in the cell. The cell can be derived from various sources, as described herein, including but not limited to cell lines, bodily fluids, xenografts and biopsies. Detection methodologies suitable for use in the practice of the invention include, but are not limited to, immunohistochemistry of cell containing samples or tissue, enzyme linked immunosorbent assays (ELISAs) including antibody sandwich assays of cell containing tissues or blood samples, mass spectroscopy, and immuno-PCR. In some embodiments, analyzing protein content comprises assessing proteomic patterns, such as by mass spectrometry, chromatography, capillary electrophoresis, immunohistochemistry or 2-D gel electrophoresis. See, e.g., Latterich M. et al. Eur J. Cancer. 44:2737-41 (2008); Conrotto P. Exp Oncol. 30:171-80 (2008). In other embodiments, reverse-phase protein lysate microarrays are used. See Paweletz, C. P., et al., Oncogene 20:1981-1989 (2001).

Compositions of the Invention

Immunoregulatory polynucleotides (IRPs) and immunoregulatory compounds (IRCs) are provided herein. Provided herein are also IRPs and IRCs for use in any of the methods described herein. Each IRP and IRC described herein comprises at least one immunoregulatory sequence (IRS). An IRP or IRC comprising an IRS may be single stranded or double stranded DNA, as well as single or double-stranded RNA. An IRP or IRC comprising an IRS may be linear, may be circular or include circular portions and/or may include a hairpin loop. IRPs and IRCs used in the invention can comprise one or more ribonucleotides (containing ribose as the only or principal sugar component) and/or deoxyribonucleotides (containing deoxyribose as the principal sugar component). The heterocyclic bases, or nucleic acid bases, which are incorporated in the IRP can be the naturally-occurring principal purine and pyrimidine bases, (namely uracil, thymine, cytosine, adenine and guanine).

As is clearly conveyed herein, it is understood that, with respect to formulae described herein, any and all parameters are independently selected. For example, if $x=0-2$, y may be independently selected regardless of the values of x (or any other selectable parameter in a formula).

In certain embodiments of any of the compositions provided herein, one or more nucleotides comprise a modification. In certain embodiments, the modification is 2'-sugar modification. In certain embodiments, the 2'-sugar modification is a 2'-O-methyl sugar modification or a 2'-O-methoxyethyl sugar modification. In certain embodiments of any of the methods or compositions provided herein, the polynucleotide is comprised of all 2'-deoxyribo polynucleotides. In certain embodiments of any of the methods or compositions provided herein, the polynucleotide is a 2'-deoxyribo polynucleotide and a 2'-sugar modification chimeric sequence. In certain embodiments of any of the methods or compositions provided herein, the polynucleotide is a 2'-deoxyribo polynucleotide and a 2'-O-methyl sugar polynucleotide chimeric sequence. In certain embodiments of any of the methods or compositions provided herein, the polynucleotide is a 2'-deoxyribo polynucleotide and a 2'-O-methoxyethyl sugar polynucleotide chimeric sequence. In certain embodiments of any of the methods or compositions provided herein, the polynucleotide has at least one nucleotide comprising a modified phosphate linkage. In certain embodiments of any of the methods or compositions provided herein, the polynucleotide comprises only phosphorothioate linkages.

In certain embodiments of any of the compositions provided herein that contain the formula: 5'-$S_1S_2S_3S_4$-3', wherein $S_1$, $S_2$, $S_3$, and $S_4$ are independently G, I, or 7-deaza-G, the nucleotides are all deoxyribonucleotides. In certain embodiments of any of the methods or compositions provided herein that contain the formula: 5'-$S_1S_2S_3S_4$-3', wherein $S_1$, $S_2$, $S_3$, and $S_4$ are independently G, I, or 7-deaza-G, the nucleotides are all 2'-deoxyribonucleotides. For instance, for methods and compositions wherein the TLR7 and/or TLR9 inhibitor is a polynucleotide comprising the nucleotide sequence of the formula: R$\gamma$JGCK$\alpha$GIGGL$\beta$-3' (SEQ ID NO:146), wherein each R, K, and L is a nucleotide, J is U or T, $\gamma$ is an integer from about 0 to 10, $\alpha$ is an integer from about 1 to about 20, and $\beta$ is an integer from about 1 to about 20, each nucleotide in the GIGG portion of the sequence is a 2'-deoxyribonucleotide (e.g., G is 2'-deoxyguanosine and I is 2'-deoxyinosine).

Provided herein are IRSs and IRCs for use in any of the methods described herein. In some embodiments, the IRS includes at least one TGC trinucleotide sequence at or near the 5' end of the polynucleotide (i.e., 5'-TGC) and/or a nucleotide sequence of the formula: 5'-$S_1S_2S_3S_4$-3', wherein $S_1$, $S_2$, $S_3$, and $S_4$ are independently G or a molecule that is capable of preventing G-tetrad formation and/or preventing Hoogsteen base pairing. In some embodiments, the TGC trinucleotide sequence is about any of 0, 1, 2, 3, 4, 5, 6, 7, 8, 9, or 10 nucleotides from the 5' end of the polynucleotide. In some embodiments, the TGC trinucleotide sequence is less than about any of 1, 2, 3, 4, 5, 6, 7, 8, 9, or 10 nucleotides from the 5' end of the polynucleotide. In some embodiments, $S_1$, $S_2$, $S_3$, and $S_4$ are G. In some instances, all of $S_1$, $S_2$, $S_3$, and $S_4$ are not G. Accordingly, the IRP or IRC does not comprise a 5'-GGGG-3' sequence. In some embodiments, $S_1$, $S_2$, $S_3$, and $S_4$ are G, I or 7-deaza G, the nucleotides are all deoxyribonucleotides. In some embodiments, polynucleotide comprising a nucleotide sequence of the formula: 5'-GIGG-3'. In some embodiments, an IRP or IRC is particularly effective when used in the single-stranded form. In some embodiments, an IRP or IRC is particularly effective when made with a phosphothioate backbone. In some embodiments, the IRP or IRC does not comprise a CG (does not comprise an unmethylated CpG). In some embodiments, the IRP or IRC is not an antisense oligonucleotide.

Provided herein are IRSs, wherein the IRS is a polynucleotide consisting of a nucleotide sequence of the formula: 5'-$R_\gamma$JGC$N_z$-3' (SEQ ID NO:147), wherein each R is a nucleotide, $\gamma$ is an integer from about 0 to 10, J is U or T, each N is a nucleotide, and z is an integer from about 1 to about 1000. For example, a polynucleotide consisting of a nucleotide sequence of the formula: 5'-$R_\gamma$JGC$N_z$-3' (SEQ ID NO:147), wherein each R is a nucleotide, $\gamma$ is an integer from about 0 to 10, J is U or T, each N is a nucleotide, and z is an integer from about 1 to about 100. In some embodiments, the polynucleotide, such as 5'-$R_\gamma$JGC$N_z$-3' (SEQ ID NO:147), further comprises another nucleotide sequence 5'-JGC-3', wherein J is U or T. For example, the polynucleotide comprises the sequence 5'-TGCTGC-3'.

In some embodiments, the polynucleotide, such as 5'-$R_\gamma$JGC$N_z$-3' (SEQ ID NO:147), further comprises a nucleotide sequence of the formula: 5'-$S_1S_2S_3S_4$-3', wherein $S_1$, $S_2$, $S_3$, and $S_4$ are independently G or a molecule that is capable of preventing G-tetrad formation and/or preventing Hoogsteen base pairing. For example, the polynucleotide consists of a nucleotide sequence of the formula: 5'-$R_\gamma$JGCK$_\alpha$$S_1S_2S_3S_4L_\beta$-3' (SEQ ID NO:148), wherein each R, K, and L is a nucleotide, $\gamma$ is an integer from about 0 to 10, J is U or T, $S_1$, $S_2$, $S_3$, and $S_4$ are independently G or a molecule that is capable of preventing G-tetrad formation and/or preventing Hoogsteen base pairing, $\alpha$ is an integer from about 1 to about 20, and $\beta$ is an integer from about 1 to about 20. In some embodiments, the molecule that is capable of preventing G-tetrad formation and/or preventing Hoogsteen base pairing disrupts or prevents formation of tetrameric/quadruplex structure of G-quadruplexes. In some embodiments, the molecule that is capable of preventing G-tetrad formation and/or preventing Hoogsteen base pairing is a nucleotide or derivative thereof. Examples of molecules that are capable of preventing G-tetrad formation and/or preventing Hoogsteen base pairing included, but are not limited to, 1,7-deaza-dG, 7-deaza-2'-deoxyxanthosine, 7-deaza-8-aza-2'-deoxyguanosine, 2'-deoxynebularine, isodeoxyguanosine, 8-oxo-2'-deoxyguanosine. In some embodiments, at least one, two, three, or four of $S_1$, $S_2$, $S_3$, and $S_4$ are molecules that are capable of preventing G-tetrad formation and/or preventing Hoogsteen base pairing. In some embodiments, at least one, two, three, or four of $S_1$, $S_2$, $S_3$, and $S_4$ are I. In some embodiments, at least one, two, three, or four of $S_1$, $S_2$, $S_3$, and $S_4$ are 7-deaza-dG. In some embodiments, at least one, two, three, or four of $S_1$, $S_2$, $S_3$, and $S_4$ are G. In some embodiments, $S_1$, $S_2$, $S_3$, and $S_4$ are G. In some embodiments, polynucleotide comprising a nucleotide sequence of the formula: 5'-GIGG-3'. In some embodiments, $S_1$, $S_2$, $S_3$, and $S_4$ are not modified and/or not further modified. In some embodiments, an IRS may comprise a sequence of the formula: $X_1$ $S_1S_2S_3S_4X_2X_3$ (SEQ ID NO:149) wherein $X_1$, $X_2$, and $X_3$ are nucleotides, provided that if $X_1$=C or A, then $X_2X_3$ is not AA. In some embodiments, an IRS may comprise a sequence of the formula SEQ ID NO:149 wherein $X_1$ is C or A. In some embodiments, an IRS may comprise a sequence of the formula: $X_1S_1S_2S_3S_4X_2X_3$ (SEQ ID NO:150) wherein $X_1$, $X_2$, and $X_3$ are nucleotides, provided that if $X_1$=C or A, then $X_2X_3$ is not AA, and wherein $X_1$ is C or A.

In some embodiments, $\gamma$ is about any of 0, 1, 2, 3, 4, 5, 6, 7, 8, 9, or 10. In some embodiments, $\gamma$ is 0 (the 5'-JGC-3' is a nucleotide sequence at the 5' end of the polynucleotide). In some embodiments, $\gamma$ is between about any of 0 to 7, 0 to 5, or 0 to 3.

In some embodiments, z is an integer of any of about between about 1 to about 750, between about 1 to about 500, between about 1 to about 250, between about 1 to about 200, between about 1 to about 150, between about 1 to about 125, between about 1 to about 100, between about 1 to about 75, between about 1 to about 50, between about 1 to about 25, between about 1 to about 20, between about 1 to about 15, between about 1 to about 10, or between about 1 to about 5. In some variation, z is an integer between about 1 to about 100. In some embodiments, z is an integer between 1 and 100. In some embodiments, z is an integer less than any of about 200, about 175, about 150, about 125, about 100, about 75, about 50, about 40, about 30, about 25, about 20, about 15 or about 10. In some embodiments, z is an integer less than 100. In some embodiments, z is an integer greater than any of about 1, about 2, about 3, about 4, about 5, about 10, about 15, or about 20.

In some embodiments, α and/or β is an integer of any of about between about 1 to about 20, between about 1 to about 15, between about 1 to about 10, or between about 1 to about 5. In some embodiments, α and/or β is an integer less than any of about 18, about 15 or about 10. In some embodiments, z is an integer less than 100. In some embodiments, α and/or β is an integer greater than any of about 1, about 2, about 3, about 4, about 5, about 10, about 15, or about 20.

Provided herein are also IRSs, wherein the IRS is a polynucleotide comprising a nucleotide sequence of the formula: 5'-$S_1S_2S_3S_4$-3', wherein $S_1$, $S_2$, $S_3$, and $S_4$ are independently G or a molecule that is capable of preventing G-tetrad formation and/or preventing Hoogsteen base pairing. In some embodiments, the polynucleotides comprising a nucleotide sequence of the formula: 5'-$K_p\ S_1S_2S_3S_4Q_r$-3' (SEQ ID NO:151), wherein each K and Q is a nucleotide, p and r is an integer from about 0 to about 500, and $S_1$, $S_2$, $S_3$, and $S_4$ are independently G or a molecule that is capable of preventing G-tetrad formation and/or preventing Hoogsteen base pairing. In some embodiments, the molecule that is capable of preventing G-tetrad formation and/or preventing Hoogsteen base pairing disrupts or prevents formation of tetrameric/quadruplex structure of G-quadruplexes. In some embodiments, the molecule that is capable of preventing G-tetrad formation and/or preventing Hoogsteen base pairing is a nucleotide or derivative thereof. In some embodiments, at least one, two, three, or four of $S_1$, $S_2$, $S_3$, and $S_4$ are molecules that are capable of preventing G-tetrad formation and/or preventing Hoogsteen base pairing. In some embodiments, at least one, two, three, or four of $S_1$, $S_2$, $S_3$, and $S_4$ are I. In some embodiments, at least one, two, three, or four of $S_1$, $S_2$, $S_3$, and $S_4$ are 7-deaza-dG. In some embodiments, at least one, two, three, or four of $S_1$, $S_2$, $S_3$, and $S_4$ are G. In some embodiments, $S_1$, $S_2$, $S_3$, and $S_4$ are G. In some embodiments, polynucleotide comprising a nucleotide sequence of the formula: 5'-GIGG-3'. In some embodiments, $S_1$, $S_2$, $S_3$, and $S_4$ are not modified and/or not further modified. The nucleotide sequence of the formula: 5'-$S_1S_2S_3S_4$-3' can be found anywhere in the polynucleotide sequence. In some variations, the nucleotide sequence of the formula: 5'-$S_1S_2S_3S_4$-3' is found internally in the polynucleotide sequence, i.e., not at the 5' end or 3' end of the nucleotide sequence. In some embodiments, wherein the TLR7 and/or TLR9 inhibitor is a polynucleotide comprising the nucleotide sequence of the formula: RγJGCKαGIGGLβ-3' (SEQ ID NO:146), wherein each R, K, and L is a nucleotide, J is U or T, γ is an integer from about 0 to 10, α is an integer from about 1 to about 20, and β is an integer from about 1 to about 20. In exemplary embodiments, the polynucleotide comprises or consists of a nucleotide sequence selected from the group consisting of SEQ ID NO:73, SEQ ID NO:134, SEQ ID NO:143, and SEQ ID NO:144.

In some embodiments, p and/or r is an integer of any of about between about 1 to about 750, between about 1 to about 500, between about 1 to about 250, between about 1 to about 200, between about 1 to about 150, between about 1 to about 125, between about 1 to about 100, between about 1 to about 75, between about 1 to about 50, between about 1 to about 25, between about 1 to about 20, between about 1 to about 15, between about 1 to about 10, or between about 1 to about 5. In some variation, p and/or r is an integer between about 1 to about 50. In some embodiments, r is an integer between 1 and 50. In some embodiments, p and/or r is an integer less than any of about 200, about 175, about 150, about 125, about 100, about 75, about 50, about 40, about 30, about 25, about 20, about 15 or about 10. In some embodiments, r is an integer less than 50. In some embodiments, r is an integer greater than any of about 1, about 2, about 3, about 4, about 5, about 10, about 15, or about 20.

In some embodiments, the polynucleotide further comprises at least one trinucleotide sequence 5'-JGC-3', J is U or T. In some embodiments, the 5'-JGC-3' is about 0-10 nucleotides from the 5' end IRS and/or IRP. The 5'-JGC-3' may be between about any of 0-7, 0-5, 0-3, or 0-2 nucleotides from the 5' end of the IRS and/or IRP. In some embodiments, the 5'-JGC-3' is a 5'-TGC or 5'-UGC nucleotide sequence at the 5' end of the polynucleotide.

For example, provided herein are IRSs, wherein the IRS consists of a sequence of the formula 5'-EζJGCFθTCCTGGAS$_1$S$_2$S$_3$S$_4$TT3φ-3' (SEQ ID NO:152), wherein each E, F, and 3 are a nucleotide, ζ, θ, and φ are an integer from about 0 to 10, J is U or T, $S_1$, $S_2$, $S_3$, and $S_4$ are independently G or a molecule that is capable of preventing G-tetrad formation and/or preventing Hoogsteen base pairing. In some embodiments, ζ, θ, and φ are about any of 0, 1, 2, 3, 4, 5, 6, 7, 8, 9, or 10. In some embodiments, the molecule that is capable of preventing G-tetrad formation and/or preventing Hoogsteen base pairing disrupts or prevents formation of tetrameric/quadruplex structure of G-quadruplexes. In some embodiments, the molecule that is capable of preventing G-tetrad formation and/or preventing Hoogsteen base pairing is a nucleotide or derivative thereof. In some embodiments, at least one, two, three, or four of $S_1$, $S_2$, $S_3$, and $S_4$ are molecules that are capable of preventing G-tetrad formation and/or preventing Hoogsteen base pairing. In some embodiments, at least one, two, three, or four of $S_1$, $S_2$, $S_3$, and $S_4$ are I. In some embodiments, at least one, two, three, or four of $S_1$, $S_2$, $S_3$, and $S_4$ are 7-deaza-dG. In some embodiments, at least one, two, three, or four of $S_1$, $S_2$, $S_3$, and $S_4$ are G. In some embodiments, $S_1$, $S_2$, $S_3$, and $S_4$ are G. In some embodiments, $S_1$, $S_2$, $S_3$, and $S_4$ are not modified and/or not further modified. The nucleotide sequence of the formula: 5'-$S_1S_2S_3S_4$-3' can be found any where in the polynucleotide sequence.

For example, the IRS is a polynucleotide consisting of one of the following sequences:

```
5'-TCCTAACGGGGAAGT-3';         (SEQ ID NO: 1)

5'-TCCTAAGGGGAAGT-3';          (SEQ ID NO: 2)

5'-TCCTAACGGGGTTGT-3';         (SEQ ID NO: 3)
```

-continued

```
                                       (SEQ ID NO: 4)
5'-TCCTAACGGGGCTGT-3';

(SEQ ID NO: 5)
5'-TCCTCAAGGGGCTGT-3';

(SEQ ID NO: 6)
5'-TCCTCAAGGGGTTGT-3';

(SEQ ID NO: 7)
5'-TCCTCATGGGGTTGT-3';

(SEQ ID NO: 8)
5'-TCCTGGAGGGGTTGT-3';

(SEQ ID NO: 9)
5'-TCCTGGAGGGGCTGT-3';

(SEQ ID NO: 10)
5'-TCCTGGAGGGGCCAT-3';

(SEQ ID NO: 11)
5'-TCCTGGAGGGGTCAT-3';

(SEQ ID NO: 12)
5'-TCCGGAAGGGGAAGT-3';

(SEQ ID NO: 13)
5'-TCCGGAAGGGGTTGT-3'

(SEQ ID NO: 14)
5'-TGACTGTAGGCGGGGAAGATGA-3';

(SEQ ID NO: 15)
5'-GAGCAAGCTGGACCTTCCAT-3';

(Z' = 7-deaza-dG; SEQ ID NO: 16)
5'-CCTCAAGCTTGAGZ'GG-3';

(SEQ ID NO: 17)
5'-TGCTTGCAAGCTTGCAAGCA-3'

(SEQ ID NO: 18)
5'-TGCTTGCAAGCTTGCAAG-3';

(SEQ ID NO: 19)
5'-TGCTTGCAAGCTTGCA-3';

(SEQ ID NO: 20)
5'-GCTTGCAAGCTTGCAAGCA-3';

(SEQ ID NO: 21)
5'-CTTGCAAGCTTGCAAGCA-3';

(SEQ ID NO: 22)
5'-TTGCAAGCTTGCAAGCA-3';

(SEQ ID NO: 23)
5'-TGCTTGCAAGCTAGCAAGCA-3';

(SEQ ID NO: 24)
5'-TGCTTGCAAGCTTGCTAGCA-3';

(SEQ ID NO: 25)
5'-TGCTTGACAGCTTGACAGCA-3';

(SEQ ID NO: 26)
5'-TGCTTAGCAGCTATGCAGCA-3';

(SEQ ID NO: 27)
5'-TGCAAGCAAGCTAGCAAGCA-3'.

(SEQ ID NO: 28)
5'-TGCAAGCTTGCAAGCTTG CAA GCT T-3'

(SEQ ID NO: 29)
5'-TGCTGCAAGCTTGCAGAT GAT-3';

(SEQ ID NO: 30)
5'-TGCTTGCAAGCTTGCAAGC-3';

(SEQ ID NO: 31)
5'-TGCAAGCTTGCAAGCTTGCAAT-3';

(SEQ ID NO: 32)
5'-TGCTTGCAAGCTTG-3';

(SEQ ID NO: 33)
5'-AGCTTGCAAGCTTGCAAGCA-3';

(SEQ ID NO: 34)
5'-TACTTGCAAGCTTGCAAGCA-3';

(SEQ ID NO: 35)
5'-TGATTGCAAGCTTGCAAGCA-3';

(SEQ ID NO: 36)
5'-AAATTGCAAGCTTGCAAGCA-3';

(SEQ ID NO: 37)
5'-TGCTGGAGGGGTTGT-3';

(SEQ ID NO: 38)
5'-AAATTGACAGCTTGACAGCA-3';

(SEQ ID NO: 39)
5'-TGATTGACAGCTTGACAGCA-3';

(SEQ ID NO: 40)
5'-TGATTGACAGATTGACAGCA-3';

(SEQ ID NO: 41)
5'-TGATTGACAGATTGACAGAC-3';

(SEQ ID NO: 42)
5'-TGCTCCTGGAGGGGTTGT-3';

(SEQ ID NO: 43)
5'-TGCTTGTCCTGGAGGGGTTGT-3';

(SEQ ID NO: 44)
5'-TGCTTGACATCCTGGAGGGGTTGT-3';

(SEQ ID NO: 45)
5'-TGCTTGACAGCTTGACAGTCCTGGAGGGGTTGT-3';

(SEQ ID NO: 46)
5'-TGCTTGACAGCTTGATCCTGGAGGGGTTGT-3';

(SEQ ID NO: 47)
5'-TGCTTGACAGCTTCCTGGAGGGGTTGT-3';

(SEQ ID NO: 48)
5'-TGCTTGACAGCTTGCTCCTGGAGGGGTTGT-3';

(SEQ ID NO: 49)
5'-TGCTTGACAGCTTGCTTGTCCTGGAGGGGTTGT-3';

(SEQ ID NO: 50)
5'-TGCTTGACAGCTTGACAGCATCCTGGAGGGGTTGT-3';

(SEQ ID NO: 51)
5'-TGCTTGACAGCTTGACAGCATCCTGGAGGGGTTGT-3';

(SEQ ID NO: 52)
5'-TGCTTGACAGCTTGACAGCATCCTGGAGGGGT-3';

(SEQ ID NO: 53)
5'-TGCTTGACAGCTTGACAGCATCCTGGAGGGG-3';

(SEQ ID NO: 54)
5'-TGCTTGCAAGCTTGCTCCTGGAGGGGTTGT-3';

(SEQ ID NO: 55)
5'-TGCTTGCAAGCTTCCTGGAGGGGTTGT-3';

(SEQ ID NO: 56)
5'-TGCTTGCAAGCTTGCAAGCATCCTGGAGGGGTTGT-3';

(SEQ ID NO: 57)
5'-TGC TGC TCC TGG AGG GGT TGT TTG T-3'
```

-continued

5'-TGC TGC TCC TTG AGG GGT TGT TTG T-3' (SEQ ID NO: 58)

5'-TGC TGC TCC TTG AGG GGT TGT-3'; (SEQ ID NO: 59)

5'-TGC TGC TCC TGG AGG GGT TGT-3'; (SEQ ID NO: 60)

5'-TGC TGC TCC TTG AGZ' GGT TGT TTG T-3', wherein Z' = 7-deaza-dG (SEQ ID NO: 61)

5'-TGC TGC TCC TTG AGI GGT TGT TTG T-3', wherein I = deoxy-inosine (SEQ ID NO: 62)

5'TGC TCC TTG AGI GGT TGT TTG T-3', wherein I = deoxy-inosine; (SEQ ID NO: 63)

5'-TGC TTG TCC TGG AGI GGT TGT AAG T-3', wherein I = deoxy-inosine; (SEQ ID NO: 64)

5'-TGC TTG TCC TGG AGI GGT GTT GT-3', wherein I = deoxy-inosine; (SEQ ID NO: 65)

5'-TGC TGC TCC TGG AGI GGT TGT-3', wherein I = deoxy-inosine; (SEQ ID NO: 66)

5'-TGC TCC TGG AGG GGT TGT AAG T-3'; (SEQ ID NO: 67)

5'-TGC TCC TGG AGG GGT TGT AAG TTT GT-3'; (SEQ ID NO: 68)

5'-TGC TCC TTG AGG GGT TGT-3'; (SEQ ID NO: 69)

5'-TGC TGC TCC TTG AGI GGT TGT-3', wherein I = deoxy-inosine; (SEQ ID NO: 70)

5'-TGC TCC TTG AGI GGT TGT-3', wherein I = deoxy-inosine; (SEQ ID NO: 71)

5'-TGC TGC TCC TTG AGI GGT GTT GT-3', wherein I = deoxy-inosine; (SEQ ID NO: 72)

5'-TGC TCC TGG AGI GGT TGT-3', wherein I = deoxy-inosine; (SEQ ID NO: 73)

5'-TGC TTG TCC TGG AGI GGT TGT-3', wherein I = deoxy-inosine; (SEQ ID NO: 74)

5'-TGC TGC TCC TTG AGI GGT TGT AAG T-3', wherein I = deoxy-inosine; (SEQ ID NO: 75)

5'-TGC TGC TCC TGG AGG GGT TGT TTG T-3'; (SEQ ID NO: 76)

5'-TGC TGC TCC TGG AGI GGT TGT AAG T-3', wherein I = deoxy-inosine; and (SEQ ID NO: 78)

5'-TGC TGC TCC TGG AGI GGT GTT GT-3', wherein I = deoxy-inosine. (SEQ ID NO: 79)

The invention further provides IRPs and IRCs comprising at least one modified IRS. A modified IRS comprises at least one modified nucleotide. The modification of at least one nucleotide may be a modified base, a modified sugar, and/or a modified phosphate. In some embodiments, the modification of at least one nucleotide may be a naturally-occurring modification. In some embodiments, the modification of at least one nucleotide may be a synthetic modification. In some embodiments, the modifications may be imparted before or after assembly of the polynucleotide. In some embodiments, the modified nucleotide comprises one or more modified nucleosides. "Modified nucleotide" or "modified nucleosides" are herein defined as being synonymous with nucleoside or nucleotide "analogs."

In some embodiments, one or more nucleotide of the IRS polynucleotide comprises at least one modification (e.g., nucleotide comprises a modification). In some embodiments, one or more nucleotides of the polynucleotide comprise a modification (e.g., sequence Nz comprises a modification). In some embodiments, the at least one modification is the same modification for multiple or each nucleotide. In some embodiments, every nucleotide of the polynucleotide is modified and the modification is a 2'-O-methyl sugar modification (i.e., nucleotide N consists of a modification and the modification is a 2'-O-methyl sugar modification). In some embodiments, the at least one modification comprises more than one different type of modifications of nucleotides.

In some embodiments, the modification of at least one nucleotide comprises a modified base. As used herein, the term "modified base" is synonymous with "base analog", for example, "modified cytosine" is synonymous with "cytosine analog." Examples of base modifications include, but are not limited to, addition of an electron-withdrawing moiety to C-5 and/or C-6 of a cytosine of the IRP. Preferably, the electron-withdrawing moiety is a halogen, e.g., 5-bromocytosine, 5-chlorocytosine, 5-fluorocytosine, 5-iodocytosine. In some embodiments, the base modifications include, but are not limited to, addition of an electron-withdrawing moiety to C-5 and/or C-6 of a uracil of the immunoregulatory polynucleotide. Preferably, the electron-withdrawing moiety is a halogen. Such modified uracils can include, but are not limited to, 5-bromouracil, 5-chlorouracil, 5-fluorouracil, 5-iodouracil. In some embodiments, the base modifications include the addition of one or more thiol groups to the base including, but not limited to, 6-thio-guanine, 4-thio-thymine, and 4-thio-uracil. In some embodiments, the base modifications include, but are not limited to, N4-ethylcytosine, 7-deazaguanine, and 5-hydroxycytosine. See, for example, Kandimalla et al. (2001) *Bioorg. Med. Chem.* 9:807-813. In some embodiments, the IRS may include 2'-deoxyuridine and/or 2-amino-2'-deoxyadenosine. In some embodiments, the modified base comprises a methylation modification. In some embodiments, the methylation modification comprises a 5'-methyl-cytosine modification. In some embodiments, an IRS comprises multiple base modifications. In some embodiments, the base modifications are the same. In some embodiments, the base modifications are different. In some embodiments, the IRS comprises any of about 1, about 2, about 3, about 4, about 5 different base modifications. Base modifications may also be made and combined with any phosphate modification and/or sugar modification in the preparation of a modified IRS.

In some embodiments, the modification of at least one nucleotide comprises a modified phosphate. In some embodiments, the modified phosphate is a phosphodiester linkage modification. For example, phosphate modifications may include, but are not limited to, methyl phosphonate, phosphorothioate, phosphoamidates, phosphoramidate (bridging or non-bridging), phosphotriester and phosphorodithioate and may be used in any combination. In some embodiments, the modified phosphate is a 3'-terminal internucleotide phosphodiester linkage modification. For example, the 3'-terminal internucleotide phosphodiester linkage modifications include, but are not limited to, an alkyl or aryl phosphotriester, an alkyl or aryl phosphonate, a hydrogen phosphonate, a phosphoramidate, and/or a phosphoroselenate linkage modification. In some embodiments, the 3'-terminal internucleotide phophodiester linkage modification is a phosphoramidate modification. In some embodiments, the modified phosphate includes, but is not limited to, embodiments wherein the phosphate is replaced by P(O)S ("thioate"), P(S)S ("dithioate"), (O)NR2 ('amidate'), P(O)R, P(R)OR', CO or CH2 ("formacetal"), in which each R or R' is independently H or substituted or unsubstituted alkyl (1-20 C), optionally containing an ether (—O—) linkage, aryl, alkenyl, cycloaklyl, cycloalkenyl, or araldyl.

In some embodiments, an IRS may comprise at least one nucleotide comprising at least phosphothioate backbone linkage. In some embodiments, polynucleotides of the IRS comprise only phosphorothioate backbones. In some embodiments, polynucleotides of the IRS comprise only phosphodiester backbones. In some embodiments, an IRS may comprise a combination of phosphate linkages in the phosphate backbone including, but not limited to, a combination of phosphodiester and phosphorothioate linkages.

The IRS can contain phosphate-modified polynucleotides, some of which may stabilize the polynucleotide. Accordingly, some embodiments include a stabilized immunoregulatory polynucleotides. In some embodiments, an IRS comprises multiple phosphate modifications. In some embodiments, the phosphate modifications are the same. In some embodiments, the phosphate modifications are different. In some embodiments, the IRS comprises any of about 1, about 2, about 3, about 4, about 5 different phosphate modifications. Phosphate modifications may also be made and combined with any base modification and/or sugar modification in the preparation of a modified IRS.

In some embodiments, the modification of at least one nucleotide comprises a modified sugar. IRPs used in the invention may comprise one or more modified sugars or sugar analogs. Thus, in addition to ribose and deoxyribose, the sugar moiety can be pentose, deoxypentose, hexose, deoxyhexose, glucose, arabinose, xylose, lyxose, and a sugar "analog" cyclopentyl group. The sugar can be in pyranosyl or in a furanosyl form. In the IRS, the sugar moiety is preferably the furanoside of ribose, deoxyribose, arabinose or 2'-O-alkylribose. In some embodiments, the sugar can be attached to the respective heterocyclic bases either in α or β anomeric configuration. In some embodiments, the sugar is modified by replacing a hydroxyl group ordinarily present. The hydroxyl group ordinarily present in the sugar may be replaced by, for example, but not limited to, phosphonate groups or phosphate groups. The 5' and 3' terminal hydroxyl group can additionally be phosphorylated or substituted with amines or organic capping group moieties of from 1 to 20 carbon atoms. In some embodiments, the modified sugars are 2'-sugar modifications including, but are not limited to, 2'-alkoxy-RNA analogs, 2'-amino-RNA analogs, 2'-fluoro-DNA, and 2'-alkoxy- or amino-RNA/DNA chimeras. In some embodiments, the modified sugars include, but are not limited to, 2'-O-methyl-, 2'-O-allyl, or 2'-azido-sugar modification. In some embodiments, the 2'-modified sugar is 2'-O-methyl sugar modification. In some embodiments, the 2'-modified sugar is 2'-O-methoxyethyl sugar modification. For example, a sugar modification in the IRS includes, but is not limited to, 2'-O-methyl-uridine, 2'-O-methyl-thymidine, 2'-O-methyl-adenine, 2'-O-methyl-guanine, or 2'-O-methyl-cytidine. In some embodiments, the sugar-modified nucleotide comprises one or more sugar modified nucleosides. The preparation of these sugars or sugar analogs and the respective "nucleosides" wherein such sugars or analogs are attached to a heterocyclic base (nucleic acid base) per se is known, and need not be described here, except to the extent such preparation can pertain to any specific example. In some embodiments, an IRS comprises multiple sugar modifications. In some embodiments, the sugar modifications are the same. In some embodiments, the sugar modifications are different. In some embodiments, the IRS comprises any of about 1, about 2, about 3, about 4, about 5 different sugar modifications. Sugar modifications may also be made and combined with any base modification and/or phosphate modification in the preparation of a modified IRS.

Any of the modified polynucleotides described herein may comprise a modification any where in the polynucleotide sequence. In some embodiments, the modification is a modification of the nucleotides at or near the 5' end of the polynucleotide sequence. In some embodiments, at the 5' end of the polynucleotide sequence, about any of 1, 2, 3, 4, 5, 6, 7, 8, 9, or 10 nucleotides are modified. In some embodiments, at the 5' end of the polynucleotide sequence, at least about any of 1, 2, 3, 4, 5, 6, 7, 8, 9, or 10 nucleotides are modified. In some embodiments, the modification is a modification of the nucleotides at or near the 3' end of the polynucleotide sequence. In some embodiments, at the 3' end of the polynucleotide sequence, about any of 1, 2, 3, 4, 5, 6, 7, 8, 9, or 10 nucleotides are modified. In some embodiments, at the 3' end of the polynucleotide sequence, at least about any of 1, 2, 3, 4, 5, 6, 7, 8, 9, or 10 nucleotides are modified. In some embodiments, both the nucleotides at or near the 5' end of the polynucleotide sequence and the nucleotides at or near the 3' end of the polynucleotide sequence are modified. In some embodiments, at the 5' end of the polynucleotide sequence and at the 3' end of the polynucleotide sequence, about any of 1, 2, 3, 4, 5, 6, 7, 8, 9, or 10 nucleotides are modified. In some embodiments, at the 5' end of the polynucleotide sequence and at the 3' end of the polynucleotide sequence, at least about any of 1, 2, 3, 4, 5, 6, 7, 8, 9, or 10 nucleotides are modified.

In some embodiments, the nucleotide sequence of the formula: 5'-$R_yGCN_z$-3' (SEQ ID NO:147) is modified. The modification may be any described above, for example, a modified base, a modified sugar, a modified phosphate. In some embodiments, modification includes a 2'-sugar modification, a 3'-terminal internucleotide phosphodiester linkage modification, and/or a 5'-methyl-cytosine modification. In some embodiments, the modification may be a phosphate or termini modification. In some embodiments, the phosphate or termini modification may be a 3' terminal internucletide phosphodiester linkage modification. In some embodiments, the 3'-terminal internucleotide phosphodiester linkage modification is selected from the group consisting of an alkyl or aryl phosphotriester, alkyl or aryl phosphonate, hydrogen phosphonate, phosphoramidate, and phosphoroselenate linkage modification. In some embodiments, 3'-terminal internucleotide phosphodiester linkage modification is a phosphoramidate modification. In some embodiments, the modification may be a sugar modification. In some embodiments, the sugar modification is a 2'-sugar modification as described herein. In some embodiments, the 2'-sugar modification is a 2'-O-methyl sugar modification or 2'-O-methoxyethyl sugar modification. In some embodiments, the modification is a base modified, for example, a 5'-methyl-cytosine modification.

In some embodiments, the modified IRS is (SEQ ID NO:80) 5'-UGC UCC UGG AGG GGU UGU-3', wherein all nucleotides are modified with phosphoramidate modification, a phosphate modification). In some embodiments, the modified IRS is (SEQ ID NO:81) 5'-UGC UCC UGG AGG GGU UGU-3', wherein all cytosines are modified with a 5-methyl dC (M) modification, a base modification).

In some embodiments, the modified IRS is modified with a 2'-O-Me modification. In some embodiments, the modified IRS modified with a 2'-O-Me modification is any of:

(SEQ ID NO: 82)
5'-*UGC UCC UGG AGG GGU UGU*-3'

(SEQ ID NO: 83)
5'-*UGC* TCC TGG AGG GGT TGT-3';

(SEQ ID NO: 84)
5'-TGC TCC TGG AGG GG*U UGU*-3';

(SEQ ID NO: 85)
5'-*UGC* TCC TGG AGG GG*U UGU*-3';

(SEQ ID NO: 86)
5'-TGC TCC TGG A*GG GG*T TGT-3';

(SEQ ID NO: 87)
5'-*UGC* TTG TCC TGG AGG GGT TGT-3';

(SEQ ID NO: 88)
5'-TGC TCC TGG AGG GGA AGT *UUG U*-3';

(SEQ ID NO: 89)
5'-*UGC* TTG TCC TGG AGG GG*U UGU*-3';

(SEQ ID NO: 90)
5'-*UGC* TTG TCC TGG AGG GGA AGT *UUG U*-3';

(SEQ ID NO: 91)
5'-*UGC* TG TCC TGG AGG GGA AGT *UUG U*-3';

(SEQ ID NO: 92)
5'-*UGC* G TCC TGG AGG GGA AGT *UUG U*-3';

(SEQ ID NO: 93)
5'-*UGC* TTG TCC TGG AGG GG TG *UUG U*-3';

(SEQ ID NO: 94)
5'-*UGC* TG TCC TGG AGG GG TG *UUG U*-3';

(SEQ ID NO: 95)
5'-*UGC* G TCC TGG AGG GG TG *UUG U*-3';

(SEQ ID NO: 96)
5'-*UGC* TTG TCC TGG AGG GGT *UGU*-3';

(SEQ ID NO: 97)
5'-*UGC* TG TCC TGG AGG GGT *UGU*-3';

(SEQ ID NO: 98)
5'-*UGC* G TCC TGG AGG GGT *UGU*-3';

(SEQ ID NO: 99)
5'-*UGC* TTG TCC TGG AGG GGT TGT *UUG U*-3';

(SEQ ID NO: 100)
5'-*UGC* TTG TCC TGG AGG GGT T*GU UUG U*-3';

(SEQ ID NO: 101)
5'-*UGC* TGC TCC TGG AGG GGT TGT *UUG U*-3';

(SEQ ID NO: 102)
5'-*UGC* TGC TCC TTG AGG GGT TGT *UUG U*-3';

(SEQ ID NO: 103)
5'-*UGC* TGC TCC TTG AGG GGT G*UU GU*-3';

(SEQ ID NO: 104)
5'-*UGC* TGC TCC TTG AGG GGT T*GU UUG U*-3';

(SEQ ID NO: 105)
5'-*UGC UGC UCC UUG AGA GGU UGU*-3';

(SEQ ID NO: 106)
5'-*UGC* TGC TCC TGG AGG GGT T*GU UUG U*-3';

(SEQ ID NO: 107)
5'-*UGC* TGC TCC TTG AGG GGT TGT T-3';
or (SEQ ID NO: 108)
5'-*UGC* TGC TCC TGG AGG GGT TGT T-3';

(SEQ ID NO: 109)
5'-*UGC* TGC TCC TTG AGI GGT TGT T-3',
wherein I = deoxy-inosine;

(SEQ ID NO: 110)
5'-*UGC* TGC TCC TTG AGZ' GGT TGT T-3',
wherein Z' = 7-deaza-dG (SEQ ID NO: 111)
5'-*UGC* TGC TCC TTG AGI GGT TGT TTG-3',
wherein I = deoxy-inosine;

(SEQ ID NO: 112)
5'-*UGC* TGC TCC TTG AGI GGT TGT TT-3',
wherein I = deoxy-inosine;

(SEQ ID NO: 113)
5'-*UGC* TGC TCC TTG AGI GGT TGT T-3',
wherein I = deoxy-inosine;

(SEQ ID NO: 114)
5'-*UGC* TGC TCC TTG AGI GGT TGT-3',
wherein I = deoxy-inosine;

(SEQ ID NO: 115)
5'-*UGC* TGC TCC TTG AGI GGT T-3',
wherein I = deoxy-inosine;

(SEQ ID NO: 116)
5'-*UGC* TGC TCC TTG AGI GGT-3',
wherein I = deoxy-inosine;

(SEQ ID NO: 117)
5'-*UGC* TGC TCC TTG AGI GG-3',
wherein I = deoxy-inosine;

(SEQ ID NO: 118)
5'-*UGC* TGC TCC TTG AGI G-3',
wherein I = deoxy-inosine;

(SEQ ID NO: 119)
5'-*UGC* TGC TCC TTG AGI-3',
wherein I = deoxy-inosine;

(SEQ ID NO: 120)
5'-*GC* TGC TCC TTG AGI GGT TGT TTG T-3',
wherein I = deoxy-inosine;

(SEQ ID NO: 121)
5'-*C* TGC TCC TTG AGI GGT TGT TTG T-3',
wherein I = deoxy-inosine;

(SEQ ID NO: 122)
5'-*UGC* TGC TCC TTG AGI GGT TG-3',
wherein I = deoxy-inosine;

(SEQ ID NO: 123)
5'-*UGC* TTG TCC TGG AGI GGT TGT-3',
wherein I = deoxy-inosine;

(SEQ ID NO: 124)
5'-*UGC* TTG TCC TGG AGI GGT GTT GT-3',
wherein I = deoxy-inosine;

(SEQ ID NO: 125)
5'-*UGC* TGC TCC TGG AGI GGT TGT-3',
wherein I = deoxy-inosine;

(SEQ ID NO: 126)
5'-*UG*C TGC TCC TTG AGI GGT TGT-3',
wherein I = deoxy-inosine;

-continued

```
                                            (SEQ ID NO: 127)
5'-UGC TGC TCC TTG AGI GGT TGT-3',
wherein I = deoxy-inosine;

(SEQ ID NO: 128)
5'-UGC TGC TCC TTG AGI GGT GTT GT-3',
wherein I = deoxy-inosine;

(SEQ ID NO: 129)
5'-UGC TGC TCC TTG AGI GGT TGT AAG T-3',
wherein I = deoxy-inosine;

(SEQ ID NO: 130)
5'-UGC TGC TCC TGG AGI GGT TGT AAG T-3',
wherein I = deoxy-inosine;

(SEQ ID NO: 131)
5'-UGC TCC TGG AGG GGU UGU-3';

(SEQ ID NO: 132)
5'-UGC TGC TCC TGG AGI GGT GTT GT-3',
wherein I = deoxy-inosine;

(SEQ ID NO: 133)
5'-UGC-ddd-TCC TGG AGI GGT TGT-3',
wherein I = deoxy-inosine and d is diethyldithio-
dicarbonate;

(SEQ ID NO: 134)
5'-UGC CAA TCC TGG AGI GGT TGT-3',
wherein I = deoxy-inosine;

(SEQ ID NO: 135)
5'-UGC CAA TCC TGG AGI GGT GTT GT-3',
wherein I = deoxy-inosine;
``` wherein the bolded and italicized nucleotides are modified with a 2'-O-Me sugar modification.

Other exemplary examples of IRPs effective in suppressing TLR7 and/or TLR9 are found, for example, in PCT/US2005/030494 and PCT/US2008/012220, which is hereby incorporated by reference in its entirety.

In some embodiments of any of the IRSs, a uridine (U) nucleoside of the modified IRS may be substituted with a thymidine (T) nucleoside. In some embodiments, all uridine (U) nucleoside of the IRS may be substituted with a thymidine (T) nucleoside. In some embodiments of any of the IRS, a thymidine (T) nucleoside of the modified IRS may be substituted with a uridine (U) nucleoside. In some embodiments, all thymidine (T) nucleoside of the IRS may be substituted with a uridine (U) nucleoside. In some embodiments, the modified IRS may comprise both uridine (U) nucleosides and thymidine (T) nucleosides.

In some embodiments, an immunoregulatory polynucleotide is less than about any of the following lengths (in bases or base pairs): 10,000; 5,000; 2500; 2000; 1500; 1250; 1000; 750; 500; 300; 250; 200; 175; 150; 125; 100; 75; 60; 50; 40; 30; 25; 20; 15; 14; 13; 12; 11; 10; 9; 8; 7; 6; 5; 4. In some embodiments, an immunoregulatory polynucleotide is greater than about any of the following lengths (in bases or base pairs): 4; 5; 6, 7, 8, 9, 10; 11; 12; 13; 14; 15; 20; 25; 30; 40; 50; 60; 75; 100; 125; 150; 175; 200; 250; 300; 350; 400; 500; 750; 1000; 2000; 5000; 7500; 10000; 20000; 50000. Alternately, the immunoregulatory polynucleotide can be any of a range of sizes having an upper limit of 10,000; 5,000; 2500; 2000; 1500; 1250; 1000; 750; 500; 300; 250; 200; 175; 150; 125; 100; 75; 60; 50; 40; 30; 25; 20; 15; 14; 13; 12; 11; 10; 9; 8; 7; 6; 5; 4 and an independently selected lower limit of 4; 5; 6; 7; 8; 9; 10; 11; 12; 13; 14; 15; 20; 25; 30; 40; 50; 60; 75; 100; 125; 150; 175; 200; 250; 300; 350; 400; 500; 750; 1000; 2000; 5000; 7500, wherein the lower limit is less than the upper limit. In some embodiments, an IRP is preferably about 200 or less bases or base pairs in length.

As demonstrated herein, particular IRPs and IRCs comprising an IRS inhibit TLR-7 dependent cell responses and/or TLR9 dependent cell responses. In some embodiments, certain IRPs do not inhibit TLR4 dependent cell responses. In some embodiments, IRPs and/or IRCs comprising a modified IRS, as described herein, inhibits and/or suppresses a measurable immune response as measured in vitro, in vivo, and/or ex vivo. In some embodiments, the immune response is an innate immune response. In some embodiments, the immune response is an adaptive immune response.

As described herein, some IRSs are particularly effective in suppressing TLR9 dependent cell responses. Such IRSs include, but are not limited to, SEQ ID NO:1-14, 16, 37, 42-79, and 83-117, and 120-145.

As described herein, some IRSs are particularly effective in suppressing TLR7 dependent cell responses. Such IRSs include, but are not limited to, SEQ ID NO:17-36, 37, 42-79, 82-145.

As described herein, some IRSs are particularly effective in suppressing TLR7 dependent cell responses. Such IRSs include, but are not limited to, SEQ ID NO:42-79 and 83-117, and 120-145.

In some embodiments, the IRPs or IRCs comprise an IRS selected from the group consisting of SEQ ID NO:64-78, SEQ ID NO:123-135, and SEQ ID NO:141-145. In some embodiments, the IRS is or comprises the IRS of one of the group consisting of SEQ ID NO:67, SEQ ID NO:68, SEQ ID NO:69, SEQ ID NO:71, SEQ ID NO:73, SEQ ID NO:78, SEQ ID NO:141, SEQ ID NO:143, and SEQ ID NO:144. In some embodiments, the IRPs or IRCs comprise an IRS selected from the group consisting of SEQ ID NO:73, SEQ ID NO:134, SEQ ID NO:143, and SEQ ID NO:144.

In some embodiments of any of the IRS, the IRS has a therapeutically acceptable safety profile and may for example, have a therapeutically acceptable histological profile including an acceptably low, if any, toxicity of the liver, kidney, pancreas, or other organs. It has been observed that IRS can exhibit toxicity to certain organs such as the liver, kidney and pancreas, and certain selected IRS provided herein can offer an improved safety profile that is unexpected and advantageous. In some embodiments, the therapeutically acceptable safety profile includes evaluation of toxicity, histological profile, and/or necrosis (for example, upon evaluation of the liver, kidneys and/or heart). In some embodiments, the IRS has a therapeutically acceptable toxicity. In some embodiments, the IRS has reduced toxicity compared to another IRS as illustrated in the examples provided herein. In some embodiments, the IRS has low or reduced toxicity (for example, compared to another IRS, e.g., SEQ ID NO:79 or SEQ ID NO:109). In some embodiments, the IRS has a therapeutically acceptable reduction in weight compared to the initial weight. In some embodiments, the IRS induces less than about any of 5%, 7.5%, 10%, 12.5, or 15% reduction in weight (for example as determined by the methods described in Example 3). In some embodiments, the IRS has a therapeutically acceptable histology profile. In some embodiments, the IRS has a better (e.g., lower score) histologic profile (for example, compared to another IRS, e.g., SEQ ID NO:79 or SEQ ID NO:109). In some embodiments, the IRS has a better and/or lower score) histologic profile upon evaluation of the liver, kidneys and heart, for example, as determined by the methods described in Example 3. In some embodiments, the IRS has a therapeutically acceptable necrosis score. In some embodiments, the IRS has reduced necrosis and/or better (e.g., lower) necrosis score (for example, compared to another IRS, e.g., SEQ ID NO:79 or SEQ ID NO:109). In some embodiments, the average necrosis score is less than or equal to about 3. In some embodiments, the average necrosis score is less than or equal to about 2. In some embodiments, the average necrosis score is less than or equal to about 1. In some embodiments, the average necrosis score is less than or equal to about 0. In some embodiments, the IRS has reduced renal and/or hepatocellular necrosis and/or better renal and/or hepatocellular necrosis score, for example, as determined by the methods described in Example 3. In some embodiments, the IRS is or comprises the IRS of one of the group consisting of SEQ ID NO:67, SEQ ID NO:68, SEQ ID NO:69, SEQ ID NO:71, SEQ ID NO:73, SEQ ID NO:78, SEQ ID NO:141, SEQ ID NO:143, and SEQ ID NO:144. In some embodiments, the IRS is selected from the group consisting of SEQ ID NO:73, SEQ ID NO:134, SEQ ID NO:143, and SEQ ID NO:144.

In some embodiments of any of the IRS, the IRS has a therapeutically acceptable pK. In some embodiments of any of the methods, the IRS has a PK profile or PK similar to another IRS as described in the examples. In some embodiments, the therapeutically acceptable safety profile is determined in mice or rats. In some embodiments, the therapeutically acceptable acceptable safety profile is determined in rats.

In some embodiments of any of the IRS, the IRS has a therapeutically acceptable B-cell activation. In some embodiments, the IRS has reduced or low B-cell-related toxicity. In some embodiments, the IRS has reduced or low B-cell activation. In some embodiments, the IRS has reduced or low B-cell activation compared to a positive control polynucleotide (e.g., an immunostimulatory sequence (ISS)), another IRS, or negative control polynucleotide and as illustrated in the examples provided herein. In some embodiments, the IRS does not induce B-cell activation to levels significantly higher than a control, e.g., a negative control polynucleotide. In some embodiments, the IRS induces B-cell activation to levels significantly lower than a control, e.g., a positive control polynucleotide (e.g., an ISS). In some embodiments, the IRS induces B-cell activation in a cell culture assay to levels less than about any of 5%, 10%, 15%, 20%, 25%, 30%, 35%, or 40% compared to a positive control polynucleotide (e.g., an ISS). In some embodiments, the IRS induces B-cell activation in a cell culture assay to levels less than about any of 5%, 10%, 15%, or 20% compared to a positive control polynucleotide (e.g., an ISS). In some embodiments, the B-cell activation of the IRS is normalized to a positive control polynucleotide (e.g., an ISS). In some embodiments normalized results of multiple IRS are compared. In some embodiments, the IRS induces B-cell activation to levels significantly lower than a second IRS. In some embodiments, the IRS does not induce B-cell activation in a cell culture assay to levels significantly higher than media alone or to a negative control polynucleotide. In some embodiments, the IRS induces B-cell activation in a cell culture assay to levels significantly less than a positive control polynucleotide (e.g., an ISS). In some embodiments, the IRS shows concentration-dependent, B-cell activation, for example over the range of about 4000 nM to about 15 nM. In some embodiments, the IRS shows low concentration-dependent, B-cell activation, for example over the range of about 4000 nM to about 15 nM. In some embodiments, B-cell activation is determined as described in Example 1 and/or FIG. 1C.

Immunostimulatory nucleic acids and other stimulators of an innate immune response have been described in the art and their activity may be readily measured using standard assays which indicate various aspects of an innate immune response, such as cytokine secretion, antibody production, NK cell activation, B cell proliferation, T cell proliferation, dendritic cell maturation. See, e.g. Krieg et al. (1995) *Nature* 374:546-549; Yamamoto et al. (1992) *J. Immunol.* 148:4072-4076; Klinman et al. (1997) *J. Immunol.* 158:3635-3639; Pisetsky (1996) *J. Immunol.* 156:421-423; Roman et al. (1997) *Nature Med.* 3:849-854; Hemmi et al. (2000), Supra; Lee et al. (2003), Supra; WO 98/16247; WO 98/55495; WO 00/61151 and U.S. Pat. No. 6,225,292. Accordingly, these and other methods can be used to identify, test and/or confirm immunoregulatory sequences, polynucleotides and/or compounds. For example, the effect of IRP or IRC can be determined when cells or individuals in which an innate immune response has been stimulated are contacted with the IRP or IRC.

Immunoregulatory Compounds

Provided herein are also IRCs, which have immunoregulatory activity and comprise a nucleic acid moiety comprising an IRS, and IRCs for use in the methods described herein. In some embodiments, the IRC comprises a modified IRS. In some embodiments, the IRC comprises an unmodified IRS. In some embodiments, the IRC comprises both modified and unmodified IRS. IRCs provided herein contain one or more nucleic acid moieties and one or more non-nucleic acid spacer moieties. Compounds conforming to a variety of structural formulas are contemplated for use as IRCs, including the core structures described in formulas I-VII, below. Formulas I-III show core sequences for "linear IRCs." Formulas IV-VI show core sequences for "branched IRCs." Formula VII shows a core structure for "single-spacer IRCs."

In each formula provided herein, "N" designates a nucleic acid moiety (oriented in either a 5'-3' or 3'-5' orientation) and "S" designates a non-nucleic acid spacer moiety. A dash ("-") designates a covalent bond between a nucleic acid moiety and a non-nucleic acid spacer moiety. A double dash ("--") designates covalent bonds between a non-nucleic acid spacer moiety and at least 2 nucleic acid moieties. A triple dash ("---") designates covalent bonds between a non-nucleic acid spacer moiety and multiple (i.e., at least 3) nucleic acid moieties. Subscripts are used to designate differently positioned nucleic acid or non-nucleic acid spacer moieties. However, the use of subscripts to distinguish different nucleic acid moieties is not intended to indicate that the moieties necessarily have a different structure or sequence. Similarly, the use of subscripts to distinguish different spacer moieties is not intended to indicate that the moieties necessarily have different structures. For example, in formula II, infra, the nucleic acid moieties designated $N_1$ and $N_2$ can have the same or different sequences, and the spacer moieties designated $S_1$ and $S_2$ can have the same or different structures. Further, it is contemplated that additional chemical moieties (e.g., phosphate, mononucleotide, additional nucleic acid moieties, alkyl, amino, thio or disulfide groups or linking groups, and/ or spacer moieties) may be covalently bound at the termini of the core structures.

Linear IRCs have structures in which the non-nucleic acid spacer moieties in the core structure are covalently bound to no more than two nucleic acid moieties. Exemplary linear IRCs conform to the following formulas:

$$N_1\text{—}S_1\text{—}N_2 \qquad (I)$$

$$N_1\text{—}S_1\text{—}N_2\text{—}S_2\text{—}N_3 \qquad (II).$$

$$N_1\text{—}S_1\text{—}N_2\text{—}S_2\text{—}[N_v\text{—}S_v]_A \qquad (III)$$

where A is an integer between 1 and about 100 and $[N_v\text{—}S_v]$ indicates A additional iterations of nucleic acid moieties conjugated to non-nucleic acid spacer moieties. The subscript "v" indicates that N and S are independently selected in each iteration of "[$N_v$—$S_v$]." "A" is sometimes between 1 and about 10, sometimes between 1 and 3, sometimes exactly 1, 2, 3, 4 or 5. In some embodiments, A is an integer in a range defined by a lower limit of 1, 2, 3, 4, or 5, and an independently selected upper limit of 10, 20, 50 or 100 (e.g., between 3 and 10).

Exemplary linear IRCs include:

| | |
|---|---|
| $N_1$-HEG-$N_2$—OH | (Id. at) |
| $N_1$-HEG-$N_1$—$PO_4$ | (Ib) |
| $N_1$-HEG-$N_2$-HEG | (Ic) |
| HEG-$N_1$-HEG-$N_1$-HEG | (Id) |
| $N_1$-HEG-$N_2$-HEG-$N_1$ | (Ie) |
| $N_1$-HEG-$N_2$—(HEG)$_4$-$N_3$ | (If) |
| (N1)$_2$-glycerol-$N_1$-HEG-$N_1$ | (Ig) |
| $PO_4$—$N_1$-HEG-$N_2$ | (Ih) |
| $N_1$—(HEG)$_{15}$-T | (Ii) |
| $N_1$-HEG-T-HEG-T | (Ik) |
| $N_1$-HEG-$N_2$-TEG-$N_3$ | (IIa) | wherein HEG refers to hexa-(ethylene glycol). TEG refers to tetra-(ethylene glycol). $N_1$ and $N_2$; and $S_1$ and $S_2$ are independently selected in examples which do not contain —[$N_v$—$S_v$]$_A$. In some embodiments of any of the IRPs, the IRP is a 2'-deoxyribo polynucleotide sequence. In some embodiments of any of the IRPs, the IRP is a 2' deoxyribo polynucleotide and/or the 2'-O-Me sugar polynucleotide chimeric sequence. In some embodiments, the IRP has at least one nucleotide comprising a modified phosphate linkage. In some embodiments, IRP comprises only phosphorothioate linkages.

Preferred linear IRCs include:

```
                                         (SEQ ID NO: 136)
5'-TGCTTGCAAGCTTGCAAGCA-HEG-TCCTGGAGGGGTTGT-3';

(SEQ ID NO: 137)
5'-TGCTTGCAAGCTAGCAAGCA-HEG-TCCTGGAGGGGTTGT-3';

(SEQ ID NO: 138)
5'-TGCTTGCAAGCTTGCTAGCA-HEG-TCCTGGAGGGGTTGT-3';

(SEQ ID NO: 139)
5'-TGCTTGCAAGCTTGCTAGCA-HEG-TCCTGGAGZGGTTGT-3';

(SEQ ID NO: 140)
5'-TCCTGGAGGGGTTGT-HEG-TGCTTGCAAGCTTGCAAGCA-3';

(SEQ ID NO: 141)
5'-TGC TCC TGG AGG GGT TGT-HEG-HEG-3';

(SEQ ID NO: 142)
5'-UGC TTG TCC TGG AGI GGT TG-HEG-T-3';

(SEQ ID NO: 143)
5'-TGC TCC TGG AGI GGT TG-HEG-T-3';

(SEQ ID NO: 144)
5'-TGC TGC TCC TGG AGI GGT TG-HEG-T-3';

(SEQ ID NO: 145)
5'-UGC HEG TCC TGG AGI GGT TGT-3';

(SEQ ID NO: 77)
5'-UGC HEG TCC TGG AGI GGT GTT GT-3';
``` wherein the bolded and italicized nucleotides are modified with a 2'-O-Me sugar modification. In some embodiments one or more nucleotides of the polynucleotide comprises a modification. In some embodiments, the modification comprises at least one phosphorothioate backbone modification. In some embodiments, the polynucleotide comprises only phosphorothioate linkages. In some preferred embodiments, the modification comprises a 2'-sugar modification. In a subset of these embodiments, the 2'-sugar modification comprises a 2'-O-methyl sugar modification or a 2'-O-methoxy-ethyl sugar modification.

Branched IRCs comprise a multivalent spacer moiety ($S_p$) covalently bound to at least three (3) nucleic acid moieties. Exemplary branched IRCs are described according to the following formulas

| | |
|---|---|
| [$N_v$]$_A$---$S_p$ | (IV) |
| [$S_v$—$N_v$]$_A$---$S_p$ | (V) |
| ($S_1$—$N_1$)—$S_p$--($N_v$—$S_v$)$_A$ | (VI) | where $S_p$ is a multivalent spacer covalently bonded to the quantity "A" independently selected nucleic acid moieties $N_v$, $S_v$—$N_v$ (which comprises a spacer moiety covalently bound to a nucleic acid moiety). The terminal iteration of "[$S_v$—$N_v$]" or "[$N_v$—$S_v$]" may include only $N_v$. For formulas IV and V, A is at least 3. In various embodiments of formulas IV and V, A is an integer between 3 and 100 (inclusive), although A may be an integer in a range defined by a lower limit of about 3, 5, 10, 50, or 100 and an independently selected upper limit of about 5, 7, 10, 50, 100, 150, 200, 250, or 500, or alternately A may be greater than 500. For formula VI, A is at least 2, an integer in a range defined by a lower limit of 2, 5, 10, 50, or 100 and an independently selected upper limit of 5, 10, 50, 100, 150, 200, 250, or 500, or greater than 500.

Exemplary branched IRCs include:

| | |
|---|---|
| ($N_1$)$_2$-glycerol-$N_1$ | (IVa) |
| ($N^2$-HEG)$_2$-glycerol-$N_1$ | (IVb) |
| ($N_1$-HEG-$N_2$)$_2$-glycerol-$N_1$ | (IVc) |
| [($N_1$)$_2$-glycerol-$N_1$]$_2$-glycerol-$N_1$ | (IVd) |
| ($N_1$-HEG)$_2$-glycerol-HEG-$N_2$ | (IVe) |
| ($N_1$-HEG)$_2$-glycerol-$N_1$-TEG-$N_1$ | (VIa) | wherein HEG refers to hexa-(ethylene glycol). TEG refers to tetra-(ethylene glycol). In some embodiments of any of the IRPs, the IRP is a 2'-deoxyribo polynucleotide sequence. In some embodiments of any of the IRPs, the IRP is a 2' deoxyribo polynucleotide and/or the 2'-O-Me sugar polynucleotide chimeric sequence. In some embodiments, the IRP has at least one nucleotide comprising a modified phosphate linkage. In some embodiments, IRP comprises only phosphorothioate linkages.

Preferred branched IRCs include (5'-$N_1$-3'-HEG)$_2$-glycerol-HEG-5'-$N_1$-3' and (5'-$N_1$-3'-HEG)$_2$-glycerol-HEG-5'-$N_1$'. In some embodiments of any of the IRPs, the IRP is a 2'-deoxyribo polynucleotide sequence. In some embodiments of any of the IRPs, the IRP is a 2' deoxyribo polynucleotide and/or the 2'-O-Me sugar polynucleotide chimeric sequence. In some embodiments, the IRP has at least one nucleotide comprising a modified phosphate linkage. In some embodiments, IRP comprises only phosphorothioate linkages.

Single spacer IRCs comprise a structure in which there is a single nucleic acid moiety covalently conjugated to a single spacer moiety, i.e., $$N_1—S_1 \qquad\qquad (VII)$$

In a preferred variation $S_1$ has the structure of a multimer comprising smaller units (e.g., HEG, TEG, glycerol, 1'2'-dideoxyribose, C2 alkyl-C12 alkyl subunits, and the like), typically connected by an ester linkage (e.g., phosphodiester or phosphorothioate ester), e.g., as described infra. See, e.g., formula VIIa, infra. The multimer can be heteromeric or homomeric. In one variation, the spacer is a heteromer of monomeric units (e.g., HEG, TEG, glycerol, 1'2'-dideoxyribose, C2 alkyl to C12 alkyl linkers, and the like) linked by an ester linkage (e.g., phosphodiester or phosphorothioate ester). See, e.g., formula VIIb, infra.

Exemplary single spacer IRCs include:

$$N_1\text{-}(HEG)_{15} \qquad\qquad (VIIa)$$

$$N_1\text{-HEG-propyl-HEG-propyl-HEG} \qquad\qquad (VIIb)$$

wherein HEG refers to hexa-(ethylene glycol). In some embodiments of any of the IRPs, the IRP is a 2'-deoxyribo polynucleotide sequence. In some embodiments of any of the IRPs, the IRP is a 2' deoxyribo polynucleotide and/or the 2'-O-Me sugar polynucleotide chimeric sequence. In some embodiments, the IRP has at least one nucleotide comprising a modified phosphate linkage. In some embodiments, IRP comprises only phosphorothioate linkages.

In certain embodiments, the terminal structures of the IRC are covalently joined (e.g., nucleic acid moiety-to-nucleic acid moiety; spacer moiety-to-spacer moiety, or nucleic acid moiety-to-spacer moiety), resulting in a circular conformation.

IRCs for use in the immunoregulatory compositions provided herein include at least one nucleic acid moiety. The term "nucleic acid moiety," as used herein, refers to a nucleotide monomer (i.e., a mononucleotide) or polymer (i.e., comprising at least 2 contiguous nucleotides). As used herein, a nucleotide comprises (1) a purine or pyrimidine base linked to a sugar that is in an ester linkage to a phosphate group, or (2) an analog in which the base and/or sugar and/or phosphate ester are replaced by analogs, e.g., as described infra. In an IRC comprising more than one nucleic acid moiety, the nucleic acid moieties may be the same or different.

Nucleic acid moieties used in IRCs incorporated in the immunoregulatory compositions may comprise any of the IRS sequences disclosed herein and may additionally be sequences of six base pairs or less. It is contemplated that in an IRC comprising multiple nucleic acid moieties, the nucleic acid moieties can be the same or different lengths. In some embodiments where the IRC comprises more than one nucleic acid moiety, only one of the moieties need comprise the IRS. In some embodiments, the IRS is a modified IRS. In some embodiments, the IRS is an unmodified IRS.

It is contemplated that in an IRC comprising multiple nucleic acid moieties, the nucleic acid moieties can be the same or different. Accordingly, in various embodiments, IRCs incorporated into the immunoregulatory compositions comprise (a) nucleic acid moieties with the same sequence, (b) more than one iteration of a nucleic acid moiety, or (c) two or more different nucleic acid moieties. Additionally, a single nucleic acid moiety may comprise more than one IRS, which may be adjacent, overlapping, or separated by additional nucleotide bases within the nucleic acid moiety.

As described herein, some IRPs are particularly effective in suppressing TLR9 dependent cell responses and some IRPs are particularly effective in suppressing TLR7 dependent cell responses. Since an IRC may comprise more than one IRP, IRPs with various activities can be combined to create an IRC with a particular activity for a particular use.

In some instances, the combination of two IRPs in an IRC leads to an immunoregulatory activity of the IRC different from either of the IRPs alone.

The IRCs comprise one or more non-nucleic acid spacer moieties covalently bound to the nucleic acid moieties. For convenience, non-nucleic acid spacer moieties are sometimes referred to herein simply as "spacers" or "spacer moieties." Spacers are generally of molecular weight about 50 to about 50,000, typically from about 75 to about 5000, most often from about 75 to about 500, which are covalently bound, in various embodiments, to one, two, three, or more than three nucleic acid moieties. A variety of agents are suitable for connecting nucleic acid moieties. For example, a variety of compounds referred to in the scientific literature as "non-nucleic acid linkers," "non-nucleotidic linkers," or "valency platform molecules" may be used as spacers in an IRC. In certain embodiments, a spacer comprises multiple covalently connected subunits and may have a homopolymeric or heteropolymeric structure. It will be appreciated that mononucleotides and polynucleotides are not included in the definition of non-nucleic acid spacers, without which exclusion there would be no difference between nucleic acid moiety and an adjacent non-nucleic acid spacer moiety.

In certain embodiments, a spacer may comprise one or more abasic nucleotides (i.e., lacking a nucleotide base, but having the sugar and phosphate portions). Exemplary abasic nucleotides include 1'2'-dideoxyribose, 1'-deoxyribose, 1'-deoxyarabinose and polymers thereof.

Other suitable spacers comprise optionally substituted alkyl, optionally substituted polyglycol, optionally substituted polyamine, optionally substituted polyalcohol, optionally substituted polyamide, optionally substituted polyether, optionally substituted polyimine, optionally substituted polyphosphodiester (such as poly(1-phospho-3-propanol), and the like. Optional substituents include alcohol, alkoxy (such as methoxy, ethoxy, and propoxy), straight or branched chain alkyl (such as C1-C12 alkyl), amine, aminoalkyl (such as amino C1-C12 alkyl), phosphoramidite, phosphate, thiophosphate, hydrazide, hydrazine, halogen, (such as F, Cl, Br, or I), amide, alkylamide (such as amide C1-C12 alkyl), carboxylic acid, carboxylic ester, carboxylic anhydride, carboxylic acid halide, sulfonyl halide, imidate ester, isocyanate, isothiocyanate, haloformate, carbodiimide adduct, aldehydes, ketone, sulfhydryl, haloacetyl, alkyl halide, alkyl sulfonate, NR1R2 wherein R1R2 is —C(=O)CH=CHC(=O) (maleimide), thioether, cyano, sugar (such as mannose, galactose, and glucose), α,β-unsaturated carbonyl, alkyl mercurial, α,β-unsaturated sulfone.

Suitable spacers may comprise polycyclic molecules, such as those containing phenyl or cyclohexyl rings. The spacer may be a polyether such as polyphosphopropanediol, polyethyleneglycol, polypropylene glycol, a bifunctional polycyclic molecule such as a bifunctional pentalene, indene, naphthalene, azulene, heptalene, biphenylene, asymindacene, sym-indacene, acenaphthylene, fluorene, phenalene, phenanthrene, anthracene, fluoranthene, acephenathrylene, aceanthrylene, triphenylene, pyrene, chrysene, naphthacene, thianthrene, isobenzofuran, chromene, xanthene, phenoxathiin, which may be substituted or modified, or a combination of the polyethers and the polycyclic molecules. The polycyclic molecule may be substituted or polysubstituted with C1-C5 alkyl, C6 alkyl, alkenyl, hydroxyalkyl, halogen or haloalkyl group. Nitrogen-containing polyheterocyclic molecules (e.g., indolizine) are typically not suitable spacers. The spacer may also be a polyalcohol, such as glycerol or pentaerythritol. In one variation, the spacer comprises 1-phosphopropane)$_3$-phosphate or 1-phosphopropane)$_4$-phosphate (also called tetraphosphopropanediol and pentaphosphopropanediol). In one variation, the spacer comprises derivatized 2,2'-ethylenedioxydiethylamine (EDDA).

Specific examples of non-nucleic acid spacers useful in IRCs include "linkers" described by Cload et al. (1991) *J. Am. Chem. Soc.* 113:6324; Richardson et al. (1991) *J. Am. Chem. Soc.* 113:5109; Ma et al. (1993) *Nucleic Acids Res.* 21:2585; Ma et al. (1993) *Biochemistry* 32:1751; McCurdy et al. (1991) *Nucleosides & Nucleotides* 10:287; Jaschke et al. (1993) *Tetrahedron Lett.* 34:301; Ono et al. (1991) *Biochemistry* 30:9914; and International Publication No. WO 89/02439.

Other suitable spacers include linkers described by Salunkhe et al. (1992) *J. Am. Chem. Soc.* 114:8768; Nelson et al. (1996) *Biochemistry* 35:5339-5344; Bartley et al. (1997) *Biochemistry* 36:14502-511; Dagneaux et al. (1996) *Nucleic Acids Res.* 24:4506-12; Durand et al. (1990) *Nucleic Acids Res.* 18:6353-59; Reynolds et al. (1996) *Nucleic Acids Res.* 24:760-65; Hendry et al. (1994) *Biochem. Biophys. Acta* 1219:405-12; Altmann et al. (1995) *Nucleic Acids Res.* 23:4827-35. Still other suitable spacers are described in European Pat. No. EP0313219B1 and U.S. Pat. No. 6,117,657.

Exemplary non-nucleic acid spacers comprise oligo-ethylene glycol (e.g., triethylene glycol, tetraethylene glycol, hexaethylene glycol spacers, and other polymers comprising up to about 10, about 20, about 40, about 50, about 100 or about 200 ethylene glycol units), alkyl spacers (e.g., propyl, butyl, hexyl, and other C2-C12 alkyl spacers, e.g., usually C2-C10 alkyl, most often C2-C6 alkyl), abasic nucleotide spacers, symmetric or asymmetric spacers derived from glycerol, pentaerythritol or 1,3,5-trihydroxycyclohexane (e.g., symmetrical doubler and trebler spacer moieties described herein). Spacers can also comprise heteromeric or homomeric oligomers and polymers of the aforementioned compounds (e.g., linked by an amide, ester, ether, thioether, disulfide, phosphodiester, phosphorothioate, phosphoramidate, phosphotriester, phosphorodithioate, methyl phosphonate or other linkage).

Suitable spacer moieties can contribute charge and/or hydrophobicity to the IRC, contribute favorable pharmacokinetic properties (e.g., improved stability, longer residence time in blood) to the IRC, and/or result in targeting of the IRC to particular cells or organs. Spacer moieties can be selected or modified to tailor the IRC for desired pharmacokinetic properties or suitability for desired modes of administration (e.g., oral administration). It will be appreciated by the reader that, for convenience, a spacer (or spacer component) is sometimes referred to by the chemical name of the compound from which the spacer component is derived (e.g., hexaethylene glycol), with the understanding that the IRC actually comprises the conjugate of the compound and adjacent nucleic acid moieties or other spacer moiety components.

In an IRC comprising more than one spacer moiety, the spacers may be the same or different. Thus, in one variation all of the non-nucleic acid spacer moieties in an IRC have the same structure. In one variation, an IRC comprises non-nucleic acid spacer moieties with at least 2, at least 3, at least 4, at least 5, or at least 6 or more different structures.

In some contemplated embodiments, the spacer moiety of an IRC is defined to exclude certain structures. Thus, in some embodiments, a spacer is other than an abasic nucleotide or polymer of abasic nucleotides. In some embodiments, a spacer is other than a oligo(ethyleneglycol) (e.g., HEG, TEG and the like) or poly(ethyleneglycol). In some embodiments a spacer is other than a C3 alkyl spacer. In some embodiments, a spacer is other than a polypeptide. Thus, in some embodiments, an immunogenic molecule, e.g., a protein or polypeptide, is not suitable as a component of spacer moieties. However, as discussed infra, it is contemplated that in certain embodiments, an IRC is a "proteinaceous IRC" i.e., comprising a spacer moiety comprising a polypeptide. However, in some embodiments, the spacer moiety is not proteinaceous and/or is not an antigen (i.e., the spacer moiety, if isolated from the IRC, is not an antigen).

Generally, suitable spacer moieties do not render the IRC of which they are a component insoluble in an aqueous solution (e.g., PBS, pH 7.0). Thus, the definition of spacers excludes microcarriers or nanocarriers. In addition, a spacer moiety that has low solubility, such as a dodecyl spacer (solubility <5 mg/ml when measured as dialcohol precursor 1,12-dihydroxydodecane) is not preferred because it can reduce the hydrophilicity and activity of the IRC. Preferably, spacer moieties have solubility much greater than 5 mg/ml (e.g., ≥20 mg/ml, ≥50 mg/ml or ≥100 mg/ml) when measured as dialcohol precursors.

The charge of an IRC may be contributed by phosphate, thiophosphate, or other groups in the nucleic acid moieties as well as groups in non-nucleic acid spacer moieties. In some embodiments, a non-nucleic acid spacer moiety carries a net charge (e.g., a net positive charge or net negative charge when measured at pH 7). In one useful variation, the IRC has a net negative charge. In some embodiments, the negative charge of a spacer moiety in an IRC is increased by derivatizing a spacer subunit described herein to increase its charge. For example, glycerol can be covalently bound to two nucleic acid moieties and the remaining alcohol can be reacted with an activated phosphoramidite, followed by oxidation or sulfurization to form a phosphate or thiophosphate, respectively. In certain embodiments the negative charge contributed by the non-nucleic acid spacer moieties in an IRC (i.e., the sum of the charges when there is more than one spacer) is greater than the negative charge contributed by the nucleic acid moieties of the IRC. Charge can be calculated based on molecular formula, or determined experimentally, e.g., by capillary electrophoresis (Li, ed., 1992, *Capillary electrophoresis, Principles, Practice and Application* Elsevier Science Publishers, Amsterdam, The Netherlands, pp 202-206).

As is noted supra, suitable spacers can be polymers of smaller non-nucleic acid (e.g., non-nucleotide) compounds, such as those described herein, that are themselves useful as spacers, including compounds commonly referred to as non-nucleotide "linkers." Such polymers (i.e., "multiunit spacers") may be heteromeric or homomeric, and often comprise monomeric units (e.g., HEG, TEG, glycerol, 1'2'-dideoxyribose, and the like) linked by an ester linkage (e.g., phosphodiester or phosphorothioate ester). Thus, in one variation the spacer comprises a polymeric (e.g., heteropolymeric) structure of non-nucleotide units (e.g., from 2 to about 100 units, alternatively 2 to about 50, e.g., 2 to about 5, alternatively e.g., about 5 to about 50, e.g., about 5 to about 20).

For illustration, IRCs containing an IRS and multiunit spacers include

> 5'-TCCTGGAGGGGTTGT-(C3)$_{15}$-T (SEQ ID NO: 153)
>
> 5'-TCCTGGAGGGGTTGT-(glycerol)$_{15}$-T (SEQ ID NO: 154)
>
> 5'-TCCTGGAGGGGTTGT-(TEG)$_8$-T (SEQ ID NO: 155)
>
> 5'-TCCTGGAGGGGTTGT-(HEG)$_4$-T (SEQ ID NO: 156)

where (C3)$_{15}$ means 15 propyl linkers connected via phosphorothioate esters; (glycerol)$_{15}$ means 15 glycerol linkers connected via phosphorothioate esters; (TEG)$_8$ means 8 triethyleneglycol linkers connected via phosphorothioate esters; and (HEG)$_4$ means 4 hexaethyleneglycol linkers connected via phosphorothioate esters. It will be appreciated that certain multiunit spacers have a net negative charge, and that the negative charge can be increased by increasing the number of e.g., ester-linked monomeric units.

In certain embodiments, a spacer moiety is a multivalent non-nucleic acid spacer moiety (i.e., a "multivalent spacer"). As used in this context, an IRC containing a multivalent spacer contains a spacer covalently bound to three (3) or more nucleic acid moieties. Multivalent spacers are sometimes referred to in the art as "platform molecules." Multivalent spacers can be polymeric or nonpolymeric. Examples of suitable molecules include glycerol or substituted glycerol (e.g., 2-hydroxymethyl glycerol, levulinyl-glycerol); tetraminobenzene, heptaminobetacyclodextrin, 1,3,5-trihydroxycyclohexane, pentaerythritol and derivatives of pentaerythritol, tetraminopentaerythritol, 1,4,8,11-tetraazacyclo tetradecane (Cyclam), 1,4,7,10-tetraazacyclododecane (Cyclen), polyethyleneimine, 1,3-diamino-2-propanol and substituted derivatives, propyloxymethyl]ethyl compounds (e.g., "trebler"), polyethylene glycol derivatives such as so-called "Star PEGs" and "bPEG" (see, e.g., Gnanou et al. (1988) *Makromol. Chem.* 189:2885; Rein et al. (1993) *Acta Polymer* 44:225; U.S. Pat. No. 5,171,264), and dendrimers.

Dendrimers are known in the art and are chemically defined globular molecules, generally prepared by stepwise or reiterative reaction of multifunctional monomers to obtain a branched structure (see, e.g., Tomalia et al. (1990) *Angew. Chem. Int. Ed. Engl.* 29:138-75). A variety of dendrimers are known, e.g., amine-terminated polyamidoamine, polyethyleneimine and polypropyleneimine dendrimers. Exemplary dendrimers useful include "dense star" polymers or "starburst" polymers such as those described in U.S. Pat. Nos. 4,587,329; 5,338,532; and 6,177,414, including so-called "poly(amidoamine) ("PAMAM") dendrimers." Still other multimeric spacer molecules suitable for use include chemically-defined, non-polymeric valency platform molecules such as those disclosed in U.S. Pat. No. 5,552,391; and PCT application publications WO 00/75105, WO 96/40197, WO 97/46251, WO 95/07073, and WO 00/34231. Many other suitable multivalent spacers can be used and will be known to those of skill in the art.

Conjugation of a nucleic acid moiety to a platform molecule can be effected in any number of ways, typically involving one or more crosslinking agents and functional groups on the nucleic acid moiety and platform molecule. Linking groups are added to platforms using standard synthetic chemistry techniques Linking groups can be added to nucleic acid moieties using standard synthetic techniques.

Multivalent spacers with a variety of valencies are useful, and in various embodiments the multivalent spacer of an IRC is bound to between about 3 and about 400 nucleic acid moieties, often from 3 to 100, sometimes from 3-50, frequently from 3-10, and sometimes more than 400 nucleic acid moieties. In various embodiments, the multivalent spacer is conjugated to more than 10, more than 25, more than 50, or more than 500 nucleic acid moieties (which may be the same or different). It will be appreciated that, in certain embodiments in which an IRC comprises a multivalent spacer, provided herein is a population of IRCs with slightly different molecular structures. For example, when an IRC is prepared using a dendrimer as a high valency the multivalent spacer, a somewhat heterogeneous mixture of molecules is produced, i.e., comprising different numbers (within or predominantly within a determinable range) of nucleic acid moieties joined to each dendrimer molecule.

Polysaccharides derivatized to allow linking to nucleic acid moieties can be used as spacers in IRCs. Suitable polysaccharides include naturally occurring polysaccharides (e.g., dextran) and synthetic polysaccharides (e.g., ficoll). For instance, aminoethylcarboxymethyl-ficoll (AECM-Ficoll) can be prepared by the method of Inman (1975) *J. Imm.* 114:704-709. AECM-Ficoll can then be reacted with a heterobifunctional crosslinking reagent, such as 6-maleimido caproic acyl N-hydroxysuccinimide ester, and then conjugated to a thiol-derivatized nucleic acid moiety (see Lee et al. (1980) *Mol. Imm.* 17:749-56). Other polysaccharides may be modified similarly.

It will be well within the ability of one of skill, guided by this specification and knowledge in the art, to prepare IRCs using routine methods. Techniques for making nucleic acid moieties (e.g., oligonucleotides and modified oligonucleotides) are known. Nucleic acid moieties can be synthesized using techniques including, but not limited to, enzymatic methods and chemical methods and combinations of enzymatic and chemical approaches. For example, DNA or RNA containing phosphodiester linkages can be chemically synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Useful solid supports for DNA synthesis include Controlled Pore Glass (Applied Biosystems, Foster City, Calif.), polystyrene bead matrix (Primer Support, Amersham Pharmacia, Piscataway, N.J.) and TentGel (Rapp Polymere GmbH, Tubingen, Germany). Once the desired oligonucleotide sequence has been synthesized, the oligonucleotide is removed from the support, the phosphate triester groups are deprotected to phosphate diesters and the nucleoside bases are deprotected using aqueous ammonia or other bases.

For instance, DNA or RNA polynucleotides (nucleic acid moieties) containing phosphodiester linkages are generally synthesized by repetitive iterations of the following steps: a) removal of the protecting group from the 5'-hydroxyl group of the 3'-solid support-bound nucleoside or nucleic acid, b) coupling of the activated nucleoside phosphoramidite to the 5'-hydroxyl group, c) oxidation of the phosphite triester to the phosphate triester, and d) capping of unreacted 5'-hydroxyl groups. DNA or RNA containing phosphorothioate linkages is prepared as described above, except that the oxidation step is replaced with a sulfurization step. Once the desired oligonucleotide sequence has been synthesized, the oligonucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in PROTOCOLS FOR OLIGONUCLEOTIDES AND ANALOGS, SYNTHESIS AND PROPERTIES (Agrawal, ed.) Humana Press, Totowa, N.J.; Warner et al. (1984) *DNA* 3:401; Tang et al. (2000) *Org. Process Res. Dev.* 4:194-198; Wyrzykiewica et al. (1994) *Bioorg. & Med. Chem. Lett.* 4:1519-1522; Radhakrishna et al. (1989) *J. Org. Chem.* 55:4693-4699. and U.S. Pat. No. 4,458,066. Programmable machines that automatically synthesize nucleic acid moieties of specified sequences are widely available. Examples include the Expedite 8909 automated DNA synthesizer (Perseptive Biosystem, Framington Mass.); the ABI 394 (Applied Biosystems, Inc., Foster City, Calif.); and the OligoPilot II (Amersham Pharmacia Biotech, Piscataway, N.J.).

Polynucleotides can be assembled in the 3' to 5' direction, e.g., using base-protected nucleosides (monomers) containing an acid-labile 5'-protecting group and a 3'-phosphoramidite. Examples of such monomers include 5'-O-(4,4'-dimethoxytrityl)-protected nucleoside-3'-O-(N,N-diisopropylamino) 2-cyanoethyl phosphoramidite, where examples of the protected nucleosides include, but are not limited to, N6-benzoyladenosine, N4-benzoylcytidine, N2-isobutyrylguanosine, thymidine, and uridine. In this case, the solid support used contains a 3'-linked protected nucleoside. Alternatively, polynucleotides can be assembled in the 5' to 3' direction using base-protected nucleosides containing an acid-labile 3'-protecting group and a 5'-phosphoramidite. Examples of such monomers include 3'-O-(4,4'-dimethoxytrityl)-protected nucleoside-5'-O—(N,N-diisopropylamino) 2-cyanoethyl phosphoramidite, where examples of the protected nucleosides include, but are not limited to, N6-benzoyladenosine, N4-benzoylcytidine, N2-isobutyrylguanosine, thymidine, and uridine (Glen Research, Sterling, Va.). In this case, the solid support used contains a 5'-linked protected nucleoside. Circular nucleic acid components can be isolated, synthesized through recombinant methods, or chemically synthesized. Chemical synthesis can be performed using any method described in the literature. See, for instance, Gao et al. (1995) *Nucleic Acids Res.* 23:2025-2029 and Wang et al. (1994) *Nucleic Acids Res.* 22:2326-2333.

Addition of non-nucleic acid spacer moieties can be accomplished using routine methods. Methods for addition of particular spacer moieties are known in the art and, for example, are described in the references cited supra. See, e.g., Durand et al. (1990) *Nucleic Acids Res.* 18:6353-6359. The covalent linkage between a spacer moiety and nucleic acid moiety can be any of a number of types, including phosphodiester, phosphorothioate, amide, ester, ether, thioether, disulfide, phosphoramidate, phosphotriester, phosphorodithioate, methyl phosphonate and other linkages. It will often be convenient to combine a spacer moiety(s) and a nucleic acid moiety(s) using the same phosphoramidite-type chemistry used for synthesis of the nucleic acid moiety. For example, IRCs described herein can be conveniently synthesized using an automated DNA synthesizer (e.g., Expedite 8909; Perseptive Biosystems, Framington, Mass.) using phosphoramidite chemistry (see, e.g., Beaucage, 1993, supra; *Current Protocols in Nucleic Acid Chemistry, supra*). However, one of skill will understand that the same (or equivalent) synthesis steps carried out by an automated DNA synthesizer can also be carried out manually, if desired. In such a synthesis, typically, one end of the spacer (or spacer subunit for multimeric spacers) is protected with a 4,4'-dimethyoxytrityl group, while the other end contains a phosphoramidite group.

A variety of spacers with the requisite protecting and reacting groups are commercially available, for example:

| | |
|---|---|
| triethylene glycol spacer or "TEG spacer" | 9-O-(4,4'-dimethoxytrityl)triethyleneglycol-1-O-[(2-cyanoethyl) N,N-diisopropylphosphoramidite] (Glen Research, 22825 Davis Drive, Sterling, VA) |
| hexaethylene glycol spacer or "HEG spacer" | 18-O-(4,4'-dimethoxytrityl)hexaethyleneglycol-1-O-[(2-cyanoethyl) N,N-diisopropylphosphoramidite] (Glen Research, Sterling, VA) |
| propyl spacer | 3-(4,4'-dimethoxytrityloxy)propyloxy-1-O-[(2-cyanoethyl) N,N-diisopropylphosphoramidite] (Glen Research, Sterling, VA); |
| butyl spacer | 4-(4,4'-dimethoxytrityloxy)butyloxy-1-O-[(2-cyanoethyl) N,N-diisopropylphosphoramidite] (Chem Genes Corporation, Ashland Technology Center, 200 Homer Ave, Ashland, MA) |
| Hexyl spacer | 6-(4,4'-dimethoxytrityloxy)hexyloxy-1-O-[(2-cyanoethyl) N,N-diisopropylphosphoramidite] |
| 2-(hydroxymethyl)ethyl spacer or "HME spacer" | 1-(4,4'-dimethoxytrityloxy)-3-(levulinyloxy)-propyloxy-2-O-[(2-cyanoethyl) N,N-diisopropylphosphoramidite]; also called "asymmetrical branched" spacer |
| "abasic nucleotide spacer" or "abasic spacer" | 5-O-(4,4'-dimethoxytrityl)-1,2-dideoxyribose-3-O-[(2-cyanoethyl) N,N-diisopropylphosphoramidite] (Glen Research, Sterling, VA) |
| "symmetrical branched spacer" or "glycerol spacer" | 1,3-O,O-bis(4,4'-dimethoxytrityl)glycerol-2-O-[(2-cyanoethyl) N,N-diisopropylphosphoramidite] (Chem Genes, Ashland, MA) |
| "trebler spacer" | 2,2,2-O,O,O-tris[3-O-(4,4'-dimethoxytrityloxy)propyloxymethyl]ethyl-1-O-[(2-cyanoethyl) N,N-diisopropylphosphoramidite] (Glen Research, Sterling, VA) |
| "symmetrical doubler spacer" | 1,3-O,O-bis[5-O-(4,4'-dimethoxytrityloxy)pentylamido]propyl-2-O-[(2-cyanoethyl) N,N-diisopropylphosphoramidite] (Glen Research, Sterling, VA) |
| "dodecyl spacer" | 12-(4,4'-dimethoxytrityloxy)dodecyloxy-1-O-[(2-cyanoethyl) N,N-diisopropylphosphoramidite] (Glen Research, Sterling, VA) |

These and a large variety of other protected spacer moiety precursors (e.g., comprising DMT and phosphoramidite group protecting groups) can be purchased or can be synthesized using routine methods for use in preparing IRCs disclosed herein. The instrument is programmed according to the manufacturer's instructions to add nucleotide monomers and spacers in the desired order.

Although use of phosphoramidite chemistry is convenient for the preparation of certain IRCs, it will be appreciated that the IRCs described herein are not limited to compounds prepared by any particular method of synthesis or preparation.

In one variation, IRCs with multivalent spacers conjugated to more than one type of nucleic acid moiety are prepared. For instance, platforms containing two maleimide groups (which can react with thiol-containing polynucleotides), and two activated ester groups (which can react with amino-containing nucleic acids) have been described (see, e.g., PCT application publication WO 95/07073). These two activated groups can be reacted independently of each other. This would result in an IRC containing a total of 4 nucleic acid moieties, two of each sequence.

IRCs with multivalent spacers containing two different nucleic acid sequences can also be prepared using the symmetrical branched spacer, described above, and conventional phosphoramidite chemistry (e.g., using manual or automated methods). The symmetrical branched spacer contains a phosphoramidite group and two protecting groups that are the same and are removed simultaneously. In one approach, for example, a first nucleic acid is synthesized and coupled to the symmetrical branched spacer, the protecting groups are removed from the spacer. Then two additional nucleic acids (of the same sequence) are synthesized on the spacer (using double the amount of reagents used for synthesis of a single nucleic acid moiety in each step).

A similar method can be used to connect three different nucleic acid moieties (referred to below as Nucleic acids I, II, and III) to a multivalent platform (e.g., asymmetrical branched spacer). This is most conveniently carried out using an automated DNA synthesizer. In one variation, the asymmetrical branched spacer contains a phosphoramidite group and two orthogonal protecting groups that can be removed independently. First, nucleic acid I is synthesized, then the asymmetrical branched spacer is coupled to nucleic acid I, then nucleic acid II is added after the selective removal of one of the protecting groups. Nucleic acid II is deprotected, and capped, and then the other protecting group on the spacer is removed. Finally, nucleic acid III is synthesized.

In some embodiments, a nucleic acid moiety(s) is synthesized, and a reactive linking group (e.g., amino, carboxylate, thio, disulfide, and the like) is added using standard synthetic chemistry techniques. The reactive linking group (which is considered to form a portion of the resulting spacer moiety) is conjugated to additional non-nucleic acid compounds to form the spacer moiety. Linking groups are added to nucleic acids using standard methods for nucleic acid synthesis, employing a variety of reagents described in the literature or commercially available. Examples include reagents that contain a protected amino group, carboxylate group, thiol group, or disulfide group and a phosphoramidite group. Once these compounds are incorporated into the nucleic acids, via the activated phosphoramidite group, and are deprotected, they provide nucleic acids with amino, carboxylate, or thiol reactivity.

Hydrophilic linkers of variable lengths are useful, for example to link nucleic acids moieties and platform molecules. A variety of suitable linkers are known. Suitable linkers include, without limitation, linear oligomers or polymers of ethylene glycol. Such linkers include linkers with the formula $R^1S(CH_2CH_2O)_nCH_2CH_2-O-(CH_2)_mCO_2R^2$ wherein n=0-200, m=1 or 2, $R^1$=H or a protecting group such as trityl, $R^2$=H or alkyl or aryl, e.g., 4-nitrophenyl ester. These linkers are useful in connecting a molecule containing a thiol reactive group such as haloaceyl, maleiamide, etc., via a thioether to a second molecule which contains an amino group via an amide bond. The order of attachment can vary, i.e., the thioether bond can be formed before or after the amide bond is formed. Other useful linkers include Sulfo-SMCC (sulfosuccinimidyl 4-[N-maleimidomethyl]-cyclohexane-1-carboxylate) Pierce Chemical Co. product 22322; Sulfo-EMCS(N[ε-maleimidocaproyloxy]sulfosuccinimide ester) Pierce Chemical Co. product 22307; Sulfo-GMBS (N-[γ-maleimidobutyryloxy]sulfosuccinimide ester) Pierce Chemical Co. product 22324 (Pierce Chemical Co., Rockford, Ill.), and similar compounds of the general formula maleimido-R—C(O)NHS ester, where R=alkyl, cyclic alkyl, polymers of ethylene glycol, and the like.

Particularly useful methods for covalently joining nucleic acid moieties to multivalent spacers are described in the references cited supra.

In certain embodiments, a polypeptide is used as a multivalent spacer moiety to which a plurality of nucleic acid moieties are covalently conjugated, directly or via linkers, to form a "proteinaceous IRC." The polypeptide can be a carrier (e.g., albumin). Typically, a proteinaceous IRC comprises at least one, and usually several or many nucleic acid moieties that (a) are between 2 and 7, more often between 4 and 7 nucleotides in length, alternatively between 2 and 6, 2 and 5, 4 and 6, or 4 and 5 nucleotides in length and/or (b) have inferior isolated immunomodulatory activity or do not have isolated immunomodulatory activity. Methods of making a proteinaceous IRC will be apparent to one of skill upon review of the present disclosure. A nucleic acid, for example, can be covalently conjugated to a polypeptide spacer moiety by art known methods including linkages between a 3' or 5' end of a nucleic acid moiety (or at a suitably modified base at an internal position in the a nucleic acid moiety) and a polypeptide with a suitable reactive group (e.g., an N-hydroxysuccinimide ester, which can be reacted directly with the $N^4$ amino group of cytosine residues). As a further example, a polypeptide can be attached to a free 5'-end of a nucleic acid moiety through an amine, thiol, or carboxyl group that has been incorporated into nucleic acid moiety. Alternatively, the polypeptide can be conjugated to a spacer moiety, as described herein. Further, a linking group comprising a protected amine, thiol, or carboxyl at one end, and a phosphoramidite can be covalently attached to a hydroxyl group of a polynucleotide, and, subsequent to deprotection, the functionality can be used to covalently attach the IRC to a peptide.

IRP and/or IRC Complexes and Compositions

IRPs or IRCs can be directly administered to the individual or they can be administered in a composition or complex to enhance IRP or IRC delivery to cells and/or uptake by cells. Compositions or complexes can also be use to enhance co-delivery of two of more different IRP and/or IRC species to a cell. In some embodiments, a mixture of IRCs and IRPs may be complexed so as to deliver at least one IRC and IRP species. In some embodiments, the IRP and/or IRC comprises a modified IRS. In some variation, the IRP and/or IRC comprises an unmodified IRS. In some embodiments, the IRP and/or IRC comprises both modified and unmodified IRSs.

Such delivery compositions or complexes include, but are not limited to, encapsulating complexes and colloidal dispersion systems as described herein and known in the art. Examples of such delivery compositions include oil-in-water emulsions, micelles, and liposomes. Delivery compositions or complexes also include IRP and/or IRC linked to a linker molecules, a platform molecule, a nanoparticle or a microparticle, as described herein. Such linkages include both covalent and non-covalent linkages. Unless otherwise noted, complex and composition formulations described herein for use with IRPs are also appropriate for use with IRCs.

In some embodiments, the IRP and/or IRC is conjugated with a linker molecule. The IRP and/or IRC portion can be coupled with the linker portion of a conjugate in a variety of ways, including covalent and/or non-covalent interactions.

The link between the portions can be made at the 3' or 5' end of the IRP and/or IRC, or at a suitably modified base at an internal position in the IRP and/or IRC. If the linker is a peptide and contains a suitable reactive group (e.g., an N-hydroxysuccinimide ester) it can be reacted directly with the $N^4$ amino group of cytosine residues. Depending on the number and location of cytosine residues in the IRP and/or IRC, specific coupling at one or more residues can be achieved.

Alternatively, modified oligonucleosides, such as are known in the art, can be incorporated at either terminus, or at internal positions in the IRP and/or IRC. These can contain blocked functional groups which, when deblocked, are reactive with a variety of functional groups which can be present on, or attached to, the linker of interest.

Where the linker is a peptide, this portion of the conjugate can be attached to the 3'-end of the IRP and/or IRC through solid support chemistry. For example, the IRP portion can be added to a peptide portion that has been pre-synthesized on a support. Haralambidis et al. (1990a) *Nucleic Acids Res.* 18:493-499; and Haralambidis et al. (1990b) *Nucleic Acids Res.* 18:501-505. Alternatively, the IRP can be synthesized such that it is connected to a solid support through a cleavable linker extending from the 3'-end. Upon chemical cleavage of the IRP from the support, a terminal thiol group is left at the 3'-end of the oligonucleotide (Zuckermann et al. (1987) *Nucleic Acids Res.* 15:5305-5321; and Corey et al. (1987) *Science* 238:1401-1403) or a terminal amino group is left at the 3'-end of the oligonucleotide (Nelson et al. (1989) *Nucleic Acids Res.* 17:1781-1794). Conjugation of the amino-modified IRP and/or IRC to amino groups of the peptide can be performed as described in Benoit et al. (1987) *Neuromethods* 6:43-72. Conjugation of the thiol-modified IRP and/or IRC to carboxyl groups of the peptide can be performed as described in Sinah et al. (1991) *Oligonucleotide Analogues: A Practical Approach*, IRL Press. Coupling of an oligonucleotide carrying an appended maleimide to the thiol side chain of a cysteine residue of a peptide has also been described. Tung et al. (1991) *Bioconjug. Chem.* 2:464-465.

The peptide linker portion of the conjugate can be attached to the 5'-end of the IRP and/or IRC through an amine, thiol, or carboxyl group that has been incorporated into the oligonucleotide during its synthesis. Preferably, while the oligonucleotide is fixed to the solid support, a linking group comprising a protected amine, thiol, or carboxyl at one end, and a phosphoramidite at the other, is covalently attached to the 5'-hydroxyl. Agrawal et al. (1986) *Nucleic Acids Res.* 14:6227-6245; Connolly (1985) *Nucleic Acids Res.* 13:4485-4502; Kremsky et al. (1987) *Nucleic Acids Res.* 15:2891-2909; Connolly (1987) *Nucleic Acids Res.* 15:3131-3139; Bischoff et al. (1987) *Anal. Biochem.* 164:336-344; Blanks et al. (1988) *Nucleic Acids Res.* 16:10283-10299; and U.S. Pat. Nos. 4,849,513, 5,015,733, 5,118,800, and 5,118,802. Subsequent to deprotection, the amine, thiol, and carboxyl functionalities can be used to covalently attach the oligonucleotide to a peptide. Benoit et al. (1987); and Sinah et al. (1991).

An IRP and/or IRC conjugate can also be formed through non-covalent interactions, such as ionic bonds, hydrophobic interactions, hydrogen bonds and/or van der Waals attractions.

Non-covalently linked conjugates can include a non-covalent interaction such as a biotin-streptavidin complex. A biotinyl group can be attached, for example, to a modified base of an IRP and/or IRC. Roget et al. (1989) *Nucleic Acids Res.* 17:7643-7651. Incorporation of a streptavidin moiety into the peptide portion allows formation of a non-covalently bound complex of the streptavidin conjugated peptide and the biotinylated oligonucleotide.

Non-covalent associations can also occur through ionic interactions involving an IRP and/or IRC through the use of a linker portion comprising charged residues that can interact with an oligonucleotide. For example, non-covalent conjugation can occur between a generally negatively-charged IRP and/or IRC and positively-charged amino acid residues of a peptide linker, e.g., polylysine, polyarginine and polyhistidine residues.

The linkage of the IRP and/or IRC to a lipid can be formed using standard methods. These methods include, but are not limited to, the synthesis of oligonucleotide-phospholipid conjugates (Yanagawa et al. (1988) *Nucleic Acids Symp. Ser.* 19:189-192), oligonucleotide-fatty acid conjugates (Grabarek et al. (1990) *Anal. Biochem.* 185:131-135; and Staros et al. (1986) *Anal. Biochem.* 156:220-222), and oligonucleotide-sterol conjugates. Boujrad et al. (1993) *Proc. Natl. Acad. Sci. USA* 90:5728-5731.

The linkage of the oligonucleotide to an oligosaccharide can be formed using standard known methods. These methods include, but are not limited to, the synthesis of oligonucleotide-oligosaccharide conjugates, wherein the oligosaccharide is a moiety of an immunoglobulin. O'Shannessy et al. (1985) *J. Applied Biochem.* 7:347-355.

The linkage of a circular IRP and/or IRC to a peptide linker can be formed in several ways. Where the circular IRP and/or IRC is synthesized using recombinant or chemical methods, a modified nucleoside is suitable. Ruth (1991) in *Oligonucleotides and Analogues: A Practical Approach*, IRL Press. Standard linking technology can then be used to connect the circular IRP and/or IRC to the peptide. Goodchild (1990) *Bioconjug. Chem.* 1:165. Where the circular IRP and/or IRC is isolated, or synthesized using recombinant or chemical methods, the linkage can be formed by chemically activating, or photoactivating, a reactive group (e.g. carbene, radical) that has been incorporated into the peptide.

Additional methods for the attachment of peptides and other molecules to oligonucleotides can be found in U.S. Pat. No. 5,391,723; Kessler (1992) "Nonradioactive labeling methods for nucleic acids" in Kricka (ed.) *Nonisotopic DNA Probe Techniques*, Academic Press; and Geoghegan et al. (1992) *Bioconjug. Chem.* 3:138-146.

An IRP and/or IRC may be proximately associated in other ways. In some embodiments, an IRP and/or IRC are proximately associated by encapsulation. In other embodiments, an IRP and/or IRC are proximately associated by linkage to a platform molecule. A "platform molecule" (also termed "platform") is a molecule containing sites which allow for attachment of the IRP and/or IRC. In other embodiments, an IRP and/or IRC are proximately associated by adsorption onto a surface, preferably a carrier particle.

In some embodiments, the methods described herein employ an encapsulating agent in association with the IRP and/or IRC. Preferably, the composition comprising IRP and/or IRC and encapsulating agent is in the form of adjuvant oil-in-water emulsions, microparticles and/or liposomes.

More preferably, adjuvant oil-in-water emulsions, microparticles and/or liposomes encapsulating an IRP and/or IRC are in the form of particles from about 0.04 µm to about 100 µm in size, preferably any of the following ranges: from about 0.1 µm to about 20 µm; from about 0.15 µm to about 10 µm; from about 0.05 µm to about 1.00 µm; from about 0.05 µm to about 0.5 µm.

Colloidal dispersion systems, such as microspheres, beads, macromolecular complexes, nanocapsules and lipid-based system, such as oil-in-water emulsions, micelles, mixed micelles and liposomes can provide effective encapsulation of IRP and/or IRC-containing compositions.

The encapsulation composition further comprises any of a wide variety of components. These include, but are not limited to, alum, lipids, phospholipids, lipid membrane structures (LMS), polyethylene glycol (PEG) and other polymers, such as polypeptides, glycopeptides, and polysaccharides.

Polypeptides suitable for encapsulation components include any known in the art and include, but are not limited to, fatty acid binding proteins. Modified polypeptides contain any of a variety of modifications, including, but not limited to glycosylation, phosphorylation, myristylation, sulfation and hydroxylation. As used herein, a suitable polypeptide is one that will protect an IRP and/or IRC-containing composition to preserve the immunoregulatory activity thereof. Examples of binding proteins include, but are not limited to, albumins such as bovine serum albumin (BSA) and pea albumin.

Other suitable polymers can be any known in the art of pharmaceuticals and include, but are not limited to, naturally-occurring polymers such as dextrans, hydroxyethyl starch, and polysaccharides, and synthetic polymers. Examples of naturally occurring polymers include proteins, glycopeptides, polysaccharides, dextran and lipids. The additional polymer can be a synthetic polymer. Examples of synthetic polymers which are suitable for use include, but are not limited to, polyalkyl glycols (PAG) such as PEG, polyoxyethylated polyols (POP), such as polyoxyethylated glycerol (POG), polytrimethylene glycol (PTG) polypropylene glycol (PPG), polyhydroxyethyl methacrylate, polyvinyl alcohol (PVA), polyacrylic acid, polyethyloxazoline, polyacrylamide, polyvinylpyrrolidone (PVP), polyamino acids, polyurethane and polyphosphazene. The synthetic polymers can also be linear or branched, substituted or unsubstituted, homopolymeric, co-polymers, or block co-polymers of two or more different synthetic monomers.

The PEGs for use in encapsulation compositions are either purchased from chemical suppliers or synthesized using techniques known to those of skill in the art.

The term "LMS", as used herein, means lamellar lipid particles wherein polar head groups of a polar lipid are arranged to face an aqueous phase of an interface to form membrane structures. Examples of the LMSs include liposomes, micelles, cochleates (i.e., generally cylindrical liposomes), microemulsions, unilamellar vesicles, multilamellar vesicles, and the like.

An optional colloidal dispersion system is a liposome. As used herein, a "liposome" or "lipid vesicle" is a small vesicle bounded by at least one and possibly more than one bilayer lipid membrane. Liposomes are made artificially from phospholipids, glycolipids, lipids, steroids such as cholesterol, related molecules, or a combination thereof by any technique known in the art, including but not limited to sonication, extrusion, or removal of detergent from lipid-detergent complexes. A liposome can also optionally comprise additional components, such as a tissue targeting component. It is understood that a "lipid membrane" or "lipid bilayer" need not consist exclusively of lipids, but can additionally contain any suitable other components, including, but not limited to, cholesterol and other steroids, lipid-soluble chemicals, proteins of any length, and other amphipathic molecules, providing the general structure of the membrane is a sheet of two hydrophilic surfaces sandwiching a hydrophobic core. For a general discussion of membrane structure, see *The Encyclopedia of Molecular Biology* by J. Kendrew (1994). For suitable lipids see e.g., Lasic (1993) "Liposomes: from Physics to Applications" Elsevier, Amsterdam.

Processes for preparing liposomes containing IRP and/or IRC compositions are known in the art. The lipid vesicles can be prepared by any suitable technique known in the art. Methods include, but are not limited to, microencapsulation, microfluidization, LLC method, ethanol injection, freon injection, the "bubble" method, detergent dialysis, hydration, sonication, and reverse-phase evaporation. Reviewed in Watwe et al. (1995) *Curr. Sci.* 68:715-724. Techniques may be combined in order to provide vesicles with the most desirable attributes.

Provided herein are uses of LMSs containing tissue or cellular targeting components. Such targeting components are components of a LMS that enhance its accumulation at certain tissue or cellular sites in preference to other tissue or cellular sites when administered to an intact animal, organ, or cell culture. A targeting component is generally accessible from outside the liposome, and is therefore preferably either bound to the outer surface or inserted into the outer lipid bilayer. A targeting component can be inter alia a peptide, a region of a larger peptide, an antibody specific for a cell surface molecule or marker, or antigen binding fragment thereof, a nucleic acid, a carbohydrate, a region of a complex carbohydrate, a special lipid, or a small molecule such as a drug, hormone, or hapten, attached to any of the aforementioned molecules. Antibodies with specificity toward cell type-specific cell surface markers are known in the art and are readily prepared by methods known in the art.

The LMSs can be targeted to any cell type toward which a therapeutic treatment is to be directed, e.g., a cell type which can regulate and/or participate in an immune response. Such target cells and organs include, but are not limited to, APCs, such as macrophages, dendritic cells and lymphocytes, lymphatic structures, such as lymph nodes and the spleen, and nonlymphatic structures, particularly those in which dendritic cells are found.

The LMS compositions provided herein can additionally comprise surfactants. Surfactants can be cationic, anionic, amphiphilic, or nonionic. A preferred class of surfactants are nonionic surfactants; particularly preferred are those that are water soluble.

In some embodiments in which an IRP and/or IRC are proximately associated by linkage to a platform molecule, the platform may be proteinaceous or non-proteinaceous (i.e., organic). Examples of proteinaceous platforms include, but are not limited to, albumin, gammaglobulin, immunoglobulin (IgG) and ovalbumin. Borel et al. (1990) *Immunol. Methods* 126:159-168; Dumas et al. (1995) *Arch. Dematol. Res.* 287: 123-128; Borel et al. (1995) *Int. Arch. Allergy Immunol.* 107: 264-267; Borel et al. (1996) *Ann. N.Y. Acad. Sci.* 778:80-87. A platform is multi-valent (i.e., contains more than one binding, or linking, site) to accommodate binding to more than 1 IRP and/or IRC. Accordingly, a platform may contain 2 or more, 3 or more, 4 or more, 5 or more, 6 or more, 7 or more, 8 or more, 9 or more, 10 or more binding or linking sites Other examples of polymeric platforms are dextran, polyacrylamide, ficoll, carboxymethylcellulose, polyvinyl alcohol, and poly D-glutamic acid/D-lysine.

In some embodiments, the polymeric platform is a polymer. In some embodiments, the polymer is dextran, polyacrylamide, ficoll, carboxymethylcellulose, polyvinyl alcohol, or poly D-glutamic acid/D-lysine. In some embodiments, the polymeric platform is ficoll. In some embodiments, the polymeric platform is ficoll 400. In some embodiments, the polymeric platform is ficoll 70. In some embodiments, the polymeric platform is Ficoll® PM 70 (Poly(sucrose-co-epichlorhydrin)). In some embodiments, the polymeric platform is Ficoll® PM 400. In some embodiments, any of between about 1 to about 200, about 1 to about 150, about 1 to about 125, about 1 to about 100, about 1 to about 75, about 1 to about 50, or about 1 to about 25 IRPs and/or IRCs are linked to the polymeric platform. In some embodiments, between about 1 to about 100 IRPs and/or IRCs are linked to the polymeric platform. In some embodiments, the IRPs and/or IRCs comprise modified IRSs. In some embodiments, the IRPs and/or IRCs comprise unmodified IRSs. In some embodiments, the IRPs and/or IRCs include both unmodified and modified IRSs.

The principles of using platform molecules are well understood in the art. Generally, a platform contains, or is derivatized to contain, appropriate binding sites for IRP and/or IRC. In addition, or alternatively, IRP and/or IRC is derivatized to provide appropriate linkage groups. For example, a simple platform is a bi-functional linker (i.e., has two binding sites), such as a peptide. Further examples are discussed below.

Platform molecules may be biologically stabilized, i.e., they exhibit an in vivo excretion half-life often of hours to days to months to confer therapeutic efficacy, and are preferably composed of a synthetic single chain of defined composition. They generally have a molecular weight in the range of about 200 to about 1,000,000, preferably any of the following ranges: from about 200 to about 500,000; from about 200 to about 200,000; from about 200 to about 50,000 (or less, such as 30,000). Examples of valency platform molecules are polymers (or are comprised of polymers) such as polyethylene glycol (PEG; preferably having a molecular weight of about 200 to about 8000), poly-D-lysine, polyvinyl alcohol, polyvinylpyrrolidone, D-glutamic acid and D-lysine (in a ratio of 3:2). Other molecules that may be used are albumin and IgG.

Other platform molecules suitable for use are the chemically-defined, non-polymeric valency platform molecules disclosed in U.S. Pat. No. 5,552,391. Other homogeneous chemically-defined valency platform molecules suitable for use are derivatized 2,2'-ethylenedioxydiethylamine (EDDA) and triethylene glycol (TEG).

Additional suitable valency platform molecules include, but are not limited to, tetraminobenzene, heptaminobetacyclodextrin, tetraminopentaerythritol, 1,4,8,11-tetraazacyclotetradecane (Cyclam) and 1,4,7,10-tetraazacyclododecane (Cyclen).

In general, these platforms are made by standard chemical synthesis techniques. PEG must be derivatized and made multivalent, which is accomplished using standard techniques. Some substances suitable for conjugate synthesis, such as PEG, albumin, and IgG are available commercially.

Conjugation of an IRP and/or IRC to a platform molecule may be effected in any number of ways, typically involving one or more crosslinking agents and functional groups on the IRP and/or IRC and platform molecule. Platforms and IRP and/or IRC must have appropriate linking groups. Linking groups are added to platforms using standard synthetic chemistry techniques. Linking groups may be added to polypeptide platforms and IRP and/or IRC using either standard solid phase synthetic techniques or recombinant techniques. Recombinant approaches may require post-translational modification in order to attach a linker, and such methods are known in the art.

As an example, polypeptides contain amino acid side chain moieties containing functional groups such as amino, carboxyl or sulfhydryl groups that serve as sites for coupling the polypeptide to the platform. Residues that have such functional groups may be added to the polypeptide if the polypeptide does not already contain these groups. Such residues may be incorporated by solid phase synthesis techniques or recombinant techniques, both of which are well known in the peptide synthesis arts. When the polypeptide has a carbohydrate side chain(s) (or if the platform is a carbohydrate), functional amino, sulfhydryl and/or aldehyde groups may be incorporated therein by conventional chemistry. For instance, primary amino groups may be incorporated by reaction of the oxidized sugar with ethylenediamine in the presence of sodium cyanoborohydride, sulfhydryls may be introduced by reaction of cysteamine dihydrochloride followed by reduction with a standard disulfide reducing agent, while aldehyde groups may be generated following periodate oxidation. In a similar fashion, the platform molecule may also be derivatized to contain functional groups if it does not already possess appropriate functional groups.

Hydrophilic linkers of variable lengths are useful for connecting IRP and/or IRC to platform molecules. Suitable linkers include linear oligomers or polymers of ethylene glycol. Such linkers include linkers with the formula $R^1S(CH_2CH_2O)_nCH_2CH_2O(CH_2)_mCO_2R^2$ wherein n=0-200, m=1 or 2, $R^1$=H or a protecting group such as trityl, $R^2$=H or alkyl or aryl, e.g., 4-nitrophenyl ester. These linkers are useful in connecting a molecule containing a thiol reactive group such as haloaceyl, maleiamide, etc., via a thioether to a second molecule which contains an amino group via an amide bond. These linkers are flexible with regard to the order of attachment, i.e., the thioether can be formed first or last.

In embodiments in which an IRP and/or IRC are proximately associated by adsorption onto a surface, the surface may be in the form of a carrier particle (for example, a nanoparticle) made with either an inorganic or organic core. Examples of such nanoparticles include, but are not limited to, nanocrystalline particles, nanoparticles made by the polymerization of alkylcyanoacrylates and nanoparticles made by the polymerization of methylidene malonate. Additional surfaces to which an IRP and/or IRC may be adsorbed include, but are not limited to, activated carbon particles and protein-ceramic nanoplates. Other examples of carrier particles are provided herein.

Adsorption of polynucleotides and polypeptides to a surface for the purpose of delivery of the adsorbed molecules to cells is well known in the art. See, for example, Douglas et al. (1987) *Crit. Rev. Ther. Drug. Carrier Syst.* 3:233-261; Hagiwara et al. (1987) *In Vivo* 1:241-252; Bousquet et al. (1999) *Pharm. Res.* 16:141-147; and Kossovsky et al., U.S. Pat. No. 5,460,831. Preferably, the material comprising the adsorbent surface is biodegradable. Adsorption of an IRP and/or IRC to a surface may occur through non-covalent interactions, including ionic and/or hydrophobic interactions.

In general, characteristics of carriers such as nanoparticles, such as surface charge, particle size and molecular weight, depend upon polymerization conditions, monomer concentration and the presence of stabilizers during the polymerization process (Douglas et al., 1987). The surface of carrier particles may be modified, for example, with a surface coating, to allow or enhance adsorption of the IRP and/or IRC. Carrier particles with adsorbed IRP and/or IRC may be further coated with other substances. The addition of such other substances may, for example, prolong the half-life of the particles once administered to the subject and/or may target the particles to a specific cell type or tissue, as described herein.

Nanocrystalline surfaces to which an IRP and/or IRC may be adsorbed have been described (see, for example, U.S. Pat. No. 5,460,831). Nanocrystalline core particles (with diameters of 1 μm or less) are coated with a surface energy modifying layer that promotes adsorption of polypeptides, polynucleotides and/or other pharmaceutical agents. Another adsorbent surface are nanoparticles made by the polymerization of alkylcyanoacrylates. Alkylcyanoacrylates can be polymerized in acidified aqueous media by a process of anionic polymerization. Depending on the polymerization conditions, the small particles tend to have sizes in the range of 20 to 3000 nm, and it is possible to make nanoparticles specific surface characteristics and with specific surface charges (Douglas et al., 1987). For example, oligonucleotides may be adsorbed to polyisobutyl- and polyisohexlcyanoacrylate nanoparticles in the presence of hydrophobic cations such as tetraphenylphosphonium chloride or quaternary ammonium salts, such as cetyltrimethyl ammonium bromide. Oligonucleotide adsorption on these nanoparticles appears to be mediated by the formation of ion pairs between negatively charged phosphate groups of the nucleic acid chain and the hydrophobic cations. See, for example, Lambert et al. (1998) *Biochimie* 80:969-976, Chavany et al. (1994) *Pharm. Res.* 11:1370-1378; Chavany et al. (1992) *Pharm. Res.* 9:441-449. Another adsorbent surface are nanoparticles made by the polymerization of methylidene malonate.

IRPs or IRCs may be administered in the form of microcarrier (MC) complexes. Accordingly, provided herein are compositions comprising IRP/MC complexes or IRC/MC complexes. IRP/MC complexes comprise an IRP bound to the surface of a microcarrier (i.e., the IRP is not encapsulated in the MC), and preferably comprise multiple molecules of IRP bound to each microcarrier. In certain embodiments, a mixture of different IRPs may be complexed with a microcarrier, such that the microcarrier is bound to more than one IRP species. The bond between the IRP and MC may be covalent or non-covalent. As will be understood by one of skill in the art, the IRP may be modified or derivatized and the composition of the microcarrier may be selected and/or modified to accommodate the desired type of binding desired for IRP/MC complex formation. This same description applies for IRC/MC complexes. In certain embodiments, a mixture of IRCs and IRPs may be complexed with a microcarrier, such that the microcarrier is bound to at least one IRC and IRP species.

Microcarriers useful are less than about 150, 120 or 100 μm in size, more commonly less than about 50-60 μm in size, preferably less than about 10 μm in size, and are insoluble in pure water. Microcarriers used are preferably biodegradable, although nonbiodegradable microcarriers are acceptable. Microcarriers are commonly solid phase, such as "beads" or other particles, although liquid phase microcarriers such as oil in water emulsions comprising a biodegradable polymers or oils are also contemplated. A wide variety of biodegradable and nonbiodegradable materials acceptable for use as microcarriers are known in the art.

Microcarriers for use in the compositions or methods described herein are generally less than about 10 μm in size (e.g., have an average diameter of less than about 10 μm, or at least about 97% of the particles pass through a 10 μm screen filter), and include nanocarriers (i.e., carriers of less than about 1 μm size). Preferably, microcarriers are selected having sizes within an upper limit of about 9, 7, 5, 2, or 1 μm or 900, 800, 700, 600, 500, 400, 300, 250, 200, or 100 nm and an independently selected lower limit of about 4, 2, or 1 μm or about 800, 600, 500, 400, 300, 250, 200, 150, 100, 50, 25, or 10 nm, where the lower limit is less than the upper limit. In some embodiments, the microcarriers have a size of about 1.0-1.5 μm, about 1.0-2.0 μm or about 0.9-1.6 μm. In certain preferred embodiments, the microcarriers have a size of about 10 nm to about 5 μm or about 25 nm to about 4.5 μm, about 1 μm, about 1.2 μm, about 1.4 μm, about 1.5 μm, about 1.6 μm, about 1.8 μm, about 2.0 μm, about 2.5 μm or about 4.5 μm. When the microcarriers are nanocarriers, preferred embodiments include nanocarriers of about 25 to about 300 nm, 50 to about 200 nm, about 50 nm or about 200 nm.

Solid phase biodegradable microcarriers may be manufactured from biodegradable polymers including, but not limited to: biodegradable polyesters, such as poly(lactic acid), poly(glycolic acid), and copolymers (including block copolymers) thereof, as well as block copolymers of poly(lactic acid) and poly(ethylene glycol); polyorthoesters such as polymers based on 3,9-diethylidene-2,4,8,10-tetraoxaspiro[5.5]undecane (DETOSU); polyanhydrides such as poly(anhydride) polymers based on relatively hydrophilic monomers such as sebacic acid; polyanhydride imides, such as polyanhydride polymers based on sebacic acid-derived monomers incorporating amino acids (i.e., linked to sebacic acid by imide bonds through the amino-terminal nitrogen) such as glycine or alanine; polyanhydride esters; polyphosphazenes, especially poly(phosphazenes) which contain hydrolysis-sensitive ester groups which can catalyze degradation of the polymer backbone through generation of carboxylic acid groups (Schacht et al., (1996) *Biotechnol. Bioeng.* 1996:102); and polyamides such as poly(lactic acid-co-lysine).

A wide variety of nonbiodegradable materials suitable for manufacturing microcarriers are also known, including, but not limited to polystyrene, polypropylene, polyethylene, silica, ceramic, polyacrylamide, dextran, hydroxyapatite, latex, gold, and ferromagnetic or paramagnetic materials. Certain embodiments exclude gold, latex, and/or magnetic beads. In certain embodiments, the microcarriers may be made of a first material (e.g., a magnetic material) encapsulated with a second material (e.g., polystyrene).

Solid phase microspheres are prepared using techniques known in the art. For example, they can be prepared by emulsion-solvent extraction/evaporation technique. Generally, in this technique, biodegradable polymers such as polyanhydrates, poly(alkyl-cyanoacrylates) and poly(hydroxy esters), for example, poly(lactic acid), poly(glycolic acid), poly(D,L-lactic-co-glycolic acid) and poly(caprolactone), are dissolved in a suitable organic solvent, such as methylene chloride, to constitute the dispersed phase (DP) of emulsion. DP is emulsified by high-speed homogenization into excess volume of aqueous continuous phase (CP) that contains a dissolved surfactant, for example, polyvinylalcohol (PVA) or polyvinylpirrolidone (PVP). Surfactant in CP is to ensure the formation of discrete and suitably-sized emulsion droplet. The organic solvent is then extracted into the CP and subsequently evaporated by raising the system temperature. The solid microparticles are then separated by centrifugation or filtration, and dried, for example, by lyophilization or application of vacuum, before storing at 4° C.

Physico-chemical characteristics such as mean size, size distribution and surface charge of dried microspheres may be determined. Size characteristics are determined, for example, by dynamic light scattering technique and the surface charge was determined by measuring the zeta potential.

Liquid phase microcarriers include liposomes, micelles, oil droplets and other lipid or oil-based particles which incorporate biodegradable polymers or oils. In certain embodiments, the biodegradable polymer is a surfactant. In other embodiments, the liquid phase microcarriers are biodegradable due to the inclusion of a biodegradable oil such as squalene or a vegetable oil. One preferred liquid phase microcarrier is oil droplets within an oil-in-water emulsion. Preferably, oil-in-water emulsions used as microcarriers comprise biodegradable substituents such as squalene.

Covalently bonded IRP/MC complexes may be linked using any covalent crosslinking technology known in the art. Typically, the IRP portion will be modified, either to incorporate an additional moiety (e.g., a free amine, carboxyl or sulfhydryl group) or incorporate modified (e.g., phosphorothioate) nucleotide bases to provide a site at which the IRP portion may be linked to the microcarrier. The link between the IRP and MC portions of the complex can be made at the 3' or 5' end of the IRP, or at a suitably modified base at an internal position in the IRP. The microcarrier is generally also modified to incorporate moieties through which a covalent link may be formed, although functional groups normally present on the microcarrier may also be utilized. The IRP/MC is formed by incubating the IRP with a microcarrier under conditions which permit the formation of a covalent complex (e.g., in the presence of a crosslinking agent or by use of an activated microcarrier comprising an activated moiety which will form a covalent bond with the IRP).

A wide variety of crosslinking technologies are known in the art, and include crosslinkers reactive with amino, carboxyl and sulfhydryl groups. As will be apparent to one of skill in the art, the selection of a crosslinking agent and crosslinking protocol will depend on the configuration of the IRP and the microcarrier as well as the desired final configuration of the IRP/MC complex. The crosslinker may be either homobifunctional or heterobifunctional. When a homobifunctional crosslinker is used, the crosslinker exploits the same moiety on the IRP and MC (e.g., an aldehyde crosslinker may be used to covalently link an IRP and MC where both the IRP and MC comprise one or more free amines). Heterobifunctional crosslinkers utilize different moieties on the IRP and MC, (e.g., a maleimido-N-hydroxysuccinimide ester may be used to covalently link a free sulfhydryl on the IRP and a free amine on the MC), and are preferred to minimize formation of inter-microcarrier bonds. In most cases, it is preferable to crosslink through a first crosslinking moiety on the microcarrier and a second crosslinking moiety on the IRP, where the second crosslinking moiety is not present on the microcarrier. One preferred method of producing the IRP/MC complex is by 'activating' the microcarrier by incubating with a heterobifunctional crosslinking agent, then forming the IRP/MC complex by incubating the IRP and activated MC under conditions appropriate for reaction. The crosslinker may incorporate a "spacer" arm between the reactive moieties, or the two reactive moieties in the crosslinker may be directly linked.

In one preferred variation, the IRP portion comprises at least one free sulfhydryl (e.g., provided by a 5'-thiol modified base or linker) for crosslinking to the microcarrier, while the microcarrier comprises free amine groups. A heterobifunctional crosslinker reactive with these two groups (e.g., a crosslinker comprising a maleimide group and a NHS-ester), such as succinimidyl 4-(N-maleimidomethyl)cyclohexane-1-carboxylate is used to activate the MC, then covalently crosslink the IRP to form the IRP/MC complex.

Non-covalent IRP/MC complexes may be linked by any non-covalent binding or interaction, including ionic (electrostatic) bonds, hydrophobic interactions, hydrogen bonds, van der Waals attractions, or a combination of two or more different interactions, as is normally the case when a binding pair is to link the IRP and MC.

Preferred non-covalent IRP/MC complexes are typically complexed by hydrophobic or electrostatic (ionic) interactions, or a combination thereof, (e.g., through base pairing between an IRP and a polynucleotide bound to an MC use of a binding pair). Due to the hydrophilic nature of the backbone of polynucleotides, IRP/MC complexes which rely on hydrophobic interactions to form the complex generally require modification of the IRP portion of the complex to incorporate a highly hydrophobic moiety. Preferably, the hydrophobic moiety is biocompatible, nonimmunogenic, and is naturally occurring in the individual for whom the composition is intended (e.g., is found in mammals, particularly humans). Examples of preferred hydrophobic moieties include lipids, steroids, sterols such as cholesterol, and terpenes. The method of linking the hydrophobic moiety to the IRP will, of course, depend on the configuration of the IRP and the identity of the hydrophobic moiety. The hydrophobic moiety may be added at any convenient site in the IRP, preferably at either the 5' or 3' end; in the case of addition of a cholesterol moiety to an IRP, the cholesterol moiety is preferably added to the 5' end of the IRP, using conventional chemical reactions (see, for example, Godard et al. (1995) *Eur. J. Biochem.* 232:404-410). Preferably, microcarriers for use in IRP/MC complexes linked by hydrophobic bonding are made from hydrophobic materials, such as oil droplets or hydrophobic polymers, although hydrophilic materials modified to incorporate hydrophobic moieties may be utilized as well. When the microcarrier is a liposome or other liquid phase microcarrier comprising a lumen and the IRP is desired to be associated with the outer surface of the MC, the IRP/MC complex is formed by mixing the IRP and the MC after preparation of the MC, in order to avoid encapsulation of the IRP during the MC preparation process.

Non-covalent IRP/MC complexes bound by electrostatic binding typically exploit the highly negative charge of the polynucleotide backbone. Accordingly, microcarriers for use in non-covalently bound IRP/MC complexes are generally positively charged (cationic) at physiological pH (e.g., about pH 6.8-7.4). The microcarrier may intrinsically possess a positive charge, but microcarriers made from compounds not normally possessing a positive charge may be derivatized or otherwise modified to become positively charged (cationic). For example, the polymer used to make the microcarrier may be derivatized to add positively charged groups, such as primary amines. Alternately, positively charged compounds may be incorporated in the formulation of the microcarrier during manufacture (e.g., positively charged surfactants may be used during the manufacture of poly(lactic acid)/poly(glycolic acid) copolymers to confer a positive charge on the resulting microcarrier particles).

For example, to prepare cationic microspheres, cationic lipids or polymers, for example, 1,2-dioleoyl-1,2,3-trimethylammoniopropane (DOTAP), cetyltrimethylammonium bromide (CTAB) or polylysine, are added either to DP or CP, as per their solubility in these phases.

IRP/MC complexes can be preformed by adsorption onto cationic microspheres by incubation of polynucleotide and the particles, preferably in an aqueous admixture. Such incubation may be carried out under any desired conditions, including ambient (room) temperature (e.g., approximately 20° C.) or under refrigeration (e.g., 4° C.). Because cationic microspheres and polynucleotides associate relatively quickly, the incubation may be for any convenient time period, such as 5, 10, 15 minutes or more, including overnight and longer incubations. For example, IRPs can be adsorbed onto the cationic microspheres by overnight aqueous incubation of polynucleotide and the particles at 4° C. However, because cationic microspheres and polynucleotides spontaneously associate, the IRP/MC complex can be formed by simple co-administration of the polynucleotide and the MC. Microspheres may be characterized for size and surface charge before and after polynucleotide association. Selected batches may then be evaluated for activity against suitable controls in, for example, human peripheral blood mononuclear cell (PBMC) and mouse splenocyte assays. The formulations may also be evaluated in suitable animal models.

Non-covalent IRP/MC complexes linked by nucleotide base pairing may be produced using conventional methodologies. Generally, base-paired IRP/MC complexes are produced using a microcarrier comprising a bound, preferably a covalently bound, polynucleotide (the "capture polynucleotide") that is at least partially complementary to the IRP. The segment of complementarity between the IRP and the capture nucleotide is preferably at least 6, 8, 10 or 15 contiguous base pairs, more preferably at least 20 contiguous base pairs. The capture nucleotide may be bound to the MC by any method known in the art, and is preferably covalently bound to the IRP at the 5' or 3' end.

In other embodiments, a binding pair may be used to link the IRP and MC in an IRP/MC complex. The binding pair may be a receptor and ligand, an antibody and antigen (or epitope), or any other binding pair which binds at high affinity (e.g., Kd less than about 10-8). One type of preferred binding pair is biotin and streptavidin or biotin and avidin, which form very tight complexes. When using a binding pair to mediate IRP/MC complex binding, the IRP is derivatized, typically by a covalent linkage, with one member of the binding pair, and the MC is derivatized with the other member of the binding pair. Mixture of the two derivatized compounds results in IRP/MC complex formation.

Isolation and Synthesis of Immunoregulatory Polynucleotides

Provided herein are also methods of making the immunoregulatory polynucleotides described herein. In some embodiments, the immunoregulatory polynucleotides comprise modified immunoregulatory sequences. In some embodiments, the immunoregulatory polynucleotides comprise unmodified immunoregulatory sequences. The methods may be any of those described herein. For example, the method could be synthesizing the IRP (for example, using solid state synthesis) and may further comprise any purification step(s). Methods of purification are known in the art.

Also provided are methods for isolating and synthesizing immunoregulatory polynucleotide (IRP). In some embodiments, the IRP is a modified IRP. In some embodiments, the IRP is an unmodified IRP.

The IRP can be synthesized using techniques and nucleic acid synthesis equipment which are well known in the art including, but not limited to, enzymatic methods, chemical methods, and the degradation of larger oligonucleotide sequences. See, for example, Ausubel et al. (1987); and Sambrook et al. (1989). When assembled enzymatically, the individual units can be ligated, for example, with a ligase such as T4 DNA or RNA ligase. U.S. Pat. No. 5,124,246. Oligonucleotide degradation can be accomplished through the exposure of an oligonucleotide to a nuclease, as exemplified in U.S. Pat. No. 4,650,675.

The IRP can also be isolated using conventional polynucleotide isolation procedures. Such procedures include, but are not limited to, hybridization of probes to genomic or cDNA libraries to detect shared nucleotide sequences, antibody screening of expression libraries to detect shared structural features and synthesis of particular native sequences by the polymerase chain reaction.

Circular immunoregulatory polynucleotide can be isolated, synthesized through recombinant methods, or chemically synthesized. Where the circular IRP is obtained through isolation or through recombinant methods, the IRP will preferably be a plasmid. The chemical synthesis of smaller circular oligonucleotides can be performed using any method described in the literature. See, for instance, Gao et al. (1995) Nucleic Acids Res. 23:2025-2029; and Wang et al. (1994) Nucleic Acids Res. 22:2326-2333.

The techniques for making polynucleotides and modified polynucleotides are known in the art. Naturally occurring DNA or RNA, containing phosphodiester linkages, is generally synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Once the desired polynucleotide sequence has been synthesized, the polynucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in Protocols for Oligonucleotides and Analogs, Synthesis and Properties (Agrawal, ed.) Humana Press, Totowa, N.J.; Warner et al. (1984) DNA 3:401 and U.S. Pat. No. 4,458,066.

Synthesis of polynucleotides containing modified phosphate linkages or non-phosphate linkages is also known in the art. For a review, see Matteucci (1997) "Oligonucleotide Analogs: an Overview" in Oligonucleotides as Therapeutic Agents, (D. J. Chadwick and G. Cardew, ed.) John Wiley and Sons, New York, N.Y. The phosphorous derivative (or modified phosphate group) which can be attached to the sugar or sugar analog moiety in the polynucleotides can be a monophosphate, diphosphate, triphosphate, alkylphosphonate, phosphorothioate, phosphorodithioate, phosphoramidate or the like. The preparation of the above-noted phosphate analogs, and their incorporation into nucleotides, modified nucleotides and oligonucleotides, per se, is also known and need not be described here in detail. Peyrottes et al. (1996) Nucleic Acids Res. 24:1841-1848; Chaturvedi et al. (1996) Nucleic Acids Res. 24:2318-2323; and Schultz et al. (1996) Nucleic Acids Res. 24:2966-2973. For example, synthesis of phosphorothioate oligonucleotides is similar to that described above for naturally occurring oligonucleotides except that the oxidation step is replaced by a sulfurization step (Zon (1993) "Oligonucleoside Phosphorothioates" in Protocols for Oligonucleotides and Analogs, Synthesis and Properties (Agrawal, ed.) Humana Press, pp. 165-190). Similarly the synthesis of other phosphate analogs, such as phosphotriester (Miller et al. (1971) JAGS 93:6657-6665), non-bridging phosphoramidates (Jager et al. (1988) Biochem. 27:7247-7246), N3' to P5' phosphoramidiates (Nelson et al. (1997) JOC 62:7278-7287) and phosphorodithioates (U.S. Pat. No. 5,453,496) has also been described. Other non-phosphorous based modified oligonucleotides can also be used (Stirchak et al. (1989) Nucleic Acids Res. 17:6129-6141).

Those skilled in the art will recognize that a large number of "synthetic" non-natural nucleosides comprising various heterocyclic bases and various sugar moieties (and sugar analogs) are available in the art, and that as long as other criteria of the present invention are satisfied, the IRP can include one or several heterocyclic bases other than the principal five base components of naturally-occurring nucleic acids. Preferably, however, the heterocyclic base in the IRP includes, but is not limited to, uracil-5-yl, cytosin-5-yl, adenin-7-yl, adenin-8-yl, guanin-7-yl, guanin-8-yl, 4-aminopyrrolo[2,3-d]pyrimidin-5-yl, 2-amino-4-oxopyrolo[2,3-d]pyrimidin-5-yl, 2-amino-4-oxopyrrolo[2,3-d]pyrimidin-3-yl groups, where the purines are attached to the sugar moiety of the IRP via the 9-position, the pyrimidines via the 1-position, the pyrrolopyrimidines via the 7-position and the pyrazolopyrimidines via the 1-position.

The preparation of base-modified nucleosides, and the synthesis of modified oligonucleotides using the base-modified nucleosides as precursors, has been described, for example, in U.S. Pat. Nos. 4,910,300, 4,948,882, and 5,093,232. These base-modified nucleosides have been designed so that they can be incorporated by chemical synthesis into either terminal or internal positions of an oligonucleotide. Such base-modified nucleosides, present at either terminal or internal positions of an oligonucleotide, can serve as sites for attachment of a peptide. Nucleosides modified in their sugar moiety have also been described (including, but not limited to, e.g., U.S. Pat. Nos. 4,849,513, 5,015,733, 5,118,800, 5,118,802) and can be used similarly.

Administration and Assessment of the Immune Response

As with all compositions for modulation of an immune response, the effective amounts and method of administration of the particular IRP and/or IRC formulation can vary based on the individual, what condition is to be treated and other factors evident to one skilled in the art. Factors to be considered include whether or not the IRP and/or IRC will be administered with or covalently attached to a delivery molecule, route of administration and the number of doses to be administered. Such factors are known in the art and it is well within the skill of those in the art to make such determinations without undue experimentation. A suitable dosage range is one that provides the desired regulation of immune response (e.g., suppression of IFN-α or other cytokine production in response to an immunostimulatory nucleic acid). When suppression of an immune response to an immunostimulatory nucleic acid is desired, a suitable dosage range is one that provides the desired suppression of immune stimulation by the immunostimulatory nucleic acid. Generally, dosage is determined by the amount of IRP and/or IRC administered to the patient, rather than the overall quantity of IRP-containing composition administered. Useful dosage ranges of the IRP and/or IRC, given in amounts of IRP and/or IRC delivered, may be, for example, from about any of the following: 0.5 to 10 mg/kg, 1 to 9 mg/kg, 2 to 8 mg/kg, 3 to 7 mg/kg, 4 to 6 mg/kg, 5 mg/kg, 1 to 10 mg/kg, or 5 to 10 mg/kg. The absolute amount given to each patient depends on pharmacological properties such as bioavailability, clearance rate and route of administration.

The effective amount and method of administration of the particular IRP and/or IRC formulation can vary based on the individual patient, desired result and/or type of disorder, the stage of the disease and other factors evident to one skilled in the art. The route(s) of administration useful in a particular application are apparent to one of skill in the art. Routes of administration include but are not limited to topical, dermal, transdermal, transmucosal, epidermal, parenteral, gastrointestinal, and naso-pharyngeal and pulmonary, including transbronchial and transalveolar. A suitable dosage range is one that provides sufficient IRP-containing composition to attain a tissue concentration of about 1-50 µM as measured by blood levels. The absolute amount given to each patient depends on pharmacological properties such as bioavailability, clearance rate and route of administration.

As described herein, tissues in which unwanted immune activation is occurring or is likely to occur are preferred targets for the IRP and/or IRC. Thus, administration of IRP and/or IRC to lymph nodes, spleen, bone marrow, blood, as well as tissue exposed to virus, are preferred sites of administration.

Provided herein are IRP and/or IRC formulations suitable for topical application including, but not limited to, physiologically acceptable implants, ointments, creams, rinses and gels. Exemplary routes of dermal administration are those which are least invasive such as transdermal transmission, epidermal administration and subcutaneous injection.

Compositions provided herein may comprise an IRP or IRC and a pharmaceutically acceptable excipient. Pharmaceutically acceptable excipients, including buffers, are described herein and well known in the art. Remington: The Science and Practice of Pharmacy, 20th edition, Mack Publishing (2000).

Transdermal administration is accomplished by application of a cream, rinse, gel, etc. capable of allowing the IRP and/or IRC to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference. Transdermal transmission may also be accomplished by iontophoresis, for example using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter.

Parenteral routes of administration include but are not limited to electrical (iontophoresis) or direct injection such as direct injection into a central venous line, intravenous, intramuscular, intraperitoneal, intradermal, or subcutaneous injection. Formulations of IRP and/or IRC suitable for parenteral administration are generally formulated in USP water or water for injection and may further comprise pH buffers, salts bulking agents, preservatives, and other pharmaceutically acceptable excipients. Immunoregulatory polynucleotide for parenteral injection may be formulated in pharmaceutically acceptable sterile isotonic solutions such as saline and phosphate buffered saline for injection.

Gastrointestinal routes of administration include, but are not limited to, ingestion and rectal routes and can include the use of, for example, pharmaceutically acceptable powders, pills or liquids for ingestion and suppositories for rectal administration.

Naso-pharyngeal and pulmonary administration include are accomplished by inhalation, and include delivery routes such as intranasal, transbronchial and transalveolar routes. Formulations of IRP and/or IRC suitable for administration by inhalation including, but not limited to, liquid suspensions for forming aerosols as well as powder forms for dry powder inhalation delivery systems are provided. Devices suitable for administration by inhalation of IRP or IRC formulations include, but are not limited to, atomizers, vaporizers, nebulizers, and dry powder inhalation delivery devices.

As is well known in the art, solutions or suspensions used for the routes of administration described herein can include any one or more of the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

As is well known in the art, pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. It may be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

As is well known in the art, sterile injectable solutions can be prepared by incorporating the active compound(s) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

The above-mentioned compositions and methods of administration are meant to describe but not limit the methods of administering the formulations of IRPs and IRCs described herein. The methods of producing the various compositions and devices are within the ability of one skilled in the art and are not described in detail here.

Combination Therapy

The IRP and/or IRC can be administered in combination with other therapeutic agent, as described herein, and can be combined with a physiologically acceptable carrier thereof (and as such includes these compositions described herein). The methods described herein may be practiced in combination with other therapies which make up the standard of care for the disorder, such as administration of anti-inflammatory agents. The IRP and/or IRC can be administered in combination with a corticosteroid, as described herein, and can be combined with a physiologically acceptable carrier thereof (and as such \includes these compositions described herein). The IRP and/or IRC may be any of those described herein. In some embodiments, the IRP and/or IRC comprises a modified IRS. In some embodiments, the IRP and/or IRC comprises both unmodified and modified IRSs.

In some embodiments, an IRP and/or IRC is administered in combination with a corticosteroid. In some embodiments, the corticosteroid is a glucocorticosteroid. In some embodiments, the corticosteroid is a mineralocorticoid. Corticosteroids include, but are not limited to, corticosterone and derivatives, prodrugs, isomers and analogs thereof, cortisone and derivatives, prodrugs, isomers and analogs thereof (i.e., Cortone), aldosterone and derivatives, prodrugs, isomers and analogs thereof, dexamethasone and derivatives, prodrugs, isomers and analogs thereof (i.e., Decadron), prednisone and derivatives, prodrugs, isomers and analogs thereof (i.e., Prelone), fludrocortisones and derivatives, prodrugs, isomers and analogs thereof (i.e. Florinef®), hydrocortisone and derivatives, prodrugs, isomers and analogs thereof (i.e., cortisol or Cortef), hydroxycortisone and derivatives, prodrugs, isomers and analogs thereof, betamethasone and derivatives, prodrugs, isomers and analogs thereof (i.e., Celestone), budesonide and derivatives, prodrugs, isomers and analogs thereof (i.e., Entocort EC), methylprednisolone and derivatives, prodrugs, isomers and analogs thereof (i.e., Medrol), prednisolone and derivatives, prodrugs, isomers and analogs thereof (i.e., Deltasone, Crtan, Meticorten, Orasone, or Sterapred), triamcinolone and derivatives, prodrugs, isomers and analogs thereof (i.e., Kenacort or Kenalog), and the like. In some embodiments, the corticosteroid is fludrocortisone or a derivative, prodrug, isomer or analog thereof. In some embodiments, the corticosteroid is fludrocortisone. In some embodiments, the corticosteroid is hydroxycortisone or a derivative, prodrug, isomer or analog thereof. In some embodiments, the corticosteroid is hydroxycortisone.

In some embodiments, the corticosteroid is administered any of between about 0.001 mg to about 1 mg, about 0.5 mg to about 1 mg, about 1 mg to about 2 mg, about 2 mg to about 20 mg, about 20 mg to about 40 mg, about 40 to about 80 mg, about 80 to about 120 mg, about 120 mg to about 200 mg, about 200 mg to about 500 mg, about 500 mg to about 1000 mg per day. In some embodiments, the corticosteroid is administered any of between about 0.1 mg/kg to about 0.5 mg/kg, about 0.5 mg/kg to about 1 mg/kg, about 1 mg/kg to about 2 mg/kg, about 2 mg/kg to about 5 mg/kg, about 5 mg/kg to about 10 mg/kg, about 10 mg/kg to about 15 mg/kg, about 15 mg/kg to about 20 mg/kg, about 20 mg/kg to about 25 mg/kg, about 25 mg/kg to 35 mg/kg, or about 35 mg/kg to about 50 mg/kg per day.

In some embodiments, the IRP and/or IRC used in combination therapy, given in amounts of IRP and/or IRC delivered, may be, for example, from about any of the following: 0.5 to 10 mg/kg, 1 to 9 mg/kg, 2 to 8 mg/kg, 3 to 7 mg/kg, 4 to 6 mg/kg, 5 mg/kg, 1 to 10 mg/kg, or 5 to 10 mg/kg.

In some embodiments, the IRP and/or IRC is administered simultaneously with the other therapeutic agent including, but not limited to, a corticosteroid (simultaneous administration). In some embodiments, the IRP and/or IRC is administered sequentially with the other therapeutic agent including, but not limited to, a corticosteroid (sequential administration). In some embodiments, the IRP and/or IRC is administered by the same route of administration as the other therapeutic agent. In some embodiments, the IRP and/or IRC is administered by a different route of administration than the other therapeutic agent. In some embodiments, the other therapeutic agent is administered parentally (e.g., central venous line, intra-arterial, intravenous, intramuscular, intraperitoneal, intradermal, or subcutaneous injection), orally, gastrointestinally, topically, naso-pharyngeal and pulmonary (e.g. inhalation or intranasally). In some embodiments, the other therapeutic agent is a corticosteroid.

In some embodiments, the combination of an IRP and/or IRC with an other therapeutic agent reduces the effective amount (including, but not limited to, dosage volume, dosage concentration, total drug dose administered) of the IRP and/or IRC and/or the other therapeutic agents compared to the effective amount when the IRP and/or IRC or other therapeutic agent is administered alone. In some embodiments, the combination of an IRP and/or IRC with a corticosteroid reduces the effective amount compared to a corticosteroid administered alone. In some embodiments, the combination of an IRP and/or IRC with another therapeutic agent reduces the frequency of administrations of the other therapeutic agent compared to administration of the other therapeutic agent alone. In some embodiments, the combination of an IRP and/or IRC with another therapeutic agent reduces the total duration of treatment compared to administration of the other therapeutic agent alone. In some embodiments, the combination of an IRP and/or IRC with another therapeutic agent reduces the side effects associated with administration of the other therapeutic agent alone. In some embodiments, the other therapeutic agent is a corticosteroid. In some embodiments, the corticosteroid is fludrocortisone or a derivative, prodrug, isomer or analog thereof. In some embodiments, the corticosteroid is fludrocortisone.

In some embodiments, the combination therapy including but not limited to the combination of an IRP and/or IRC and a corticosteroid is used in the treatment of an inflammatory disease. In some embodiments, the inflammatory disease is an autoimmune disease. In some embodiments, the autoimmune disease is rheumatoid arthritis. In some embodiments, the autoimmune disease is lupus. In some embodiments, the autoimmune disease systemic lupus erythematosus (SLE). In some embodiments, the lupus is associated with renal flares. In some embodiments, the renal flares are moderate renal flares. In some embodiments, the renal flares are severe renal flares.

Kits

Provided here are kits. In certain embodiments, the kits described herein generally comprise one or more containers comprising any IRP and/or IRC as described herein. In some embodiments, the kits comprise an IRP and/or IRC with a modified IRS. In some embodiments, the kits comprise an IRP and/or IRC with an unmodified IRS. In some variation, the kit comprises IRPs and/or IRCs with both modified and unmodified IRSs. In some embodiments, the kits may further provide another therapeutic agent. In some embodiments, the other therapeutic agent is a corticosteroid.

The kits may further comprise a suitable set of instructions, generally written instructions, relating to the use of the IRP and/or IRC for any of the methods described herein (e.g., suppression of a response to an immunostimulatory nucleic acid, suppression of a TLR7 and/or TLR9 dependent response, ameliorating one or more symptoms of an autoimmune disease, ameliorating a symptom of chronic inflammatory disease, decreasing cytokine production in response to a virus).

The kits may comprise IRP and/or IRC packaged in any convenient, appropriate packaging. For example, if the IRP or IRC is a dry formulation (e.g., freeze dried or a dry powder), a vial with a resilient stopper is normally used, so that the IRP or IRC may be easily resuspended by injecting fluid through the resilient stopper. Ampoules with non-resilient, removable closures (e.g., sealed glass) or resilient stoppers are most conveniently used for liquid formulations of IRP or IRC. Also contemplated are packages for use in combination with a specific device, such as an inhaler, nasal administration device (e.g., an atomizer), a syringe or an infusion device such as a minipump.

The instructions relating to the use of IRP and/or IRC generally include information as to dosage, dosing schedule, and route of administration for the intended method of use. The containers of IRP or IRC may be unit doses, bulk packages (e.g., multi-dose packages) or sub-unit doses. Instructions supplied in the kits described herein are typically written instructions on a label or package insert (e.g., a paper sheet included in the kit), but machine-readable instructions (e.g., instructions carried on a magnetic or optical storage disk) are also acceptable.

In some embodiments, kits described herein comprise materials for production of IRP and/or IRC as complexes for administration, for example, encapsulation material, microcarrier complex material and so on. Generally, the kit includes separate containers of IRP or IRC and the complex material(s). The IRP or IRC and complexes are preferably supplied in a form which allows formation of IRP- or IRC-complex upon mixing of the supplied IRP or IRC and complex material. This configuration is preferred when the IRP- or IRC-complex is linked by non-covalent bonding. This configuration is also preferred when the IRP- or IRC-complex are to be crosslinked via a heterobifunctional crosslinker; either IRP/IRC or the complex is supplied in an "activated" form (e.g., linked to the heterobifunctional crosslinker such that a moiety reactive with the IRP/IRC is available).

EXAMPLES

The following examples are provided to illustrate, but not limit, the invention. The IRPs used in the examples were synthesized as 2'-deoxyribo polynucleotide sequences with all phosphorothioate linkages, unless otherwise noted (e.g., particular nucleotides noted as 2'-O-methyl sugar modifications).

Abbreviations: ELHA (enzyme-linked hybridization assay); ELISA (enzyme-linked immunosorbent assay); GC (glucocorticoids); IC50 (half maximal inhibitory concentration); IC90 (90% maximal inhibitory concentration); IFN (interferon); IP (intraperitoneal); IRP (immunoregulatory polynucleotide); ISS (immunostimulatory sequence); IV (intravenous); MOI (multiplicity of infection); PBMC (peripheral blood mononuclear cells); PDC (plasmacytoid dendritic cells); SC (subcutaneous); SLE (systemic lupus erythematosus); TLR (toll-like receptor).

Example 1

Human B-cells Cultured in the Presence of IRPs

To further investigate the effect of IRPs on B-cell stimulatory activity, various sequences or control samples were assayed for IL-6.

For the human B-cell assay, B-cells were purified from total blood cells obtained from healthy donors using magnetic beads (CD19 positive). Cells were resuspended in fresh medium (RPMI 1640 with 10% fetal calf serum, 50 units/mL penicillin, 50 µg/mL streptomycin, and 2 mM glutamine). The cells were then incubated with various concentrations of IRPs or a control sequences as indicated in the figures. At 48 hours, supernatants were collected and cytokine levels, IL-6, were measured using immunoassay. A description for the IRPs tested is found in Table 1-1.

FIGS. 1A and 1B show IL-6 produced (pg/mL) in the presence of the tested IRPs or controls. Phosphorothioate-modified oligodeoxynucleotides induce some human B-cell response due to their backbone in vitro, but no evidence of B-cell activation has been shown in vivo in primates. However, B-cells can infiltrate organs in rodents. C532, DV177, and SEQ ID NO:109 induced a B-cell response as evidenced by increased IL-6. Surprisingly, SEQ ID NO:42 was different and did not induce any B-cell response.

FIG. 1C shows the percent IL-6 from CpG-ISS stimulated with ISS (TLR9 ligand) either alone or in the presence of the tested IRPs. SEQ ID NO: 79, SEQ ID NO:73, SEQ ID NO:134, SEQ ID NO:143, and SEQ ID NO:144 had low B-cell stimulatory activity.

TABLE 1-1

Sequences of IRPs and Controls

| Sequence (SEQ ID NO) | Comments* |
|---|---|
| CpG-ISS<br>5'-TGA CTG TGA ACG TTC GAG ATG A-3' (SEQ ID NO: 157) | |
| CpG-ISS<br>5'-TCG TCG AAC GTT CGA GAT GAT-3' (SEQ ID NO: 158) | |
| CTRL SEQ<br>5'-NNN NNN NNN NNN NNN NNN NNN N-3' (SEQ ID NO: 159) | random oligonucleotide |
| CTRL SEQ<br>5'-TCC TGC AGG TTA AGT-3' (SEQ ID NO: 160) | |
| 5'-TGC TCC TGG AGG GGT TGT-3' (SEQ ID NO: 42) | |
| 5'-*UGC* TGC TCC TTG AGI GGT TGT TTG T-3' (SEQ ID NO: 109) | 2'OMe on 5'-UGC, |
| 5'-TGC TCC TGG AGI GGT TGT-3' (SEQ ID NO: 73) | |
| 5'-TGC TCC TGG AGI GGT TG-HEG-T-3' (SEQ ID NO: 143) | |
| 5'-TGC TGC TCC TGG AGI GGT TG-HEG-T-3' (SEQ ID NO: 144) | |
| 5'-TGC TGC TCC TGG AGI GGT GTT GT-3' (SEQ ID NO: 79) | |
| 5'-*UGC* CAA TCC TGG AGI GGT TGT-3' (SEQ ID NO: 134) | 2'OMe on 5'-UGC, |

*I = deoxy-inosine

Example 2

Monomer and Tetramer Formation of IRPs

Theoretically IRP containing the quad-G repeat can form a parallel stranded G-tetrad. To further investigate tetramer formation, the effects of substituting inosine for guanine in the quad-G repeat was assessed.

Solutions were prepared of the by mixing 100 mg/mL of the IRP sequences in PBS and 0.5M KCl and storing at room temperature for three to five weeks. The solutions were subsequently analyzed by size-exclusion HPLC.

After storage at room temperature for three weeks, 45.99% of SEQ ID NO:42, which includes 5'-GGGG-3', in the solution was in a tetramer form while only 54.01% was in monomer form. In contrast, 100% of SEQ ID NO:109, which includes 5'-GIGG-3', was in monomer form.

After storage at room temperature for five weeks, 100% of SEQ ID NO:73, SEQ ID NO:79, SEQ ID NO:109, SEQ ID NO:134, SEQ ID NO:143, and SEQ ID NO:144, all of which include 5'-GIGG-3', were in monomer form.

Example 3

High Dosages of IRPs in Rats

To test the activity of IRPs at high dosages in rats, IRPs (SEQ ID NO:42 and SEQ ID NO:109) or a control (PBS) were subcutaneously administered to 8-9 weeks old, female Sprague Dawley rats at a dosage of 100 mg/kg or 10 mg/kg on days 0, 3, 6, and 9 (n=6 per group). Rats were weighed prior to administration and on days 1, 3, 4, 6, 7, and 9. Organs were harvested at the end of the study, and organ weights and tissues levels of the oligonucleotides were determined. In addition, histolocial evaluation of the liver, kidney, and heart was performed.

There was no significant difference in organ weight of the liver, heart, kidney, or spleen upon administration of either 10 mg/kg or 100 mg/kg of SEQ ID NO:42 and SEQ ID NO:109. At 100 mg/kg of SEQ ID NO:109, a decrease in total weight and % weight gain/loss was observed as shown in FIGS. 2A and 2B.

To further test the activity of IRPs at high dosages, IRPs (SEQ ID NO:73, SEQ ID NO: 79, SEQ ID NO:109, SEQ ID NO:134, SEQ ID NO:143, and SEQ ID NO:144) or a control (saline) were subcutaneously administered to 8-9 weeks old, female Sprague Dawley rats at a dosage of 90 mg/kg on days 0, 3, 6, and 9 (n=6 per group). Rats were weighed prior to administration and on days 1, 3, 6, 7, and 9. Organs were harvested at the end of the study, and organ weights and tissues levels of the oligonucleotides were determined. In addition, histological evaluation of the liver, kidney, and heart was performed.

In the group administered SEQ ID NO:109, one rat died two days after the administration of the first dose. In the group administered SEQ ID NO:79, two rats died two days after the administration of the first dose and one rat died two days after the administration of the second dose. Rat total body weight and percent weight gain/loss is shown in FIGS. 2C and 2D.

The histology evaluation of the liver, kidneys and heart is shown in Table 3-1.

TABLE 3-1

Rat Histology.

| Group | Saline | SEQ ID NO: 42 90 mg/kg | SEQ ID NO: 42 10 mg/kg | SEQ ID NO: 109 90 mg/kg | SEQ ID NO: 109 10 mg/kg | SEQ ID NO: 79 90 mg/kg | SEQ ID NO: 79 10 mg/kg |
|---|---|---|---|---|---|---|---|
| Number of Animals | 6 | 6 | 6 | 6 | 6 | 6 | 6 |
| Liver: | | | | | | | |
| No significant changes | 3 | 0 | 3 | 0 | 0 | 0 | 0 |
| Liver changes | 0 | 6 (2.3) | 1 (1.0) | 6 (3.5) | 6 (1.0) | 3 (1.8) | 0 |
| Necrosis | 0 | 1 (3.5) | 0 | 6 (2.0) | 0 | 2 (2.8) | 0 |
| Vacuolation | 0 | 0 | 0 | 6 (2.0) | 0 | 3 (2.3) | 0 |
| Mixed cell infiltration, | 3 (1.7) | 4 (2.1) | 2 (1.5) | 6 (2.0) | 6 (2.5) | 3 (2.5) | 6 (1.8) |
| Right Kidney: | | | | | | | |
| No significant changes | 5 | 0 | 0 | 0 | 0 | 0 | 1 |
| Tubular changes | 0 | 6 (2.0) | 6 (1.0) | 5 (2.0) | 6 (1.0) | 3 (2.0) | 5 (1.1) |
| Tubular basophilia | 0 | 4 (1.5) | 0 | 5 (3.0) | 6 (1.5) | 2 (2.8) | 0 |
| Mineralization | 1 (2.0) | 1 (1.0) | 3 (2.0) | 1 (1.0) | 0 | 1 (2.0) | 2 (1.0) |
| Hydronephrosis | 0 | 0 | 0 | 0 | 0 | 0 | 0 |
| Necrosis | 0 | 0 | 0 | 1 (4.0) | 0 | 3 (4.0) | 0 |
| Heart: | | | | | | | |
| No significant changes | 6 | 6 | 5 | 0 | 6 | 1 | 6 |
| Mononuclear Cell Infiltration | 0 | 0 | 1 (2.0) | 0 | 0 | 0 | 0 |
| Cell Vacuolation | 0 | 0 | 0 | 5 (1.8) | 0 | 2 (1.5) | 0 |
| Hemorrhage | 0 | 0 | 0 | 1 (3.0) | 0 | 2 (3.5) | 0 |
| Necrosis | 0 | 0 | 0 | 1 (1.0) | 0 | 3 (2.0) | 0 |

| Group | SEQ ID NO: 73 90 mg/kg | SEQ ID NO: 73 10 mg/kg | SEQ ID NO: 134 90 mg/kg | SEQ ID NO: 134 10 mg/kg | SEQ ID NO: 143 90 mg/kg | SEQ ID NO: 143 10 mg/kg |
|---|---|---|---|---|---|---|
| Number of Animals | 6 | 6 | 6 | 6 | 6 | 6 |
| Liver: | | | | | | |
| No significant changes | 0 | 0 | 0 | 0 | 0 | 1 |
| Liver changes | 6 (1.9) | 0 | 6 (2.5) | 0 | 6 (2.1) | 0 |
| Necrosis | 0 | 0 | 0 | 0 | 0 | 0 |
| Vacuolation | 0 | 0 | 6 (3.0) | 3 (2.0) | 5 (2.7) | 2 (1.5) |
| Mixed cell infiltration, | 2 (2.0) | 6 (1.8) | 6 (2.0) | 6 (2.2) | 1 (1.0) | 5 (1.4) |
| Right Kidney: | | | | | | |
| No significant changes | 0 | 0 | 0 | | 0 | 0 |
| Tubular changes | 6 (2.0) | 6 (1.3) | 6 (2.0) | 0 | 6 (1.8) | 6 (1.1) |
| Tubular basophilia | 0 | 0 | 6 (3.0) | 6 (1.7) | 3 (1.0) | 0 |
| Mineralization | 2 (1.5) | 1 (1.0) | 0 | 0 | 2 (2.0) | 1 (2.0) |
| Hydronephrosis | 0 | 1 (2.0) | 0 | 0 | 0 | 0 |
| Necrosis | 0 | 0 | 0 | 0 | 0 | 0 |
| Heart: | | | | | | |
| No significant changes | 6 | 6 | 1 | 6 | 1 | 6 |
| Mononuclear Cell Infiltration | 0 | 0 | 0 | 0 | 0 | 0 |
| Cell Vacuolation | 0 | 0 | 5 (1.0) | 0 | 5 (1.0) | 0 |
| Hemorrhage | 0 | 0 | 0 | 0 | 0 | 0 |
| Necrosis | 0 | 0 | 0 | 0 | 0 | 0 |

( ) = Mean severity score where 0 = no change, 1 = minimal, 2 = mild, 3 = moderate and 4 = severe.

SEQ ID NO:73, SEQ ID NO:143, and SEQ ID NO:134 have favorable toxicity profiles. Probable treatment-related changes were noted in the heart, kidney and liver. Cardiac changes were characterized by hemorrhage, necrosis and cell vacuolation. The hemorrhage and necrosis were noted in SEQ ID NO:109 (90 mg/kg) and SEQ ID NO:79 (90 mg/kg) groups. Cellular vacuolation (characterized by a few interstitial cells with vacuolated bluish cytoplasm) was present in some animals from groups SEQ ID NO:109, SEQ ID NO:79, SEQ ID NO:134, SEQ ID NO:143, and SEQ ID NO:144 (90 mg/kg). Kidney changes consisted of tubular changes, tubular basophilia and necrosis. Tubular changes (characterized by increased eosinophilia with some cytoplasmic stippling of proximal tubules) occurred in various incidences in all treated groups. Tubular basophilia and atrophy involved cortical tubules and ranged from multifocal to diffuse, and was also occasionally associated with individual tubular cell necrosis and mild interstitial mononuclear cell infiltration. The tubular basophilia occurred in groups SEQ ID NO:42, SEQ ID NO:79, SEQ ID NO:134, SEQ ID NO:143, and SEQ ID NO:144 (90 mg/kg) and SEQ ID NO:109 (90 mg/kg and 10 mg/kg). Renal necrosis was noted only in the SEQ ID NO:109 and SEQ ID NO:79 (90 mg/kg) groups. Liver changes were characterized by: a) hepatocellular necrosis (either individual cell necrosis or foci of necrosis) in groups SEQ ID NO:42, SEQ ID NO:109, SEQ ID NO:79, and SEQ ID NO:144 (90 mg/kg) and b) hepatocellular cytoplasmic vacuolation in groups SEQ ID NO:109, SEQ ID NO:79, SEQ ID NO:134, SEQ ID NO:143, and SEQ ID NO:144 (90 mg/kg) and SEQ ID NO:134 and SEQ ID NO:144 (10 mg/kg).

Example 4

High Dosages of IRPs in Mice

To test the activity of IRPs at high dosages in mice, IRPs or a control (saline) were subcutaneously administered to BALB/c mice at a dosage of 4 mg/kg, 20 mg/kg, 50 mg/kg, or 100 mg/kg on days 1, 4, 7, and 10 (n=5 per group). Mice were weighed prior to administration and on days 2, 4, 7, 9, and 11. Serum cytokines were assayed at two hours post the first and third injections and 24 hours post the fourth injection. Organs were harvested at the end of the study, and organ weights and tissues levels of the oligonucleotides were determined. In addition, histological evaluation of the liver, kidney, and heart was performed.

Figure 3A:
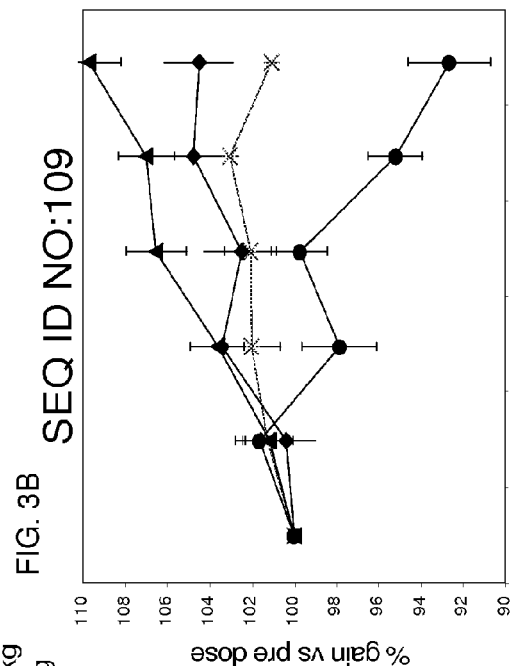
FIGS. 3A-B shows percent weight gain versus pre-dose over time after administration of SEQ ID NO:42 (A) and SEQ ID NO:109 (B) at the indicated doses.
Figure 3B:
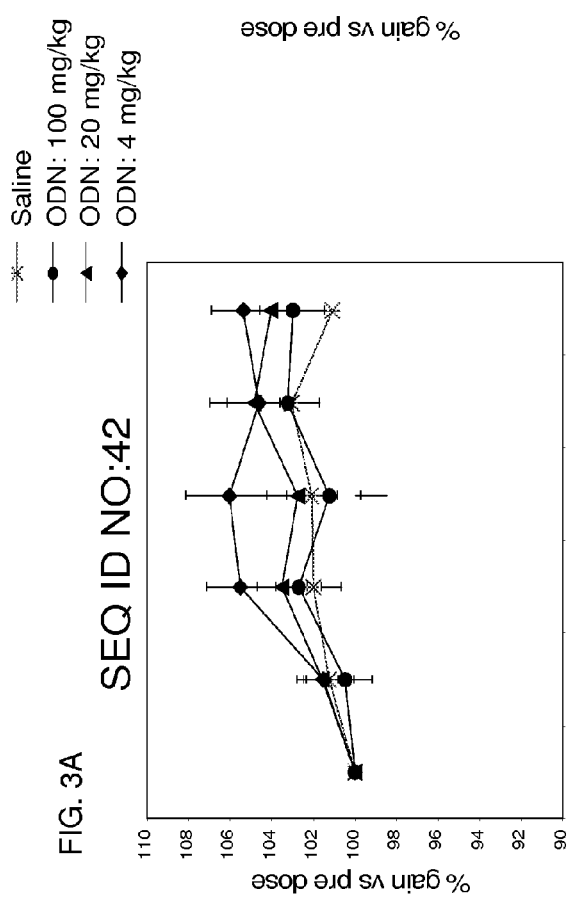

SEQ ID NO:109 at 100 mg/kg, but not SEQ ID NO:42 provoked weight loss as indicated by % gain versus pre-dose in mice as shown in FIGS. 3A and 3B.

To further test the activity of IRPs at high dosages, IRPs (SEQ ID NO:42, SEQ ID NO:73, SEQ ID NO: 79, SEQ ID NO:134, SEQ ID NO:143, and SEQ ID NO:144 at 100 mg/kg) or a control (saline and ISS (5 mg/kg)) were subcutaneously administered to BALB/c mice on days 0, 3, 6, and 9 (n=6 per group). Mice were weighed prior to administration and on days 1, 3, 4, 6, 7, and 9. Organs were harvested at the end of the study, and organ weights and tissues levels of the oligonucleotides were determined. In addition, histological evaluation of the liver, kidney, and heart was performed.

Figure 3C:
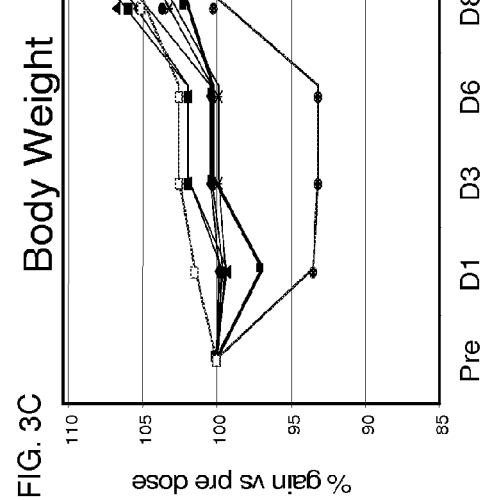
FIG. 3C shows percent weight gain versus pre-dose over time after administration of SEQ ID NO:42, SEQ ID NO:79, SEQ ID NO:73, SEQ ID NO:134, SEQ ID NO:143 and SEQ ID NO:144 at 100 mg/kg.
Figure 4B:
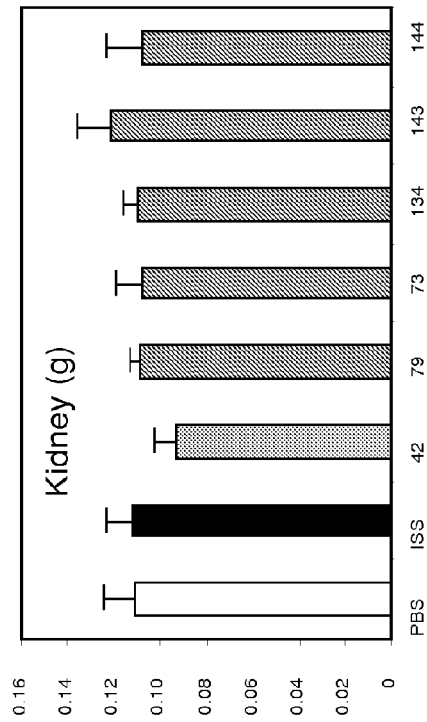
FIGS. 4A-D shows organ weight of the liver, heart, kidney or spleen after administration of SEQ ID NO:42, SEQ ID NO:79, SEQ ID NO:73, SEQ ID NO:134, SEQ ID NO:143 and SEQ ID NO:144 at 100 mg/kg.
Figure 4D:
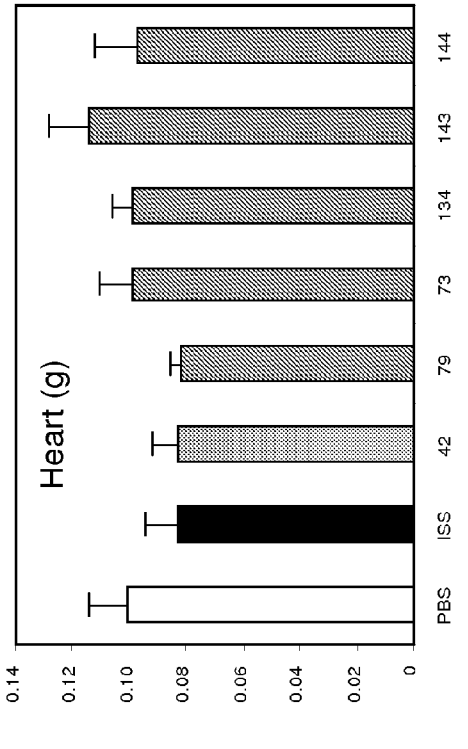
Figure 4A:
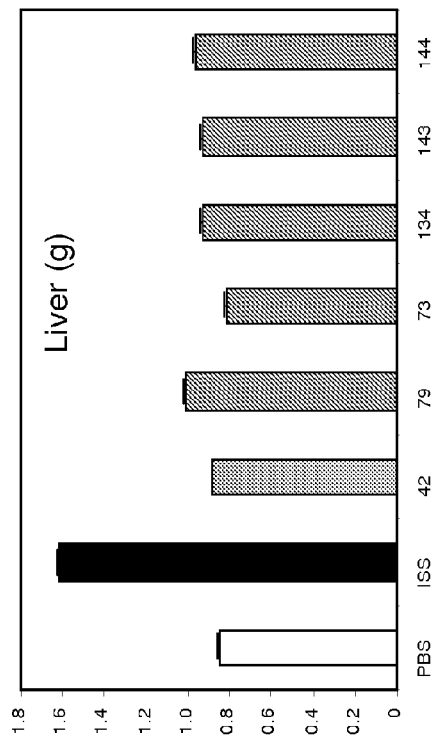
Figure 4C:
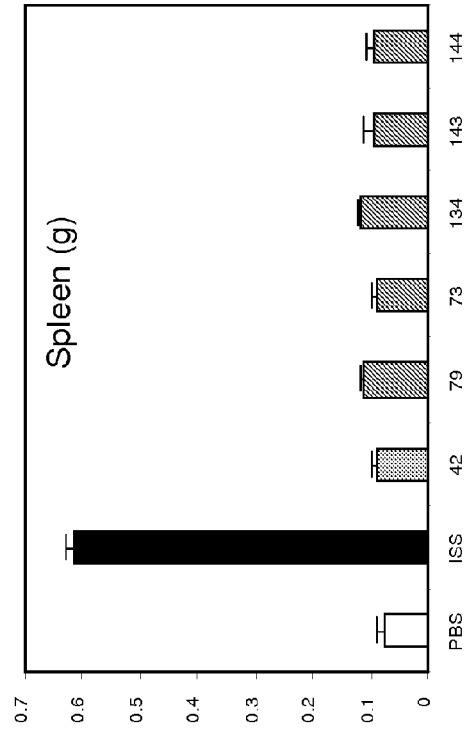

As shown in FIG. 3C, the tested IRS sequences did not significantly effect body weight as determined by % gain versus pre-dose. Further, there was no significant difference in organ weight of the liver, heart, kidney, or spleen as shown in FIGS. 4A-D. The histology evaluation of the liver, kidneys and heart is shown in Table 4-1.

No treatment-related changes were noted in the heart. Observed cardiac changes included mineralization, and/or chronic inflammation in the subpericardial regions of the right ventricle represent a common finding in some strains of mice. Probable treatment-related liver changes were characterized by: a) hypertrophy of some sinusoidal cells with cytoplasmic vacuolation and a bluish staining of the cytoplasm of the sinusoidal cells, b) mixed cell infiltration, characterized by both hemapoietic elements and what appeared to be inflammatory components (this change was difficult to distinguish from a normal focal mixed cell infiltration, which is commonly seen in the mouse but was definitely treatment related.), and c) mild increase in cytoplasmic vacuolation consistent with fat. Renal changes that were probably associated with treatment were characterized by: a) tubular changes, which consisted of varying degrees, generally minimal to mild, of black stippling in the cytoplasm of convoluted tubules, particularly in the subcapsular regions and b) focal areas of mild tubular basophilia in cortical regions (this is found occasionally in mice and therefore may not be treatment related, although a treatment effect cannot be excluded).

TABLE 4-1

Mice Histology

| Group | Saline | ISS | SEQ ID NO: 42 100 mg/kg | SEQ ID NO: 42 50 mg/kg | SEQ ID NO: 79 100 mg/kg | SEQ ID NO: 79 50 mg/kg |
|---|---|---|---|---|---|---|
| Number of Animals | 6 | 6 | 6 | 6 | 6 | 6 |
| Liver: | | | | | | |
| No significan changes | 5 | 0 | 0 | 0 | 0 | 0 |
| Mixed cell infiltration, | 1 (1.0) | 6 (3.0) | 4 (2.0) | 4 (1.8) | 6 (2.0) | 4 (1.0) |
| Liver changes | 0 | 6 (2.0) | 6 (1.8) | 5 (1.0) | 6 (2.0) | 6 (1.0) |
| Right Kidney: | | | | | | |
| No significant changes | 6 | 5 | 0 | 1 | 0 | 6 |
| Tubular changes | 0 | 0 | 6 (1.0) | 5 (1.0) | 6 (2.0) | 0 |
| Tubular basophilia | 0 | 1 (2.0) | 0 | 0 | 0 | 0 |
| Heart: | | | | | | |
| No significant changes | 3** | 1** | 3** | 2** | 1** | 1** |
| Mineralization, | 1 (3.0) | 1 (4.0) | 1 (2.0) | 1 (3.0) | 2 (2.5) | 1 (2.0) |
| Chronic inflammation. | 0 | 2 (2.0) | 0 | 1 (2.0) | 1 (3.0) | 2 (2.0) |

| Group | SEQ ID NO: 73 100 mg/kg | SEQ ID NO: 73 50 mg/kg | SEQ ID NO: 134 100 mg/kg | SEQ ID NO: 134 50 mg/kg | SEQ ID NO: 143 100 mg/kg | SEQ ID NO: 143 50 mg/kg | SEQ ID NO: 144 100 mg/kg |
|---|---|---|---|---|---|---|---|
| Number of Animals | 6 | 6 | 6 | 6 | 6 | 6 | 6 |
| Liver: | | | | | | | |
| No significan changes | 1 | 3 | 0 | 0 | 5 | 0 | 0 |
| Mixed cell infiltration, | 1 (1.0) | 2 (1.0) | 4 (2.0) | 4 (1.8) | 1 (1.0) | 6 (3.0) | 6 (2.0) |
| Liver changes | 5 (1.0) | 1 (1.0) | 6 (1.8) | 5 (1.0) | 0 | 6 (2.0) | 6 (2.0) |
| Right Kidney: | | | | | | | |
| No significant changes | 0 | 6 | 0 | 1 | 6 | 5 | 0 |
| Tubular changes | 6 (1.0) | 0 | 6 (1.0) | 5 (1.0) | 0 | 0 | 6 (2.0) |
| Tubular basophilia | 0 | 0 | 0 | 0 | 0 | 1 (2.0) | 0 |
| Heart: | | | | | | | |
| No significant changes | 2** | 2** | 3** | 2** | 3** | 1** | 1** |
| Mineralization, | 1 (3.0) | 2 (3.0) | 1 (2.0) | 1 (3.0) | 1 (3.0) | 1 (4.0) | 2 (2.5) |
| Chronic inflammation. | 1 (2.0) | 0 | 0 | 1 (2.0) | 0 | 2 (2.0) | 1 (3.0) |

**= Tissue missing in two animals ( ) = Mean severity score where 0 = no change, 1 = minimal, 2 = mild, 3 = moderate and 4 = severe.

Example 5

Mouse Splenocytes Stimulated with 1018 ISS (TLR9 Ligand) or R848 (TLR7 Ligand) in the Presence of IRPs IRPs or control samples were assayed for immunoregulatory activity on mouse cells. For mouse cell assays, splenocytes from 6-12 week-old BALB/c mice spleen were harvested and mechanically dispersed by forcing the digested fragments through metal screens. The dispersed splenocytes were pelleted by centrifugation, then resuspended in fresh medium (RPMI 1640 with 10% fetal calf serum, plus 50 units/mL penicillin, 50 µg/mL streptomycin, 2 mM glutamine, and 0.05 mM β-mercaptoethanol). In a dose-dependent manner, the cells were then stimulated with 1 mM of 1018 ISS (TLR9 ligand; 5'-TGACTGTGAACGTTC-GAGATGA-3' (SEQ ID NO:157)) or 1 µM of R848 (TLR7 ligand; a small molecule imidazoquinoline also called resiquimod) either alone or in the presence of the tested IRPs. At 48 hours, supernatants were collected and cytokine levels, IL-6, were measured using immunoassays. Three separate experiments were conducted.

FIG. 5A shows the percentage of IL-6 produced compared to R848 alone when stimulated with R848 (TLR7 ligand) either alone or in the presence of the tested IRPs. FIG. 5B shows the percentage of IL-6 produced compared to CpG-ISS alone when stimulated with CpG-ISS (TLR9 ligand) either alone or in the presence of the tested IRPs.

Example 6

Rat Splenocytes and B-cells Stimulated with 1018 ISS (TLR9 Ligand) or R848 (TLR7 Ligand) in the Presence of IRPs IRPs or control samples were assayed for immunoregulatory activity on rat cells. For rat cell assays, splenocytes and B-cells from 8-9 weeks old, female Sprague Dawley rats were harvested and mechanically dispersed by forcing the digested fragments through metal screens. The dispersed splenocytes and B-cells were pelleted by centrifugation, then resuspended in fresh medium (RPMI 1640 with 10% fetal calf serum, plus 50 units/mL penicillin, 50 µg/mL streptomycin, 2 mM glutamine, and 0.05 mM β-mercaptoethanol). In a dose-dependent manner, the cells were then stimulated with 1 mM of CpG-ISS1018 ISS (TLR9 ligand; 5'-TGACTGTGAACGT-TCGAGATGA-3' (SEQ ID NO:157)) or 1 µM of R848 (TLR7 ligand; a small molecule imidazoquinoline also called resiquimod) either alone or in the presence of the tested IRPs. At 48 hours, supernatants were collected and cytokine levels, IL-6, were measured using immunoassays. Two separate experiments were conducted for the splenocytes and one experiment was conducted for the B-cells.

FIGS. 6A and 6B show the percentage of IL-6 produced compared to R848 alone or level of IL-6 (pg/ml) produced when stimulated with R848 (TLR7 ligand) either alone or in the presence of the tested IRPs in splenocytes and B-cells, respectively. FIGS. 6C and 6D show the percentage of IL-6 produced compared to CpG-ISS alone or level of IL-6 (pg/ml) produced when stimulated with CpG-ISS (TLR9 ligand) either alone or in the presence of the tested IRPs in splenocytes and B-cells, respectively.

Example 7

Human B-Cells Stimulated in the Presence of IRPs

To further investigate the effect of IRPs on TLR7 and TLR9 activation, various IRPs or control samples were assayed for immunoregulatory activity on human B-cells. Human B-cells were stimulated with 1 mM of CpG-ISS1018 ISS (TLR9 ligand; 5'-TGACTGTGAACGTTCGAGATGA-3' (SEQ ID NO:157)) or 1 µM of R848 (TLR7 ligand; a small molecule imidazoquinoline also called resiquimod) either alone or in the presence of the tested IRPs.

Figure 7A:
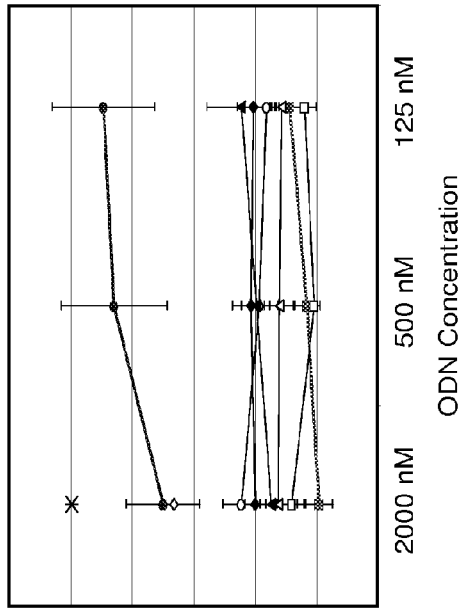
FIG. 7A shows the percentage of IL-6 produced compared to CpG-ISS alone when stimulated with CpG-ISS either alone or in the presence of the tested IRPs.
Figure 7B:
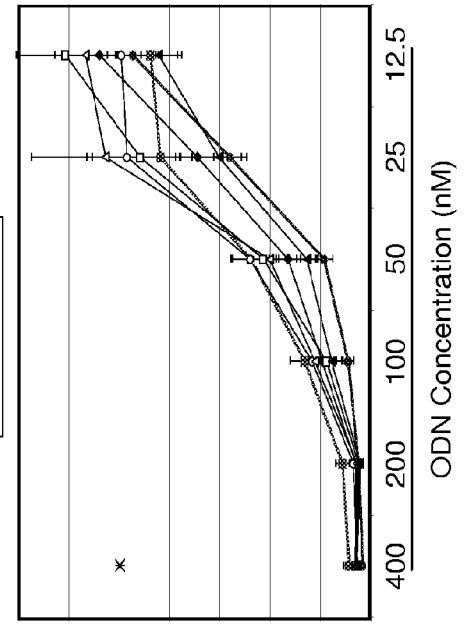
FIG. 7B shows the percentage of IL-6 produced compared to R848 alone when stimulated with R848 either alone or in the presence of the tested IRPs.

FIG. 7A shows the percentage of IL-6 produced compared to CpG-ISS alone when stimulated with CpG-ISS (TLR9 ligand) either alone or in the presence of the tested IRPs. FIG. 7B shows the percentage of IL-6 produced compared to R848 alone when stimulated with R848 (TLR7 ligand) either alone or in the presence of the tested IRPs.

Example 8

Human Plasmacytoid Dendritic Cells (PDCs) Stimulated in the Presence of IRPs

To further investigate the effect of IRPs on TLR7 and TLR9 activation, various IRPs or control samples were assayed for immunoregulatory activity on human PDCs.

Human PDCs infected with herpes simplex virus type 1 (HSV-1 KOS strain) respond by producing IFN-α and this response is dependent on TLR-9 signaling. Human PDCs infected with influenza virus (FLU H1N1 strain, A/PR/8/34 from a patient in Puerto Rico 1934; See ATCC catalog VR-95) also respond by producing IFN-α, however, this response is dependent on TLR-7 signaling and independent of TLR-9. The effect of IRPs on innate immune response cytokine production by infected cells was examined. In a dose-dependent manner, the primary human PDCs were thus stimulated with HSV-1 (4 MOI) or influenza (2 MOI), either alone or in the presence of the tested IRPs. At 24 hours, supernatants were collected and cytokine levels, IFN-alpha, were measured by immunoassay.

Human PDCs from 16-18 donors were purified and infected with influenza virus (strain PR/8) or HSV-1. HSV was used at 4 MOI, while the influenza virus was used at 2 MOI. The amount of IFN-α produced by the cells was measured and compared to the amount of virus used for infection.

Figure 7C:
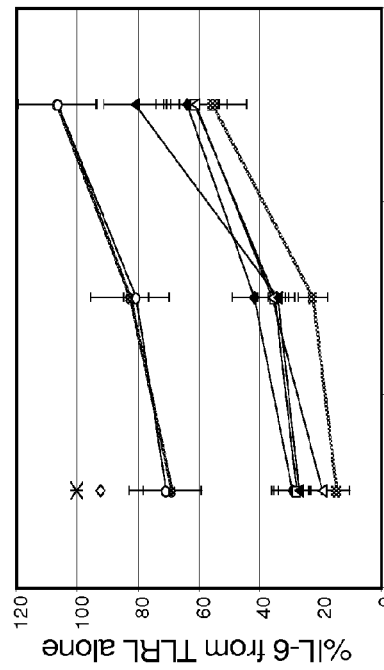
FIGS. 7C-D show the percentage of IFN-α produced compared to virus alone when stimulated with influenza virus (C) or HSV (D) either alone or in the presence of the tested IRPs.
Figure 7D:
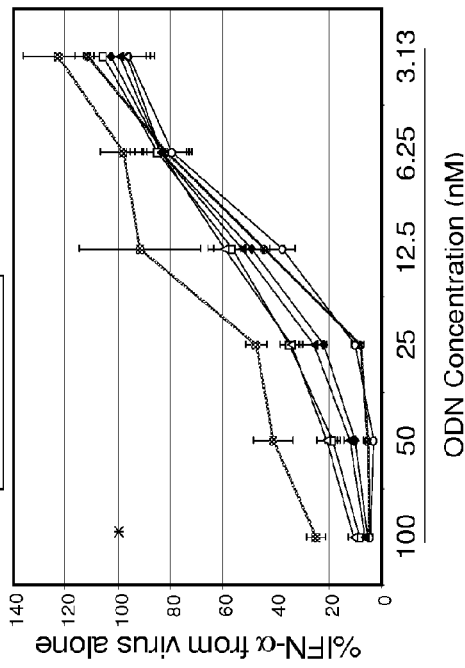

FIGS. 7C and 7D show the percentage of IFN-α produced compared to virus alone when stimulated with influenza virus (TLR7 ligand) or stimulated with HSV (TLR9 ligand), respectively, either alone or in the presence of the tested IRPs.

Human PDC were stimulated with TLR9L CpG-ISS 274 (5'-TCG TCG AAC GTT CGA GAT GAT-3' (SEQ ID NO:158)) or with TLR9L DNA-IC or TLR7L RNP-IC either alone or in the presence of 1 µM of the tested IRPs. DNA-IC (anti-double strand DNA immune complexes) trigger TLR9 in human PDC by inducing the release of IFN-α. DNA-IC were obtained from anti-dsDNA positive plasma from SLE patients and used at 10% culture well volume. RNP-IC (anti-ribonuclear protein immune complexes) trigger TLR7 in human PDC by inducing the release of IFN-α. RNP-IC were purified IgG from anti-RNP positive plasma from SLE patients and was used at 0.5 mg/ml. After 24 hours of culture at 37° C., supernatants were harvested and IFN-α was measured by immunoassay.

FIG. 8A shows the level of IFN-α produced when stimulated with CpG-ISS alone or in the presence of the tested IRPs. FIGS. 8B and 8C show the percentage of IFN-α produced compared to DNA-IC alone when stimulated with DNA-IC, respectively, either alone or in the presence of the tested IRPs.

Example 9

IC50 and IC90 Values of IRPs for TLR7- and TLR9-Stimulated Human PDC

To further investigate the effectiveness of IRPs on TLR7 and TLR9 activation, various IRPs or control samples were assayed for immunoregulatory activity on human PDCs as described in Example 8.

Figure 9A:
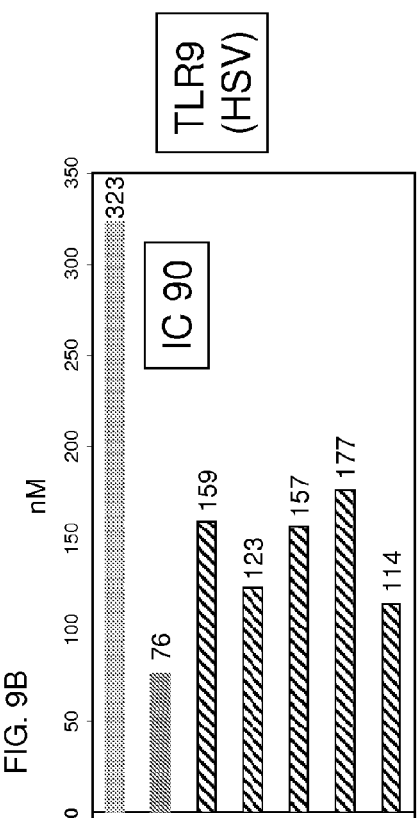
FIGS. 9A-B shows IC50 values for the tested IRPs in PDC when stimulated with HSV.
Figure 9B:
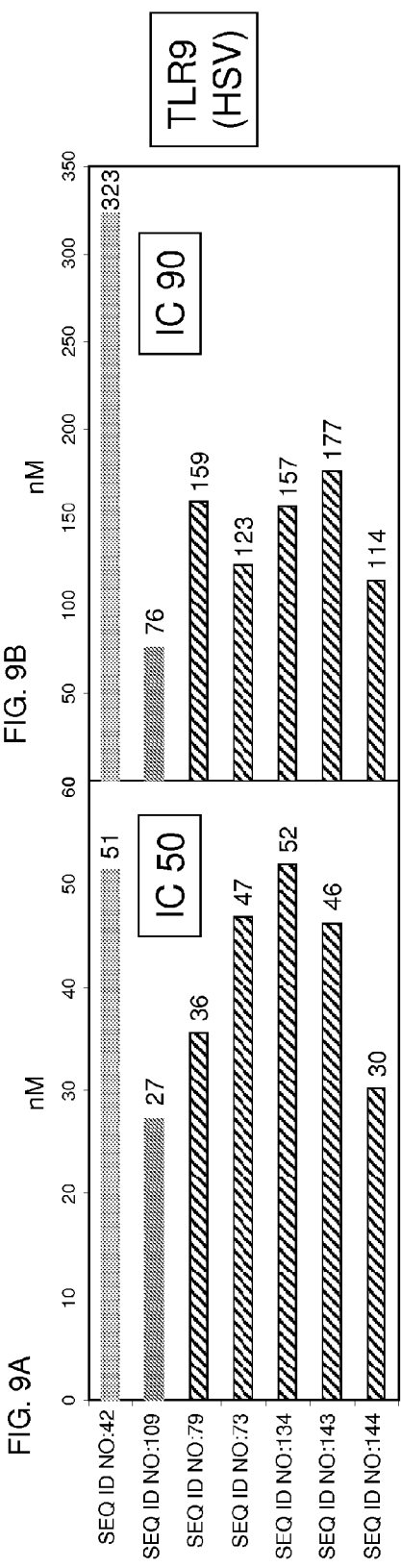
Figure 9C:
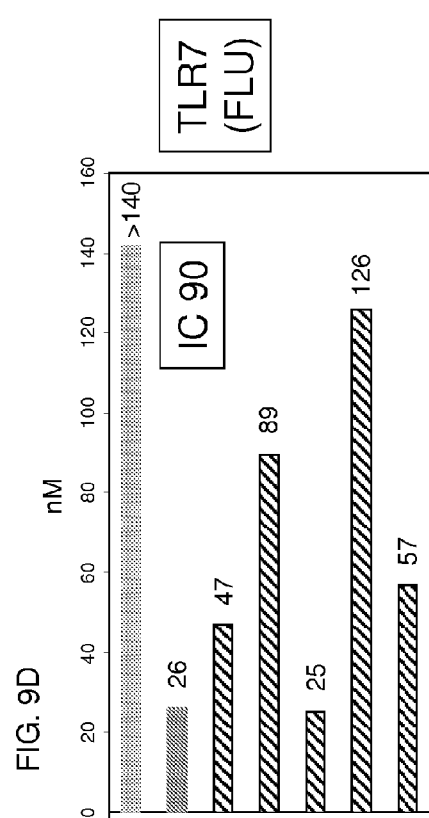
FIGS. 9C and D show IC90 values for the tested IRPs in PDC when stimulated with influenza virus.
Figure 9D:
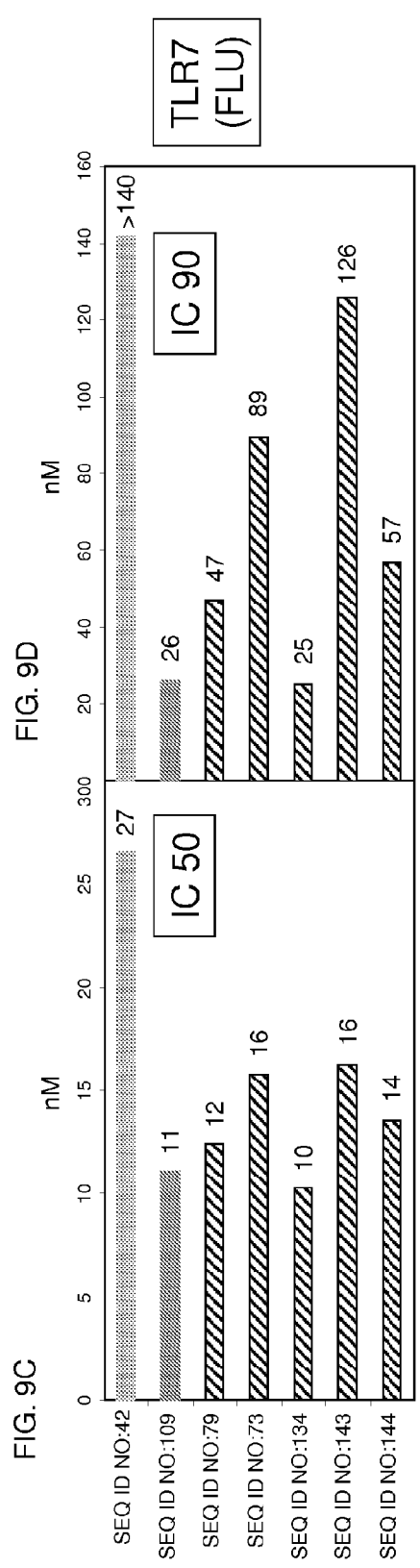

FIGS. 9A and 9B show IC50 values (half maximal inhibitory concentration) when stimulated with HSV (TLR9 ligand). FIGS. 9C and 9D show IC90 values (90% maximal inhibitory concentration) when stimulated with FLU (TLR7 ligand).

FIG. 10A shows dose response curve of human PDC stimulated with TLR9L HSV or TLR71FLU either alone or in the presence of various concentration of SEQ ID 73. IC50 (nM) values are 25 and 13 for HSV and FLU, respectively. IC90 (nM) values are 99 and 101 for HSV and FLU, respectively.

Example 10

Monkey PBMC Stimulated in the Presence of IRPs

To further investigate the effect of IRPs on TLR7 and TLR9 activation, various IRPs or control samples were assayed for immunoregulatory activity on monkey PBMCs.

PBMC from Rhesus Macque monkeys were stimulated with TLR7L FLU at MOI 10 either alone or in the presence of various concentrations of the tested IRPs. Supernatants were collected 24 hr later and assayed for IFN-α by immunoassay.

FIG. 10B shows show the percentage of IFN-α produced compared to virus alone when stimulated with influenza virus (TLR7 ligand), either alone or in the presence of the tested IRPs.

Example 11

In Vivo Activity of Modified IRPs When Stimulated by an ISS

IRPs effect on TLR7 and TLR9 activation was assayed in vivo on 6 to 12 week-old BALB/c mice. Mice were injected subcutaneously (SC) with 25 µg of 1018 ISS (5'-TGACTGT-GAACGTTCG AGATGA-3' (SEQ ID NO:157)) alone or in the presence of various concentrations of tested IRPs. Two hours following injections, blood was harvested and serum prepared using standard procedures. IL-6 levels were measured.

FIGS. 10C and 10D show the level of IL-6 (pg/ml) produced or the percentage of IL-6 produced compared to CpG-ISS alone when stimulated with CpG-ISS (TLR9 ligand) either alone or in the presence of the tested IRPs. The tested IRPs have strong activity in vivo.

TABLE 11-1

Provides a Summary of the IRPs Tested in Mice.

| SEQ ID | Inhibition of Spenocyte IL-6 | | Inhibition of B-Cell IL-6 | | Inhibition of PDC IFN-a | | | | | Mice IL-6 |
|---|---|---|---|---|---|---|---|---|---|---|
| | ISS | R848 | ISS | R848 | ISS | HSV | FLU | DNA IC | RNP IC | In Vivo |
| NO: 42 | +++ | ++ | +++ | +++ | + | ++ | + | +++ | +++ | ++ |
| NO: 109 | +++ | +++ | + | + | +++ | +++ | ++ | ++ | +++ | +++ |
| NO: 79 | +++ | ++ | +++ | ++ | ++ | +++ | ++ | ++ | +++ | ++ |
| NO: 73 | +++ | ++ | +++ | +++ | ++ | +++ | ++ | ++ | | ++ |
| NO: 134 | ++ | +++ | + | ++ | ++ | ++ | ++ | +++ | +++ | ++ |
| NO: 143 | +++ | ++ | +++ | ++ | ++ | ++ | ++ | +++ | +++ | ++ |
| NO: 144 | +++ | ++ | +++ | ++ | ++ | ++ | ++ | +++ | +++ | ++ |

Example 12 pK Studies

To investigate the pharmacokinetics (pK) of various IRP candidates, IRPs were subcutaneously administered to BALB/C mice or female Sprague Dawley rats as described below.

Tissue samples were prepared by placing approximately 30-60 mg of tissue pieces into an eppendorf tubes. Tissue homogenization buffer (20 mM Tris, pH 8, 20 mM EDTA, 100 mM NaCl, 0.2% SDS; 20 µL/mg of tissue) was added and tissues were homogenized on a TissueLyzer (Qiagen). Proteinase K was added (2 µg/mg of tissue) and sample incubated for 2-18 hrs at 50° C. Then the Proteinase K was heat-inactivated and three dilutions of each tissue homogenate were analyzed in the Enzyme-linked Hybridization Assay (ELHA).

Dilutions of the Proteinase K-treated homogenate samples were mixed with detection probe (50 µg/mL final concentration). The detection probe is a biotinylated oligonucleotide complementary to the 3' end of the target sequence or analyte. This probe-homogenate mixture was added to an assay plate (NUNC Immobilizer Amino plate) whose wells were coated with a capture probe. The capture probe is complementary to the 5' end of the target sequence or analyte and has an amino functional group that allows covalent attachment to the assay plate. After incubation (37° C. for 1 hour), plates were washed (Tris-buffered saline, 0.05% Tween-20) followed by incubation (room temperature, 30 minutes) with streptavidin-horse radish peroxidase (HRP). Unbound streptavidin-HRP was washed away and HRP substrate was added to detect and quantify the amount of target sequence or analyte. The dilution of homogenate that provided a value within the range of the assay was used to determine the concentration of target sequence or analyte. The amount of analyte (oligonucleotide) was back-calculated against a standard curve to provide a microgram of analyte (oligonucleotide) per gram of tissue value.

In FIGS. 11A and 11B, IRPs were subcutaneously administered to BALB/C mice at a dosage of 5 mg/kg (n=6 per group). Organs were harvested at day 1, 3, 6, and 9 post injection. Liver and kidney tissue was analyzed for tested IRPs. Tissue concentrations for the liver and kidney are shown in FIGS. 11A and 11B.

As shown in FIGS. 11C and 11D, SEQ ID NO:73 and SEQ ID NO:109 were subcutaneously administered to BALB/c mice at a dosage of 50 mg/kg or 100 mg/kg on days 0, 3, 7, and 10 (n=6 per group). Organs were harvested 24 hours after last injection. Liver, kidney, spleen, and heart tissue was analyzed for SEQ ID NO:73 and SEQ ID NO:109 as described above. Tissue concentrations for the liver, kidney, spleen, and heart are shown in FIGS. 11C and 11D.

For FIGS. 12A and 12B, SEQ ID NO:73 were subcutaneously administered to female Sprague Dawley rats at a dosage of 5 mg/kg on days 0.25, 1, 3, 6, and 9 (n=6 per group). Organs were harvested at the end of the study. Liver, kidney, spleen, and heart tissue was analyzed for SEQ ID NO:73 and analyzed as described above. Tissue concentrations for the liver, kidney, spleen, and heart are shown in FIGS. 12A and 12B.

For FIGS. 12C and 12D, SEQ ID NO:73 and SEQ ID NO:109 were subcutaneously administered to female Sprague Dawley rats at a dosage of 10 mg/kg or 90 mg/kg on days 0, 3, 7, and 10 (n=6 per group). Organs were harvested at the end of the study. Liver, kidney, spleen, and heart tissue was analyzed for SEQ ID NO:73 and SEQ ID NO:109 as described above. Tissue concentrations for the liver, kidney, and spleen are shown in FIGS. 12C and 12D.

Example 13

Methods and Reagents Used in Examples 14 to 17

Reagents.

Phosphorothioate ODNs were prepared as previously described (Duramad et al, 2005). The prototype for ISS class C used was: CpG-ISS(C274): 5'-TCGTCGAACG TTC-GAGATGA T (SEQ ID NO:158). The prototype for inhibitor of TLR7 and 9 used was 5'-TGCTCCTGGA GGGGTTGT-3'(SEQ ID NO:42). Control oligonucleotide was 5'-TCCTG-CAGGT TAAGT-3' (SEQ ID NO:160). Heat inactivated influenza virus (FLU H1N1, strain A/PR/8/34) was obtained from ATCC (Manassas, Va.). Hydrocortisone and dexamethasone were purchased from SIGMA. Purification of anti-RNP IC was performed as previously described (Barrat et al., 2005). Human IFN-α ELISA set were purchased from PBL Biomedical Laboratories (Piscataway, N.J.). PI3K inhibitors LY294002 (LY), p38 MAPK inhibitors, SB203580 and p38 MAPK III and NF-kB inhibitor (IKK-2 IV) were purchased from Calbiochem. P50 and NEMO inhibitory peptides were purchase from Imgenex.

Patients and Healthy Donors

Pediatric patients were recruited at Baylor University Medical Center, Texas Scottish Rite Hospital, and Children's Medical Center, all in Dallas, Tex. The study was approved by the institutional review board of all three institutions. Informed consents were obtained from all patients (legal representatives and patients over 10 years of age). The demographic characteristics of 71 SLE patients are displayed in Table 13-1. Briefly, there were 85% females, 15% males; 42% Hispanic, 32% African Americans, 15% White. The average patient age was 14.1±2.4 years. The average SLEDAI was 8.2±6.1. Forty one healthy age- and ethnicity-matched children were included in Microarray and Nanostring experiments as controls.

TABLE 13-1

| Patient Information | | | |
|---|---|---|---|
| Subject | Ethic | Gender | Age |
| SLE-20 | AA | Female | 16 |
| SLE-29 | Hispanic | Male | 16 |
| SLE-31 | Hispanic | Female | 12 |
| SLE-33 | Asian | Female | 11 |
| SLE-34 | Hispanic | Female | 16 |
| SLE-40 | AA | Female | 15 |
| SLE-55 | AA | Female | 16 |
| SLE-60 | Hispanic | Female | 15 |
| SLE-64 | White | Female | 16 |
| SLE-79 | Hispanic | Female | 14 |
| SLE-80 | AA | Female | 16 |
| SLE-83 | AA | Female | 15 |
| SLE-87 | White | Female | 17 |
| SLE-91 | Asian | Female | 14 |
| SLE-95 | AA | Female | 17 |
| SLE-110 | AA | Female | 15 |
| SLE-121 | Hispanic | Female | 15 |
| SLE-123 | Hispanic | Male | 13 |
| SLE-125 | Hispanic | Female | 15 |
| SLE-128 | AA | Female | 16 |
| SLE-141 | Hispanic | Male | 14 |
| SLE-142 | White | Female | 17 |
| SLE-143 | Hispanic | Female | 15 |
| SLE-144 | White | Female | 14 |
| SLE-154 | Hispanic | Male | 13 |
| SLE-157 | AA | Female | 17 |
| SLE-158 | Hispanic | Female | 17 |
| SLE-163 | White | Female | 11 |
| SLE-168 | Hispanic | Female | 17 |
| SLE-169 | Hispanic | Female | 14 |
| SLE-171 | Hispanic | Female | 13 |
| SLE-172 | Hispanic | Female | 11 |
| SLE-175 | White | Female | 12 |
| SLE-179 | Hispanic | Female | 13 |
| SLE-181 | Hispanic | Female | 12 |
| SLE-182 | Hispanic | Male | 15 |
| SLE-183 | Hispanic | Female | 11 |
| SLE-184 | AA | Female | 7 |
| SLE-185 | Asian | Female | 13 |
| SLE-186 | Asian | Female | 18 |
| SLE-187 | Hispanic | Female | 13 |
| SLE-188 | Hispanic | Female | 12 |
| SLE-189 | AA | Female | 14 |
| SLE-191 | AA | Female | 16 |
| SLE-192 | Hispanic | Male | 16 |
| SLE-196 | AA | Female | 14 |
| SLE-198 | AA | Male | 18 |
| SLE-208 | AA | Female | 14 |
| SLE-212 | AA | Female | 14 |
| SLE-213 | White | Female | 12 |
| SLE-214 | Hispanic | Female | 16 |
| SLE-215 | Other | Female | 12 |
| SLE-216 | White | Male | 12 |
| SLE-225 | Hispanic | Female | 16 |
| SLE-226 | Asian | Male | 15 |
| SLE-229 | AA | Female | 17 |
| SLE-231 | AA | Female | 17 |
| SLE-233 | White | Female | 11 |
| SLE-237 | Hispanic | Female | 12 |
| SLE-238 | White | Female | 17 |
| SLE-240 | Hispanic | Female | 15 |
| SLE-241 | AA | Female | 13 |
| SLE-242 | Hispanic | Female | 10 |
| SLE-244 | Hispanic | Female | 9 |
| SLE-249 | AA | Male | 9 |
| SLE-252 | AA | Female | 14 |
| SLE-260 | AA | Female | 12 |
| SLE-270 | Asian | Female | 14 |
| SLE-276 | White | Male | 12 |
| SLE-277 | Hispanic | Female | 17 |
| SLE-282 | AA | Female | 17 |

Blood Sample Collection

Blood samples for gene expression analysis were collected in Tempus tubes and immediately delivered to Baylor Institute for Immunology Research (Dallas, Tex.) at room temperature and stored at −20° C. before processing. For flow cytometry analysis, 100 μL of blood and 3-10 μL of each antibody were incubated for 30 min. The blood was then lysed with FACS Lysing Solution (BD Biosciences), rinsed with PBS, centrifuged at 300 g for 10 min, and resuspended in 1% paraformaldehyde. Samples were then acquired on a FACSCalibur flow cytometer and analyzed with CellQuest software (BD Biosciences). The following fluorochrome-conjugated anti-human antibodies were used for whole-blood stainings: LINEAGE-fluorescein isothiocyanate (FITC) cocktail (containing CD3, CD 14, CD 16, CD 19, CD20, and CD56), CD123-phycoerythrin (PE), HLA-DR-peridin chlorophyll protein (PerCP), CD11c-allophycocyanin (APC), CD4-FITC, CD8-PE, CD3-PerCP, and CD14-APC (BD Biosciences).

Modular Analysis

A set of transcriptional modules was used as a framework for the analysis of microarray data. The approach used for the construction of such framework was previously reported (Chaussabel et al., 2008). Briefly, genes with coordinate expression within or across whole blood datasets corresponding to nine human diseases where selected in multiple rounds of clique and paraclique clustering to form a transcriptional module framework. Ingenuity Pathway Analysis (IPA) (Ingenuity Systems, Redwood City, Calif.), PUBMED and iHOP databases were used for module annotation and functional analysis. Module expression level is defined as the average normalized data for all the genes in the module (Table I). Color intensity indicates the proportion of genes within each module that are expressed at significantly different levels in SLE patients. Red: over expressed. Blue: under expressed. Expression was normalized to an age- and ethnicity-matched control group (n=9).

NanoString nCounter Assay

The details of the nCounter Analysis System (NanoString Technologies) were described previously (Geiss et al., 2008). The nCounter code set includes 240 genes of interest and 20 control genes. Samples were hybridized using 100 ng of total RNA. The expression levels of each gene were normalized to those of 20 control genes.

Isolation and In Vitro Stimulation of Purified PDC and Measurement of Cell Survival Buffy coats were obtained either from the Stanford Blood Center (Palo Alto, Calif.) and cells were used under internal Institutional Review Board-approved protocols, or from adult healthy donors (Saint-Antoine Crozatier Blood Bank, Paris, France) where all donors signed informed consent to allow the use of their blood for research purposes. PDC were isolated either by using positive selection using BDCA-4 conjugated beads or by using negative depletion (Miltenyi Biotech) as previously described (Guiducci et al., 2006). PDC were 94-99% BDCA2+ CD123+ as determined by flow cytometry. For viability 1×10$^5$ PDC were stimulated in 96-well U-bottom plates with CpG-C (0.5 μM), or FLU (2 MOI) in the presence of different doses of hydrocortisone. Alternatively, 1×10$^5$ PDCs were cultured with 50,000 UV-irradiated (60 mJ) U937 cells in the presence of 0.5 mg/ml of purified IgG from anti-RNP-positive SLE patients (Barrat et al., 2005). When indicated, soluble IFN-α was used at 20 ng/ml and blocking IFN was achieved using a combination of anti-IFN-α (5000 neutralizing U/ml), anti-IFN-β (2000 neutralizing U/ml) and mouse anti-IFN-α/β receptor MAb (20 μg/ml). Cell survival was assessed at 24-48 hr by flow cytometry using Invitrogen's "live or dead cell viability kit" according to manufacture instructions.

Measurement of NF-kB Transcriptional Activity

Untouched naïve PDC were purified using the PDC negative selection kit from Miltenyi Biotech and stimulated for 3 hr as indicated. Alternatively monocytes were purified from human blood using CD14-conjugated beads (Miltenyi Biotech) and stimulated as indicated for 1 hr. Nuclear extracts were prepared using Active Motif nuclear extraction kit according to manufacture's instructions. Nuclear extracts (2 μg) were analyzed for the binding activity of NF-kB p65 subunit using TransAM NF-kB kit (Active Motif) according to manufacture's instructions.

Treatment of Mice and Cellular Analysis.

8-12 weeks old C57BL/6 and 129 mice were purchased from Charles River Laboratories. (NZBxNZW)F1 female mice were purchased from Jackson laboratories and used at 16-17 weeks of age. In some experiments (NZBxNZW)F1 female mice were used at 3 weeks of age. TLR7.6 transgenic mice overexpressing TLR7 (C57BL/6 background) were previously described (Deane et al., 2007) and used at 8 weeks of age. Mice were pre-bled in the morning and immediately treated with intra peritoneal (IP) glucocorticoid, dexamethasone (DEX, SIGMA). In some experiments IP DEX was administered with SC TLR7 and TLR9 inhibitors (IRPs) as specified in the figure legends. Mice were analyzed 18 hr after DEX administration. Flow cytometric analyses was performed using fluorochrome-conjugated monoclonal antibodies to mouse CD3, CD1 1b, GR1, B220, CD11c (BD bioscience), PDCA1 (Miltenyi Biotech) and 120G8 (Invivogen). Specific gating was done as follow: PDC were CD11c low, B220+, GR1+, PDCA1+; conventional DC were CD11c high B220-; B cells were B220+; T cells were CD3+; granulocytes GR1+. For quantification of cellular subsets in the spleen, collagenase D treated splenocyte suspension was counted before performing flow cytometric analysis and total number of specific subsets was calculated according to %. Absolute cell number in blood was calculated by adding an internal microsphere counting standard to the flow cytometry samples (CountBright counting beads; Invitrogen).

Real-Time Quantitative PCR (TaqMan) Analysis

PCR reactions were performed as described previously (Barrat et al., 2005). In brief, RNA was extracted from collagenase D-treated splenocyte suspensions with Qiagen RNA and cDNA was generated with SuperScript First-Strand Synthesis System (Invitrogen). ECT was threshold cycle (CT) values for each gene were normalized to the housekeeping genes ubiquitin or β-actin using the formula Eq. 1.8(HSKGENE) (100,000), where HSK is the mean CT of triplicate housekeeping gene runs, GENE is the mean CT of duplicate runs of the gene of interest, and 100,000 is arbitrarily chosen as a factor to bring all values above 0.

Statistical Analysis

Data were analyzed using a Mann-Whitney U-test (2-tailed Student's t test using non parametric criteria for independent samples). All analyses were performed using Prism software (GraphPad Software, San Diego, Calif.). Differences were considered significant at a P level less than 0.05.

Example 14

Figure 13:
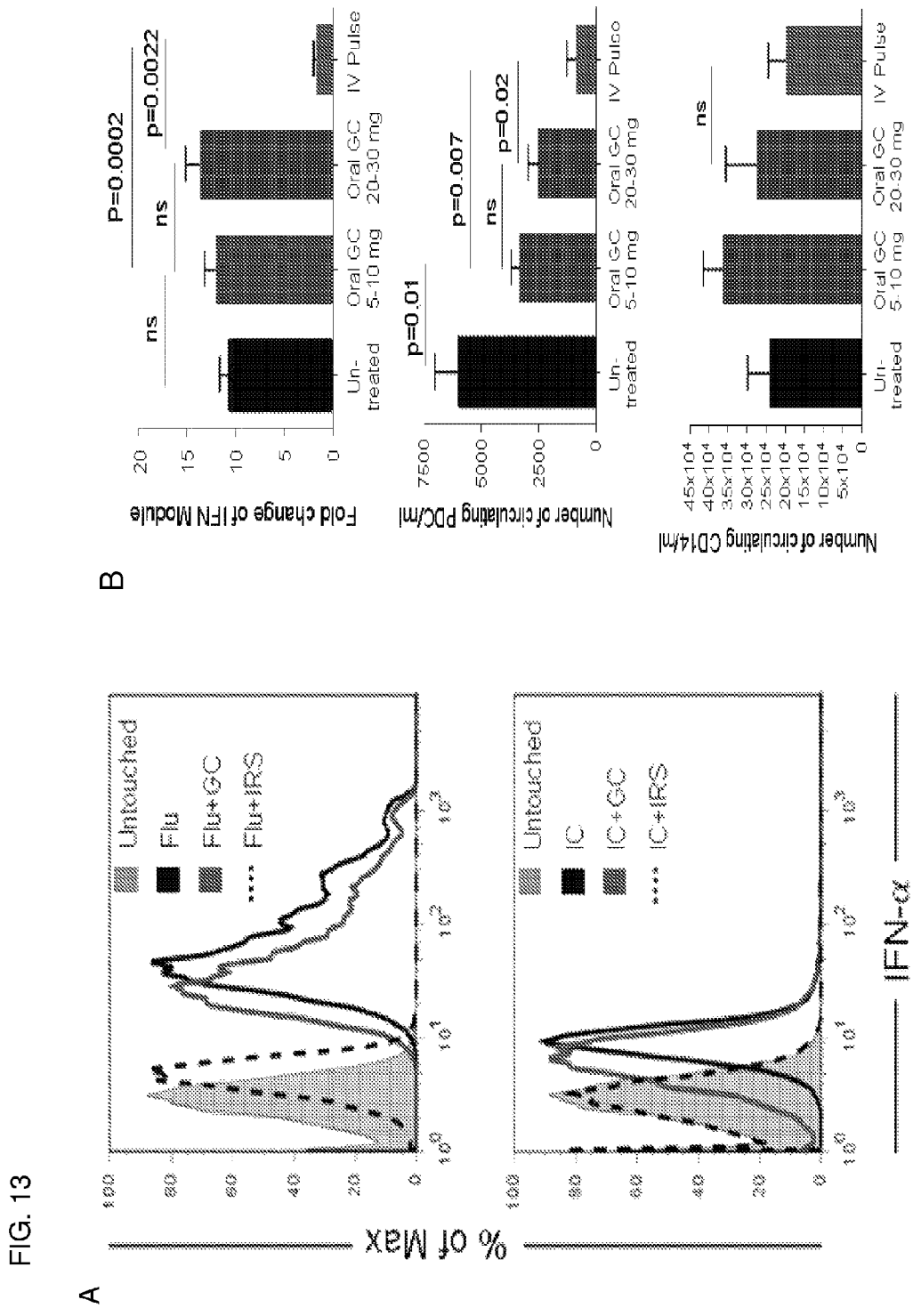
FIGS. 13A-D shows that the level of expression of the PDC-induced IFN signature in GC-treated SLE patients strictly correlated with circulating blood PDC. (A) Purified PDC were cultured alone or with Flu or purified anti-RNP-IC either alone or with GC ($10^{-5}$M) or IRS and assayed for IFN-α secretion at 3 h. (B) Top panel: Interferon module expression levels (average from transcripts within the IFN module) in SLE patients untreated (n=30), on 5-10 mg (n=29) or on 20-30 mg (n=6) daily oral Prednisone and on IV methylprednisolone pulse (3 consecutive doses, n=6). Medium and lower panels: blood PDC and monocyte numbers in SLE patients untreated (n=13), under 5-10 mg daily oral GC (n=27), oral daily GC 20-30 mg (n=16) and the day after IV pulse (n=6). (C) Representative flow cytometry analysis of PDC before and 1 and 6 days post IV pulse. (D) Top: Quantification of the average Interferon module level expression (Nanostring, see FIG. 17) in healthy controls (n=9), SLE patients before IV pulse (n=26) and at Day 1 (n=1) and Day 8 after the pulse (n=2). Bottom: PDCs frequency in the CD11c population patients before IV pulse (D0, n=10) and at Day 1 (n=9) and Day 6 after pulse (n=2). Data are plotted as mean±SEM.
Figure 13:
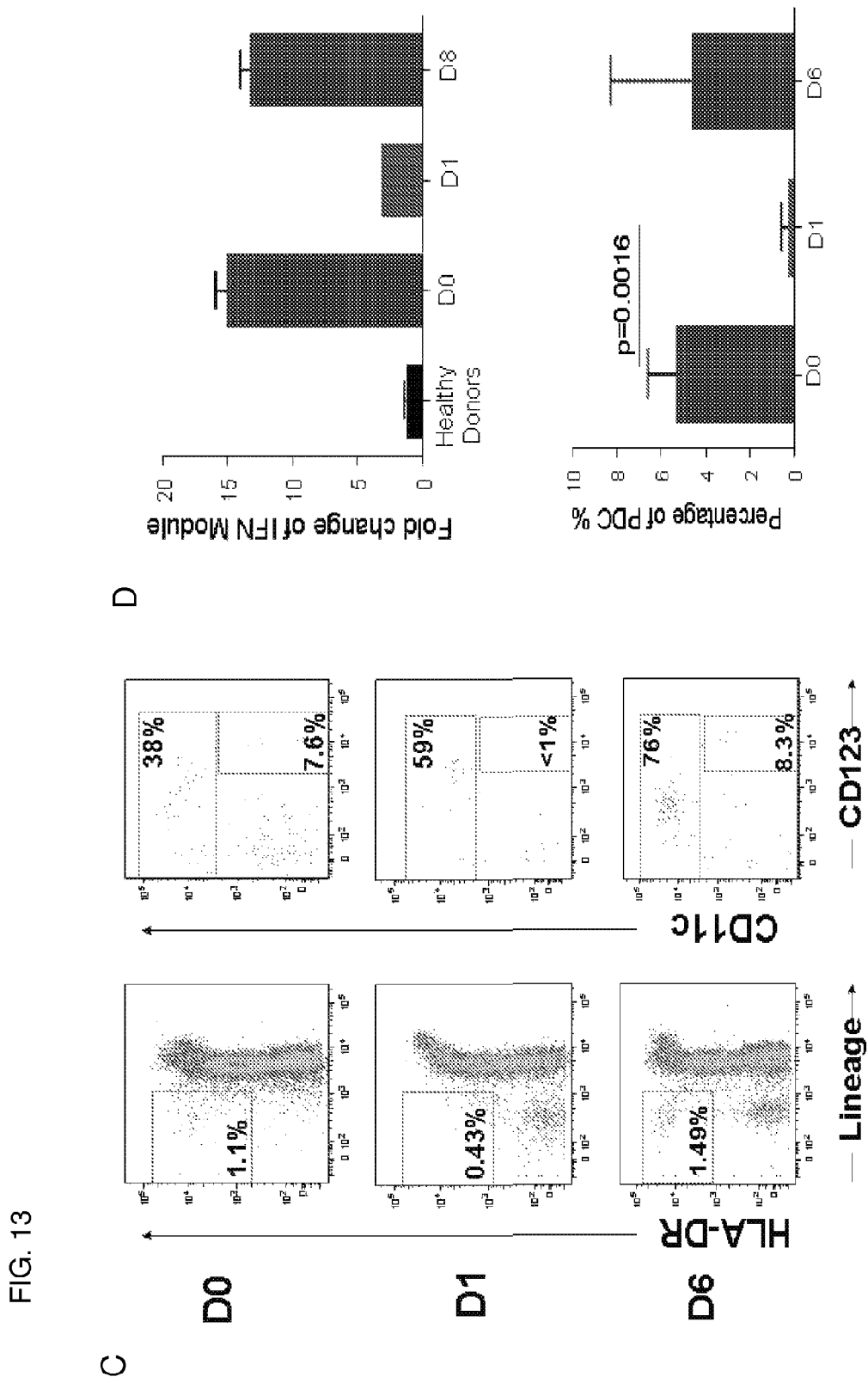
Figure 18:
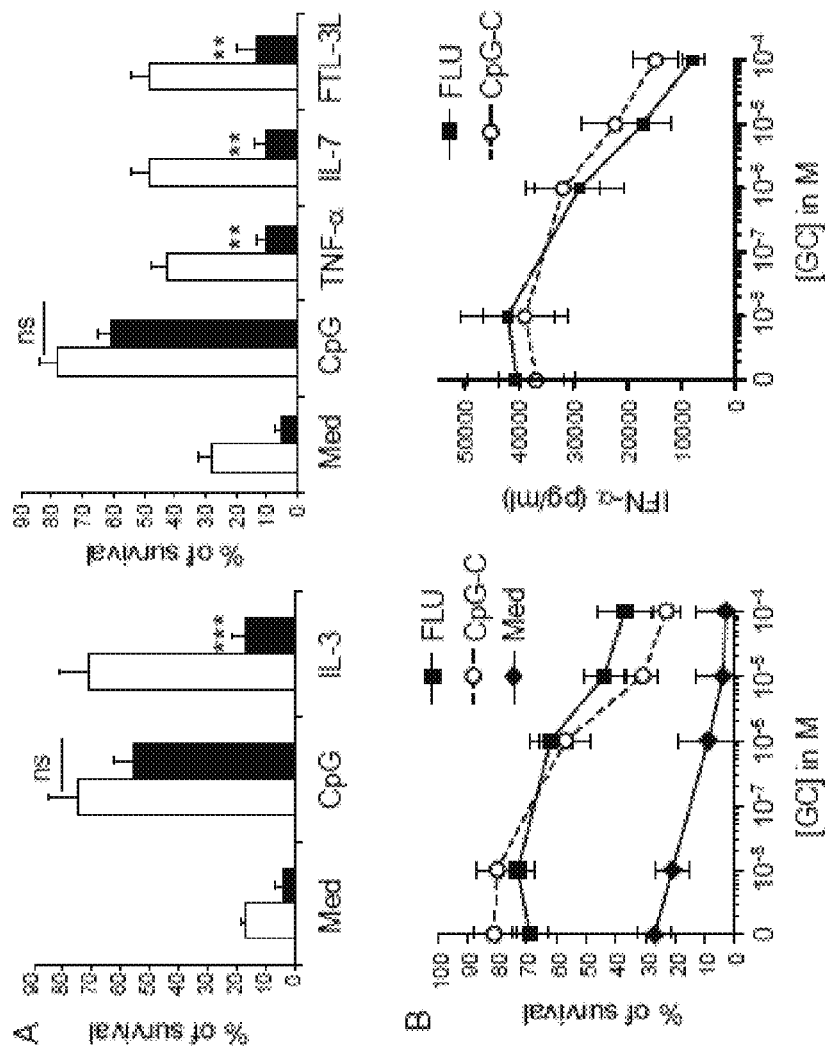
Figure 18:
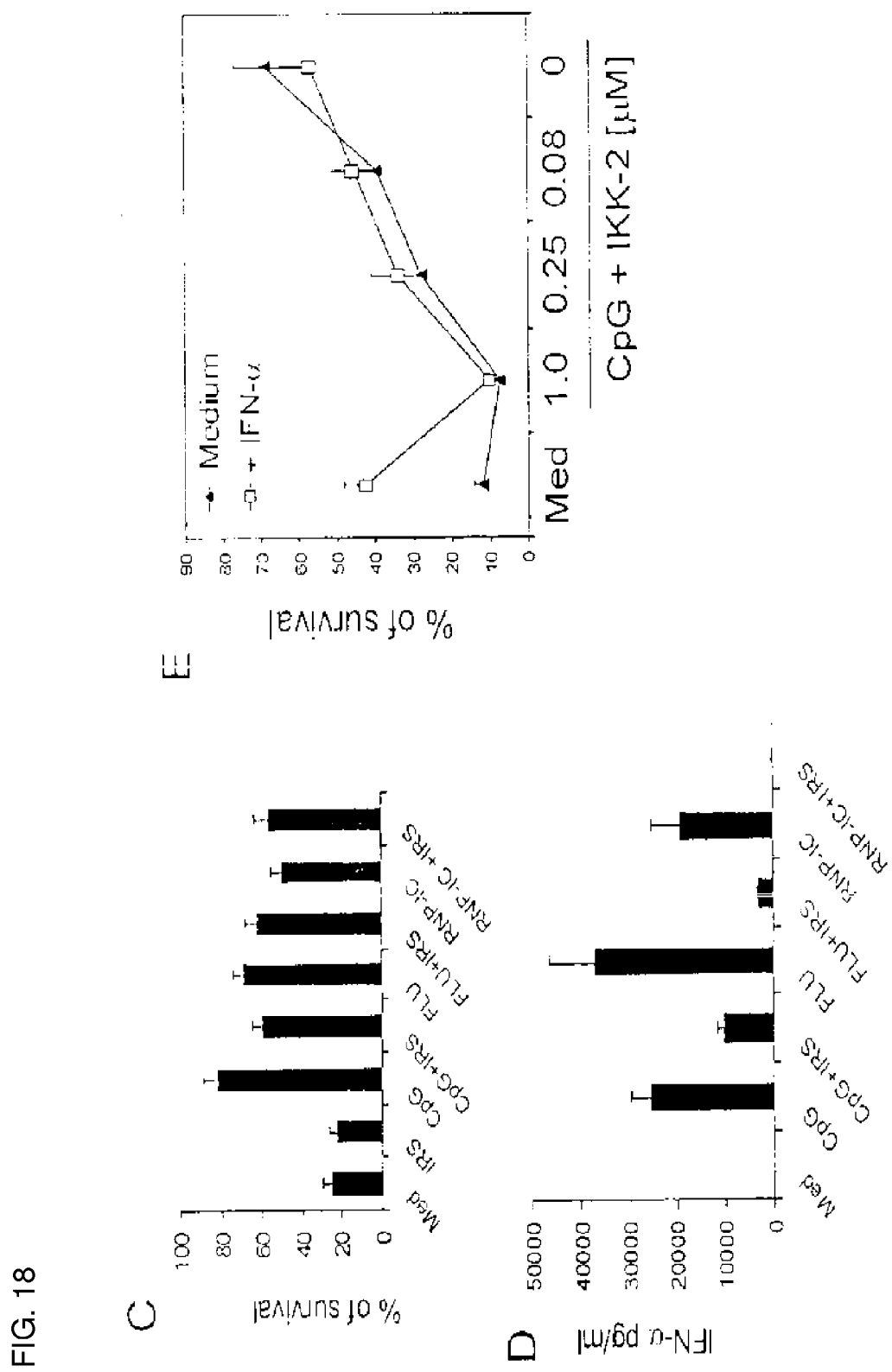
Figure 38:
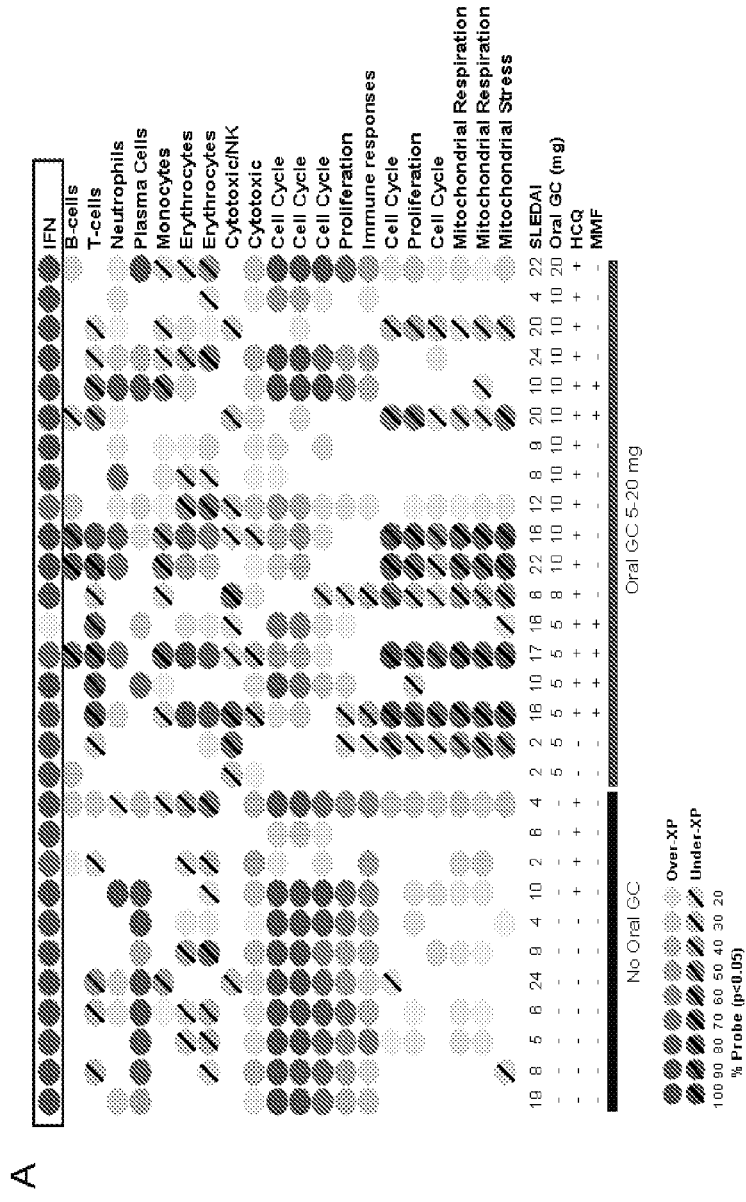
Figure 38:
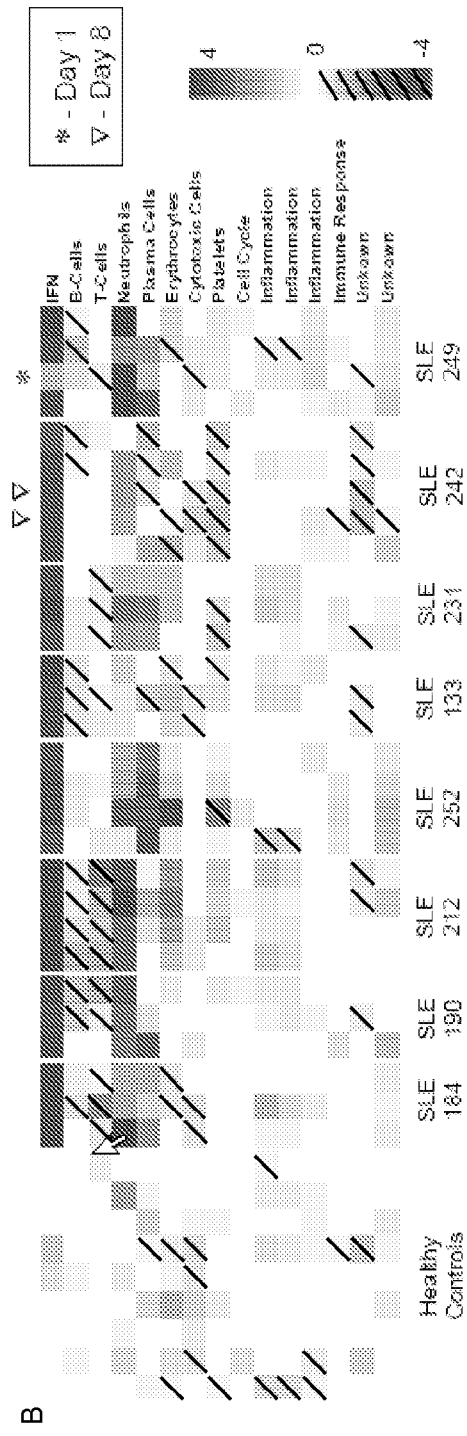

Level of Expression of PDC-Induced IFN Signature in GC-Treated SLE Patients Correlates with Circulating Blood PDC Lupus patients without treatment or with maintenance hydroxychloroquine (HCQ) treatment (200-400 mg/day) displayed characteristic transcriptional changes in their blood cells. These changes can be analyzed using "modules" of transcriptionally co-regulated genes (Chaussabel et al., 2008). In FIGS. 38a and b, modules with a slash correspond to decreased expression relative to control genes and modules without slashes correspond to increased expression. As previously published (Bennett et al. J. Exp. Med, 2003) and confirmed here (See FIG. 38), multiple transcriptional modules normalized in patients receiving oral glucocorticoids (GC) (5-20 mg/day) and/or mycophenolate mofetil reflecting the strong immunosuppressive effect of GC affecting most of the disregulated pathways in SLE patients (Bennett et al, 2003 and FIG. 38a). However, the IFN pathway was not affected in patients treated by oral GC (Bennett et al, 2003 and FIG. 38a and FIG. 13b upper panel that summarize data from 71 SLE patients). Consistent with this, GC did not significantly reduce the production of IFN-α upon PDC activation with the TLR7 and TLR9 ligands influenza virus (FLU) or CpG-ISS, or with IC from SLE patients (FIG. 13a and FIG. 17). This was confirmed by measuring IFN-α protein levels (FIG. 18b). Addition of a bifunctional TLR7/9 inhibitor (IRS, dashed line) (Barrat et al., 2005) however, was effective at blocking IFN-α production (FIG. 13a and FIG. 17).

In contrast, IV pulse therapy normalized the IFN signature (Bennett et al, 2003, FIG. 38b (* is after pulse therapy) and FIG. 13b). This demonstrated that the level of GC used in these patients correlated with reduction of the IFN signature in patients. This also correlated with a reduction in PDC (FIG. 13b) but not other cells, such as CD14+ monocytes in the blood (FIG. 13b). Similar reduction in PDC was observed in healthy donors but at much lower GC doses (15 mg/day) (Shodell et al., 2003) suggesting that continuous triggering of TLR7 and TLR9 on PDC by ICs in SLE patients counteracted the activity of GC on the IFN pathway. The partial reduction in PDC number with oral GC treatment did not significantly affect IFN module expression, which represents genes induced with varying sensitivity by IFN. The inhibition of the IFN-signature by pulse therapy was transient, returning to pre-pulse levels by day 8 (FIG. 13d and FIG. 38b). Similarly, the number of PDC was dramatically reduced 1 day after pulse therapy but rebounded by day 6 (FIG. 13c,d)

Example 15

Figure 14:
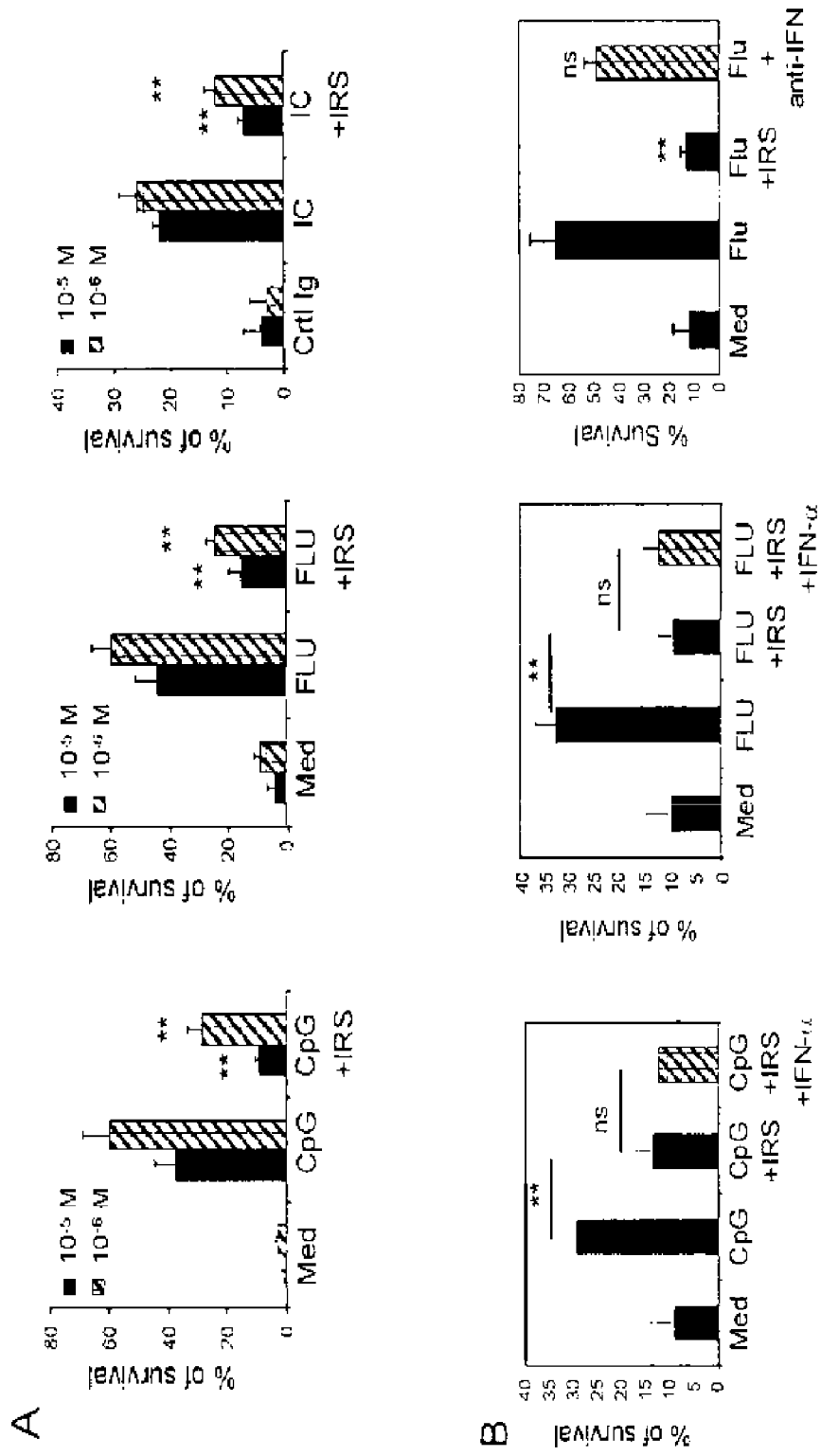
FIGS. 14A-G shows that GC did not affect viability of TLR7&9-activated PDC due to its lack of activity on TLR-induced NF-kB activation. (A-D) Purified PDC were cultured as indicated and viability was assessed after 24 hr. (A) PDC were cultured with GC ($10^{-5}$M or $10^{-6}$M) either alone or as indicated. Average of 6-12 independent donors is shown±SEM. ** p≤0.01 TLRL alone versus cultured with IRS. (B) PDC were cultured with GC ($10^{-5}$M) either alone or as indicated. Average of 5-8 independent donors±SEM. (C-D) PDC were cultured with CpG-C either alone or with p38 MAPK, PI3Kinase or NF-kB inhibitors. Average of 6-8 independent donors±SEM is shown. (E-G) Nuclear extracts from purified PDC (E-F) or monocytes (G) were prepared following cultures as indicated and the transcriptional activity of NF-kB was assessed. IKK-2 was used at 0.5 μM. Data are shown as OD values (mean±SEM) of at least four independent experiments.
Figure 14:
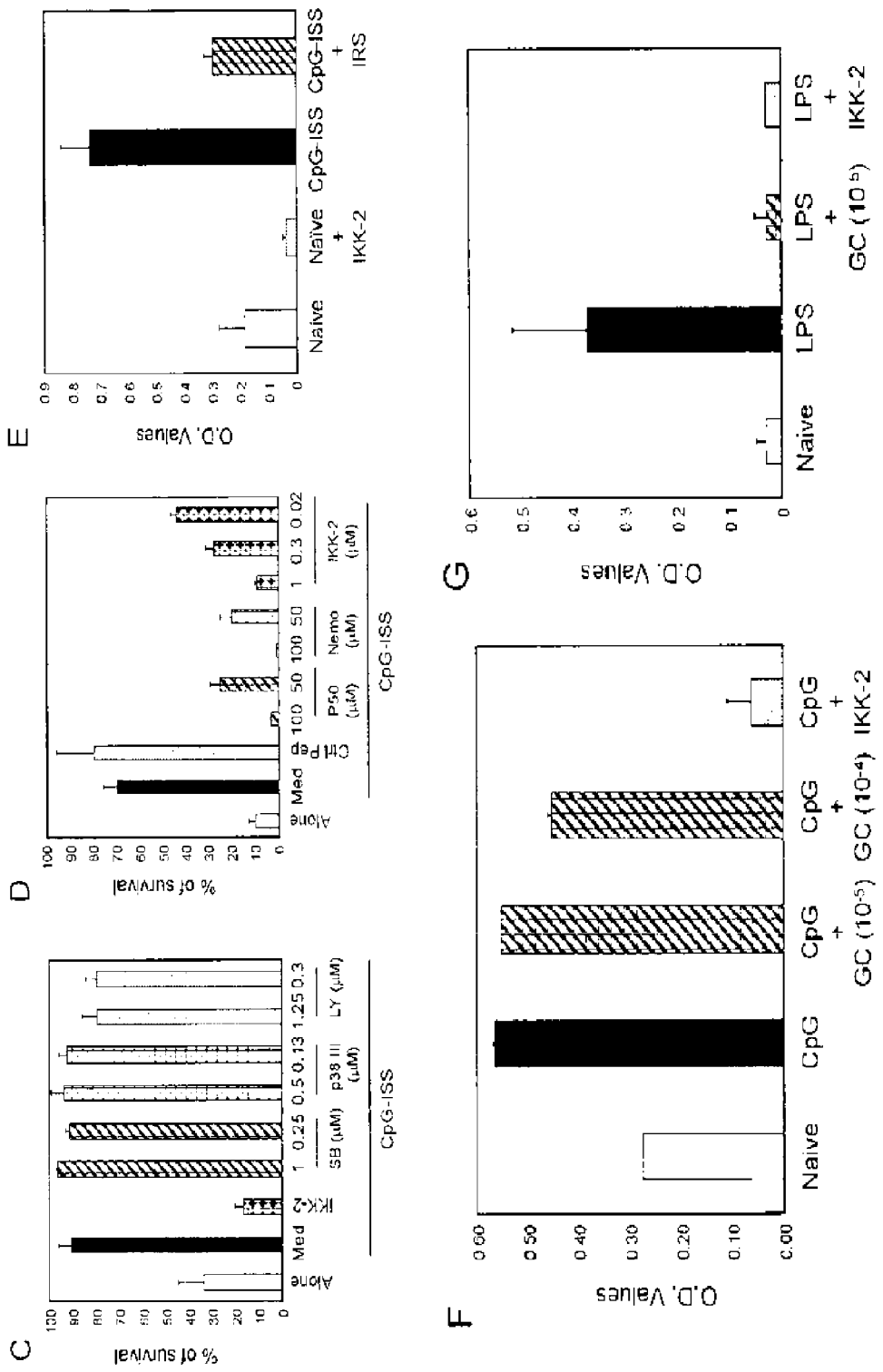

GC do not Affect Viability of TLR7 and TLR9-Activated PDC Due to its Lack of Activity on TLR-Induced NF-κB Activation GC induce apoptosis in many cell types (Montague et al., 1995), including PDC, where TLR signaling confers partial protection. Freshly isolated PDC from healthy donors stimulated with TLR7 or TLR9 ligands, were protected from GC-induced cell death (FIG. 14a, and FIG. 18a,b). This dose-dependent protection correlated with the production of IFN-α by PDC (FIG. 18b) supporting data obtained at a single cell level (FIG. 13a). Blocking this pathway with SEQ ID NO:42 (Barrat et al, 2005) restored GC sensitivity to PDC in vitro (FIG. 14a,b) although IRS itself was not cytotoxic (FIG. 18c). Likewise, RNP-IC from SLE patients protected PDC (FIG. 14a), a finding directly relevant to SLE. Type I IFNs were not required for protection by TLR7 and TLR9 ligands as neutralizing antibodies for type I IFN did inhibit protection (FIG. 14b) and IRS-mediated cell death was not reversed by exogenous IFN-α (FIG. 14b). Thus signaling through TLR7 or TLR9 protects human PDC from GC-induced cell death.

The signaling pathway of TLR-mediated PDC survival, was examined with specific inhibitors of molecules involved in TLR signaling: PI-3Kinase, P38 MAPK and NF-kB. Inhibitors of NF-kB, but not of p38 or PI-3Kinase blocked PDC survival induced by stimulation through TLR9 (FIG. 14c) and TLR7 (not shown). This observation was confirmed with three different NF-kB inhibitors (FIG. 14d). Exogenous IFN-α had no effect as well (FIG. 18e). Increased NF-kB transcriptional activity was observed in TLR9-stimulated PDC relative to unstimulated cells (FIG. 14e). Although GC inhibited NF-kB in many cellular systems (FIG. 14g and Parker et al., 2003), no inhibition of NF-kB measured by DNA-binding activity (FIG. 14f) or p65 phosphorylation after TLR7 and TLR9 triggering in PDC (FIG. 19a,b) was observed. The inability of GC to interfere with the NF-kB pathway in PDC may explain why TLR-activated PDC were resistant to GC-mediated death.

Example 16

TLR9 Activation In Vivo Renders PDC More Resistant to GC Treatment

Figure 15:
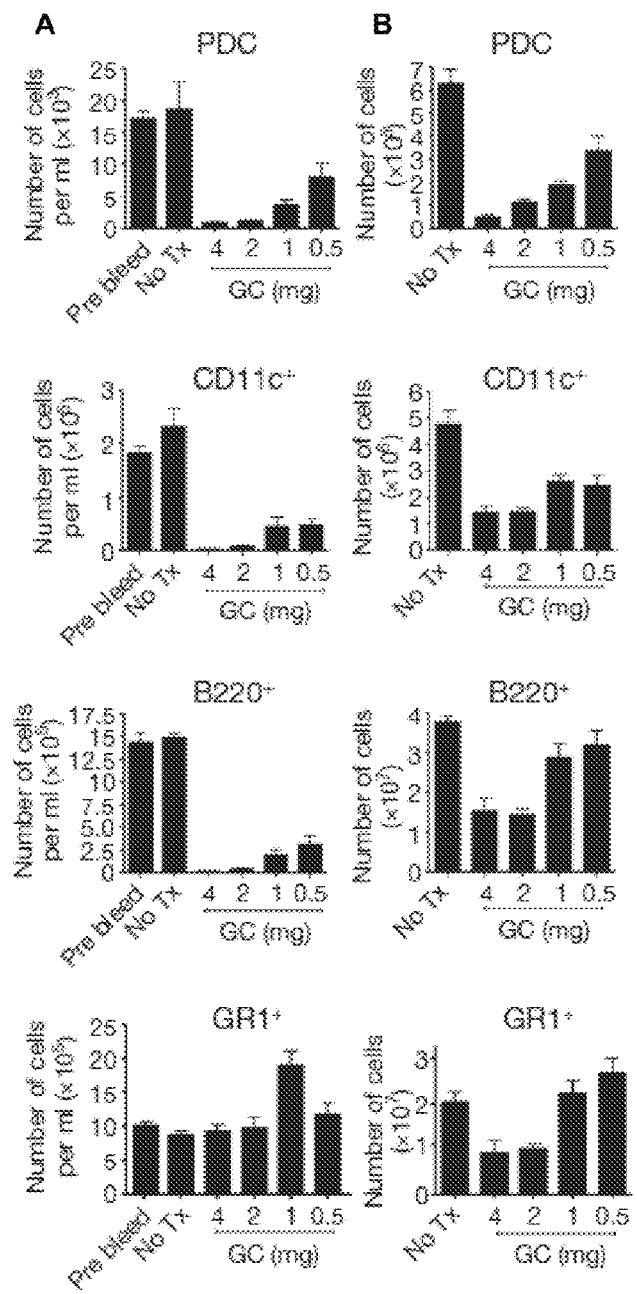
FIGS. 15A-D shows that TLR9 activation in vivo rendered PDC more resistant to GC treatment. (A, B) 129 mice were injected with graded doses of dexamethasone and cells prepared from blood (A) or spleens (B) after 18 hr. In blood (A), data are expressed as number of cells/ml of blood and as total number of cells in spleens (B). n=6 mice per group. (C-D) 129 mice were either left untreated or treated with 1 mg dexamethasone alone or in the presence of either CpG-C ISS (50 μg/mouse) or with CpG-C ISS plus IRS (100 μg/mouse); Number of cells/ml in blood is shown in (C) and total number of cells in spleen is shown in (D). Cumulative data of two independent experiments; n=8 mice per group is shown. Plotted data represent averages±standard error of the mean  p≤0.01, * p≤0.001.
Figure 15:
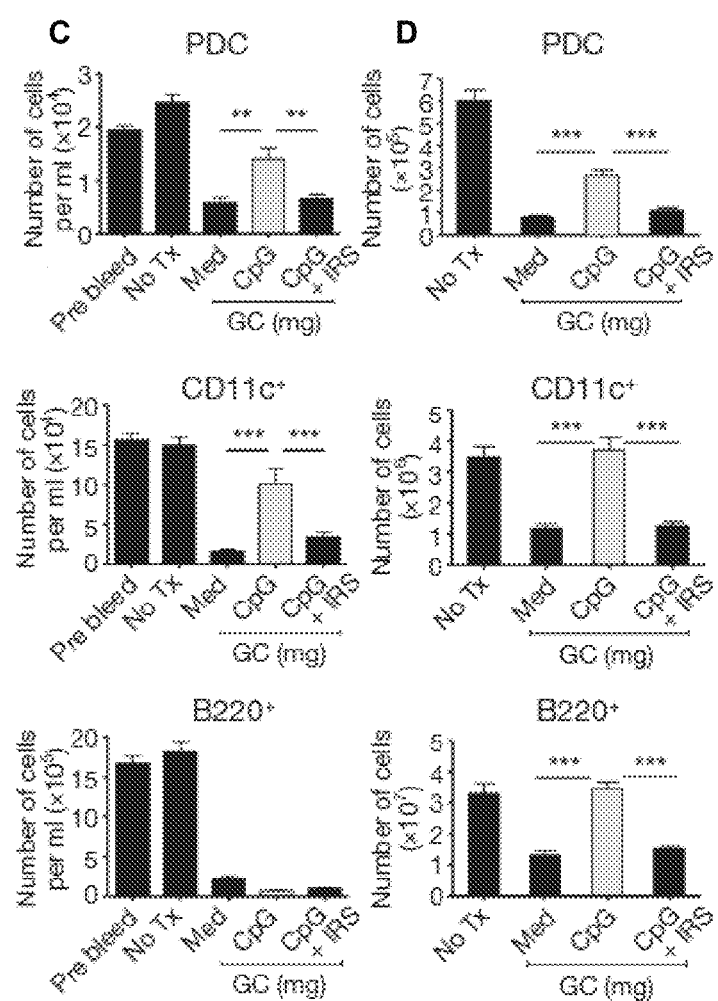

Next, the effect of GC on PDC in mouse models was investigated in vivo. In normal mice, PDC were extremely sensitive to GC treatment and promptly disappeared from blood (FIG. 15a) and spleen (FIG. 15b). Other TLR9+ cell types, including conventional DC (CD 11c+) and B cells (B220+) were similarly reduced (FIG. 15a,b). In contrast, neutrophils (GR1+) were not responsive to GC treatment, consistent with observations that GC promote survival, not death, of human neutrophils in vitro. TLR9 activation in vivo with CpG-ISS afforded significant protection from GC-induced cell death to conventional and plasmacytoid DC in both spleen and blood (FIG. 15c,d). Splenic B cells were similarly protected from death by TLR9 activation, but circulating blood B cells were not (FIG. 15c,d). Co-injection of IRS prevented CpG-ISS-induced activation (FIG. 20), resulting in increased GC-induced cell death in both blood and spleen (FIG. 15c,d). Thus, naïve circulating PDC are significantly more susceptible to GC-induced cell death than TLR-activated PDC in vivo.

Example 17

PDC from Lupus Prone Mice have Intrinsic Resistance to GC-Induced Cell Death as Compared to WT Mice Due to TLR7 and TLR9 Activation by Self Nucleic Acid This phenomenon was further studied in a disease model using the lupus-prone mouse strains (NZBxNZW)F1 and TLR7.Tg.6. (NZBxNZW)F1. These mice spontaneously develop a disease resembling human SLE with increased nucleic acid-containing ICs. Type I IFNs are associated with development of disease (Rozzo et al., 2001; Santiago-Raber et al., 2003; and Mathian et al., 2005) and blocking TLR7 and TLR9 reduced autoantibody titers and end-organ damage (Barrat et al., 2007). The TLR7.Tg.6 strain displays increased TLR7 expression, accumulation of anti-RNA autoantibodies, upregulation of type I IFN gene signature and an autoimmune syndrome resembling human SLE (Deane et al., 2007). Both strains are models of spontaneous autoimmunity due to recognition of endogenous nucleic acids by TLR7 and TLR9 as in SLE patients.

Figure 22:
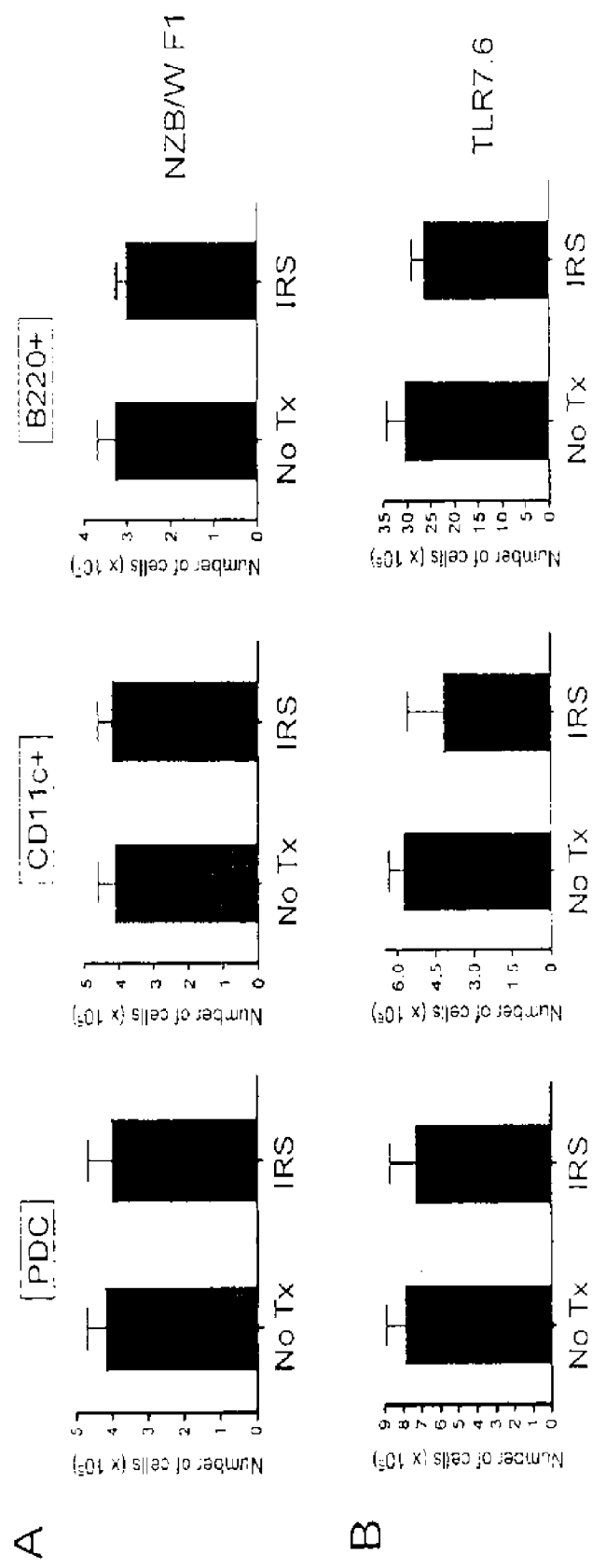
Figure 22:
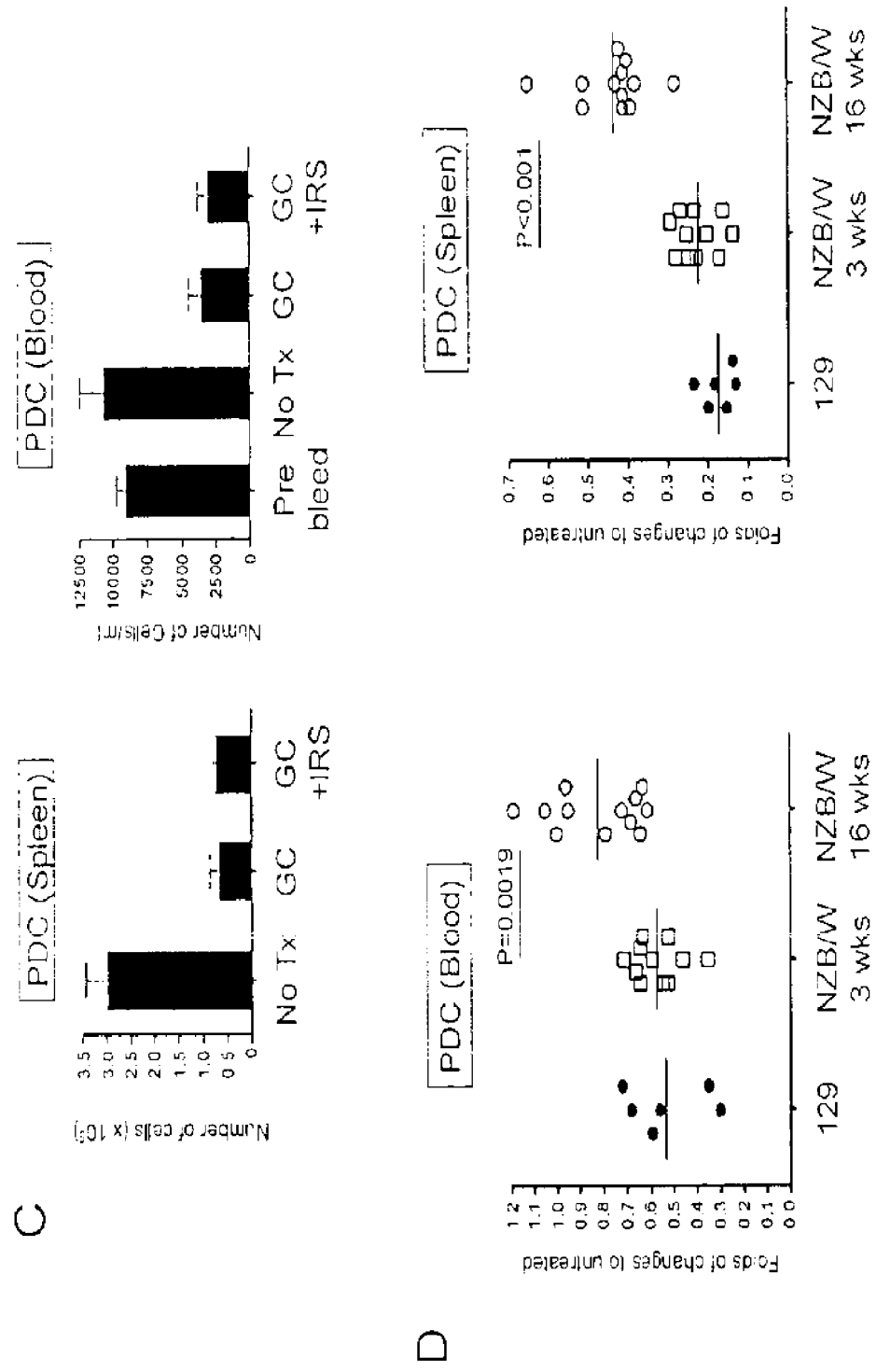

TLR7 and TLR9 bearing cells such as PDC, cDC and B cells were significantly more resistant to GC induced death in lupus-prone mice compared to normal strains such as 129 or C57/BL6, in which 0.5 mg GC induced a 50-75% reduction in live PDC (FIG. 16a,b). In both lupus strains, as in SLE patients, chronically activated cells thus had a reduced response to GC treatment. Blocking TLR7 and TLR9 in vivo with SEQ ID NO:42 enhanced the sensitivity to GC of PDC, cDC and B cells in both spleen (FIG. 16c,d) and blood (FIG. 21a,b). The expansion of neutrophils upon GC treatment (FIG. 21a,b) is consistent with the expansion of granulocytes in mice and humans following GC administration (Shodell et al., 2003; Athens et al., 1961; Laakko et al., 2002; and Trottier et al., 2008) and with the persistence of a low density neutrophil gene signature after high dose steroids in SLE patients (Bennet et al., 2003). Interestingly, a reduction of the GC-induced neutrophil expansion was observed upon IRS administration (FIG. 21a,b) perhaps indicating that blocking TLR7 and TLR9 could impact the dysregulated granulopoiesis in SLE Inhibition of TLR7 and TLR9 was similar in both lupus-prone mouse strains and specific for nucleic acid-induced inflammation as i) IRS did not induce cell death without GC (FIG. 22a,b), ii) blocking TLR7 and TLR9 had no effect on PDC in normal mice injected with GC (FIG. 22c) and iii) PDC from young (NZBxNZW)F1 mice (before disease onset) were more sensitive to GC than PDC from older mice (FIG. 22d). The increased GC activity in mice pre-treated with IRS was significant at GC doses that had no effect on PDC survival in normal mice (FIG. 23a). These findings support the hypothesis that innate inflammation through self-nucleic acid recognition is a dominant feature in the unresponsiveness of SLE patients to GC treatment. As observed in human SLE, type I IFN-regulated genes are stimulated to some extent in both (NZBxNZW)F1 and TLR7.Tg.6 model (Trottier et al., 2008; and Rozzo et al., 2001). In both lupus-prone strains, IRS pre-treatment reduced the expression of IFN-regulated genes but not TNF-$\alpha$(FIG. 23b,c), demonstrating that activation through TLR7 and TLR9 is central to inflammation in these mice.

These results demonstrate, in vitro and in vivo, that stimulation of PDC through TLR7 and TLR9 can account for the reduced activity of GC to inhibit the IFN pathway in SLE patients and in two lupus-prone mouse strains. The triggering of PDC through TLR7 and TLR9 by nucleic acid-containing immune complexes or by synthetic ligands activates the NF-kB pathway essential for PDC survival. GC do not affect NF-kB activation in PDC, preventing GC induction of PDC death and the consequent reduction of systemic IFN-$\alpha$ levels. These findings unveil a novel understanding of the role of self recognition of DNA and RNA by TLR as an important inflammatory amplifier in SLE and indicate that inhibitors of TLR7 and TLR9 signaling could prove to be effective corticosteroid-sparing drugs. These data also stress the potential utilization of bi-functional TLR7/9 inhibitors (e.g., IRS) as corticosteroid-sparing drugs.

Example 18

Methods and Reagents Used in Examples 19 to 23

Reagents

Phosphorothioate ODNs were prepared as previously described (Duramad et al., 2003). The prototype TLR7 and TLR9 inhibitors used were 5'-TGCTCCTGGA GGGGT-TGT-3 (SEQ ID NO:42) and/or 5'-UGC TGC TCC TTG AGI GGT TGT TTG T-3' (SEQ ID NO:109), wherein I=deoxy-inosine (Barrat et al., 2005). Control oligonucleotide used was 5'-TCCTGCAGGT TAAGT-3 (SEQ ID NO:160). Mouse IFN-$\alpha$ ELISA sets were purchased from PBL Biomedical Laboratories (Piscataway, N.J.).

Animals and In Vivo Treatments.

C57BL/6 and 129 mice were purchased from Charles River Laboratories. (NZBxNZW)F1 female mice were purchased from Jackson Laboratories and used at 18-22 weeks of age. MyD88/KO and TLR9/KO mouse colonies were maintained at Simonsen Laboratories and used with age matched C57BL/6 wild type controls at 8-12 weeks of age. Tape stripping was performed after shaving the dorsal area (3×3 cm) using 10 strokes with duct tape. IRS was administered just before tape stripping SC at a distant site. Alternatively, in (NZBxNZW)F1 mice, IRS was administered long term. In certain experiments PDC and neutrophils were depleted with 250 µg of antibody given IP at day −2 and day 0, eight hours before tape stripping. Anti-120G8 (Imgenex) was used for depletion of PDC (Asselin-Paturel et al., 2003), and anti-GR1-LY6G (clone 1A8; Biolegend) was used for depletion of neutrophils (Daley et al., 2008). Over 95% cellular depletion was achieved in both blood stream and skin infiltrate. In experiments where PDC were depleted, long term 120G8 depleting antibody was administered. Experiments in (NZBxNZW)F1 were terminated between 15-23 days after initial tape stripping, depending on the progression of the lesions in the untreated groups in each experiment. Percentage of area with open lesions in (NZBxNZW)F1 and normal mice was evaluated with Nikon software NIS-elements.

Histological Analysis of Skin Inflammation and Tissue Pathology

The biopsy specimens were fixed in formalin and embedded in paraffin. Sections were stained with hematoxylin-eosin. Multiple skin sections of 12-30 mice per group were evaluated in a blinded fashion. The following histological features were assessed and graded on a scale of 1 to 3: i) epidermis thickness ii) degree of ulceration iii) intraepithelial inflammation, iv) dermal inflammation, and v) panniculum inflammation. Histological grading was assigned as follows: 0, normal skin architecture, few dermal leukocytes and regular adnexa; 1, mild inflammation, slight epidermal hyperplasia and signs of dermal fibroblast proliferation; 2, moderate inflammation, noticeable epidermal hyperplasia (two- to four-fold increase in epithelial thickness) with hyperkeratosis, significant leukocyte/neutrophil-granulocyte dermal infiltrate with few macrophages, moderate fibrosclerosis of the dermis, reduction in the number of adnexa, slight degenerative changes of the hypodermic adipose tissue; 3, severe inflammation, marked epidermal hyperplasia (>four-fold increase in epithelial thickness) with hyperkeratosis, formation of keratin-filled craters and cysts, diffuse discontinuity of the epidermal layer (ulceration), extensive dermal infiltrate with abundant neutrophils and macrophages, pronounced dermal fibrosclerosis, vanishing of adnexa and evident degenerative changes of the hypodermic adipose tissue. The different parameters were scored separately and summed to obtained a total disease score (Table 22-1). Statistical significance among groups was calculated with a Mann-Whitney U-test.

Skin Sample Processing and Flow Cytometry

For analysis of cellular infiltrate mice were sacrificed 24 hr later and epidermis and derma were mechanically separated followed by enzymatic digestion with 0.28 U/ML of Liberase 3 (Roche) for 20 minutes at 37° C., passed trough a 70 µm filter washed in RPMI without serum, counted and stained for flow cytometric analyses. Flow cytometric analyses was performed using fluorochrome-conjugated monoclonal antibodies to mouse CD3, CD8, CD4, B220, CD11c (BD bioscience), GR1-LY6G (1A8 clone), F4/80 (Biolegend), PDCA1 (Miltenyi Biotech) and 120G8 (Imgenex). Specific gating to characterize skin infiltrate was done as follows: PDC were CD11c+, PDCA1+; 120G8+, Ly-6C+, myeloid DC were CD11c+ PDCA1− 120G8− Ly-6C−; T cells were CD3+ CD4+; CD3+ CD8+, neutrophils were GR1-Ly6-G high F4/80−, macrophages were GR1− Ly6-G low F480+. In these experiments IFN-α production by PDC was evaluated by FACS analysis, skin was processed as described above but in the presence of 5 μg/ml of Brefeldin A. Cellular infiltrate was seeded in non coated plastic plates at a concentration of $1 \times 10^6$/ml in RPMI medium (supplemented with 10% FCS) with the addition of 5 μg/ml of Brefeldin A for 2 hr. Afterwards cells were stained for surface markers with anti-CD11c plus anti-PDCA1 conjugated antibodies to identify PDC. Cells were then fixed in 2% paraformaldyde and permeabilized for 10 minutes in 0.5% Saponin 1% BSA in PBS and then stained in the same buffer with anti-IFN-α conjugated antibody (5 μg/ml) (PBL Biomedical Laboratories). As a positive control, BM-derived PDC were stimulated for 4 hr with CpG-C ISS, and 5 μg/ml of Brefeldin A was added in the last 2 hr of stimulation. In some experiments, the ability of skin infiltrating neutrophils to produce NET was assayed as previously described (Brinkmann et al., 2004; Fuchs et al., 2007; Kessenbrock et al., 2009; and Wartha and Henriques-Normark, 2008). In brief, skin infiltrating cells were seeded on coated glass (0.001% polylysin; SIGMA) at a concentration of $1 \times 10^6$/ml for 10 minutes at 37° C. in RPMI with 2% FCS. Afterwards cells were stained with anti-LY6G conjugated antibody for 10 minutes on ice and immediately fixed in 2% paraformaldyde and counterstained for DNA with SYTOX green (1 to 5000 Invitrogen) (Fuchs et al., 2007). In some experiments, after fixation, neutrophils were further stained with anti-LL37/CRAMP antibody (Innovagen) (5 μg/ml) and then counterstained for DNA with SYTOX green (1 to 5000 Invitrogen) or with a specific RNA dye SYTO RNA Select (1 to 5000 Invitrogen).

Real-Time Quantitative PCR (TaqMan) Analysis

PCR reactions were performed as described previously (Barrat et al., 2005). In brief, RNA was extracted from skin infiltrating cells using RNA micro kit (Qiagen) and from skin tissues with a fibrous tissue RNA extraction kit (Qiagen) according to the manufacturer's instructions. RNA and cDNA was generated with SuperScript First-Strand Synthesis System (Invitrogen). ECT was threshold cycle (CT) values for each gene were normalized to the housekeeping gene ubiquitin or β-actin using the formula Eq. 1.8 (HSKGENE) (100,000), where HSK is the mean CT of triplicate housekeeping gene runs, GENE is the mean CT of duplicate runs of the gene of interest, and 100,000 is arbitrarily chosen as a factor to bring all values above. Primers sequences used were as follow:

```
IFI202R
                                     (SEQ ID NO: 184)
5'-CTAGGATGCCACTGCTGTTG-3',

IFI202F
                                     (SEQ ID NO: 185)
5'-CAAGCCTCTCCTGGACCTAA-3',

IRF7R
                                     (SEQ ID NO: 186)
5'-TCCAAGCTCCCGGCTAAGT-3',

IRF7F
                                     (SEQ ID NO: 187)
5'-ACAGGGCGTTTTATCTTGCG-3',

ISG15R
                                     (SEQ ID NO: 188)
5'-CCCCTTTCGTTCCTCACCAG-3',

ISG15F
                                     (SEQ ID NO: 189)
5'-ACGGTCTTACCCTTTCCAGTC-3',

ISG20R
                                     (SEQ ID NO: 190)
5'-CCACCAGCTTGCCTTTCAGAA-3',

ISG20F
                                     (SEQ ID NO: 191)
5'-GTCACGCCTCAGCACATGGT-3',

NMIR
                                     (SEQ ID NO: 192)
5'-AATGCCTTCTAATCCGGTCA-3',

NMIF
                                     (SEQ ID NO: 193)
5'-AGTGGAAAGCGTGGATTATGA-3',

IFIT1R
                                     (SEQ ID NO: 194)
5'-TCTGGATTTAACCGGACAGC-3',

IFIT1F
                                     (SEQ ID NO: 195)
5'-AGGCTGGAGTGTGCTGAGAT-3',

IL-1AR
                                     (SEQ ID NO: 196)
5'-CCGACAGCACGAGGCTTT-3',

IL-1*F
                                     (SEQ ID NO: 197)
5'-TGGTGTGTGACGTTCCCATT-3',

TNF-AR
                                     (SEQ ID NO: 198)
5'-GGTCTGGGCCATAGAACTGATG-3'

TNF-AF
                                     (SEQ ID NO: 199)
5'-GCCACCACGCTCTTCTGTCT-3',

IL-1-BR
                                     (SEQ ID NO: 200)
5'-AAACCGTTTTTCCATCTTCTTCTTT-3',

IL-1-BF
                                     (SEQ ID NO: 201)
5'-GACGGCACACCCACCCT-3',

IP-10F
                                     (SEQ ID NO: 202)
5'-GACGGTCCGCTGCAACTG-3',
and IP-10R
                                     (SEQ ID NO: 203)
5'-GCTTCCCTATGGCCCTCATT-3'.
```

Statistical Analysis

Data were analyzed using a 2-tailed Student's t test. All analyses were performed using Prism software (GraphPad Software, San Diego, Calif.). Differences were considered significant at a P level less than 0.05.

Example 19

Activated PDC and Neutrophils Infiltrate Skin Rapidly after Tape Stripping

Tape-stripping was employed as a method to induce mild cutaneous injury and inflammation. This method was previously used to provoke disease in mouse models of psoriasis and atopic-dermatitis (Inoue et al., 2005; Jin et al., 2009; and Sano et al., 2005). Tape stripping has also been used as a non-invasive method for detecting and diagnosing lupus, as lupus patients overreact to this mild cutaneous injury as compared to healthy individuals. The nature of the inflammatory response to tape-stripping however has not been well characterized at the cellular or molecular level. At 24 hr following tape stripping, a pronounced increase of inflammatory cells in the skin was observed (FIG. 24A) compared to untreated skin, including a cell population expressing the PDC markers, CD11c+ and PDCA1+ (FIG. 24A) as well as 120G8+, Ly-6C (not shown). The PDC were functionally active as they produced IFN-α, measured by intracellular staining in cells isolated from the skin (FIG. 24B). Flow cytometric analysis also revealed a massive influx of neutrophils (Ly6G+ cells) and a lesser increase in macrophages (F4/80+ cells), along with CD4+ and CD8+ T cells (FIG. 24A).

Activated neutrophils produce neutrophil extracellular trap (NET), which are essential to kill bacteria in vivo (Brinkmann et al., 2004; Fuchs et al., 2007; and Wartha and Henriques-Normark, 2008). Neutrophils infiltrating tape-stripped skin were activated, producing abundant NETs with long chromatin fibers (FIG. 24D), whereas no NET formation was observed in unstimulated bone marrow neutrophils that were used as controls (FIG. 24C). In skin neutrophils, the long fibers of the NETs contained both DNA and RNA and were associated with LL37/CRAMP (FIGS. 24E and F), a cationic antimicrobial peptide secreted by activated neutrophils (Kessenbrock et al., 2009; and Wartha and Henriques-Normark, 2008).

Example 20

Figure 25:
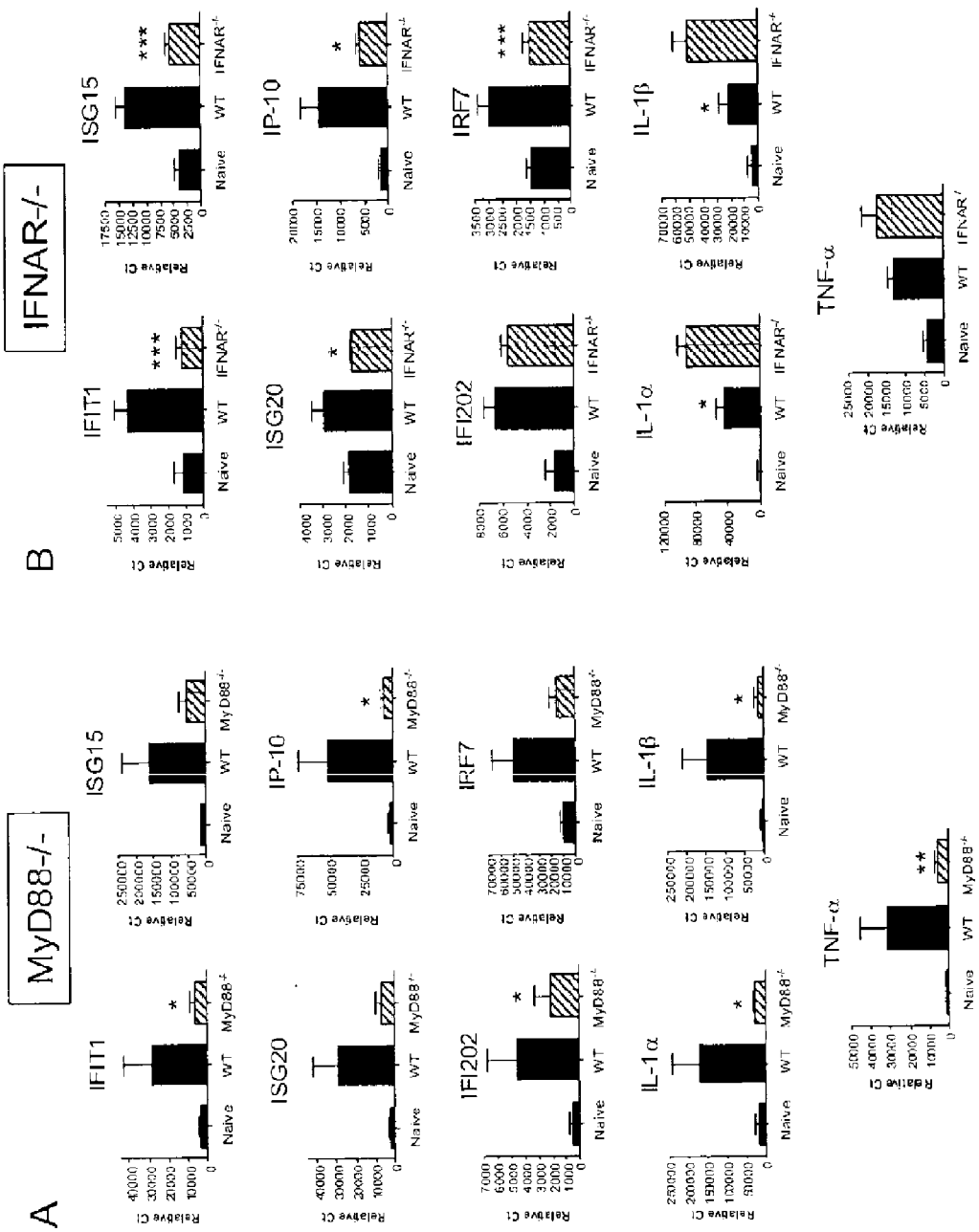
Figure 31:
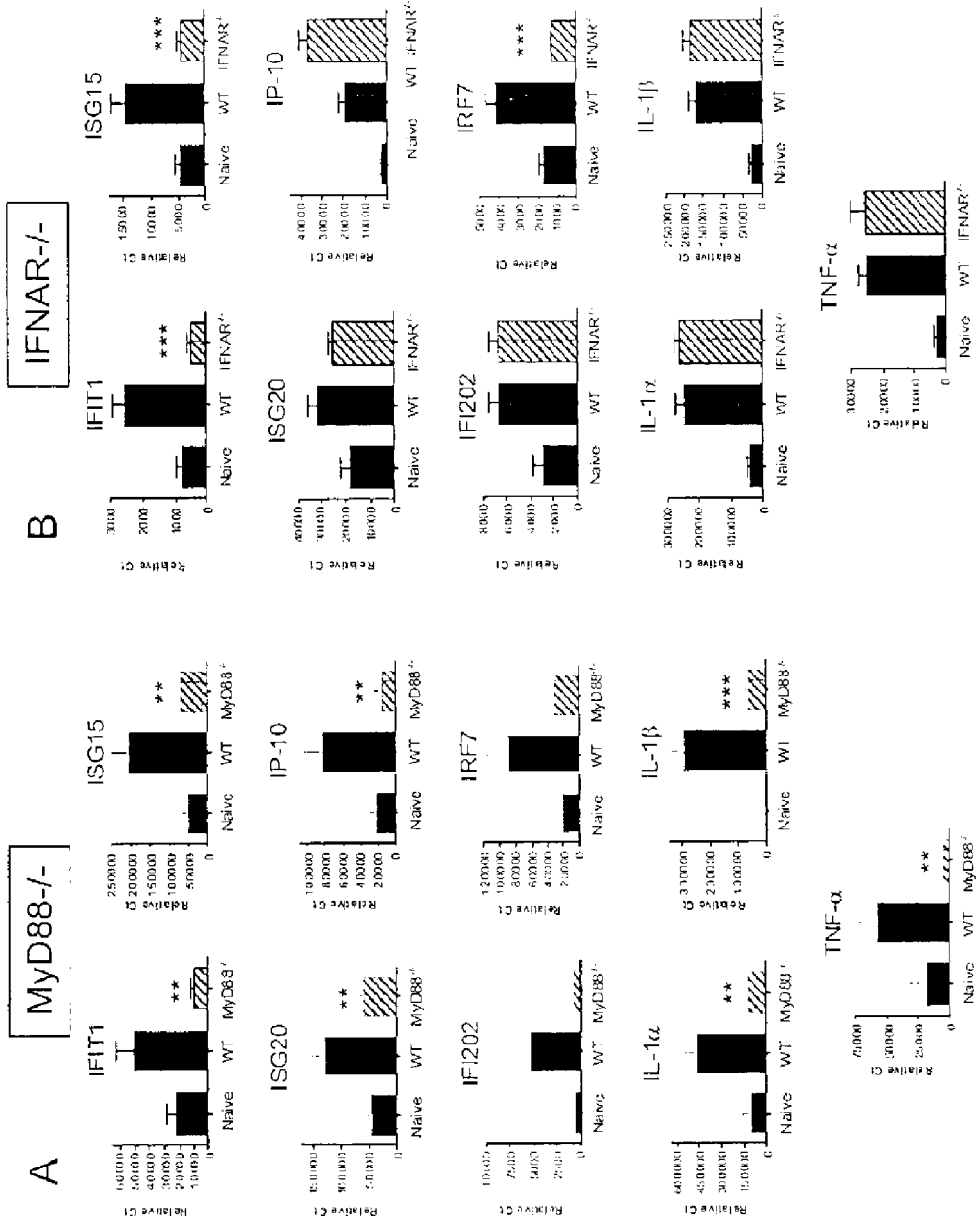

Signaling Through TLR7 and TLR9 Lead to Rapid Induction of IFN-Regulated and Pro-Inflammatory Genes at the Site of Cutaneous Injury Accompanying the cellular infiltration, epidermal injury resulted in strong induction of many prominent inflammatory genes in mRNA isolated from both skin biopsies and infiltrating leukocytes (FIG. 25 and FIG. 31). The induction of these genes required MyD88, as shown by the lack of gene induction in MyD88-deficient mice (FIG. 25A and FIG. 31A). To define the regulation of these genes, the experiment was repeated using IFNAR−/− mice, lacking one chain of the type I IFN receptor. In these IFNα/β-unresponsive mice, IFIT1, ISG15, IRF7 and ISG20, all IFN-regulated genes, were not induced (FIG. 25B and FIG. 31B) in either compartment and IP-10 was reduced in the skin (FIG. 25B) but not in the infiltrating cells (FIG. 31B). Another IFN-regulated gene IFI202 was induced in IFNAR−/− mice, consistent with previous studies showing an IFN-independent signaling pathway for this gene in mice (Asefa et al., 2004; and Choubey and Panchanathan, 2008). In contrast, the lack of IFNα/β signaling did not reduce the induction of TNF-α or IL-1α or β (FIG. 25B and FIG. 31B). Instead, expression of these inflammatory genes was somewhat increased in the IFNAR−/− in mRNA from total skin (FIG. 25B), but not in infiltrating cells (FIG. 33B), possibly reflecting the previously reported reciprocal regulation of the Type I IFN and TNF pathways (Banchereau et al., 2004). The clear requirement for MyD88 in the induction of all three pro-inflammatory genes demonstrates an important role for signaling through members of IL-1R or TLR receptor families.

To test whether the two nucleic acid-specific TLR, TLR7 and TLR9, were involved in the induction of these inflammatory genes signatures, tape-stripped mice were treated with SEQ ID NO:42 (IRS), a bifunctional oligonucleotide antagonist that blocks activation by TLR7 or TLR9 agonists in vitro (Barrat et al., 2005) and in vivo (Barrat et al., 2007). Treatment with SEQ ID NO:42 (IRS) significantly reduced the expression of both IFN-α regulated genes and pro-inflammatory genes, in some cases, reducing expression to the levels found in untreated mouse skin (FIG. 26B and FIG. 33). Thus, signaling through TLR7 and/or TLR9 is central to the principal gene expression changes induced by tape-stripping. In contrast, SEQ ID NO:42 (IRS) treatment had no measurable effect on infiltration of cells, including PDC and neutrophils into the site of injury (FIG. 26B and FIG. 32). This shows clearly that cell migration and cytokine secretion, although they appear coordinately regulated, are induced by different stimuli arising from tissue injury.

Example 21

Figure 27:
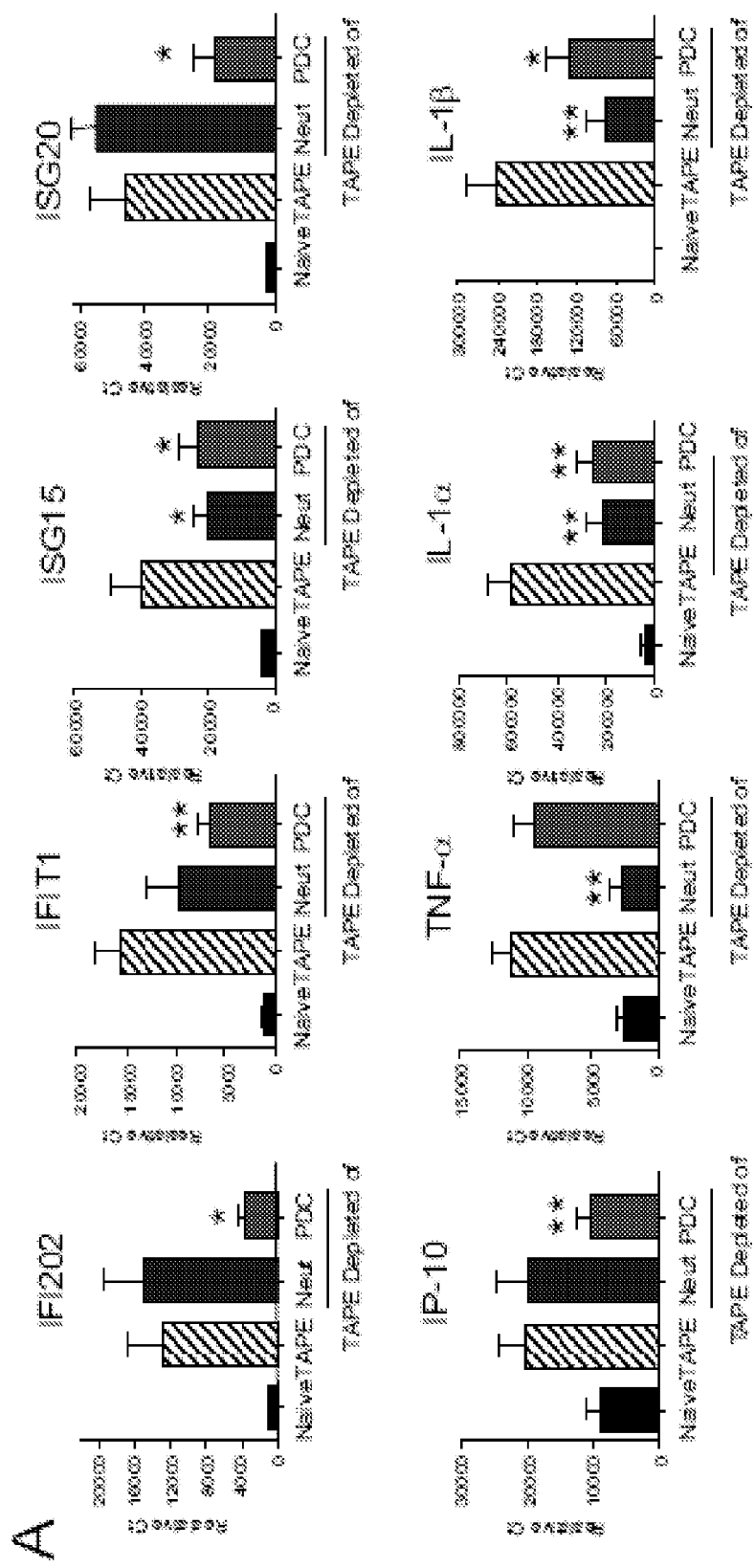
Figure 27:
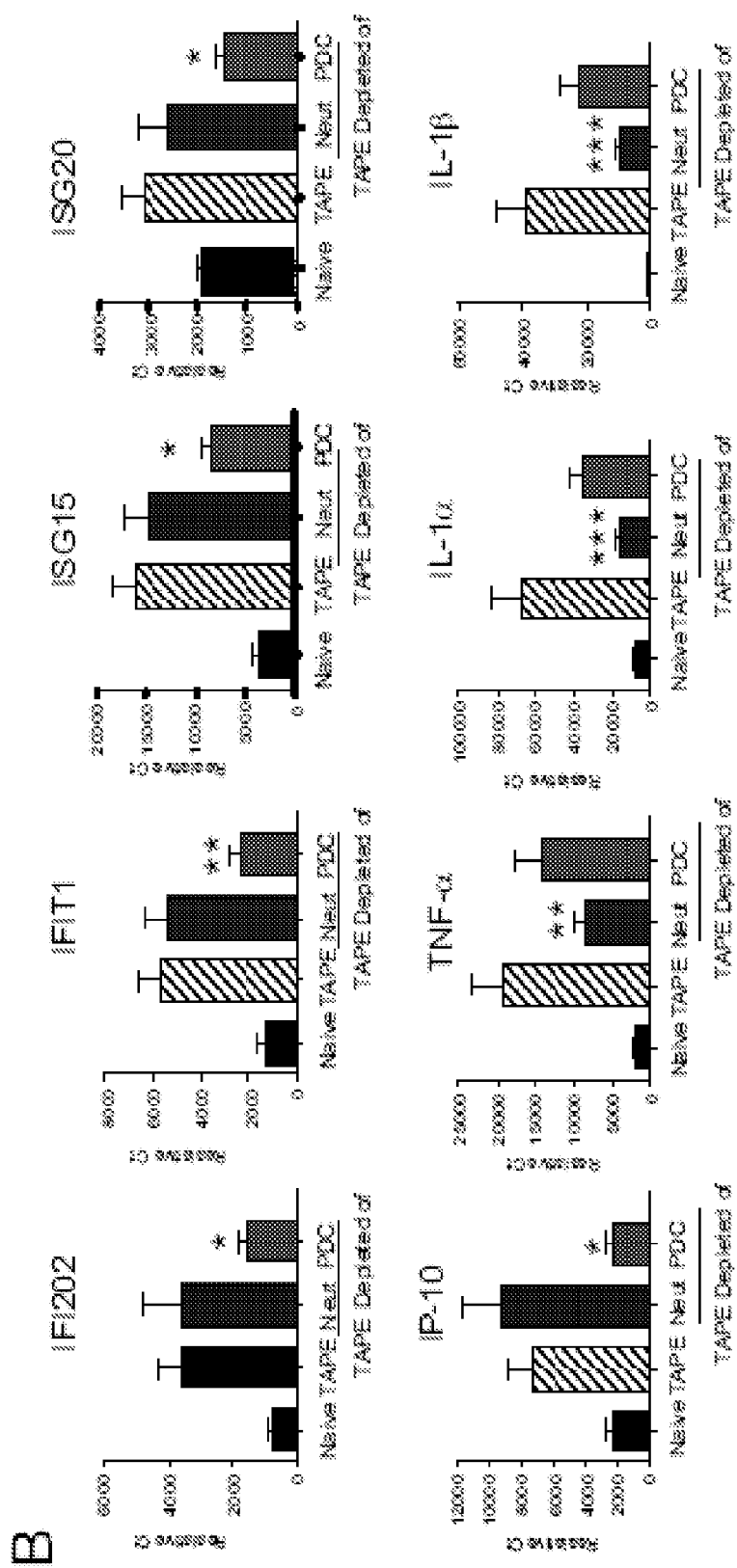

PDC and Neutrophils are Responsible for Different Patterns of Cytokine Induction in Response to Tape Stripping To determine the relative contribution of each of these two prominent cell types in this model of skin inflammation, each cell type was specifically depleted prior to tape stripping. Depletion of PDC with the 120G8 monoclonal antibody led to strong reduction of the type I IFN-regulated genes (IFI202, IFIT, ISG15, ISG20, IP-10) in infiltrating cells (FIG. 27A) and skin biopsies (FIG. 27B), whereas these genes were relatively unaffected by depletion of neutrophils (FIG. 27). In contrast, neutrophil depletion resulted in a 70-90% reduction in TNF-α, IL1-α and IL1-β mRNA, whereas depletion of PDC led to a more modest 20-50% reduction in expression of these genes. Concurrent depletion of both cell types, as expected, resulted in large reductions in expression of both groups of genes (not shown). Collectively, these results suggest that in this acute skin injury model, PDC and neutrophils are major components of the TLR l and TLR9, MyD88 dependent inflammation, but promote two separate inflammatory responses, one regulated by the type I IFNs produced by PDC and one that involves neutrophil-dependent pro-inflammatory cytokines.

Example 22

Lupus Prone (NZBxNZW)F1 Mice Develop Chronic Skin Lesions Resembling Human CLE after Tape Stripping Patients with SLE or CLE are often much more sensitive to mild cutaneous irritation and injury, suggesting that injury initiates a process that is exacerbated and sustained by autoimmune processes. Hybrid (NZBxNZW)F1 mice spontaneously develop high levels of circulating anti-DNA and anti-RNA autoantibodies (Furukawa and Yoshimasu, 2005), leading to immune complex formation and lupus nephritis resembling that observed in SLE patients. Although these mice rarely show spontaneous development of skin lesions, there is an accumulation of immune complexes at the epidermis-dermis junction, similar to those observed in human CLE (Furukawa and Yoshimasu, 2005; McCauliffe, 1996). As immune complexes containing endogenous RNA or DNA are potent ligands for TLR7 and TLR9, respectively (Barrat et al., 2005; and Means et al., 2005), (NZBxNZW)F1 mice may exhibit a prolonged or exacerbated response to tape stripping.

Figure 28:
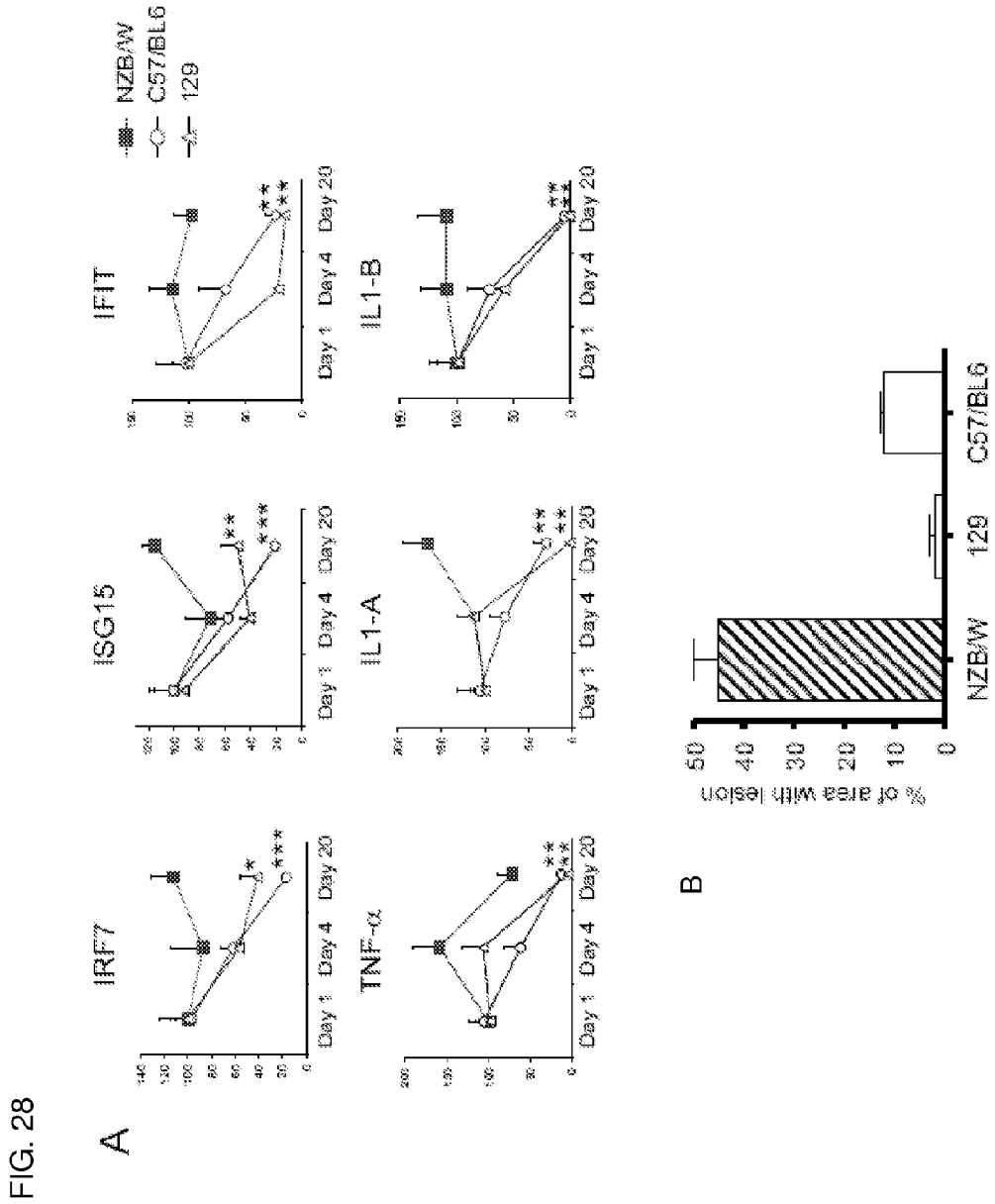
Figure 28:
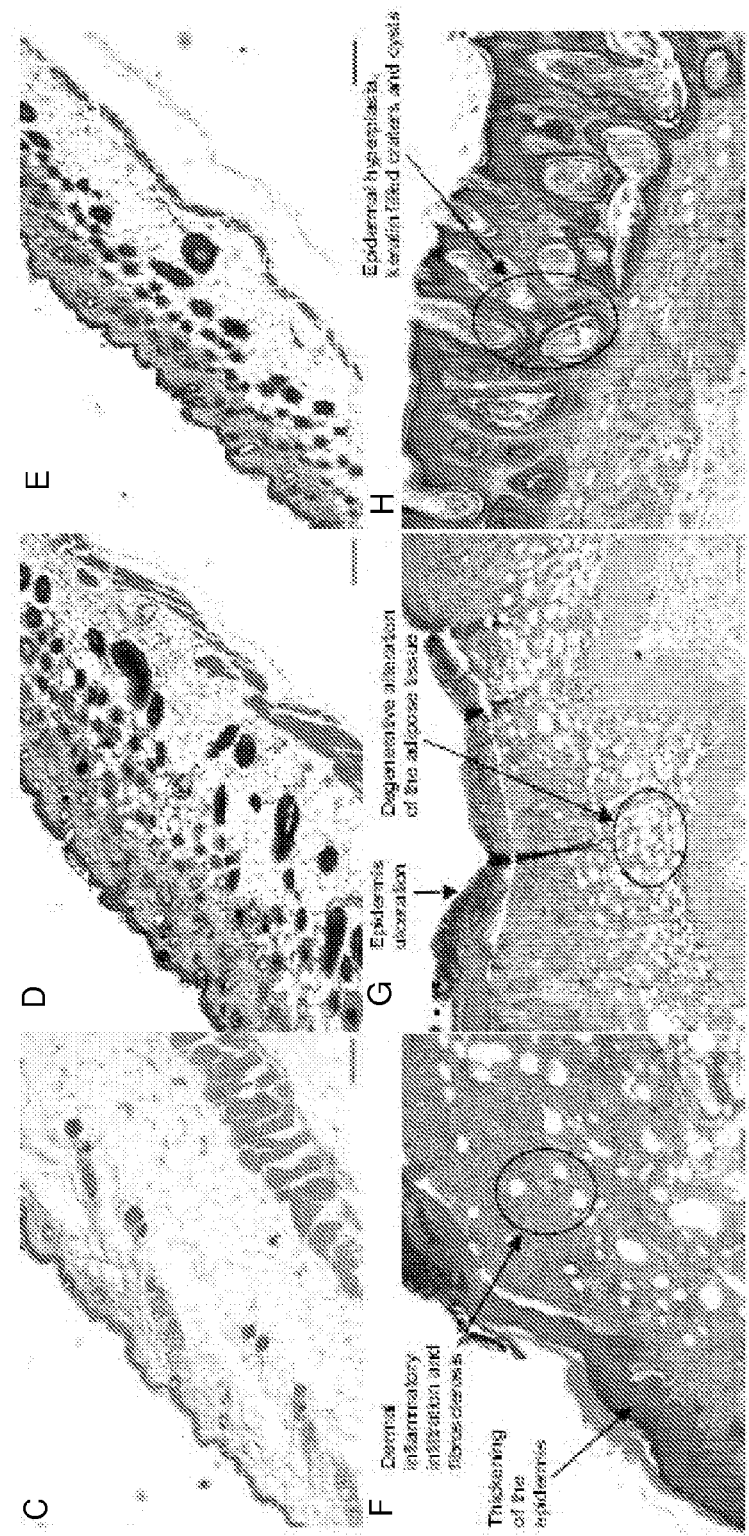
Figure 34:
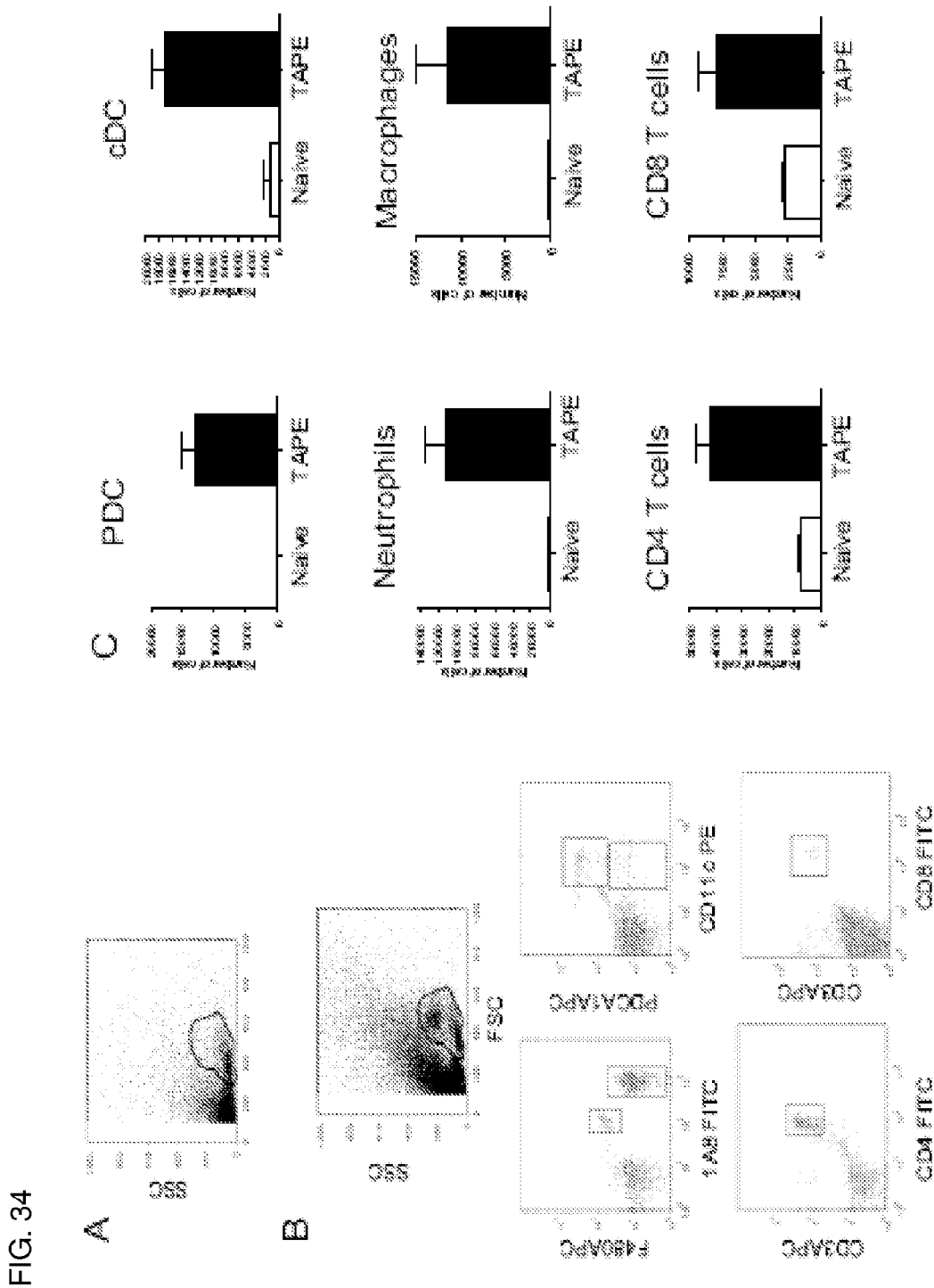
Figure 34:
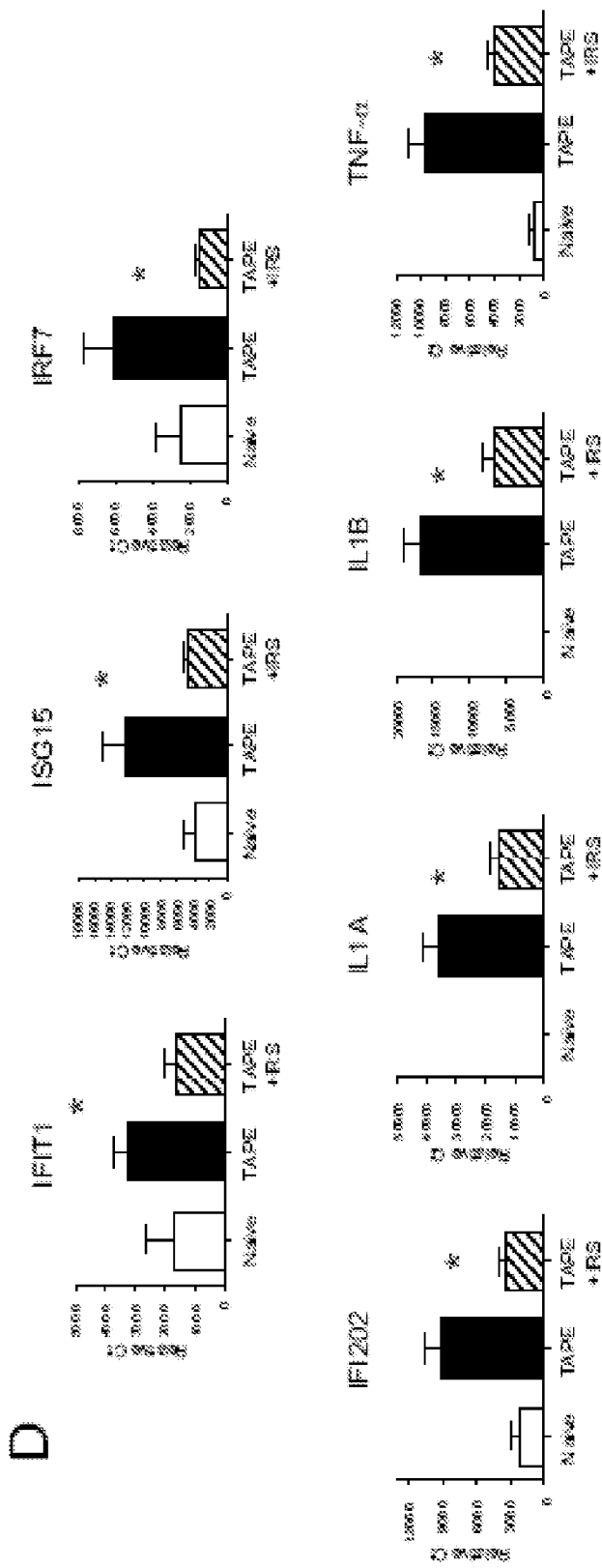
Figure 35:
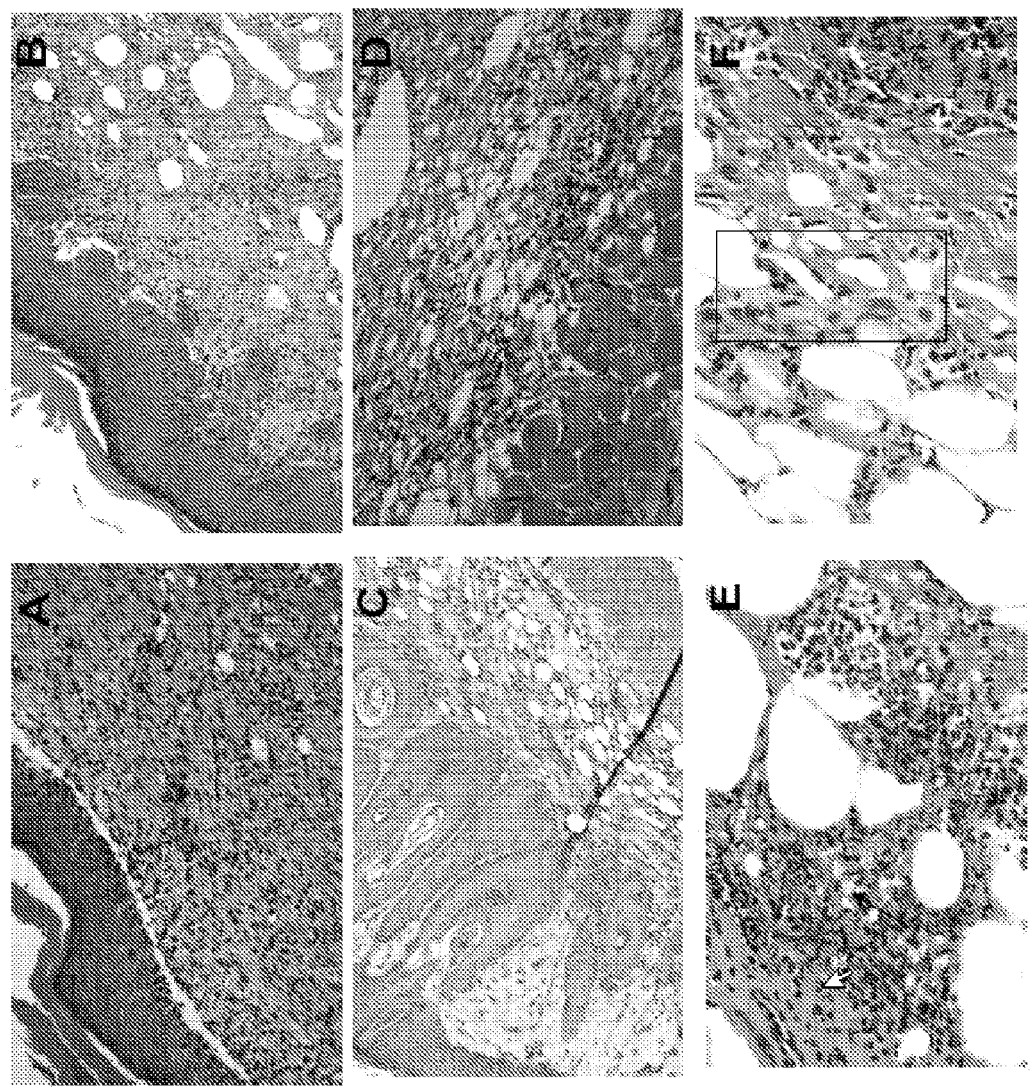

The initial response to tape stripping in (NZBxNZW)F1 mice was very similar to that in normal mice, with involved skin showing a consistent increase in the number of PDC and neutrophils (FIGS. 34A-C). The abundant cellular infiltrate was accompanied by increased expression of IFN-regulated and pro-inflammatory genes. A single injection of SEQ ID NO:42 (IRS) prior to tape stripping efficiently inhibited this gene induction, consistent with a role of TLR7 and TLR9 in driving the acute response in this strain (FIG. 34D). However, in contrast to the transient course of inflammation in normal mice, the inflammatory response in (NZBxNZW)F1 mice was sustained for many days, with mRNA for both IFN-regulated genes and proinflammatory cytokines remaining significantly elevated for up to three weeks after tape stripping (FIG. 28A). This suggests that either these mice fail to properly resolve the inflammation or conditions exist to perpetuate the inflammatory signals once initiated by the injury of tape stripping. Three weeks after tape stripping, skin lesions of (NZBxNZW)F1 mice extended over 50% of tape stripped area, while in normal mice lesions were healed (FIG. 28C). At very early time points, 1 and 4 days after tape stripping, (NZBxNZW)F1 mice had severe multifocal thinning of the epidermis with epidermal necrosis and diffuse dermo-epidermal leukocytic infiltrates composed largely of neutrophils and macrophages. By about three weeks after the initial tape stripping, (NZBxNZW)F1 mice showed prominent epidermal hyperplasia with hyperkeratosis, keratin-filled craters or cysts, dermal fibrosclerosis and degenerative changes of the subcutaneous fat tissue (FIGS. 28F-H and FIG. 35). In man, epidermal changes and vacuolar degeneration of the dermoepidermal junction is characteristic of all the forms of CLE while other features of this model, such as the presence of keratin filled cysts and the degeneration of subcutaneous fat are more prominent in discoid CLE (DLE) and verrucous DLE (Baltaci and Fritsch, 2009). Cutaneous lesions in (NZBxNZW)F1 mice showed persistent leukocyte infiltration, composed mainly of neutrophils, macrophages and T cells, involving the epidermis, dermis and adnexa, as well as the subcutaneous fat (FIGS. 28F-H and FIG. 35). In the non-autoimmune mouse strains, 129 and C57/BL6, although a transient inflammation was observed involving the dermis (early time points 1 day and 4 days), it resolved spontaneously without producing sclerotic lesions and at the same time points, infiltrating leukocytes were scarce and similar in number to untreated control skin (FIGS. 28D and E). A systematic review of the histopathological changes, based on the semi-quantitative evaluation of multiple disease parameters: epidermis thickness, degree of ulceration, degree of intraepithelial, dermal and panniculum inflammation is shown in Table 22-1. Overall disease score in lesions was significantly higher in (NZBxNZW)F1 compared to normal mice.

Example 23

PDC and Signaling Through TLR7 and TLR9 are Required for the Initiation and Maintenance of Cutaneous Lesions in (NZBxNZW)F1 Mice To demonstrate that PDC and recognition of nucleic acids by TLR7 and TLR9 are central to the tape-stripping response in (NZBxNZW)F1 mice, animals were treated with SEQ ID NO:42 (IRS) before skin injury and for the duration of the experiment, according to the schedule in FIG. 36. In contrast to untreated mice (FIGS. 29A and C), IRS-treated mice healed completely or had small lesions (less than 15% of the stripped area) (FIG. 29A). Skin from IRS treated mice showed a very mild hyperplasia of the epithelium with slight hyperkeratosis and absence of ulceration. The inflammatory infiltrate and fibrotic reaction of the dermis appeared greatly reduced as compared to untreated animals and no cellular infiltration was present in the epidermis (FIGS. 29D and E). Depletion of PDC starting before tape stripping (FIG. 36) produced a very similar inhibition of the response to tape-stripping. PDC-depleted mice had normal appearance (FIG. 29A) with normal to slight hyperplasic epithelium, negligible alterations of the dermis, epidermis and adnexa and minimal presence of inflammatory infiltration of the dermis (FIGS. 29F and G). Histological disease score confirmed these results and showed a significant difference between untreated mice and mice treated with IRS or depleted of PDC (Table 22-1). These results indicate that PDC are key cells in the response to cutaneous injury through their ability to sense DNA and RNA through the two nucleic acid-specific TLRs expressed by PDC.

To evaluate whether TLR7 and TLR9 signaling continues to be required for the prolonged response in (NZBxNZW)F1 mice, or is primarily involved in the initiation of the response, the first IRS treatment was delayed until 4 days after the tape stripping, at a time when the lesions were fully developed. Strikingly, the cutaneous lesions of mice treated with IRS beginning at day 4 were almost completely healed by day 15-23 with only 10% of the surface still covered by open lesions (FIG. 30A). In contrast, untreated animals had substantial unhealed lesions (FIGS. 30A and B) at these time points. Skin specimens from IRS treated mice presented moderate alterations with very modest dermal inflammatory infiltration and fibrosclerosis and negligible involvement of the adipose tissue (FIGS. 30D and E and Table 22-1). These

TABLE 22-1

Pathologic Evaluation Of Skin Lesions Following Tape Stripping

| Mice | Epidermis thickness | Ulceration | Intraepithelial inflammation | Dermal inflammation | Panniculum inflammation | Total Disease Score |
|---|---|---|---|---|---|---|
| (NZBxNZW)F1 | $2.9 \pm 1.7$ | $1.6 \pm 0.2$ | $1.0 \pm 0.16$ | $2.3 \pm 0.14$ | $1.7 \pm 0.12$ | $8.4 \pm 0.6$ |
| C57/BL6 | $0.4 \pm 0.3$ | $0.4 \pm 0.4$ | $0.4 \pm 0.4$ | $0.8 \pm 0.2$ | $1.4 \pm 0.3$ | $3.4 \pm 0.8$ |
|  | $p < 0.001$ | $p < 0.05$ | $p < 0.05$ | $p < 0.001$ | $p < 0.05$ | $p < 0.001$ |
| 129 | $1.0 \pm 0.2$ | $0.0 \pm 0.0$ | $0.0 \pm 0.0$ | $1.6 \pm 0.2$ | $1.2 \pm 0.2$ | $3.1 \pm 0.4$ |
|  | $p < 0.001$ | $p < 0.001$ | $p < 0.001$ | $p < 0.001$ | $p < 0.001$ | $p < 0.001$ |
| (NZBxNZW)F1 + IRS (pre-injury) | $0.7 \pm 0.2$ | $0.0 \pm 0.0$ | $0.2 \pm 0.2$ | $1.3 \pm 0.2$ | $0.8 \pm 0.1$ | $3.2 \pm 0.5$ |
|  | $p < 0.001$ | $p < 0.001$ | $p < 0.05$ | $p < 0.001$ | $p < 0.001$ | $p < 0.001$ |
| (NZBxNZW)F1 + IRS (therapeutic) | $1.0 \pm 0.2$ | $0.2 \pm 0.1$ | $0.2 \pm 0.2$ | $1.2 \pm 0.1$ | $1.0 \pm 0.0$ | $3.5 \pm 0.4$ |
|  | $p < 0.001$ | $p < 0.001$ | $p < 0.001$ | $p < 0.001$ | $p < 0.001$ | $p < 0.001$ |
| (NZBxNZW)F1 depleted of PDC | $1.4 \pm 0.3$ | $0.1 \pm 0.1$ | $0.1 \pm 0.1$ | $1.4 \pm 0.2$ | $1.0 \pm 0.2$ | $4.0 \pm 0.5$ |
|  | $p < 0.05$ | $p < 0.001$ | $p < 0.05$ | $p < 0.001$ | $p < 0.001$ | $p < 0.001$ | findings demonstrate that the chronic activation of TLR7 and/or TLR9 in PDC is required both to initiate and maintain the inflammation in the skin of (NZBxNZW)F1 mice. These results also indicate that blocking this process with a specific TLR7/9 inhibitor is effective in a therapeutic setting to resolve ongoing skin inflammation.

Studies of the pathogenic mechanisms of CLE and development of new therapies for CLE have been hampered by the absence of animal models of interface dermatitis that replicate key features and pathway of the human disease. Examples 19 to 23 report that skin injury due to tape-striping in normal mice is followed by an acute inflammatory response accompanied by conspicuous infiltration of innate immune cells including PDC and neutrophils, paralleled with induction of Type I IFN-regulated genes and pro-inflammatory cytokines. This increased expression of cytokine genes is completely abrogated in MyD88 deficient mice and in mice treated with a specific inhibitor of TLR7 and TLR9 indicating a central role for stimulation by RNA and/or DNA. Among the leukocytes that infiltrate the lesional skin, both PDC and neutrophils express TLR7 and TLR9 receptors (Edwards et al., 2003; Hayashi et al., 2003; and Kadowaki et al., 2001). The magnitude and composition of the cellular infiltrate is not significantly altered by TLR7 and TLR9 inhibition suggesting that these pathways are not required for extravasation and homing. Using specific depleting antibodies, it is demonstrated that PDC, not neutrophils are the source of Type I IFN response, while pro-inflammatory cytokines IL1-α, IL1-β and TNF-α are profoundly inhibited by neutrophil depletion. The reduction in cytokine gene expression in skin depleted of PDC or neutrophils is similar in RNA samples extracted from infiltrating leukocytes or from whole skin biopsies, indicating that keratinocytes or endothelial cells are not major contributors to this gene expression pattern. The finding that both IRS and neutrophil depletion inhibit pro-inflammatory cytokines to a similar extent suggest that neutrophils do respond directly through one or both of TLR7 and TLR9. Alternatively, the inhibition of TLR7 and TLR9 may prevent induction of factor made by another cell type (not PDC) that activates neutrophils.

The most likely ligands for TLR7 and TLR9 in injured skin are endogenous nucleic acids released from keratinocytes and other cell types dying as a consequence of mechanical injury or neutrophil cytotoxicity. A second potential source is DNA specifically extruded from neutrophils in the form of NETs. This is not likely the major source of the initial TLR stimulation, as neutrophil depletion prior to injury does not reduce the activation of PDC (FIG. 27), however this may be a relevant source in the chronic activation observed in autoimmune mice. Tissue injury in a largely sterile environment has been shown to stimulate a similar nucleic acid-dependent inflammatory response. Indeed, DNA release from necrotic hepatocytes stimulate cytokine production by neutrophils in a TLR9 dependent manner, and this has been suggested to be a primary mechanism of liver damage following some forms of hepatic injury (Bamboat et al., 2010; and Imaeda et al., 2009).

In 129 or C57/BL6 mice, the burst of mRNA encoding inflammatory cytokines is transient and gene expression levels return to pretreatment levels within 10 days of tape stripping. This is paralleled by reduction in cellular infiltration and progressive wound healing. Thus, this model represents an acute activation of pathways that are activated chronically in lupus, CLE and related diseases. In contrast, tape stripping of lupus-prone (NZBxNZW)F1 mice produces a lesion quite similar to that in non-autoimmune strains, but instead of healing spontaneously, it evolves into lesions that resemble the human CLE situation both clinically and histologically.

Although the initial source of TLR ligands may be similar in normal and autoimmune mice, an important difference may be the continued presence of ligands for TLR7 and TLR9 in (NZBxNZW)F1 mice, specifically the IC that accumulate at the derma-epidermis junction (Furukawa and Yoshimasu, 2005; and McCauliffe, 1996), and the presence of circulating anti-DNA and anti-RNA autoantibodies in these mice (Furukawa and Yoshimasu, 2005). A similar phenomenon may take place in human CLE, where anti-DNA and RNA IC, in circulation and deposited in skin tissue have been extensively described (McCauliffe, 1996; and Wenzel and Tuting, 2008). Another source of DNA and RNA for this continued stimulation might be the neutrophils themselves. Skin neutrophils are highly activated after tape stripping and produce abundant NET fibers containing DNA and RNA molecules. NET-producing neutrophils were found in normal mice only at early time points, before the inflammatory response is resolved. In (NZBxNZW)F1 mice, however significant infiltration of NET-producing neutrophils are detectable at later time points in well-established lesions, suggesting that they may constitute a source of endogenous nucleic-acid leading to chronic TLR signaling. Interestingly, it was found that the antimicrobial peptide LL37 was associated with the fibers of the NETs from skin neutrophils. LL37 is a cationic antimicrobial peptide highly inducible in keratinocytes and has been shown to convert endogenous DNA and RNA into a potent TLR9 or TLR7 agonists by promoting aggregation and enhanced uptake by PDC in vitro (Ganguly et al., 2009; and Lande et al., 2007).

The development of cutaneous lesions following injury in lupus prone mice is similar to the Koebner phenomenon observed in patients with CLE and other autoimmune disease of the skin after skin trauma (Ueki, 2005). Indeed, these patients are highly sensitive to skin trauma and even minor skin scratches can result in development chronic lesions within weeks. The development of the lesions in (NZBxNZW)F1 is characterized by a persistent IFN-signature and a high level of pro-inflammatory mediators such as IL-1α, IL-1β and TNF-α. Similarly, in human CLE, both the IFN-signature but also TNF-α and IL-1 overexpression correlate with disease severity (Clancy et al., 2004; Popovic et al., 2005; Werth, 2007; and Werth et al., 2002). The absence of spontaneous macroscopic lesions in lupus-prone mice is not surprising as many mouse models of other skin diseases such as atopic dermatitis or psoriasis, develop the pathology exclusively after mild wounding (Matsunaga et al., 2007; Sano et al., 2005; and Spergel et al., 1999).

Figure 29:
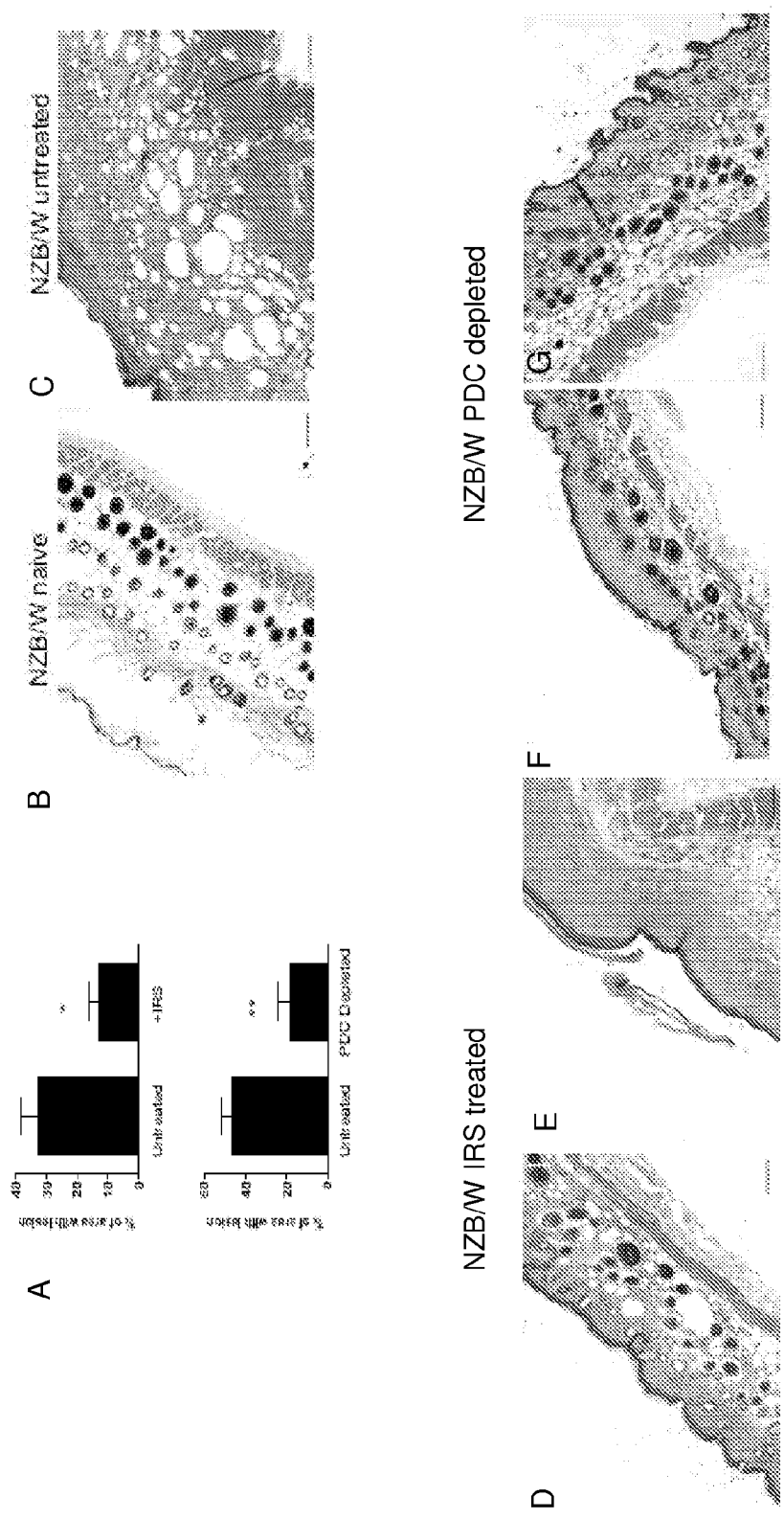
Figure 30:
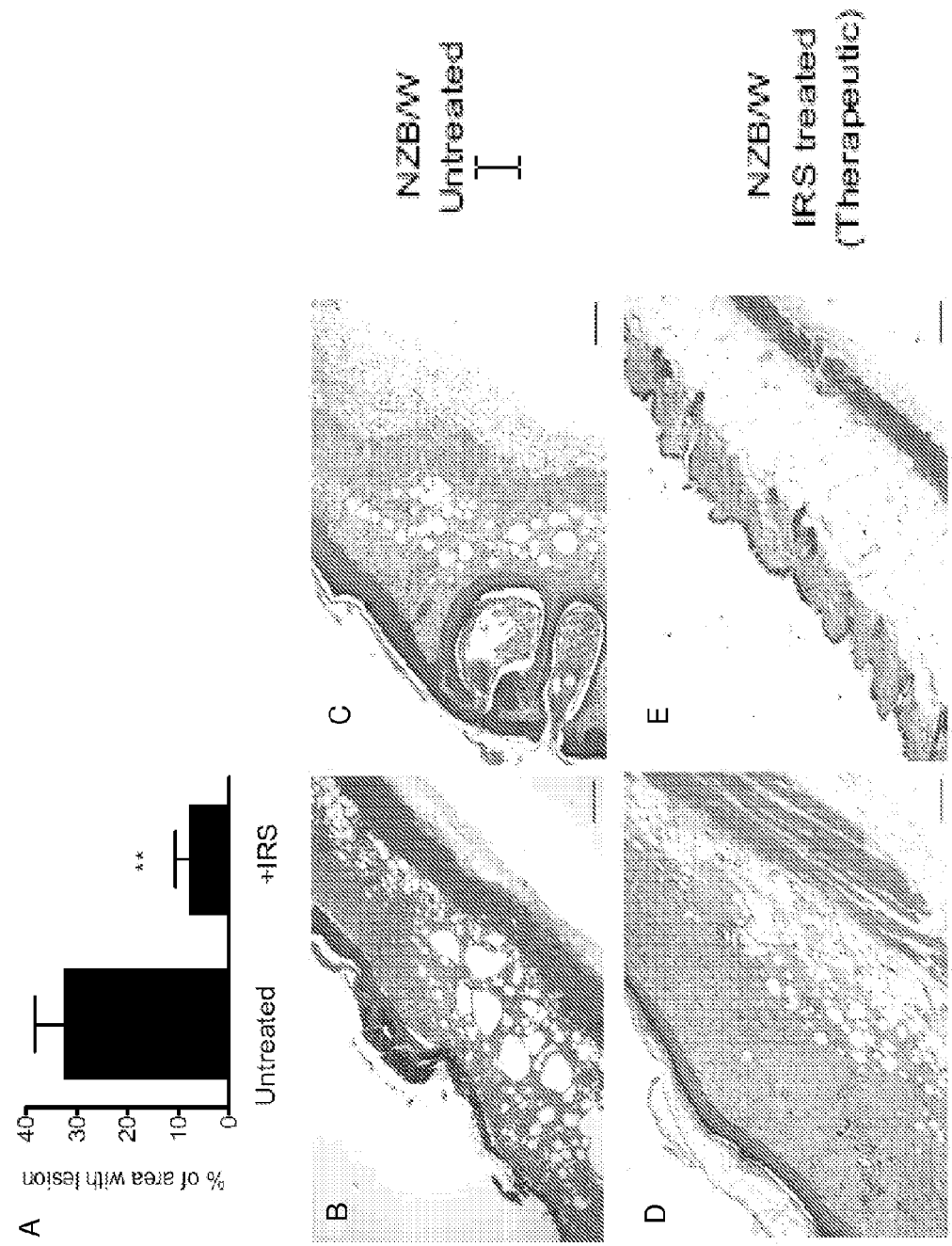

The difference in outcome in lupus-prone versus normal mice following mild injury in the skin thus reflects the nature of the response, acute vs chronic, by PDC and neutrophils to endogenous nucleic acids in the skin. The inflammation is mediated by TLR7 and TLR9 as the treatment of (NZBxNZW)F1 mice with the specific TLR7/9 inhibitor SEQ ID NO:42 (IRS) is able to prevent disease onset as shown by gross appearance of the skin, histological examination and by the normalization of the gene signatures. The outcome was similar in mice depleted of PDC suggesting that PDC are the key cells that respond to TLR7 and TLR9 ligands and are responsible to establish the disease (FIG. 29-30). However, this does not exclude the possibility that the inhibitors and depletion of PDC might act differently in breaking the inflammatory loop that leads to disease. TLR7 and TLR9 activation is required not only for the induction of the inflammatory response but also for continuation of the chronic response seen in lupus-prone mice. This is shown clearly by the fact that SEQ ID NO:42 (IRS) treatment initiated after the development of the initial cellular infiltrate and cutaneous lesions leads to accelerated healing. This finding identifies TLR7 and TLR9 as important targets for therapy in CLE and related cutaneous autoimmune diseases.

In conclusion, the results shown in Examples 19-23 provide evidence that an abnormal response to endogenous ligands leading to chronic activation of both TLR7 and TLR9 constitutes a fundamental trigger of autoimmunity in the skin. These data indicate that an abnormal, chronic response to TLR7 and TLR9 ligands can establish a self-perpetuating inflammatory loop driving diseases such as CLE or other diseases with interface dermatitis. These studies also demonstrate that novel oligonucleotide-based inhibitors of TLR7 and TLR9 are valuable therapeutics for skin autoimmune diseases.

Example 24

TLR7 and TLR9 Contribution to Response

To test the role of TLR7 and TLR9 in the inflammatory response, the response to tape stripping in the individual receptor deficient animals was measured. A partial reduction of the levels of gene expression in the skin was observed following injury in either TLR7- (FIG. 37A) or TLR9- (FIG. 37B) deficient mice. However, none of the genes was exclusively dependent on any one of these receptors. As expected, the addition of the bifunctional TLR7/9 inhibitor SEQ ID NO:42 completed the inhibition in the TLR9-deficient animals (FIG. 37B). FIG. 37 shows that the upregulation of Type I IFN-regulated and inflammatory genes was dependent on both TLR7 and TLR9 receptors. No exacerbation of skin inflammation was observed in the TLR9-deficient animals. Both TLR7 and TLR9 contributed to the response and blocking only one of these did not fully prevent inflammation.

Example 25

Human B-cells Cultured in the Presence of IRPs

To further investigate the effect of IRPs on B-cell stimulatory activity, a wide variety of IRP sequences were assayed for IL-6, along with positive and negative controls. The experiment was performed as described in Example 1 using doses of IRP of either 4.0 µM or 2.0 µM. The positive control was an immunostimulatory sequence (ISS) with SEQ ID NO:157. The amount of IL-6 induced by the IRP was divided by that induced by the positive control to normalize the results across individual experiments and the results are presented in Tables 25-1 and 25-2. The results are presented as the average normalized IL-6 response over several experiments.

The results in the following tables show that different IRP sequences induce a range of IL-6 responses from B cells, ranging from 4%-63% of the IL-6 response of the positive control. It is preferable that IRPs minimally activate B cells (e.g., induce less than 20% IL-6 compared to the positive control).

TABLE 25-1

Normalized IL-6 Response (Percentage of Positive Control).

| SEQ ID NO | | Experiment # 1 4.0 uM | 2 4.0 uM | 3 Max Conc 4.0 uM | 4 4.0 uM | 5 4.0 uM | 6 4.0 uM |
|---|---|---|---|---|---|---|---|
| 42 | 5'-TGC TCC TGG AGG GGT TGT | 13% | 14% | 5% | 9% | 10% | 6% |
| 204 | 5'-TGC TTG TCC TGG AGG GGT TGT | | | | 9% | | |
| 141 | 5'-TGC TCC TGG AGG GGT TGT-HEG-HEG-3' | | | | 8% | | |
| 67 | 5'-TGC TCC TGG AGG GGT TGT AAG T | | | | 8% | 7% | 4% |
| 68 | 5'-TGC TCC TGG AGG GGT TGT AAG TTT GT | | | | | 12% | 6% |
| 83 | 5'-UGC TCC TGG AGG GGT TGT | | | | 6% | | |
| 87 | 5'-UGC TTG TCC TGG AGG GGT TGT | | | | | 16% | 12% |
| 69 | 5'-TGC TCC TTG AGG GGT TGT | | | | 11% | | |
| 104 | 5'-UGC TGC TCC TTG AGG GGT TGU U UG U | | | | 7% | | |
| 59 | 5'-TGC TGC TCC TTG AGG GGT TGT | | | | 12% | | |
| 60 | 5'-TGC TGC TCC TGG AGG GGT TGT | | | | 10% | | |
| 71 | 5'-TGC TCC TTG AGI GGT TGT | | | | 12% | 15% | 10% |
| 73 | 5'-TGC TCC TGG AGI GGT TGT | 11% | 13% | 6% | | | |
| 143 | 5'-TGC TCC TGG AGI GGT TG-HEG-T | | | | 5% | | |
| 144 | 5'-TGC TGC TCC TGG AGI GGT TG-HEG-T | | | | 10% | | |
| 85 | 5'-UGC TCC TGG AGG GGU UGU | | | | | 18% | |

TABLE 25-1-continued

Normalized IL-6 Response (Percentage of Positive Control).

| SEQ ID NO | | Experiment # | | | | | |
|---|---|---|---|---|---|---|---|
| | | 1 | 2 | 3 | 4 Max Conc | 5 | 6 |
| | | 4.0 uM | 4.0 uM | 4.0 uM | 4.0 uM | 4.0 uM | 4.0 uM |
| 57 | 5'-TGC TGC TCC TGG AGG GGT TGT TTG T | | | | | 22% | 17% |
| 117 | 5'-*UGC* TGC TCC TTG AGI GG | | | | | 17% | 13% |
| 78 | 5'-TGC TGC TCC TGG AGI GGT TGT AAG T | 26% | | | | | |
| 79 | 5'-TGC TGC TCC TGG AGI GGT GTT GT | 33% | | 18% | | | |
| 74 | 5'-TGC TTG TCC TGG AGI GGT TGT | 21% | 25% | | | | |
| 134 | 5'-*UGC* CAA TCC TGG AGI GGT TGT | | 31% | 21% | | | |
| 66 | 5'-TGC TGC TCC TGG AGI GGT TGT | 20% | | | | | |
| 77 | 5'-*UGC* HEG TCC TGG AGI GGT GTT GT | | | 24% | | | |
| 58 | 5'-TGC TGC TCC TTG AGG GGT TGT TTG T | | | | | 33% | 29% |
| 62 | 5'-TGC TGC TCC TTG AGI GGT TGT TTG T | | | | 49% | | |
| 107 | 5'-*UGC* TGC TCC TTG AGG GGT TGT TTG T | | | | 43% | | |
| 109 | 5'-*UGC* TGC TCC TTG AGI GGT TGT TTG T | 58% | 52% | 39% | 45% | 53% | 58% |
| 114 | 5'-*UGC* TGC TCC TTG AGI GGT TGT | | | | 40% | 39% | 39% |
| 63 | 5'-TGC TCC TTG AGI GGT TGT TTG T | | | | 46% | 48% | 41% |
| 125 | 5'-*UGC* TGC TCC TGG AGI GGT TGT | | | | | | |
| 126 | 5'-*UGC* TGC TCC TTG AGI GGT TGT | | | | | | |
| 127 | 5'-*UGC* TGC TCC TTG AGI GGT TGT | | | | | | |
| 179 | 5'-TGC TGC TCC TTG AGI GGT GTT GT | | | | | | |
| 180 | 5'-*UGC* TGC TCC TTG AGI GGT GTT GT | | | | | | |
| 175 | 5'-TGC TGC TCC TTG AGI GGT TGT AAG T | | | | | | |
| 129 | 5'-*UGC* TGC TCC TTG AGI GGT TGT AAG T | | | | | | |
| 130 | 5'-*UGC* TGC TCC TGG AGI GGT TGT AAG T | | | | | | |
| 182 | 5'-*UGC* TGC TCC TGG AGI GGT GTT GT | | | | | | |
| 123 | 5'-*UGC* TTG TCC TGG AGI GGT TGT | | 35% | | | | |
| 124 | 5'-*UGC* TTG TCC TGG AGI GGT GTT GT | | | | | | |
| 135 | 5'-*UGC* CAA TCC TGG AGI GGT GTT GT | | | | | | |
| 142 | 5'-*UGC* TTG TCC TGG AGI GGT TG-HEG-T | | 35% | | | | |
| 64 | 5'-TGC TTG TCC TGG AGI GGT TGT AAG T | 33% | | | | | |
| 65 | 5'-TGC TTG TCC TGG AGI GGT GTT GT | 38% | | | | | |

TABLE 25-2

| | | Normalized IL-6 Response (Percentage of Positive Control). | | | | | |
|---|---|---|---|---|---|---|---|
| | | | colspan=5: Experiment # |
| | | | 7 | 8 | 9 | 10 | 11 |
| SEQ ID NO | | | colspan=5: Max Conc |
| | | | 4.0 uM | 2.0 uM | 2.0 uM | 2.0 uM | 2.0 uM |
| 42 | 5'-TGC TCC TGG AGG GGT TGT | | 9% | 8% | 6% | 18% | 10% |
| 43 | 5'-TGC TTG TCC TGG AGG GGT TGT | | 9% | | | | |
| 141 | 5'-TGC TCC TGG AGG GGT TGT-HEG-HEG-3' | | 8% | | | | |
| 67 | 5'-TGC TCC TGG AGG GGT TGT AAG T | | 8% | | | | |
| 68 | 5'-TGC TCC TGG AGG GGT TGT AAG TTT GT | | | | | | |
| 83 | 5'-*UGC* TCC TGG AGG GGT TGT | | 6% | | | | |
| 87 | 5'-*UGC* TTG TCC TGG AGG GGT TGT | | | | | | |
| 69 | 5'-TGC TCC TTG AGG GGT TGT | | 11% | | | | |
| 104 | 5'-*UGC* TGC TCC TTG AGG GGT *TGU U UG U* | | 7% | | | | |
| 59 | 5'-TGC TGC TCC TTG AGG GGT TGT | | 12% | | | | |
| 60 | 5'-TGC TGC TCC TGG AGG GGT TGT | | 10% | | | | |
| 71 | 5'-TGC TCC TTG AGI GGT TGT | | 12% | 4% | 14% | | |
| 73 | 5'-TGC TCC TGG AGI GGT TGT | | | | 11% | | |
| 143 | 5'-TGC TCC TGG AGI GGT TG-HEG-T | | | | | | |
| 144 | 5'-TGC TGC TCC TGG AGI GGT TG-HEG-T | | | | | | |
| 85 | 5'-*UGC* TCC TGG AGG GG*U UGU* | | 18% | | | | |
| 57 | 5'-TGC TGC TCC TGG AGG GGT TGT TTG T | | | | | | |
| 117 | 5'-*UGC* TGC TCC TTG AGI GG | | | | | | |
| 78 | 5'-TGC TGC TCC TGG AGI GGT TGT AAG T | | | | | | 29% |
| 79 | 5'-TGC TGC TCC TGG AGI GGT GTT GT | | | | | | 28% |
| 74 | 5'-TGC TTG TCC TGG AGI GGT TGT | | | | 23% | | |
| 134 | 5'-*UGC* CAA TCC TGG AGI GGT TGT | | | 22% | | | |
| 66 | 5'-TGC TGC TCC TGG AGI GGT TGT | | | | 18% | | |
| 77 | 5'-*UGC* HEG TCC TGG AGI GGT GTT GT | | | | | | |
| 58 | 5'-TGC TGC TCC TTG AGG GGT TGT TTG T | | | | | | |
| 62 | 5'-TGC TGC TCC TTG AGI GGT TGT TTG T | | 49% | | | | |
| 107 | 5'-*UGC* TGC TCC TTG AGG GGT TGT TTG T | | 43% | | | | |
| 109 | 5'-*UGC* TGC TCC TTG AGI GGT TGT TTG T | | 45% | 42% | 64% | 63% | 54% |
| 114 | 5'-*UGC* TGC TCC TTG AGI GGT TGT | | 40% | | | | |
| 63 | 5'-TGC TCC TTG AGI GGT TGT TTG T | | 46% | | | | |
| 125 | 5'-*UGC* TGC TCC TGG AGI GGT TGT | | | | | | 38% |
| 126 | 5'-*UGC* TGC TCC TTG AGI GGT TGT | | | | | | 37% |
| 127 | 5'-*UGC* TGC TCC TTG AGI GGT TGT | | | | | 46% | |
| 179 | 5'-TGC TGC TCC TTG AGI GGT GTT GT | | | | | | 40% |
| 180 | 5'-*UGC* TGC TCC TTG AGI GGT GTT GT | | | | | 46% | |
| 181 | 5'-TGC TGC TCC TTG AGI GGT TGT AAG T | | | | | | 38% |

TABLE 25-2-continued

Normalized IL-6 Response (Percentage of Positive Control).

| | | Experiment # | | | | |
|---|---|---|---|---|---|---|
| | | 7 | 8 | 9 | 10 | 11 |
| SEQ ID NO | | | | Max Conc | | |
| | | 4.0 uM | 2.0 uM | 2.0 uM | 2.0 uM | 2.0 uM |
| 129 | 5'-UGC TGC TCC TTG AGI GGT TGT AAG T | | | | 51% | |
| 130 | 5'-UGC TGC TCC TGG AGI GGT TGT AAG T | | | | 49% | |
| 182 | 5'-UGC TGC TCC TGG AGI GGT GTT GT | | | | 53% | |
| 123 | 5'-UGC TTG TCC TGG AGI GGT TGT | | | 35% | | |
| 124 | 5'-UGC TTG TCC TGG AGI GGT GTT GT | | 33% | | | |
| 135 | 5'-UGC CAA TCC TGG AGI GGT GTT GT | | 42% | | | |
| 142 | 5'-UGC TTG TCC TGG AGI GGT TG-HEG-T | | 22% | | | |
| 64 | 5'-TGC TTG TCC TGG AGI GGT TGT AAG T | | 19% | | | |
| 65 | 5'-TGC TTG TCC TGG AGI GGT GTT GT | | | | 21% | |

Example 26

Administration of an IRS to Systemic Lupus Erythematosus (SLE) Patients

A clinical trial is conducted to determine the safety and efficacy of an IRS in subjects with a diagnosis of SLE according to the revised American College of Rheumatology classification criteria. Eligible subjects have active disease graded on SELENA (safety of estrogen in lupus erythematosus national assessment)-modified SLEDAI (SLE disease activity index). Additionally subjects have an elevated interferon signature score during screening based on nanostring analysis. The interferon signature is a component of an inflammatory gene expression pattern. The interferon signature is also a component of an SLE signature. In some instances, an elevated interferon signature is a score of at least 1.5-, 2.0-, 2.5-, 3.0-, 4.0-, 5.0-, 7.5-10-, 15-, or 30-fold over control or reference sample(s). In other instances, an elevated interferon signature is a score of at least +1, +2 or +3 standard deviations over the average of the control or reference samples. In some instances, the control or reference sample(s) are from healthy adult subject(s).

A pharmaceutical composition comprising an IRS is administered to subjects at a dose of 15, 30, 60, 120 or more mg SC on a weekly basis for eight weeks. The following samples are collected to determine the impact of treatment on the gene expression levels in SLE patients (IFN-signature alone or as part of a SLE signature): i) plasma—pre-dose and several time points post start of treatment; and ii) PBMC—at least two pre-dose to establish the baseline, and then at least at 4 weeks, 8 weeks and 12 weeks post start of treatment will be collected and analyzed. Additional time points may be added to provide additional data points for curve. Gene analysis is performed by nanostring.

Endpoints include but are not limited to the following listing. A decrease in IFN-signature score from initial to week 8 and other time points. A decrease in SLE signature score from initial to week 8 and other time points. Proportion of subjects with a reduction in any gene signature scores over 8 weeks. The decrease can be determined using various statistical approaches, such as but not limited to comparison of area of the curve of treated vs. placebo-treat subjects. Change in clinical disease activity measures including SELENA-SEL-DAI and BILAG index (e.g., decrease in disease severity). Change in serologic disease measures such as a reduction in complement or autoantibodies (e.g., anti-nuclear antigen antibodies: anti-dsDNA, anti-Sm [Smith antigen], anti-histone, anti-RNP, anti-Ro [SSA], anti-La [SSB], etc.; see e.g., Riemekasten and Hahn, Rheumatology, 44:975-982, 2005). An increase in PDCs in peripheral blood over 8 weeks as determined by flow cytometry. A corticosteroid-sparing effect in the treated groups as compared to the placebo group.

REFERENCES

Asefa, B., K. D. Klarmann, N. G. Copeland, D. J. Gilbert, N. A. Jenkins, and J. R. Keller. 2004. The interferon-inducible p200 family of proteins: a perspective on their roles in cell cycle regulation and differentiation. Blood Cells Mol Dis 32:155-167.

Asselin-Paturel, C., G. Brizard, J. J. Pin, F. Briere, and G. Trinchieri. 2003. Mouse strain differences in plasmacytoid dendritic cell frequency and function revealed by a novel monoclonal antibody. J Immunol 171:6466-6477.

Baltaci, M., and P. Fritsch. 2009. Histologic features of cutaneous lupus erythematosus. Autoimmun Rev 8:467-473.

Bamboat, Z. M., V. P. Balachandran, L. M. Ocuin, H. Obaid, G. Plitas, and R. P. DeMatteo. 2010. Toll-like receptor 9 inhibition confers protection from liver ischemia-reperfusion injury. Hepatology 51:621-632.

Banchereau, J., V. Pascual, and A. K. Palucka. 2004. Autoimmunity through cytokine-induced dendritic cell activation. Immunity 20:539-550.

Barrat, F. J., and R. L. Coffman. 2008. Development of TLR inhibitors for the treatment of autoimmune diseases. Immunol Rev 223:271-283.

Barrat, F. J., T. Meeker, J. H. Chan, C. Guiducci, and R. L. Coffman. 2007. Treatment of lupus-prone mice with a dual inhibitor of TLR7 and TLR9 leads to reduction of autoantibody production and amelioration of disease symptoms. Eur J Immunol 37:3582-3586.

Barrat, F. J., T. Meeker, J. Gregorio, J. H. Chan, S. Uematsu, S. Akira, B. Chang, O. Duramad, and R. L. Coffman. 2005. Nucleic Acids of Mammalian Origin Can Act as Endogenous Ligands for Toll-like Receptors and May Promote Systemic Lupus Erythematosus. J. Exp. Med 202:1131-1139.

Blomberg, S., M. L. Eloranta, B. Cederblad, K. Nordlin, G. V. Alm, and L. Ronnblom. 2001. Presence of cutaneous interferon-alpha producing cells in patients with systemic lupus erythematosus. Lupus 10:484-490.

Brinkmann, V., U. Reichard, C. Goosmann, B. Fauler, Y. Uhlemann, D. S. Weiss, Y. Weinrauch, and A. Zychlinsky. 2004. Neutrophil extracellular traps kill bacteria. Science 303:1532-1535.

Choubey, D., and R. Panchanathan. 2008. Interferon-inducible Ifi200-family genes in systemic lupus erythematosus. Immunol Lett 119:32-41.

Clancy, R. M., C. B. Backer, X. Yin, M. W. Chang, S. R. Cohen, L. A. Lee, and J. P. Buyon. 2004. Genetic association of cutaneous neonatal lupus with HLA class II and tumor necrosis factor alpha: implications for pathogenesis. Arthritis Rheum 50:2598-2603.

Coxon, A., X. Cullere, S. Knight, S. Sethi, M. W. Wakelin, G. Stavrakis, F. W. Luscinskas, and T. N. Mayadas. 2001. Fc gamma RIII mediates neutrophil recruitment to immune complexes. a mechanism for neutrophil accumulation in immune-mediated inflammation. Immunity 14:693-704.

Daley, J. M., A. A. Thomay, M. D. Connolly, J. S. Reichner, and J. E. Albina. 2008. Use of Ly6G-specific monoclonal antibody to deplete neutrophils in mice. J Leukoc Biol 83:64-70.

Duramad, O., K. L. Fearon, J. H. Chan, H. Kanzler, J. D. Marshall, R. L. Coffman, and F. J. Barrat. 2003. IL-10 regulates plasmacytoid dendritic cell response to CpG-containing immunostimulatory sequences. Blood 102: 4487-4492.

Edwards, A. D., S. S. Diebold, E. M. Slack, H. Tomizawa, H. Hemmi, T. Kaisho, S. Akira, and C. Reis e Sousa. 2003. Toll-like receptor expression in murine DC subsets: lack of TLR7 expression by CD8 alpha+DC correlates with unresponsiveness to imidazoquinolines. Eur J Immunol 33:827-833.

Farkas, L., K. Beiske, F. Lund-Johansen, P. Brandtzaeg, and F. L. Jahnsen. 2001. Plasmacytoid dendritic cells (natural interferon-alpha/beta-producing cells) accumulate in cutaneous lupus erythematosus lesions. Am J Pathol 159:237-243.

Fuchs, T. A., U. Abed, C. Goosmann, R. Hurwitz, I. Schulze, V. Wahn, Y. Weinrauch, V. Brinkmann, and A. Zychlinsky. 2007. Novel cell death program leads to neutrophil extracellular traps. J Cell Biol 176:231-241.

Furukawa, F., and T. Yoshimasu. 2005. Animal models of spontaneous and drug-induced cutaneous lupus erythematosus. Autoimmun Rev 4:345-350.

Ganguly, D., G. Chamilos, R. Lande, J. Gregorio, S. Meller, V. Facchinetti, B. Homey, F. J. Barrat, T. Zal, and M. Gilliet. 2009. Self-RNA-antimicrobial peptide complexes activate human dendritic cells through TLR7 and TLR8. J Exp Med 206:1983-1994.

Guiducci, C., R. L. Coffman, and F. J. Barrat. 2009. Signalling pathways leading to IFN-alpha production in human plasmacytoid dendritic cell and the possible use of agonists or antagonists of TLR7 and TLR9 in clinical indications. J Intern Med 265:43-57.

Hayashi, F., T. K. Means, and A. D. Luster. 2003. Toll-like receptors stimulate human neutrophil function. Blood 102: 2660-2669.

Imaeda, A. B., A. Watanabe, M. A. Sohail, S. Mahmood, M. Mohamadnejad, F. S. Sutterwala, R. A. Flavell, and W. Z. Mehal. 2009. Acetaminophen-induced hepatotoxicity in mice is dependent on T1r9 and the Nalp3 inflammasome. J Clin Invest 119:305-314.

Inoue, J., S. Yotsumoto, T. Sakamoto, S. Tsuchiya, and Y. Aramaki. 2005. Changes in immune responses to antigen applied to tape-stripped skin with CpG-oligodeoxynucleotide in mice. J Control Release 108:294-305.

Jin, H., M. K. Oyoshi, Y. Le, T. Bianchi, S. Koduru, C. B. Mathias, L. Kumar, S. Le Bras, D. Young, M. Collins, M. J. Grusby, J. Wenzel, T. Bieber, M. Boes, L. E. Silberstein, H. C. Oettgen, and R. S. Geha. 2009. IL-21R is essential for epicutaneous sensitization and allergic skin inflammation in humans and mice. J Clin Invest 119:47-60.

Kadowaki, N., S. Ho, S. Antonenko, R. W. Malefyt, R. A. Kastelein, F. Bazan, and Y. J. Liu. 2001. Subsets of human dendritic cell precursors express different toll-like receptors and respond to different microbial antigens. J Exp Med 194:863-869.

Kessenbrock, K., M. Krumbholz, U. Schonermarck, W. Back, W. L. Gross, Z. Werb, H. J. Grone, V. Brinkmann, and D. E. Jenne. 2009. Netting neutrophils in autoimmune small-vessel vasculitis. Nat Med 15:623-625.

Lande, R., J. Gregorio, V. Facchinetti, B. Chatterjee, Y. H. Wang, B. Homey, W. Cao, Y. H. Wang, B. Su, F. O, Nestle, T. Zal, I. Mellman, J. M. Schroder, Y. J. Liu, and M. Gilliet. 2007. Plasmacytoid dendritic cells sense self-DNA coupled with antimicrobial peptide. Nature 449:564-569.

Lipsker, D., and J. H. Saurat. 2008. Neutrophilic cutaneous lupus erythematosus. At the edge between innate and acquired immunity? Dermatology 216:283-286.

Marshak-Rothstein, A. 2006. Toll-like receptors in systemic autoimmune disease. Nat Rev Immunol 6:823-835.

Martinelli, S., M. Urosevic, A. Daryadel, P. A. Oberholzer, C. Baumann, M. F. Fey, R. Dummer, H. U. Simon, and S. Yousefi. 2004. Induction of genes mediating interferon-dependent extracellular trap formation during neutrophil differentiation. J Biol Chem 279:44123-44132.

Matsunaga, Y., Y. Ogura, R. Ehama, S. Amano, T. Nishiyama, and H. Tagami. 2007. Establishment of a mouse skin model of the lichenification in human chronic eczematous dermatitis. Br J Dermatol 156:884-891.

McCauliffe, D. P. 1996. Antibody penetration into the cells of mice and men. J Invest Dermatol 107:3-4.

Means, T. K., E. Latz, F. Hayashi, M. R. Murali, D. T. Golenbock, and A. D. Luster. 2005. Human lupus autoantibody-DNA complexes activate DCs through cooperation of CD32 and TLR9. J Clin Invest 115:407-417.

Popovic, K., M. Ek, A. Espinosa, L. Padyukov, H. E. Harris, M. Wahren-Herlenius, and F. Nyberg. 2005. Increased expression of the novel proinflammatory cytokine high mobility group box chromosomal protein 1 in skin lesions of patients with lupus erythematosus. Arthritis Rheum 52:3639-3645.

Sano, S., K. S. Chan, S. Carbajal, J. Clifford, M. Peavey, K. Kiguchi, S. Itami, B. J. Nickoloff, and J. DiGiovanni 2005. Stat3 links activated keratinocytes and immunocytes required for development of psoriasis in a novel transgenic mouse model. Nat Med 11:43-49.

Spergel, J. M., E. Mizoguchi, H. Oettgen, A. K. Bhan, and R. S. Geha. 1999. Roles of TH1 and TH2 cytokines in a murine model of allergic dermatitis. J Clin Invest 103: 1103-1111.

Tsuboi, N., K. Asano, M. Lauterbach, and T. N. Mayadas. 2008. Human neutrophil Fcgamma receptors initiate and play specialized nonredundant roles in antibody-mediated inflammatory diseases. Immunity 28:833-846.

Ueki, H. 2005. Koebner phenomenon in lupus erythematosus with special consideration of clinical findings. Autoimmun Rev 4:219-223.

Ueno, H., E. Klechevsky, R. Morita, C. Aspord, T. Cao, T. Matsui, T. Di Pucchio, J. Connolly, J. W. Fay, V. Pascual, A. K. Palucka, and J. Banchereau. 2007. Dendritic cell subsets in health and disease. Immunol Rev 219:118-142.

Wartha, F., and B. Henriques-Normark. 2008. ETosis: a novel cell death pathway. Sci Signal 1:pe25.

Wenzel, J., and T. Tuting. 2007. Identification of type I interferon-associated inflammation in the pathogenesis of cutaneous lupus erythematosus opens up options for novel therapeutic approaches. Exp Dermatol 16:454-463.

Wenzel, J., and T. Tuting. 2008. An IFN-Associated Cytotoxic Cellular Immune Response against Viral, Self-, or Tumor Antigens Is a Common Pathogenetic Feature in "Interface Dermatitis". J Invest Dermatol Werth, V. P. 2007. Cutaneous lupus: insights into pathogenesis and disease classification. Bull NYU Hosp Jt Dis 65:200-204.

Werth, V. P., J. P. Callen, G. Ang, and K. E. Sullivan. 2002. Associations of tumor necrosis factor alpha and HLA polymorphisms with adult dermatomyositis: implications for a unique pathogenesis. J Invest Dermatol 119:617-620.

Hahn, B. Antibodies to DNA. New England Journal of Medicine 338, 1359-1368 (1998).

Chatham, W. W. & Kimberly, R. P. Treatment of lupus with corticosteroids. Lupus 10, 140-7 (2001).

Franchin, G. & Diamond, B. Pulse steroids: how much is enough? Autoimmun Rev 5, 111-3 (2006).

Parker, B. J. & Bruce, I. N. High dose methylprednisolone therapy for the treatment of severe systemic lupus erythematosus. Lupus 16, 387-93 (2007).

De Bosscher, K., Vanden Berghe, W. & Haegeman, G. The interplay between the glucocorticoid receptor and nuclear factor-kappaB or activator protein-1: molecular mechanisms for gene repression. Endocr Rev 24, 488-522 (2003).

Barrat, F. J. & Coffman, R. L. Development of TLR inhibitors for the treatment of autoimmune diseases. Immunol Rev 223, 271-83 (2008).

Banchereau, J. & Pascual, V. Type I interferon in systemic lupus erythematosus and other autoimmune diseases. Immunity 25, 383-92 (2006).

Wenzel, J. & Tuting, T. An IFN-Associated Cytotoxic Cellular Immune Response against Viral, Self-, or Tumor Antigens Is a Common Pathogenetic Feature in "Interface Dermatitis". J Invest Dermatol (2008).

Tucci, M. et al. Glomerular accumulation of plasmacytoid dendritic cells in active lupus nephritis: role of interleukin-18. Arthritis Rheum 58, 251-62 (2008).

Chaussabel, D. et al. A modular analysis framework for blood genomics studies: application to systemic lupus erythematosus. Immunity 29, 150-64 (2008).

Barrat, F. J. et al. Nucleic Acids of Mammalian Origin Can Act as Endogenous Ligands for Toll-like Receptors and May Promote Systemic Lupus Erythematosus. J. Exp. Med 202, 1131-9 (2005).

Shodell, M., Shah, K. & Siegal, F. P. Circulating human plasmacytoid dendritic cells are highly sensitive to corticosteroid administration. Lupus 12, 222-30 (2003).

Montague, J. W. & Cidlowski, J. A. Glucocorticoid-induced death of immune cells: mechanisms of action. Curr Top Microbiol Immunol 200, 51-65 (1995).

Boor, P. P. et al. Prednisolone suppresses the function and promotes apoptosis of dendritic cells. Am J Transplant 6, 2332-41 (2006).

Takauji, R. et al. CpG-DNA-induced IFN-alpha production involves p38 MAPK-dependent STAT 1 phosphorylation in human plasmacytoid dendritic cell precursors. J Leukoc Biol 72, 1011-9 (2002).

Guiducci, C. et al. PI3K is critical for the nuclear translocation of IRF-7 and type I IFN production by human plasmacytoid predendritic cells in response to TLR activation. J Exp Med 205, 315-22 (2008).

Strickland, I. et al. High constitutive glucocorticoid receptor beta in human neutrophils enables them to reduce their spontaneous rate of cell death in response to corticosteroids. J Exp Med 193, 585-93 (2001).

Rozzo, S. J. et al. Evidence for an interferon-inducible gene, Ifi202, in the susceptibility to systemic lupus. Immunity 15, 435-43 (2001).

Santiago-Raber, M. L. et al. Type-I interferon receptor deficiency reduces lupus-like disease in NZB mice. J Exp Med 197, 777-88 (2003).

Mathian, A., Weinberg, A., Gallegos, M., Banchereau, J. & Koutouzov, S. IFN-alpha induces early lethal lupus in preautoimmune (New Zealand Black×New Zealand White) F1 but not in BALB/c mice. J Immunol 174, 2499-506 (2005).

Agrawal, H. et al. Deficiency of type I IFN receptor in lupus-prone New Zealand mixed 2328 mice decreases dendritic cell numbers and activation and protects from disease. J Immunol 183, 6021-9 (2009).

Barrat, F. J., Meeker, T., Chan, J. H., Guiducci, C. & Coffman, R. L. Treatment of lupus-prone mice with a dual inhibitor of TLR7 and TLR9 leads to reduction of autoantibody production and amelioration of disease symptoms. Eur J Immunol 37, 3582-3586 (2007).

Deane, J. A. et al. Control of Toll-like Receptor 7 Expression Is Essential to Restrict Autoimmunity and Dendritic Cell Proliferation. Immunity 27, 801-10 (2007).

Athens, J. W. et al. Leukokinetic studies. IV. The total blood, circulating and marginal granulocyte pools and the granulocyte turnover rate in normal subjects. J Clin Invest 40, 989-95 (1961).

Laakko, T. & Fraker, P. Rapid changes in the lymphopoietic and granulopoietic compartments of the marrow caused by stress levels of corticosterone. Immunology 105, 111-9 (2002).

Trottier, M. D., Newsted, M. M., King, L. E. & Fraker, P. J. Natural glucocorticoids induce expansion of all developmental stages of murine bone marrow granulocytes without inhibiting function. Proc Natl Acad Sci USA 105, 2028-33 (2008).

Bennett, L. et al. Interferon and granulopoiesis signatures in systemic lupus erythematosus blood. Exp Med 197, 711-23 (2003).

Duramad, O. et al Inhibitors of TLR-9 act on multiple cell subsets in mouse and man in vitro and prevent death in vivo from systemic inflammation. J Immunol 174, 5193-200 (2005).

Geiss, G. K. et al. Direct multiplexed measurement of gene expression with color-coded probe pairs. Nat Biotechnol 26, 317-25 (2008).

Guiducci, C. et al. Properties regulating the nature of the plasmacytoid dendritic cell response to Toll-like receptor 9 activation. J Exp Med 203, 1999-2008 (2006).

Guiducci et al., TLR recognition of self nucleic acids hampers glucocorticoid activity in lupus, Nature, 465:937-942 (2010).

Guiducci et al., Autoimmune skin inflammation is dependent on plasmacytoid dendritic cell activation by nucleic acids via TLR7 and TLR9, J Exp Med, 207:2931-2942, 2010.

What is claimed is:

1. A polynucleotide comprising a nucleotide sequence selected from the group consisting of SEQ ID NO:73, SEQ ID NO:134, SEQ ID NO:143 and SEQ ID NO:144, wherein the polynucleotide is less than 100 bases or base pairs in length.

2. The polynucleotide of claim 1, wherein the polynucleotide consists of the nucleotide sequence selected from the group consisting of SEQ ID NO:73, SEQ ID NO:134, SEQ ID NO:143 and SEQ ID NO:144.

3. The polynucleotide of claim 2, wherein one or more nucleotides comprises a modification.

4. The polynucleotide of claim 3, wherein the modification comprises at least one phosphorothioate backbone modification.

5. The polynucleotide of claim 3, wherein the modification comprises a 2'-sugar modification.

6. The polynucleotide of claim 5, wherein the 2'-sugar modification comprises a 2'-O-methyl sugar modification or a 2'-O-methoxyethyl sugar modification.

7. The polynucleotide of claim 1, wherein the polynucleotide is less than 50 bases or base pairs in length.

8. The polynucleotide of claim 1, wherein the polynucleotide does not comprise a CG dinucleotide.

9. A method of treating an autoimmune disease, comprising administering to an individual having an autoimmune disease an effective amount of the polynucleotide of claim 1.

10. The method of claim 9, wherein the polynucleotide is administered in an amount effective to achieve one or more of the following outcomes:
   a) reduce a clinical disease activity measure of the autoimmune disease;
   b) reduce a serologic disease measure of the autoimmune disease; and
   c) increase plasmacytoid dendritic cells in a post-treatment peripheral blood mononuclear cell sample from the individual.

11. The method of claim 9, further comprising administering a second therapeutic agent to the individual.

12. The method of claim 11, wherein the second therapeutic agent is selected from the group consisting of a corticosteroid, a nonsteroidal anti-inflammatory drug (NSAID), an IFN-alpha inhibitor, and an anti-malarial.

13. The method of claim 12, wherein the corticosteroid is a glucocorticoid and the administering the polynucleotide is effective in reducing the glucocorticoid use by the individual.

14. The method of claim 9, wherein the individual is a human.

15. The method of claim 9, wherein the autoimmune disease is systemic lupus erythematosus (SLE) or cutaneous lupus erythematosus (CLE).

16. The polynucleotide of claim 1, wherein the polynucleotide consists of the nucleotide sequence of SEQ ID NO:73.

17. The polynucleotide of claim 1, wherein the polynucleotide consists of the nucleotide sequence selected of SEQ ID NO:134.

18. The polynucleotide of claim 1, wherein the polynucleotide consists of the nucleotide sequence of SEQ ID NO:143.

19. The polynucleotide of claim 1, wherein the polynucleotide consists of the nucleotide sequence of SEQ ID NO:144.

20. The polynucleotide of claim 1, wherein the polynucleotide is less than 40 bases or base pairs in length.

21. The polynucleotide of claim 1, wherein the polynucleotide is less than 30 bases or base pairs in length.

22. The polynucleotide of claim 1, wherein the polynucleotide is less than 25 bases or base pairs in length.

23. The polynucleotide of claim 1, wherein the polynucleotide is less than 20 bases or base pairs in length.

24. The polynucleotide of claim 4, wherein the polynucleotide contains only phosphorothioate linkages.

25. The polynucleotide of claim 1, wherein the polynucleotide is single stranded.

26. The polynucleotide of claim 1, wherein the polynucleotide is double stranded.

27. A pharmaceutical composition comprising the polynucleotide of claim 1 and a pharmaceutically acceptable excipient.

28. The pharmaceutical composition of claim 27 comprising a sterile, isotonic solution.

29. The polynucleotide of claim 16, wherein the polynucleotide contains only phosphorothioate linkages.

30. The polynucleotide of claim 16, wherein the polynucleotide is single stranded.

31. The polynucleotide of claim 16, wherein the polynucleotide is single stranded and contains only phosphorothioate linkages.

32. A pharmaceutical composition comprising the polynucleotide of claim 16 and a pharmaceutically acceptable excipient.

33. The pharmaceutical composition of claim 32 comprising a sterile, isotonic solution.

* * * * *

SEQUENCE LISTING

<160> NUMBER OF SEQ ID NOS: 207

<210> SEQ ID NO 1
<211> LENGTH: 15
<212> TYPE: DNA
<213> ORGANISM: Artificial Sequence
<220> FEATURE:
<223> OTHER INFORMATION: Synthetic Construct

<400> SEQUENCE: 1
tcctaacggg gaagt                                                        15

<210> SEQ ID NO 2
<211> LENGTH: 15
<212> TYPE: DNA
<213> ORGANISM: Artificial Sequence
<220> FEATURE:
<223> OTHER INFORMATION: Synthetic Construct

<400> SEQUENCE: 2
tcctaagggg gaagt                                                        15

<210> SEQ ID NO 3
<211> LENGTH: 15
<212> TYPE: DNA
<213> ORGANISM: Artificial Sequence
<220> FEATURE:
<223> OTHER INFORMATION: Synthetic Construct

<400> SEQUENCE: 3
tcctaacggg gttgt                                                        15

<210> SEQ ID NO 4
<211> LENGTH: 15
<212> TYPE: DNA
<213> ORGANISM: Artificial Sequence
<220> FEATURE:
<223> OTHER INFORMATION: Synthetic Construct

<400> SEQUENCE: 4
tcctaacggg gctgt                                                        15

<210> SEQ ID NO 5
<211> LENGTH: 15
<212> TYPE: DNA
<213> ORGANISM: Artificial Sequence
<220> FEATURE:
<223> OTHER INFORMATION: Synthetic Construct

<400> SEQUENCE: 5
tcctcaaggg gctgt                                                        15

<210> SEQ ID NO 6
<211> LENGTH: 15
<212> TYPE: DNA
<213> ORGANISM: Artificial Sequence
<220> FEATURE:
<223> OTHER INFORMATION: Synthetic Construct

<400> SEQUENCE: 6
tcctcaaggg gttgt                                                        15

<210> SEQ ID NO 7
<211> LENGTH: 15
<212> TYPE: DNA
<213> ORGANISM: Artificial Sequence

```
<220> FEATURE:
<223> OTHER INFORMATION: Synthetic Construct

<400> SEQUENCE: 7
tcctcatggg gttgt                                                          15

<210> SEQ ID NO 8
<211> LENGTH: 15
<212> TYPE: DNA
<213> ORGANISM: Artificial Sequence
<220> FEATURE:
<223> OTHER INFORMATION: Synthetic Construct

<400> SEQUENCE: 8
tcctggaggg gttgt                                                          15

<210> SEQ ID NO 9
<211> LENGTH: 15
<212> TYPE: DNA
<213> ORGANISM: Artificial Sequence
<220> FEATURE:
<223> OTHER INFORMATION: Synthetic Construct

<400> SEQUENCE: 9
tcctggaggg gctgt                                                          15

<210> SEQ ID NO 10
<211> LENGTH: 15
<212> TYPE: DNA
<213> ORGANISM: Artificial Sequence
<220> FEATURE:
<223> OTHER INFORMATION: Synthetic Construct

<400> SEQUENCE: 10
tcctggaggg gccat                                                          15

<210> SEQ ID NO 11
<211> LENGTH: 15
<212> TYPE: DNA
<213> ORGANISM: Artificial Sequence
<220> FEATURE:
<223> OTHER INFORMATION: Synthetic Construct

<400> SEQUENCE: 11
tcctggaggg gtcat                                                          15

<210> SEQ ID NO 12
<211> LENGTH: 15
<212> TYPE: DNA
<213> ORGANISM: Artificial Sequence
<220> FEATURE:
<223> OTHER INFORMATION: Synthetic Construct

<400> SEQUENCE: 12
tccggaaggg gaagt                                                          15

<210> SEQ ID NO 13
<211> LENGTH: 15
<212> TYPE: DNA
<213> ORGANISM: Artificial Sequence
<220> FEATURE:
<223> OTHER INFORMATION: Synthetic Construct

<400> SEQUENCE: 13
tccggaaggg gttgt                                                          15
```

<210> SEQ ID NO 14
<211> LENGTH: 22
<212> TYPE: DNA
<213> ORGANISM: Artificial Sequence
<220> FEATURE:
<223> OTHER INFORMATION: Synthetic Construct

<400> SEQUENCE: 14
tgactgtagg cggggaagat ga                                         22

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct

<400> SEQUENCE: 15
gagcaagctg gaccttccat                                            20

<210> SEQ ID NO 16
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 14
<223> OTHER INFORMATION: n = 7-deaza-dG

<400> SEQUENCE: 16
cctcaagctt gagngg                                                16

<210> SEQ ID NO 17
<211> LENGTH: 20
<212> TYPE: DNA
<213> ORGANISM: Artificial Sequence
<220> FEATURE:
<223> OTHER INFORMATION: Synthetic Construct

<400> SEQUENCE: 17
tgcttgcaag cttgcaagca                                            20

<210> SEQ ID NO 18
<211> LENGTH: 18
<212> TYPE: DNA
<213> ORGANISM: Artificial Sequence
<220> FEATURE:
<223> OTHER INFORMATION: Synthetic Construct

<400> SEQUENCE: 18
tgcttgcaag cttgcaag                                              18

<210> SEQ ID NO 19
<211> LENGTH: 16
<212> TYPE: DNA
<213> ORGANISM: Artificial Sequence
<220> FEATURE:
<223> OTHER INFORMATION: Synthetic Construct

<400> SEQUENCE: 19
tgcttgcaag cttgca                                                16

<210> SEQ ID NO 20
<211> LENGTH: 19

```
<212> TYPE: DNA
<213> ORGANISM: Artificial Sequence
<220> FEATURE:
<223> OTHER INFORMATION: Synthetic Construct

<400> SEQUENCE: 20
gcttgcaagc ttgcaagca                                              19

<210> SEQ ID NO 21
<211> LENGTH: 18
<212> TYPE: DNA
<213> ORGANISM: Artificial Sequence
<220> FEATURE:
<223> OTHER INFORMATION: Synthetic Construct

<400> SEQUENCE: 21
cttgcaagct tgcaagca                                               18

<210> SEQ ID NO 22
<211> LENGTH: 17
<212> TYPE: DNA
<213> ORGANISM: Artificial Sequence
<220> FEATURE:
<223> OTHER INFORMATION: Synthetic Construct

<400> SEQUENCE: 22
ttgcaagctt gcaagca                                                17

<210> SEQ ID NO 23
<211> LENGTH: 20
<212> TYPE: DNA
<213> ORGANISM: Artificial Sequence
<220> FEATURE:
<223> OTHER INFORMATION: Synthetic Construct

<400> SEQUENCE: 23
tgcttgcaag ctagcaagca                                             20

<210> SEQ ID NO 24
<211> LENGTH: 20
<212> TYPE: DNA
<213> ORGANISM: Artificial Sequence
<220> FEATURE:
<223> OTHER INFORMATION: Synthetic Construct

<400> SEQUENCE: 24
tgcttgcaag cttgctagca                                             20

<210> SEQ ID NO 25
<211> LENGTH: 20
<212> TYPE: DNA
<213> ORGANISM: Artificial Sequence
<220> FEATURE:
<223> OTHER INFORMATION: Synthetic Construct

<400> SEQUENCE: 25
tgcttgacag cttgacagca                                             20

<210> SEQ ID NO 26
<211> LENGTH: 20
<212> TYPE: DNA
<213> ORGANISM: Artificial Sequence
<220> FEATURE:
<223> OTHER INFORMATION: Synthetic Construct

<400> SEQUENCE: 26
```

-continued tgcttagcag ctatgcagca                                                     20

<210> SEQ ID NO 27
<211> LENGTH: 20
<212> TYPE: DNA
<213> ORGANISM: Artificial Sequence
<220> FEATURE:
<223> OTHER INFORMATION: Synthetic Construct

<400> SEQUENCE: 27
tgcaagcaag ctagcaagca                                                     20

<210> SEQ ID NO 28
<211> LENGTH: 25
<212> TYPE: DNA
<213> ORGANISM: Artificial Sequence
<220> FEATURE:
<223> OTHER INFORMATION: Synthetic Construct

<400> SEQUENCE: 28
tgcaagcttg caagcttgca agctt                                               25

<210> SEQ ID NO 29
<211> LENGTH: 21
<212> TYPE: DNA
<213> ORGANISM: Artificial Sequence
<220> FEATURE:
<223> OTHER INFORMATION: Synthetic Construct

<400> SEQUENCE: 29
tgctgcaagc ttgcagatga t                                                   21

<210> SEQ ID NO 30
<211> LENGTH: 19
<212> TYPE: DNA
<213> ORGANISM: Artificial Sequence
<220> FEATURE:
<223> OTHER INFORMATION: Synthetic Construct

<400> SEQUENCE: 30
tgcttgcaag cttgcaagc                                                      19

<210> SEQ ID NO 31
<211> LENGTH: 22
<212> TYPE: DNA
<213> ORGANISM: Artificial Sequence
<220> FEATURE:
<223> OTHER INFORMATION: Synthetic Construct

<400> SEQUENCE: 31
tgcaagcttg caagcttgca at                                                  22

<210> SEQ ID NO 32
<211> LENGTH: 14
<212> TYPE: DNA
<213> ORGANISM: Artificial Sequence
<220> FEATURE:
<223> OTHER INFORMATION: Synthetic Construct

<400> SEQUENCE: 32
tgcttgcaag cttg                                                           14

<210> SEQ ID NO 33
<211> LENGTH: 20
<212> TYPE: DNA
<213> ORGANISM: Artificial Sequence

```
<220> FEATURE:
<223> OTHER INFORMATION: Synthetic Construct

<400> SEQUENCE: 33
agcttgcaag cttgcaagca                                          20

<210> SEQ ID NO 34
<211> LENGTH: 20
<212> TYPE: DNA
<213> ORGANISM: Artificial Sequence
<220> FEATURE:
<223> OTHER INFORMATION: Synthetic Construct

<400> SEQUENCE: 34
tacttgcaag cttgcaagca                                          20

<210> SEQ ID NO 35
<211> LENGTH: 20
<212> TYPE: DNA
<213> ORGANISM: Artificial Sequence
<220> FEATURE:
<223> OTHER INFORMATION: Synthetic Construct

<400> SEQUENCE: 35
tgattgcaag cttgcaagca                                          20

<210> SEQ ID NO 36
<211> LENGTH: 20
<212> TYPE: DNA
<213> ORGANISM: Artificial Sequence
<220> FEATURE:
<223> OTHER INFORMATION: Synthetic Construct

<400> SEQUENCE: 36
aaattgcaag cttgcaagca                                          20

<210> SEQ ID NO 37
<211> LENGTH: 15
<212> TYPE: DNA
<213> ORGANISM: Artificial Sequence
<220> FEATURE:
<223> OTHER INFORMATION: Synthetic Construct

<400> SEQUENCE: 37
tgctggaggg gttgt                                               15

<210> SEQ ID NO 38
<211> LENGTH: 20
<212> TYPE: DNA
<213> ORGANISM: Artificial Sequence
<220> FEATURE:
<223> OTHER INFORMATION: Synthetic Construct

<400> SEQUENCE: 38
aaattgacag cttgacagca                                          20

<210> SEQ ID NO 39
<211> LENGTH: 20
<212> TYPE: DNA
<213> ORGANISM: Artificial Sequence
<220> FEATURE:
<223> OTHER INFORMATION: Synthetic Construct

<400> SEQUENCE: 39
tgattgacag cttgacagca                                          20
```

```
<210> SEQ ID NO 40
<211> LENGTH: 20
<212> TYPE: DNA
<213> ORGANISM: Artificial Sequence
<220> FEATURE:
<223> OTHER INFORMATION: Synthetic Construct

<400> SEQUENCE: 40
tgattgacag attgacagca                                                   20

<210> SEQ ID NO 41
<211> LENGTH: 20
<212> TYPE: DNA
<213> ORGANISM: Artificial Sequence
<220> FEATURE:
<223> OTHER INFORMATION: Synthetic Construct

<400> SEQUENCE: 41
tgattgacag attgacagac                                                   20

<210> SEQ ID NO 42
<211> LENGTH: 18
<212> TYPE: DNA
<213> ORGANISM: Artificial Sequence
<220> FEATURE:
<223> OTHER INFORMATION: Synthetic Construct

<400> SEQUENCE: 42
tgctcctgga ggggttgt                                                     18

<210> SEQ ID NO 43
<211> LENGTH: 21
<212> TYPE: DNA
<213> ORGANISM: Artificial Sequence
<220> FEATURE:
<223> OTHER INFORMATION: Synthetic Construct

<400> SEQUENCE: 43
tgcttgtcct ggagggttg t                                                  21

<210> SEQ ID NO 44
<211> LENGTH: 24
<212> TYPE: DNA
<213> ORGANISM: Artificial Sequence
<220> FEATURE:
<223> OTHER INFORMATION: Synthetic Construct

<400> SEQUENCE: 44
tgcttgacat cctggagggg ttgt                                              24

<210> SEQ ID NO 45
<211> LENGTH: 33
<212> TYPE: DNA
<213> ORGANISM: Artificial Sequence
<220> FEATURE:
<223> OTHER INFORMATION: Synthetic Construct

<400> SEQUENCE: 45
tgcttgacag cttgacagtc ctggagggt tgt                                     33

<210> SEQ ID NO 46
<211> LENGTH: 30
<212> TYPE: DNA
<213> ORGANISM: Artificial Sequence
<220> FEATURE:
<223> OTHER INFORMATION: Synthetic Construct
```

<400> SEQUENCE: 46
tgcttgacag cttgatcctg gagggttgt           30

<210> SEQ ID NO 47
<211> LENGTH: 27
<212> TYPE: DNA
<213> ORGANISM: Artificial Sequence
<220> FEATURE:
<223> OTHER INFORMATION: Synthetic Construct

<400> SEQUENCE: 47
tgcttgacag cttcctggag gggttgt           27

<210> SEQ ID NO 48
<211> LENGTH: 30
<212> TYPE: DNA
<213> ORGANISM: Artificial Sequence
<220> FEATURE:
<223> OTHER INFORMATION: Synthetic Construct

<400> SEQUENCE: 48
tgcttgacag cttgctcctg gagggttgt           30

<210> SEQ ID NO 49
<211> LENGTH: 33
<212> TYPE: DNA
<213> ORGANISM: Artificial Sequence
<220> FEATURE:
<223> OTHER INFORMATION: Synthetic Construct

<400> SEQUENCE: 49
tgcttgacag cttgcttgtc ctggaggggt tgt           33

<210> SEQ ID NO 50
<211> LENGTH: 35
<212> TYPE: DNA
<213> ORGANISM: Artificial Sequence
<220> FEATURE:
<223> OTHER INFORMATION: Synthetic Construct

<400> SEQUENCE: 50
tgcttgacag cttgacagca tcctggaggg gttgt           35

<210> SEQ ID NO 51
<211> LENGTH: 35
<212> TYPE: DNA
<213> ORGANISM: Artificial Sequence
<220> FEATURE:
<223> OTHER INFORMATION: Synthetic Construct

<400> SEQUENCE: 51
tgcttgacag cttgacagca tcctggaggg gttgt           35

<210> SEQ ID NO 52
<211> LENGTH: 32
<212> TYPE: DNA
<213> ORGANISM: Artificial Sequence
<220> FEATURE:
<223> OTHER INFORMATION: Synthetic Construct

<400> SEQUENCE: 52
tgcttgacag cttgacagca tcctggaggg gt           32

<210> SEQ ID NO 53

-continued

<211> LENGTH: 31
<212> TYPE: DNA
<213> ORGANISM: Artificial Sequence
<220> FEATURE:
<223> OTHER INFORMATION: Synthetic Construct

<400> SEQUENCE: 53
tgcttgacag cttgacagca tcctggaggg g                              31

<210> SEQ ID NO 54
<211> LENGTH: 30
<212> TYPE: DNA
<213> ORGANISM: Artificial Sequence
<220> FEATURE:
<223> OTHER INFORMATION: Synthetic Construct

<400> SEQUENCE: 54
tgcttgcaag cttgctcctg gaggggttgt                                30

<210> SEQ ID NO 55
<211> LENGTH: 27
<212> TYPE: DNA
<213> ORGANISM: Artificial Sequence
<220> FEATURE:
<223> OTHER INFORMATION: Synthetic Construct

<400> SEQUENCE: 55
tgcttgcaag cttcctggag gggttgt                                   27

<210> SEQ ID NO 56
<211> LENGTH: 35
<212> TYPE: DNA
<213> ORGANISM: Artificial Sequence
<220> FEATURE:
<223> OTHER INFORMATION: Synthetic Construct

<400> SEQUENCE: 56
tgcttgcaag cttgcaagca tcctggaggg gttgt                          35

<210> SEQ ID NO 57
<211> LENGTH: 25
<212> TYPE: DNA
<213> ORGANISM: Artificial Sequence
<220> FEATURE:
<223> OTHER INFORMATION: Synthetic Construct

<400> SEQUENCE: 57
tgctgctcct ggaggggttg tttgt                                     25

<210> SEQ ID NO 58
<211> LENGTH: 25
<212> TYPE: DNA
<213> ORGANISM: Artificial Sequence
<220> FEATURE:
<223> OTHER INFORMATION: Synthetic Construct

<400> SEQUENCE: 58
tgctgctcct tgaggggttg tttgt                                     25

<210> SEQ ID NO 59
<211> LENGTH: 21
<212> TYPE: DNA
<213> ORGANISM: Artificial Sequence
<220> FEATURE:
<223> OTHER INFORMATION: Synthetic Construct

<400> SEQUENCE: 59
tgctgctcct tgaggggttg t                                              21

<210> SEQ ID NO 60
<211> LENGTH: 21
<212> TYPE: DNA
<213> ORGANISM: Artificial Sequence
<220> FEATURE:
<223> OTHER INFORMATION: Synthetic Construct

<400> SEQUENCE: 60
tgctgctcct ggaggggttg t                                              21

<210> SEQ ID NO 61
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15
<223> OTHER INFORMATION: n = 7-deaza-dG

<400> SEQUENCE: 61
tgctgctcct tgagnggttg tttgt                                          25

<210> SEQ ID NO 62
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15
<223> OTHER INFORMATION: n = deoxy-inosine

<400> SEQUENCE: 62
tgctgctcct tgagnggttg tttgt                                          25

<210> SEQ ID NO 63
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 12
<223> OTHER INFORMATION: n = deoxy-inosine

<400> SEQUENCE: 63
tgctccttga gnggttgttt gt                                             22

<210> SEQ ID NO 64
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15
<223> OTHER INFORMATION: n = deoxy-inosine

<400> SEQUENCE: 64
tgcttgtcct ggagnggttg taagt                                          25

<210> SEQ ID NO 65
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15
<223> OTHER INFORMATION: n = deoxy-inosine

<400> SEQUENCE: 65
tgcttgtcct ggagnggtgt tgt                                    23

<210> SEQ ID NO 66
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15
<223> OTHER INFORMATION: n = deoxy-inosine

<400> SEQUENCE: 66
tgctgctcct ggagnggttg t                                      21

<210> SEQ ID NO 67
<211> LENGTH: 22
<212> TYPE: DNA
<213> ORGANISM: Artificial Sequence
<220> FEATURE:
<223> OTHER INFORMATION: Synthetic Construct

<400> SEQUENCE: 67
tgctcctgga ggggttgtaa gt                                     22

<210> SEQ ID NO 68
<211> LENGTH: 26
<212> TYPE: DNA
<213> ORGANISM: Artificial Sequence
<220> FEATURE:
<223> OTHER INFORMATION: Synthetic Construct

<400> SEQUENCE: 68
tgctcctgga ggggttgtaa gtttgt                                 26

<210> SEQ ID NO 69
<211> LENGTH: 18
<212> TYPE: DNA
<213> ORGANISM: Artificial Sequence
<220> FEATURE:
<223> OTHER INFORMATION: Synthetic Construct

<400> SEQUENCE: 69
tgctccttga ggggttgt                                          18

<210> SEQ ID NO 70
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15
<223> OTHER INFORMATION: n = deoxy-inosine

<400> SEQUENCE: 70
tgctgctcct tgagnggttg t                                              21

<210> SEQ ID NO 71
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 12
<223> OTHER INFORMATION: n = deoxy-inosine

<400> SEQUENCE: 71
tgctccttga gnggttgt                                                  18

<210> SEQ ID NO 72
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15
<223> OTHER INFORMATION: n = deoxy-inosine

<400> SEQUENCE: 72
tgctgctcct tgagnggtgt tgt                                            23

<210> SEQ ID NO 73
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 12
<223> OTHER INFORMATION: n = deoxy-inosine

<400> SEQUENCE: 73
tgctcctgga gnggttgt                                                  18

<210> SEQ ID NO 74
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15
<223> OTHER INFORMATION: n = deoxy-inosine

<400> SEQUENCE: 74
tgcttgtcct ggagnggttg t                                              21

<210> SEQ ID NO 75
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15

```
<223> OTHER INFORMATION: n = deoxy-inosine

<400> SEQUENCE: 75
tgctgctcct tgagnggttg taagt                                         25

<210> SEQ ID NO 76
<211> LENGTH: 25
<212> TYPE: DNA
<213> ORGANISM: Artificial Sequence
<220> FEATURE:
<223> OTHER INFORMATION: Synthetic Construct

<400> SEQUENCE: 76
tgctgctcct ggaggggttg tttgt                                         25

<210> SEQ ID NO 77
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: 4
<223> OTHER INFORMATION: n = hexa- (ethylene glycol)
<220> FEATURE:
<221> NAME/KEY: misc_feature
<222> LOCATION: 13
<223> OTHER INFORMATION: n = deoxy-inosine

<400> SEQUENCE: 77
nnnntcctgg agnggtgttg t                                             21

<210> SEQ ID NO 78
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15
<223> OTHER INFORMATION: n = deoxy-inosine

<400> SEQUENCE: 78
tgctgctcct ggagnggttg taagt                                         25

<210> SEQ ID NO 79
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15
```

<223> OTHER INFORMATION: n = deoxy-inosine

<400> SEQUENCE: 79
tgctgctcct ggagnggtgt tgt                                           23

<210> SEQ ID NO 80
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(18)
<223> OTHER INFORMATION: bases are modified with a phosphoramidate
      modification

<400> SEQUENCE: 80
ugcuccugga gggguugu                                                 18

<210> SEQ ID NO 81
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 3
<223> OTHER INFORMATION: n = C modified with a 5-methyl dC (M)
      modification
<220> FEATURE:
<221> NAME/KEY: misc_feature
<222> LOCATION: (5)...(6)
<223> OTHER INFORMATION: n = C modified with a 5-methyl dC (M)
      modification

<400> SEQUENCE: 81
ugnunnugga gggguugu                                                 18

<210> SEQ ID NO 82
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(18)
<223> OTHER INFORMATION: nucleotides modified with a 2'-O-Me sugar
      modification

<400> SEQUENCE: 82
ugcuccugga gggguugu                                                 18

<210> SEQ ID NO 83
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification

```
<220> FEATURE:
<221> NAME/KEY: misc_feature
<222> LOCATION: 3
<223> OTHER INFORMATION: n = C modified with a 2'-O-Me sugar
      modification

<400> SEQUENCE: 83
nnntcctgga ggggttgt                                                     18

<210> SEQ ID NO 84
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15
<223> OTHER INFORMATION: n = U modified with a 2'-O-Me sugar
      modification
<220> FEATURE:
<221> NAME/KEY: misc_feature
<222> LOCATION: 16
<223> OTHER INFORMATION: n = U modified with a 2'-O-Me sugar
      modification
<220> FEATURE:
<221> NAME/KEY: misc_feature
<222> LOCATION: 17
<223> OTHER INFORMATION: n = G modified with a 2'-O-Me sugar
      modification
<220> FEATURE:
<221> NAME/KEY: misc_feature
<222> LOCATION: 18
<223> OTHER INFORMATION: n = U modified with a 2'-O-Me sugar
      modification

<400> SEQUENCE: 84
tgctcctgga ggggnnnn                                                     18

<210> SEQ ID NO 85
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: U modified with a 2'-O-Me sugar modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: 15
<223> OTHER INFORMATION: n = U modified with a 2'-O-Me sugar
      modification
<220> FEATURE:
<221> NAME/KEY: misc_feature
<222> LOCATION: 16
<223> OTHER INFORMATION: n = U modified with a 2'-O-Me sugar
      modification
<220> FEATURE:
<221> NAME/KEY: misc_feature
<222> LOCATION: (17)...(17)
<223> OTHER INFORMATION: n = G modified with a 2'-O-Me sugar
      modification
<220> FEATURE:
```

```
<221> NAME/KEY: misc_feature
<222> LOCATION: (18)...(18)
<223> OTHER INFORMATION: n = U modified with a 2'-O-Me sugar
      modification

<400> SEQUENCE: 85
ugcuccugga gggguugu                                                    18

<210> SEQ ID NO 86
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (11)...(14)
<223> OTHER INFORMATION: n = G modified with a 2'-O-Me sugar
      modification

<400> SEQUENCE: 86
tgctcctgga nnnnttgt                                                    18

<210> SEQ ID NO 87
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification

<400> SEQUENCE: 87
nnnttgtcct ggaggggttg t                                                21

<210> SEQ ID NO 88
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (19)...(20)
<223> OTHER INFORMATION: n = U modified with a 2'-O-Me sugar
      modification
<220> FEATURE:
<221> NAME/KEY: misc_feature
<222> LOCATION: 21
<223> OTHER INFORMATION: n = G modified with a 2'-O-Me sugar
      modification
<220> FEATURE:
<221> NAME/KEY: misc_feature
<222> LOCATION: 22
<223> OTHER INFORMATION: n = U modified with a 2'-O-Me sugar
      modification

<400> SEQUENCE: 88
tgctcctgga ggggaagtnn nn                                               22
```

<210> SEQ ID NO 89
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: (18)...(19)
<223> OTHER INFORMATION: U modified with a 2'-O-Me sugar modification
<220> FEATURE:
<221> NAME/KEY: misc_feature
<222> LOCATION: 20
<223> OTHER INFORMATION: n = G modified with a 2'-O-Me sugar
      modification
<220> FEATURE:
<221> NAME/KEY: misc_feature
<222> LOCATION: 21
<223> OTHER INFORMATION: n = U modified with a 2'-O-Me sugar
      modification

<400> SEQUENCE: 89
nnnttgtcct ggagggnnn n                                           21

<210> SEQ ID NO 90
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: (22)...(23)
<223> OTHER INFORMATION: n = U modified with a 2'-O-Me sugar
      modification
<220> FEATURE:
<221> NAME/KEY: misc_feature
<222> LOCATION: 24
<223> OTHER INFORMATION: n = G modified with a 2'-O-Me
<220> FEATURE:
<221> NAME/KEY: misc_feature
<222> LOCATION: 25
<223> OTHER INFORMATION: n = U modified with a 2'-O-Me sugar
      modification

```
<400> SEQUENCE: 90
nnnttgtcct ggaggggaag tnnnn                                          25

<210> SEQ ID NO 91
<211> LENGTH: 24
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: (21)...(22)
<223> OTHER INFORMATION: n = U modified with a 2'-O-Me sugar
      modification
<220> FEATURE:
<221> NAME/KEY: misc_feature
<222> LOCATION: 23
<223> OTHER INFORMATION: n = G modified with a 2'-O-Me
<220> FEATURE:
<221> NAME/KEY: misc_feature
<222> LOCATION: 24
<223> OTHER INFORMATION: n = U modified with a 2'-O-Me sugar
      modification

<400> SEQUENCE: 91
nnntgtcctg gagggaagt nnnn                                            24

<210> SEQ ID NO 92
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: (20)...(21)
<223> OTHER INFORMATION: n = U modified with a 2'-O-Me sugar
      modification
<220> FEATURE:
<221> NAME/KEY: misc_feature
<222> LOCATION: 22
<223> OTHER INFORMATION: n = G modified with a 2'-O-Me
<220> FEATURE:
<221> NAME/KEY: misc_feature
<222> LOCATION: 23
```

```
<223> OTHER INFORMATION: n = U modified with a 2'-O-Me sugar
      modification

<400> SEQUENCE: 92
nnngtcctgg aggggaagtn nnn                                              23

<210> SEQ ID NO 93
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: (20)...(21)
<223> OTHER INFORMATION: n = U modified with a 2'-O-Me sugar
      modification
<220> FEATURE:
<221> NAME/KEY: misc_feature
<222> LOCATION: 22
<223> OTHER INFORMATION: n = G modified with a 2'-O-Me
<220> FEATURE:
<221> NAME/KEY: misc_feature
<222> LOCATION: 23
<223> OTHER INFORMATION: n = U modified with a 2'-O-Me sugar
      modification

<400> SEQUENCE: 93
nnnttgtcct ggaggggtgn nnn                                              23

<210> SEQ ID NO 94
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: (19)...(20)
<223> OTHER INFORMATION: n = U modified with a 2'-O-Me sugar
      modification
<220> FEATURE:
<221> NAME/KEY: misc_feature
<222> LOCATION: 21
<223> OTHER INFORMATION: n = G modified with a 2'-O-Me
```

```
<220> FEATURE:
<221> NAME/KEY: misc_feature
<222> LOCATION: 22
<223> OTHER INFORMATION: n = U modified with a 2'-O-Me sugar
      modification

<400> SEQUENCE: 94
nnntgtcctg gaggggtgnn nn                                                    22

<210> SEQ ID NO 95
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: (18)...(19)
<223> OTHER INFORMATION: n = U modified with a 2'-O-Me sugar
      modification
<220> FEATURE:
<221> NAME/KEY: misc_feature
<222> LOCATION: 20
<223> OTHER INFORMATION: n = G modified with a 2'-O-Me
<220> FEATURE:
<221> NAME/KEY: misc_feature
<222> LOCATION: 21
<223> OTHER INFORMATION: n = U modified with a 2'-O-Me sugar
      modification

<400> SEQUENCE: 95
nnngtcctgg aggggtgnnn n                                                     21

<210> SEQ ID NO 96
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: 19
<223> OTHER INFORMATION: n = U modified with a 2'-O-Me sugar
      modification
<220> FEATURE:
```

<221> NAME/KEY: misc_feature
<222> LOCATION: 20
<223> OTHER INFORMATION: n = G modified with a 2'-O-Me
<220> FEATURE:
<221> NAME/KEY: misc_feature
<222> LOCATION: 21
<223> OTHER INFORMATION: n = U modified with a 2'-O-Me sugar
    modification

<400> SEQUENCE: 96
nnnttgtcct ggaggggtnn n        21

<210> SEQ ID NO 97
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
    modification
<220> FEATURE:
<221> NAME/KEY: misc_feature
<222> LOCATION: 2
<223> OTHER INFORMATION: n = G modified with a 2'-O-Me sugar
    modification
<220> FEATURE:
<221> NAME/KEY: misc_feature
<222> LOCATION: 3
<223> OTHER INFORMATION: n = C modified with a 2'-O-Me sugar
    modification
<220> FEATURE:
<221> NAME/KEY: misc_feature
<222> LOCATION: 18
<223> OTHER INFORMATION: n = U modified with a 2'-O-Me sugar
    modification
<220> FEATURE:
<221> NAME/KEY: misc_feature
<222> LOCATION: 19
<223> OTHER INFORMATION: n = G modified with a 2'-O-Me
<220> FEATURE:
<221> NAME/KEY: misc_feature
<222> LOCATION: 20
<223> OTHER INFORMATION: n = U modified with a 2'-O-Me sugar
    modification

<400> SEQUENCE: 97
nnntgtcctg gaggggtnnn        20

<210> SEQ ID NO 98
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
    modification
<220> FEATURE:
<221> NAME/KEY: misc_feature
<222> LOCATION: 2
<223> OTHER INFORMATION: n = G modified with a 2'-O-Me sugar
    modification
<220> FEATURE:
<221> NAME/KEY: misc_feature
<222> LOCATION: 3
<223> OTHER INFORMATION: n = C modified with a 2'-O-Me sugar
    modification
<220> FEATURE:
<221> NAME/KEY: misc_feature
<222> LOCATION: 17

<223> OTHER INFORMATION: n = U modified with a 2'-O-Me sugar
      modification
<220> FEATURE:
<221> NAME/KEY: misc_feature
<222> LOCATION: 18
<223> OTHER INFORMATION: n = G modified with a 2'-O-Me
<220> FEATURE:
<221> NAME/KEY: misc_feature
<222> LOCATION: 19
<223> OTHER INFORMATION: n = U modified with a 2'-O-Me sugar
      modification

<400> SEQUENCE: 98
nnngtcctgg aggggtnnn                                                   19

<210> SEQ ID NO 99
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: (22)...(23)
<223> OTHER INFORMATION: n = U modified with a 2'-O-Me sugar
      modification
<220> FEATURE:
<221> NAME/KEY: misc_feature
<222> LOCATION: 24
<223> OTHER INFORMATION: n = G modified with a 2'-O-Me
<220> FEATURE:
<221> NAME/KEY: misc_feature
<222> LOCATION: 25
<223> OTHER INFORMATION: n = U modified with a 2'-O-Me sugar
      modification

<400> SEQUENCE: 99
nnnttgtcct ggaggggttg tnnnn                                            25

<210> SEQ ID NO 100
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification

```
<220> FEATURE:
<221> NAME/KEY: misc_feature
<222> LOCATION: 20
<223> OTHER INFORMATION: n = G modified with a 2'-O-Me sugar
      modification
<220> FEATURE:
<221> NAME/KEY: misc_feature
<222> LOCATION: (21)...(23)
<223> OTHER INFORMATION: n = U modified with a 2'-O-Me sugar
      modification
<220> FEATURE:
<221> NAME/KEY: misc_feature
<222> LOCATION: 24
<223> OTHER INFORMATION: n = G modified with a 2'-O-Me sugar
      modification
<220> FEATURE:
<221> NAME/KEY: misc_feature
<222> LOCATION: 25
<223> OTHER INFORMATION: n = U modified with a 2'-O-Me sugar
      modification

<400> SEQUENCE: 100
nnnttgtcct ggaggggttn nnnnn                                           25

<210> SEQ ID NO 101
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: (22)...(23)
<223> OTHER INFORMATION: n = U modified with a 2'-O-Me sugar
      modification
<220> FEATURE:
<221> NAME/KEY: misc_feature
<222> LOCATION: 24
<223> OTHER INFORMATION: n = G modified with a 2'-O-Me sugar
      modification
<220> FEATURE:
<221> NAME/KEY: misc_feature
<222> LOCATION: 25
<223> OTHER INFORMATION: n = U modified with a 2'-O-Me sugar
      modification

<400> SEQUENCE: 101
nnntgctcct ggaggggttg tnnnn                                           25

<210> SEQ ID NO 102
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
```

<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: (22)...(23)
<223> OTHER INFORMATION: n = U modified with a 2'-O-Me sugar
      modification
<220> FEATURE:
<221> NAME/KEY: misc_feature
<222> LOCATION: 24
<223> OTHER INFORMATION: n = G modified with a 2'-O-Me sugar
      modification
<220> FEATURE:
<221> NAME/KEY: misc_feature
<222> LOCATION: 25
<223> OTHER INFORMATION: n = U modified with a 2'-O-Me sugar
      modification

<400> SEQUENCE: 102
nnntgctcct tgagggttg tnnnn                                          25

<210> SEQ ID NO 103
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: (20)...(21)
<223> OTHER INFORMATION: n = U modified with a 2'-O-Me sugar
      modification
<220> FEATURE:
<221> NAME/KEY: misc_feature
<222> LOCATION: 22
<223> OTHER INFORMATION: n = G modified with a 2'-O-Me sugar
      modification
<220> FEATURE:
<221> NAME/KEY: misc_feature
<222> LOCATION: 23
<223> OTHER INFORMATION: n = U modified with a 2'-O-Me sugar
      modification

<400> SEQUENCE: 103
nnntgctcct tgagggggtgn nnn                                          23

<210> SEQ ID NO 104
<211> LENGTH: 25
<212> TYPE: DNA
<213> ORGANISM: Artificial Sequence
<220> FEATURE:
<223> OTHER INFORMATION: Synthetic Construct

```
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: 20
<223> OTHER INFORMATION: n = G modified with a 2'-O-Me sugar
      modification
<220> FEATURE:
<221> NAME/KEY: misc_feature
<222> LOCATION: (21)...(23)
<223> OTHER INFORMATION: n = U modified with a 2'-O-Me sugar
      modification
<220> FEATURE:
<221> NAME/KEY: misc_feature
<222> LOCATION: 24
<223> OTHER INFORMATION: n = G modified with a 2'-O-Me sugar
      modification
<220> FEATURE:
<221> NAME/KEY: misc_feature
<222> LOCATION: 25
<223> OTHER INFORMATION: n = U modified with a 2'-O-Me sugar
      modification

<400> SEQUENCE: 104
nnntgctcct tgaggggttn nnnnn                                         25

<210> SEQ ID NO 105
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(21)
<223> OTHER INFORMATION: nucleotides are modified with a 2'-O-Me sugar
      modification

<400> SEQUENCE: 105
ugcugcuccu ugagagguug u                                             21

<210> SEQ ID NO 106
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
```

```
<220> FEATURE:
<221> NAME/KEY: misc_feature
<222> LOCATION: 20
<223> OTHER INFORMATION: n = G modified with a 2'-O-Me sugar
      modification
<220> FEATURE:
<221> NAME/KEY: misc_feature
<222> LOCATION: (21)...(23)
<223> OTHER INFORMATION: n = U modified with a 2'-O-Me sugar
      modification
<220> FEATURE:
<221> NAME/KEY: misc_feature
<222> LOCATION: 24
<223> OTHER INFORMATION: n = G modified with a 2'-O-Me sugar
      modification
<220> FEATURE:
<221> NAME/KEY: misc_feature
<222> LOCATION: 25
<223> OTHER INFORMATION: n = U modified with a 2'-O-Me sugar
      modification

<400> SEQUENCE: 106
nnntgctcct ggaggggttn nnnnn                                       25

<210> SEQ ID NO 107
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification

<400> SEQUENCE: 107
nnntgctcct tgaggggttg tttgt                                       25

<210> SEQ ID NO 108
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification

<400> SEQUENCE: 108
nnntgctcct ggaggggttg tttgt                                       25
```

```
<210> SEQ ID NO 109
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 109
nnntgctcct tgagnggttg tttgt                                           25

<210> SEQ ID NO 110
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: 15
<223> OTHER INFORMATION: n = 7-deaza-dG

<400> SEQUENCE: 110
nnntgctcct tgagnggttg tttgt                                           25

<210> SEQ ID NO 111
<211> LENGTH: 24
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
```

```
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 111
nnntgctcct tgagnggttg tttg                                              24

<210> SEQ ID NO 112
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = G modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 112
nnntgctcct tgagnggttg ttt                                               23

<210> SEQ ID NO 113
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 113
nnntgctcct tgagnggttg tt                                                22

<210> SEQ ID NO 114
<211> LENGTH: 21
```

```
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 114
nnntgctcct tgagnggttg t                                               21

<210> SEQ ID NO 115
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 115
nnntgctcct tgagnggtt                                                  19

<210> SEQ ID NO 116
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
```

```
<223> OTHER INFORMATION: n = C modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 116
nnntgctcct tgagnggt                                                18

<210> SEQ ID NO 117
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification,
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 117
nnntgctcct tgagngg                                                 17

<210> SEQ ID NO 118
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 118
nnntgctcct tgagng                                                  16

<210> SEQ ID NO 119
<211> LENGTH: 15
<212> TYPE: DNA
<213> ORGANISM: Artificial Sequence
<220> FEATURE:
```

```
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 119
nnntgctcct tgagn                                                     15

<210> SEQ ID NO 120
<211> LENGTH: 24
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = G modified with a 2'-O-Me sugar
      modification
<220> FEATURE:
<221> NAME/KEY: misc_feature
<222> LOCATION: 2
<223> OTHER INFORMATION: n = C modified with a 2'-O-Me sugar
      modification
<220> FEATURE:
<221> NAME/KEY: misc_feature
<222> LOCATION: 14
<223> OTHER INFORMATION: n = deoxy-inosine

<400> SEQUENCE: 120
nntgctcctt gagnggttgt ttgt                                           24

<210> SEQ ID NO 121
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = C modified with a 2'-O-Me sugar
      modification
<220> FEATURE:
<221> NAME/KEY: misc_feature
<222> LOCATION: 13
<223> OTHER INFORMATION: n = deoxy-inosine

<400> SEQUENCE: 121
ntgctccttg agnggttgtt tgt                                            23

<210> SEQ ID NO 122
<211> LENGTH: 20
<212> TYPE: DNA
<213> ORGANISM: Artificial Sequence
<220> FEATURE:
<223> OTHER INFORMATION: Synthetic Construct
```

-continued

```
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 122
nnntgctcct tgagnggttg                                              20

<210> SEQ ID NO 123
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 123
nnnttgtcct ggagnggttg t                                            21

<210> SEQ ID NO 124
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
```

```
<222> LOCATION: 15
<223> OTHER INFORMATION: n = deoxy-inosine

<400> SEQUENCE: 124
nnnttgtcct ggagnggtgt tgt                                              23

<210> SEQ ID NO 125
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 125
nnntgctcct ggagnggttg t                                                21

<210> SEQ ID NO 126
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 126
nnctgctcct tgagnggttg t                                                21

<210> SEQ ID NO 127
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 15
```

```
<223> OTHER INFORMATION: n = deoxy-inosine

<400> SEQUENCE: 127
ngctgctcct tgagnggttg t                                              21

<210> SEQ ID NO 128
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 128
nnntgctcct tgagnggtgt tgt                                            23

<210> SEQ ID NO 129
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 129
nnntgctcct tgagnggttg taagt                                          25

<210> SEQ ID NO 130
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
```

```
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 130
nnntgctcct ggagnggttg taagt                                           25

<210> SEQ ID NO 131
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: (15)...(16)
<223> OTHER INFORMATION: n = U modified with a 2'-O-Me sugar
      modification
<220> FEATURE:
<221> NAME/KEY: misc_feature
<222> LOCATION: 17
<223> OTHER INFORMATION: n = G modified with a 2'-O-Me sugar
      modification
<220> FEATURE:
<221> NAME/KEY: misc_feature
<222> LOCATION: 18
<223> OTHER INFORMATION: n = U modified with a 2'-O-Me sugar
      modification

<400> SEQUENCE: 131
nnntcctgga ggggnnnn                                                   18

<210> SEQ ID NO 132
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
```

```
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 132
nnntgctcct ggagnggtgt tgt                                               23

<210> SEQ ID NO 133
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: (4)...(6)
<223> OTHER INFORMATION: n = diethyldithiodicarbonate
<220> FEATURE:
<221> NAME/KEY: misc_feature
<222> LOCATION: 15
<223> OTHER INFORMATION: n = deoxy-inosine

<400> SEQUENCE: 133
nnnnnntcct ggagnggttg t                                                 21

<210> SEQ ID NO 134
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 134
nnncaatcct ggagnggttg t                                                 21
```

```
<210> SEQ ID NO 135
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: 15
<223> OTHER INFORMATION: n = deoxy-inosine

<400> SEQUENCE: 135
nnncaatcct ggagnggtgt tgt                                           23

<210> SEQ ID NO 136
<211> LENGTH: 36
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 21
<223> OTHER INFORMATION: n = hexa- (ethylene glycol)

<400> SEQUENCE: 136
tgcttgcaag cttgcaagca ntcctggagg ggttgt                             36

<210> SEQ ID NO 137
<211> LENGTH: 36
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 21
<223> OTHER INFORMATION: n = hexa- (ethylene glycol)

<400> SEQUENCE: 137
tgcttgcaag ctagcaagca ntcctggagg ggttgt                             36

<210> SEQ ID NO 138
<211> LENGTH: 36
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 21
<223> OTHER INFORMATION: n = hexa- (ethylene glycol)

<400> SEQUENCE: 138
tgcttgcaag cttgctagca ntcctggagg ggttgt                             36
```

<210> SEQ ID NO 139
<211> LENGTH: 36
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 21
<223> OTHER INFORMATION: n = hexa- (ethylene glycol)
<220> FEATURE:
<221> NAME/KEY: misc_feature
<222> LOCATION: 30
<223> OTHER INFORMATION: n = 7-deaza-dG

<400> SEQUENCE: 139
tgcttgcaag cttgctagca ntcctggagn ggttgt          36

<210> SEQ ID NO 140
<211> LENGTH: 36
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16
<223> OTHER INFORMATION: n = hexa- (ethylene glycol)

<400> SEQUENCE: 140
tcctggaggg gttgtntgct tgcaagcttg caagca          36

<210> SEQ ID NO 141
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (19)...(20)
<223> OTHER INFORMATION: n = hexa- (ethylene glycol)

<400> SEQUENCE: 141
tgctcctgga ggggttgtnn          20

<210> SEQ ID NO 142
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
     modification
<220> FEATURE:
<221> NAME/KEY: misc_feature
<222> LOCATION: 2
<223> OTHER INFORMATION: n = G modified with a 2'-O-Me sugar
     modification
<220> FEATURE:
<221> NAME/KEY: misc_feature
<222> LOCATION: 3
<223> OTHER INFORMATION: n = C modified with a 2'-O-Me sugar
     modification
<220> FEATURE:
<221> NAME/KEY: misc_feature
<222> LOCATION: 15
<223> OTHER INFORMATION: n = deoxy-inosine -continued

```
<220> FEATURE:
<221> NAME/KEY: misc_feature
<222> LOCATION: 21
<223> OTHER INFORMATION: n = hexa- (ethylene glycol)

<400> SEQUENCE: 142
nnnttgtcct ggagnggttg nt                                              22

<210> SEQ ID NO 143
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 12
<223> OTHER INFORMATION: n = deoxy-inosine
<220> FEATURE:
<221> NAME/KEY: misc_feature
<222> LOCATION: 18
<223> OTHER INFORMATION: n = hexa- (ethylene glycol)

<400> SEQUENCE: 143
tgctcctgga gnggttgnt                                                  19

<210> SEQ ID NO 144
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15
<223> OTHER INFORMATION: n = deoxy-inosine
<220> FEATURE:
<221> NAME/KEY: misc_feature
<222> LOCATION: 21
<223> OTHER INFORMATION: n = hexa- (ethylene glycol)

<400> SEQUENCE: 144
tgctgctcct ggagnggttg nt                                              22

<210> SEQ ID NO 145
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-O-Me sugar
      modification
<220> FEATURE:
<221> NAME/KEY: misc_feature
<222> LOCATION: 2
<223> OTHER INFORMATION: n = G modified with a 2'-O-Me sugar
      modification
<220> FEATURE:
<221> NAME/KEY: misc_feature
<222> LOCATION: 3
<223> OTHER INFORMATION: n = C modified with a 2'-O-Me sugar
      modification
<220> FEATURE:
<221> NAME/KEY: misc_feature
<222> LOCATION: 4
<223> OTHER INFORMATION: n = hexa- (ethylene glycol)
<220> FEATURE:
<221> NAME/KEY: misc_feature
<222> LOCATION: 13
<223> OTHER INFORMATION: n = deoxy-inosine
```

<400> SEQUENCE: 145
nnnntcctgg agnggttgt                                                   19

<210> SEQ ID NO 146
<211> LENGTH: 57
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(10)
<223> OTHER INFORMATION: n = any nucleotide or absent
<220> FEATURE:
<221> NAME/KEY: misc_feature
<222> LOCATION: 11
<223> OTHER INFORMATION: n = U or T,
<220> FEATURE:
<221> NAME/KEY: misc_feature
<222> LOCATION: 14
<223> OTHER INFORMATION: n = any nucleotide
<220> FEATURE:
<221> NAME/KEY: misc_feature
<222> LOCATION: (15)...(33)
<223> OTHER INFORMATION: n = any nucleotide or absent
<220> FEATURE:
<221> NAME/KEY: misc_feature
<222> LOCATION: (34)...(37)
<223> OTHER INFORMATION: n = nucleotides are a 2'-deoxyribonucleotide
<220> FEATURE:
<221> NAME/KEY: misc_feature
<222> LOCATION: (35)...(35)
<223> OTHER INFORMATION: n = deoxy-inosine
<220> FEATURE:
<221> NAME/KEY: misc_feature
<222> LOCATION: (38)...(38)
<223> OTHER INFORMATION: n = any nucleotide
<220> FEATURE:
<221> NAME/KEY: misc_feature
<222> LOCATION: (39)...(57)
<223> OTHER INFORMATION: n = any nucleotide or absent

<400> SEQUENCE: 146
nnnnnnnnnn ngcnnnnnnn nnnnnnnnnn nnngnggnnn nnnnnnnnnn nnnnnnn        57

<210> SEQ ID NO 147
<211> LENGTH: 113
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(10)
<223> OTHER INFORMATION: n = any nucleotide or absent
<220> FEATURE:
<221> NAME/KEY: misc_feature
<222> LOCATION: 11
<223> OTHER INFORMATION: n = u or t
<220> FEATURE:
<221> NAME/KEY: misc_feature
<222> LOCATION: 14
<223> OTHER INFORMATION: n = any nucleotide
<220> FEATURE:
<221> NAME/KEY: misc_feature
<222> LOCATION: (15)...(113)
<223> OTHER INFORMATION: n = any nucleotide or absent

<400> SEQUENCE: 147
nnnnnnnnnn ngcnnnnnnn nnnnnnnnnn nnnnnnnnnn nnnnnnnnnn nnnnnnnnnn     60
nnnnnnnnnn nnnnnnnnnn nnnnnnnnnn nnnnnnnnnn nnnnnnnnnn nnn          113

```
<210> SEQ ID NO 148
<211> LENGTH: 57
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(10)
<223> OTHER INFORMATION: n = any nucleotide or absent
<220> FEATURE:
<221> NAME/KEY: misc_feature
<222> LOCATION: 11
<223> OTHER INFORMATION: n = u or t
<220> FEATURE:
<221> NAME/KEY: misc_feature
<222> LOCATION: 14
<223> OTHER INFORMATION: n = any nucleotide
<220> FEATURE:
<221> NAME/KEY: misc_feature
<222> LOCATION: (15)...(33)
<223> OTHER INFORMATION: n = any nucleotide or absent
<220> FEATURE:
<221> NAME/KEY: misc_feature
<222> LOCATION: (34)...(37)
<223> OTHER INFORMATION: n = g or a molecule that is capable of
      preventing G-tetrad formation and/or preventing Hoogsteen
      base pairing
<220> FEATURE:
<221> NAME/KEY: misc_feature
<222> LOCATION: (38)...(38)
<223> OTHER INFORMATION: n = any nucleotide
<220> FEATURE:
<221> NAME/KEY: misc_feature
<222> LOCATION: (39)...(57)
<223> OTHER INFORMATION: n = any nucleotide or absent

<400> SEQUENCE: 148
nnnnnnnnnn ngcnnnnnnn nnnnnnnnnn nnnnnnnnnn nnnnnnnnnn nnnnnnn          57

<210> SEQ ID NO 149
<211> LENGTH: 7
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = any nucleotide
<220> FEATURE:
<221> NAME/KEY: misc_feature
<222> LOCATION: (2)...(5)
<223> OTHER INFORMATION: n = G or a molecule that is capable of
      preventing G-tetrad formation and/or preventing Hoogsteen
      base pairing
<220> FEATURE:
<221> NAME/KEY: misc_feature
<222> LOCATION: (6)...(7)
<223> OTHER INFORMATION: n = any nucleotide unless base 1 is C or A, if
      base 1 is C or A bases 6 and 7 are  not AA

<400> SEQUENCE: 149 nnnnnnn                                                                   7

<210> SEQ ID NO 150
<211> LENGTH: 8
<212> TYPE: DNA
<213> ORGANISM: Artificial Sequence
<220> FEATURE:
<223> OTHER INFORMATION: Syntehtic Construct 150
<220> FEATURE:
<221> NAME/KEY: misc_feature
<222> LOCATION: 1
```

```
<223> OTHER INFORMATION: n = C or A
<220> FEATURE:
<221> NAME/KEY: misc_feature
<222> LOCATION: (2)...(5)
<223> OTHER INFORMATION: n = G or a molecule that is capable of
      preventing G-tetrad formation and/or
<220> FEATURE:
<221> NAME/KEY: misc_feature
<222> LOCATION: 6
<223> OTHER INFORMATION: n = any nucleotide
<220> FEATURE:
<221> NAME/KEY: misc_feature
<222> LOCATION: 7
<223> OTHER INFORMATION: n = any nucleotide but not A if base 8 is A
<220> FEATURE:
<221> NAME/KEY: misc_feature
<222> LOCATION: 8
<223> OTHER INFORMATION: n = any nucleotide by not A if base 7 is A

<400> SEQUENCE: 150 nnnnnnnn                                                              8

<210> SEQ ID NO 151
<211> LENGTH: 1004
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(500)
<223> OTHER INFORMATION: n = any nucleotide or absent
<220> FEATURE:
<221> NAME/KEY: misc_feature
<222> LOCATION: (501)...(504)
<223> OTHER INFORMATION: n = G or a molecule that is capable of
      preventing G-tetrad formation and/or preventing Hoogsteen
      base pairing
<220> FEATURE:
<221> NAME/KEY: misc_feature
<222> LOCATION: (505)...(1004)
<223> OTHER INFORMATION: n = any nucleotide or absent

<400> SEQUENCE: 151
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
```

```
nnnnnnnnnn nnnnnnnnnn nnnnnnnnnn nnnnnnnnnn nnnn          1004

<210> SEQ ID NO 152
<211> LENGTH: 46
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(10)
<223> OTHER INFORMATION: n = any nucleotide or absent
<220> FEATURE:
<221> NAME/KEY: misc_feature
<222> LOCATION: 11
<223> OTHER INFORMATION: n = u or t
<220> FEATURE:
<221> NAME/KEY: misc_feature
<222> LOCATION: (14)...(23)
<223> OTHER INFORMATION: n = any nucleotide or absent
<220> FEATURE:
<221> NAME/KEY: misc_feature
<222> LOCATION: (31)...(34)
<223> OTHER INFORMATION: n = G, I, 7-deaza-dG or or a molecule that is
      capable of preventing G-tetrad formation and/or
      preventing Hoogsteen base pairing
<220> FEATURE:
<221> NAME/KEY: misc_feature
<222> LOCATION: (37)...(46)
<223> OTHER INFORMATION: n = any nucleotide or absent

<400> SEQUENCE: 152
nnnnnnnnnn ngcnnnnnnn nnntcctgga nnnnttnnnn nnnnnn          46

<210> SEQ ID NO 153
<211> LENGTH: 31
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)...(30)
<223> OTHER INFORMATION: n = propyl linkers connected via
      phosphorothioate esters

<400> SEQUENCE: 153
tcctggaggg gttgtnnnnn nnnnnnnnnn t          31

<210> SEQ ID NO 154
<211> LENGTH: 31
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)...(30)
<223> OTHER INFORMATION: n = glycerol linkers connected via
      phosphorothioate esters

<400> SEQUENCE: 154
tcctggaggg gttgtnnnnn nnnnnnnnnn t          31

<210> SEQ ID NO 155
<211> LENGTH: 24
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
```

```
<222> LOCATION: (16)...(23)
<223> OTHER INFORMATION: n = triethyleneglycol linkers connected via
      phosphorothioate esters

<400> SEQUENCE: 155
tcctggaggg gttgtnnnnn nnnt                                          24

<210> SEQ ID NO 156
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)...(19)
<223> OTHER INFORMATION: n = hexaethyleneglycol linkers connected via
      phosphorothioate esters

<400> SEQUENCE: 156
tcctggaggg gttgtnnnnt                                               20

<210> SEQ ID NO 157
<211> LENGTH: 22
<212> TYPE: DNA
<213> ORGANISM: Artificial Sequence
<220> FEATURE:
<223> OTHER INFORMATION: Synthetic Construct

<400> SEQUENCE: 157
tgactgtgaa cgttcgagat ga                                            22

<210> SEQ ID NO 158
<211> LENGTH: 21
<212> TYPE: DNA
<213> ORGANISM: Artificial Sequence
<220> FEATURE:
<223> OTHER INFORMATION: Synthetic Construct

<400> SEQUENCE: 158
tcgtcgaacg ttcgagatga t                                             21

<210> SEQ ID NO 159
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(22)
<223> OTHER INFORMATION: n = a, c, t, or g

<400> SEQUENCE: 159
nnnnnnnnnn nnnnnnnnnn nn                                            22

<210> SEQ ID NO 160
<211> LENGTH: 15
<212> TYPE: DNA
<213> ORGANISM: Artificial Sequence
<220> FEATURE:
<223> OTHER INFORMATION: Synthetic Construct

<400> SEQUENCE: 160
tcctgcaggt taagt                                                    15

<210> SEQ ID NO 161
```

<211> LENGTH: 18
<212> TYPE: DNA
<213> ORGANISM: Artificial Sequence
<220> FEATURE:
<223> OTHER INFORMATION: Synthetic Construct

<400> SEQUENCE: 161
ctatctgacg ttctctgt                                                       18

<210> SEQ ID NO 162
<211> LENGTH: 18
<212> TYPE: DNA
<213> ORGANISM: Artificial Sequence
<220> FEATURE:
<223> OTHER INFORMATION: Synthetic Construct

<400> SEQUENCE: 162
ctatctgucg ttctctgt                                                       18

<210> SEQ ID NO 163
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 10
<223> OTHER INFORMATION: n = 2'-deoxy-7-deazaguanosine linker

<400> SEQUENCE: 163
ctatctgacn ttctctgt                                                       18

<210> SEQ ID NO 164
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 10
<223> OTHER INFORMATION: n = 2'-deoxy-7-deazaguanosine linker

<400> SEQUENCE: 164
ctatctgucn ttctctgt                                                       18

<210> SEQ ID NO 165
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 7
<223> OTHER INFORMATION: n = G modified with a 2'O-methyl-ribonucleotide
<220> FEATURE:
<221> NAME/KEY: misc_feature
<222> LOCATION: 8
<223> OTHER INFORMATION: n = A modified with a 2'O-methyl-ribonucleotide

<400> SEQUENCE: 165
ctatctnncg ttctctgt                                                       18

<210> SEQ ID NO 166
<211> LENGTH: 18
<212> TYPE: DNA
<213> ORGANISM: Artificial Sequence

```
<220> FEATURE:
<223> OTHER INFORMATION: Synthetic Construct
<220> FEATURE:
<221> NAME/KEY: misc_feature
<222> LOCATION: 7
<223> OTHER INFORMATION: n = G modified with a 2'O-methyl-ribonucleotide
<220> FEATURE:
<221> NAME/KEY: misc_feature
<222> LOCATION: 8
<223> OTHER INFORMATION: n = U modified with a 2'O-methyl-ribonucleotide

<400> SEQUENCE: 166
ctatctnncg ttctctgt                                                       18

<210> SEQ ID NO 167
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 7
<223> OTHER INFORMATION: n = G modified with a 2'O-methyl-ribonucleotide
<220> FEATURE:
<221> NAME/KEY: misc_feature
<222> LOCATION: 8
<223> OTHER INFORMATION: n = A modified with a 2'O-methyl-ribonucleotide
<220> FEATURE:
<221> NAME/KEY: misc_feature
<222> LOCATION: 10
<223> OTHER INFORMATION: n = 2'-deoxy-7-deazaguanosine linker

<400> SEQUENCE: 167
ctatctnncn ttctctgt                                                       18

<210> SEQ ID NO 168
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 7
<223> OTHER INFORMATION: n = G modified with a 2'O-methyl-ribonucleotide
<220> FEATURE:
<221> NAME/KEY: misc_feature
<222> LOCATION: 8
<223> OTHER INFORMATION: n = U modified with a 2'O-methyl-ribonucleotide
<220> FEATURE:
<221> NAME/KEY: misc_feature
<222> LOCATION: 10
<223> OTHER INFORMATION: n = 2'-deoxy-7-deazaguanosine linker

<400> SEQUENCE: 168
ctatctnncn ttctctgt                                                       18

<210> SEQ ID NO 169
<211> LENGTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 4
<223> OTHER INFORMATION: n = G modified with a 2'-OMe
<220> FEATURE:
<221> NAME/KEY: misc_feature
<222> LOCATION: 5
<223> OTHER INFORMATION: n = A modified with a 2'-OMe
```

```
<400> SEQUENCE: 169
tctnncgttc t                                                        11

<210> SEQ ID NO 170
<211> LENTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 4
<223> OTHER INFORMATION: n = G modified with a 2'-OMe
<220> FEATURE:
<221> NAME/KEY: misc_feature
<222> LOCATION: 5
<223> OTHER INFORMATION: n = A modified with a 2'-OMe
<220> FEATURE:
<221> NAME/KEY: misc_feature
<222> LOCATION: 7
<223> OTHER INFORMATION: n = 7-deaza-dG

<400> SEQUENCE: 170
tctnncnttc t                                                        11

<210> SEQ ID NO 171
<211> LENGTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 4
<223> OTHER INFORMATION: n = G modified with a 2'-OMe
<220> FEATURE:
<221> NAME/KEY: misc_feature
<222> LOCATION: 5
<223> OTHER INFORMATION: n = A modified with a 2'-OMe
<220> FEATURE:
<221> NAME/KEY: misc_feature
<222> LOCATION: 7
<223> OTHER INFORMATION: n = araG

<400> SEQUENCE: 171
tctnncnttc t                                                        11

<210> SEQ ID NO 172
<211> LENGTH: 11
<212> TYPE: DNA
<213> ORGANISM: Artificial Sequence
<220> FEATURE:
<223> OTHER INFORMATION: Synthetic Construct

<400> SEQUENCE: 172
tctctgacgt t                                                        11

<210> SEQ ID NO 173
<211> LENGTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 4
<223> OTHER INFORMATION: n =G modified with a 2'-OMe
<220> FEATURE:
<221> NAME/KEY: misc_feature
<222> LOCATION: 5
<223> OTHER INFORMATION: n = U modified with a 2'-OMe
```

<400> SEQUENCE: 173
tctnncgttc t                                                                                      11

<210> SEQ ID NO 174
<211> LENGTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 4
<223> OTHER INFORMATION: n = G modified with a 2'-OMe
<220> FEATURE:
<221> NAME/KEY: misc_feature
<222> LOCATION: 5
<223> OTHER INFORMATION: n = U modified with a 2'-OMe
<220> FEATURE:
<221> NAME/KEY: misc_feature
<222> LOCATION: 7
<223> OTHER INFORMATION: n = 7-deaza-dG

<400> SEQUENCE: 174
tctnncnttc t                                                                                      11

<210> SEQ ID NO 175
<211> LENGTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 4
<223> OTHER INFORMATION: n = G modified with a 2'-OMe
<220> FEATURE:
<221> NAME/KEY: misc_feature
<222> LOCATION: 5
<223> OTHER INFORMATION: n = A modified with a 2'-OMe
<220> FEATURE:
<221> NAME/KEY: misc_feature
<222> LOCATION: 7
<223> OTHER INFORMATION: n = araG

<400> SEQUENCE: 175
tctnncnttc t                                                                                      11

<210> SEQ ID NO 176
<211> LENGTH: 9
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 4
<223> OTHER INFORMATION: n = G modified with a 2'-OMe
<220> FEATURE:
<221> NAME/KEY: misc_feature
<222> LOCATION: 5
<223> OTHER INFORMATION: n = A modified with a 2'-OMe
<220> FEATURE:
<221> NAME/KEY: misc_feature
<222> LOCATION: 7
<223> OTHER INFORMATION: n = 7-deaza-dG

<400> SEQUENCE: 176 tctnncntt                                                                                          9

<210> SEQ ID NO 177

```
<211> LENGTH: 9
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-OMe
<220> FEATURE:
<221> NAME/KEY: misc_feature
<222> LOCATION: 2
<223> OTHER INFORMATION: n = G modified with a 2'-OMe
<220> FEATURE:
<221> NAME/KEY: misc_feature
<222> LOCATION: 3
<223> OTHER INFORMATION: n = U modified with a 2'-OMe
<220> FEATURE:
<221> NAME/KEY: misc_feature
<222> LOCATION: 5
<223> OTHER INFORMATION: n = 7-deaza-dG

<400> SEQUENCE: 177 nnncnttct                                                                9

<210> SEQ ID NO 178
<211> LENGTH: 9
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = U modified with a 2'-OMe
<220> FEATURE:
<221> NAME/KEY: misc_feature
<222> LOCATION: 2
<223> OTHER INFORMATION: n = G modified with a 2'-OMe
<220> FEATURE:
<221> NAME/KEY: misc_feature
<222> LOCATION: 3
<223> OTHER INFORMATION: n = A modified with a 2'-OMe
<220> FEATURE:
<221> NAME/KEY: misc_feature
<222> LOCATION: 5
<223> OTHER INFORMATION: n = 7-deaza-dG

<400> SEQUENCE: 178 nnncnttct                                                                9

<210> SEQ ID NO 179
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15
<223> OTHER INFORMATION: n = deoxy-inosine

<400> SEQUENCE: 179
tgctgctcct tgagnggtgt tgt                                               23

<210> SEQ ID NO 180
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
```

```
<222> LOCATION: 15
<223> OTHER INFORMATION: n = deoxy-inosine

<400> SEQUENCE: 180
ugctgctcct tgagnggtgt tgt                                          23

<210> SEQ ID NO 181
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15
<223> OTHER INFORMATION: n = deoxy-inosine

<400> SEQUENCE: 181
tgctgctcct tgagnggttg taagt                                        25

<210> SEQ ID NO 182
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 15
<223> OTHER INFORMATION: n = deoxy-inosine

<400> SEQUENCE: 182
ugctgctcct ggagnggtgt tgt                                          23

<210> SEQ ID NO 183
<211> LENGTH: 16
<212> TYPE: DNA
<213> ORGANISM: Artificial Sequence
<220> FEATURE:
<223> OTHER INFORMATION: Synthetic Construct

<400> SEQUENCE: 183
ccatgtggtt atgggt                                                  16

<210> SEQ ID NO 184
<211> LENGTH: 20
<212> TYPE: DNA
<213> ORGANISM: Artificial Sequence
<220> FEATURE:
<223> OTHER INFORMATION: Synthetic Construct

<400> SEQUENCE: 184
ctaggatgcc actgctgttg                                              20

<210> SEQ ID NO 185
<211> LENGTH: 20
<212> TYPE: DNA
<213> ORGANISM: Artificial Sequence
<220> FEATURE:
<223> OTHER INFORMATION: Synthetic Construct

<400> SEQUENCE: 185
caagcctctc ctggacctaa                                              20

<210> SEQ ID NO 186
<211> LENGTH: 19
<212> TYPE: DNA
```

```
<213> ORGANISM: Artificial Sequence
<220> FEATURE:
<223> OTHER INFORMATION: Synthetic Construct

<400> SEQUENCE: 186
tccaagctcc cggctaagt                                                    19

<210> SEQ ID NO 187
<211> LENGTH: 20
<212> TYPE: DNA
<213> ORGANISM: Artificial Sequence
<220> FEATURE:
<223> OTHER INFORMATION: Synthetic Construct

<400> SEQUENCE: 187
acagggcgtt ttatcttgcg                                                   20

<210> SEQ ID NO 188
<211> LENGTH: 20
<212> TYPE: DNA
<213> ORGANISM: Artificial Sequence
<220> FEATURE:
<223> OTHER INFORMATION: Synthetic Construct

<400> SEQUENCE: 188
cccctttcgt tcctcaccag                                                   20

<210> SEQ ID NO 189
<211> LENGTH: 21
<212> TYPE: DNA
<213> ORGANISM: Artificial Sequence
<220> FEATURE:
<223> OTHER INFORMATION: Synthetic Construct

<400> SEQUENCE: 189
acggtcttac cctttccagt c                                                 21

<210> SEQ ID NO 190
<211> LENGTH: 21
<212> TYPE: DNA
<213> ORGANISM: Artificial Sequence
<220> FEATURE:
<223> OTHER INFORMATION: Synthetic Construct

<400> SEQUENCE: 190
ccaccagctt gcctttcaga a                                                 21

<210> SEQ ID NO 191
<211> LENGTH: 20
<212> TYPE: DNA
<213> ORGANISM: Artificial Sequence
<220> FEATURE:
<223> OTHER INFORMATION: Synthetic Construct

<400> SEQUENCE: 191
gtcacgcctc agcacatggt                                                   20

<210> SEQ ID NO 192
<211> LENGTH: 20
<212> TYPE: DNA
<213> ORGANISM: Artificial Sequence
<220> FEATURE:
<223> OTHER INFORMATION: Synthetic Construct

<400> SEQUENCE: 192
aatgccttct aatccggtca                                                   20
```

<210> SEQ ID NO 193
<211> LENGTH: 21
<212> TYPE: DNA
<213> ORGANISM: Artificial Sequence
<220> FEATURE:
<223> OTHER INFORMATION: Synthetic Construct

<400> SEQUENCE: 193
agtggaaagc gtggattatg a                                              21

<210> SEQ ID NO 194
<211> LENGTH: 20
<212> TYPE: DNA
<213> ORGANISM: Artificial Sequence
<220> FEATURE:
<223> OTHER INFORMATION: Synthetic Construct

<400> SEQUENCE: 194
tctggattta accggacagc                                                20

<210> SEQ ID NO 195
<211> LENGTH: 20
<212> TYPE: DNA
<213> ORGANISM: Artificial Sequence
<220> FEATURE:
<223> OTHER INFORMATION: Synthetic Construct

<400> SEQUENCE: 195
aggctggagt gtgctgagat                                                20

<210> SEQ ID NO 196
<211> LENGTH: 18
<212> TYPE: DNA
<213> ORGANISM: Artificial Sequence
<220> FEATURE:
<223> OTHER INFORMATION: Synthetic Construct

<400> SEQUENCE: 196
ccgacagcac gaggcttt                                                  18

<210> SEQ ID NO 197
<211> LENGTH: 20
<212> TYPE: DNA
<213> ORGANISM: Artificial Sequence
<220> FEATURE:
<223> OTHER INFORMATION: Synthetic Construct

<400> SEQUENCE: 197
tggtgtgtga cgttcccatt                                                20

<210> SEQ ID NO 198
<211> LENGTH: 22
<212> TYPE: DNA
<213> ORGANISM: Artificial Sequence
<220> FEATURE:
<223> OTHER INFORMATION: Synthetic Construct

<400> SEQUENCE: 198
ggtctgggcc atagaactga tg                                             22

<210> SEQ ID NO 199
<211> LENGTH: 20
<212> TYPE: DNA
<213> ORGANISM: Artificial Sequence
<220> FEATURE:

<223> OTHER INFORMATION: Synthetic Construct

<400> SEQUENCE: 199
gccaccacgc tcttctgtct                                           20

<210> SEQ ID NO 200
<211> LENGTH: 25
<212> TYPE: DNA
<213> ORGANISM: Artificial Sequence
<220> FEATURE:
<223> OTHER INFORMATION: Synthetic Construct

<400> SEQUENCE: 200
aaaccgtttt tccatcttct tcttt                                     25

<210> SEQ ID NO 201
<211> LENGTH: 17
<212> TYPE: DNA
<213> ORGANISM: Artificial Sequence
<220> FEATURE:
<223> OTHER INFORMATION: Synthetic Construct

<400> SEQUENCE: 201
gacggcacac ccaccct                                              17

<210> SEQ ID NO 202
<211> LENGTH: 18
<212> TYPE: DNA
<213> ORGANISM: Artificial Sequence
<220> FEATURE:
<223> OTHER INFORMATION: Synthetic Construct

<400> SEQUENCE: 202
gacggtccgc tgcaactg                                             18

<210> SEQ ID NO 203
<211> LENGTH: 20
<212> TYPE: DNA
<213> ORGANISM: Artificial Sequence
<220> FEATURE:
<223> OTHER INFORMATION: Synthetic Construct

<400> SEQUENCE: 203
gcttccctat ggccctcatt                                           20

<210> SEQ ID NO 204
<211> LENGTH: 20
<212> TYPE: DNA
<213> ORGANISM: Artificial Sequence
<220> FEATURE:
<223> OTHER INFORMATION: Synthetic Construct

<400> SEQUENCE: 204
tgcttgtcct ggagggttgt                                           20

<210> SEQ ID NO 205
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = any nucleotide, a nucleotide derivator or
      non-nucleotdie linkage
<220> FEATURE:

```
<221> NAME/KEY: misc_feature
<222> LOCATION: (2)...(3)
<223> OTHER INFORMATION: n = a nucleotide derivative or non-nucleotide
      linkage modification that suppresses the activity
      of the oligonucleotide motif
<220> FEATURE:
<221> NAME/KEY: misc_feature
<222> LOCATION: 4
<223> OTHER INFORMATION: n = a nucleotide, nucleotide derivator, or
      non-nucleotide linkage modification that
      suppresses the activity of the oligonucleotide
      motif
<220> FEATURE:
<221> NAME/KEY: misc_feature
<222> LOCATION: 5
<223> OTHER INFORMATION: n = c or pyrimidine nucleotide derivative
<220> FEATURE:
<221> NAME/KEY: misc_feature
<222> LOCATION: 6
<223> OTHER INFORMATION: n = g or purine nucleotide derivative
<220> FEATURE:
<221> NAME/KEY: misc_feature
<222> LOCATION: (7)...(9)
<223> OTHER INFORMATION: n = a nucleotide or nucleotide derivative
<220> FEATURE:
<221> NAME/KEY: misc_feature
<222> LOCATION: (10)...(10)
<223> OTHER INFORMATION: n = a nucleotide, nucleotide derivator, or
      non-nucleotide linkage

<400> SEQUENCE: 205 nnnnnnnnnn                                                              10

<210> SEQ ID NO 206
<211> LENGTH: 54
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(12)
<223> OTHER INFORMATION: n = any nucleotide or absent
<220> FEATURE:
<221> NAME/KEY: misc_feature
<222> LOCATION: (13)...(14)
<223> OTHER INFORMATION: n = cytidine or a derivative thereof, wherein
      at least one is a cytidine derivative
<220> FEATURE:
<221> NAME/KEY: misc_feature
<222> LOCATION: (15)...(17)
<223> OTHER INFORMATION: n = any nucleotide
<220> FEATURE:
<221> NAME/KEY: misc_feature
<222> LOCATION: (18)...(38)
<223> OTHER INFORMATION: n = any nucleotide or absent
<220> FEATURE:
<221> NAME/KEY: misc_feature
<222> LOCATION: 39
<223> OTHER INFORMATION: = any nucleotide
<220> FEATURE:
<221> NAME/KEY: misc_feature
<222> LOCATION: (43)...(54)
<223> OTHER INFORMATION: n = any nucleotide or absent

<400> SEQUENCE: 206
nnnnnnnnnn nnnnnnnnnn nnnnnnnnnn nnnnnnnng ggnnnnnnnn nnnn             54

<210> SEQ ID NO 207
<211> LENGTH: 43
<212> TYPE: DNA
<213> ORGANISM: Artificial Sequence
<220> FEATURE:
<223> OTHER INFORMATION: Synthetic Construct
<220> FEATURE:
```

```
<221> NAME/KEY: misc_feature
<222> LOCATION: (2)...(3)
<223> OTHER INFORMATION: n = cytidine or a derivative thereof,
<220> FEATURE:
<221> NAME/KEY: misc_feature
<222> LOCATION: 6
<223> OTHER INFORMATION: n = any nucleotide
<220> FEATURE:
<221> NAME/KEY: misc_feature
<222> LOCATION: (7)...(27)
<223> OTHER INFORMATION: n = any nucleotide or absent,
<220> FEATURE:
<221> NAME/KEY: misc_feature
<222> LOCATION: 28
<223> OTHER INFORMATION: n = any nueclotide
<220> FEATURE:
<221> NAME/KEY: misc_feature
<222> LOCATION: (29)...(31)
<223> OTHER INFORMATION: n = guanosine or a deaza derivative thereof
<220> FEATURE:
<221> NAME/KEY: misc_feature
<222> LOCATION: (32)...(43)
<223> OTHER INFORMATION: n =  any nucleotide or absent

<400> SEQUENCE: 207
tnntgnnnnn nnnnnnnnnn nnnnnnnnnn nnnnnnnnnn nnn                    43
```